United States Patent
Welcher et al.

(10) Patent No.: US 11,230,597 B2
(45) Date of Patent: *Jan. 25, 2022

(54) METHODS OF TREATMENT USING AN INTERFERON GAMMA INHIBITOR

(71) Applicant: AMGEN INC., Thousand Oaks, CA (US)

(72) Inventors: Andrew A. Welcher, Ventura, CA (US); Michael J. Boedigheimer, Newbury Park, CA (US); James B. Chung, Thousand Oaks, CA (US)

(73) Assignee: AMGEN INC., Thousand Oaks, CA (US)

( * ) Notice: Subject to any disclaimer, the term of this patent is extended or adjusted under 35 U.S.C. 154(b) by 707 days.

This patent is subject to a terminal disclaimer.

(21) Appl. No.: 15/693,160

(22) Filed: Aug. 31, 2017

(65) Prior Publication Data

US 2018/0030132 A1 Feb. 1, 2018

Related U.S. Application Data

(63) Continuation of application No. 14/862,096, filed on Sep. 22, 2015, now abandoned, which is a continuation of application No. 13/683,684, filed on Nov. 21, 2012, now abandoned.

(60) Provisional application No. 61/651,900, filed on May 25, 2012, provisional application No. 61/616,846, filed on Mar. 28, 2012, provisional application No. 61/563,357, filed on Nov. 23, 2011.

(51) Int. Cl.
| | |
|---|---|
| *C07K 16/24* | (2006.01) |
| *A61K 39/395* | (2006.01) |
| *A61K 39/00* | (2006.01) |
| *C12Q 1/6883* | (2018.01) |
| *G01N 33/68* | (2006.01) |
| *A61K 31/42* | (2006.01) |
| *A61K 31/519* | (2006.01) |
| *A61K 31/52* | (2006.01) |
| *A61K 31/5377* | (2006.01) |
| *A61K 31/573* | (2006.01) |
| *A61K 45/06* | (2006.01) |
| *A61K 31/365* | (2006.01) |

(52) U.S. Cl.
CPC .......... *C07K 16/249* (2013.01); *A61K 31/365* (2013.01); *A61K 31/42* (2013.01); *A61K 31/519* (2013.01); *A61K 31/52* (2013.01); *A61K 31/5377* (2013.01); *A61K 31/573* (2013.01); *A61K 39/0005* (2013.01); *A61K 39/3955* (2013.01); *A61K 45/06* (2013.01); *C12Q 1/6883* (2013.01); *G01N 33/68* (2013.01); *A61K 2039/505* (2013.01); *A61K 2039/545* (2013.01); *C07K 2317/21* (2013.01); *C07K 2317/56* (2013.01); *C07K 2317/565* (2013.01); *C07K 2317/76* (2013.01); *C12Q 2600/106* (2013.01); *C12Q 2600/158* (2013.01); *G01N 2800/52* (2013.01)

(58) Field of Classification Search
None
See application file for complete search history.

(56) References Cited

U.S. PATENT DOCUMENTS

| | | | | |
|---|---|---|---|---|
| 7,335,743 B2 * | 2/2008 | Welcher | ... | A61P 37/06 530/388.15 |
| 7,790,859 B2 * | 9/2010 | Welcher | ... | A61P 3/10 530/387.3 |
| 8,529,893 B2 * | 9/2013 | Welcher | ... | A61P 43/00 424/130.1 |
| 8,906,371 B2 * | 12/2014 | Welcher | ... | A61P 19/04 424/133.1 |
| 2005/0004353 A1 * | 1/2005 | Welcher | ... | A61P 15/00 530/388.22 |

FOREIGN PATENT DOCUMENTS

| | | |
|---|---|---|
| JP | 2006/508689 A | 3/2006 |
| WO | 2001/0142474 A | 6/2001 |
| WO | 2004/035747 A | 4/2004 |
| WO | 2013/078378 A | 5/2013 |

OTHER PUBLICATIONS

Marrizzua et al. Annu. Rev. Blophys. Biophys. Chem. 1987; 16: 139-159. (Year: 1987).*
Baechler et al. (2003, PNAS, vol. 5, p. 2610-2615) (Year: 2003).*
Bauer et al. (2009, Arthritis Rheum., 60(10), p. 3098-3107) (Year: 2009).*
Brown, M., et al. "Tolerance of Single, but Not Multiple, Amino Acid Replacements in Antibody VH CDR2: A Means of Minimizing B Cell Wastage from Somatic Hypermutation?" *The Journal of Immunology* (1996): 3285-3291.
Giusti, A. M., et al. "Somatic Diversification of S107 from an Antiphosphocholine to an Anti-DNA Autoantibody Is Due to a Single Base Change in Its Heavy Chain Variable Region," *Proceedings of the National Academy of Sciences* 84.9 (1987): 2926-2930.
Jordan et al., An animal model of hemophagocytic lymphohistiocytosis (HLH): CD8+ T cells and interferon gamma are essential for the disorder; Blood, Aug. 1, 2004, vol. 104, No. 3, pp. 734-743.

(Continued)

*Primary Examiner* — Gary B Nickol
*Assistant Examiner* — Jegatheesan Seharaseyon
(74) *Attorney, Agent, or Firm* — Lawrence H. Kong

(57) ABSTRACT

The invention encompasses methods of treatment of interferon gamma (IFN-γ)-mediated diseases using IFN-γ inhibitors, such as anti-huIFN-γ antibodies, wherein levels of expression of one or more biomarkers are determined either before administration of the IFN-γ inhibitor and/or after administration. Also contemplated are methods of treatment using particular, pharmacodynamically effective doses of an anti-huIFN-γ antibody.

29 Claims, 14 Drawing Sheets

Specification includes a Sequence Listing.

(56) References Cited

OTHER PUBLICATIONS

Kono, Michihito, et al., (The Journal of the Japanese Society of Internal Medicine), Oct. 10, 2011, vol. 100, No. 10, pp. 2954-2959.
Martin, David A, et al., AMG 811 (anti-IFN-gamma) Treatment Leads to a Reduction in the Whole Blood IFN-Signature and Serum CXCL10 In Subjects With Systemic Lupus Erythematosus Results Of Two Phase I Studies'. Arthritis & Rheumatism, vol. 65, Oct. 2013 Abstract Supplement; Abstracts of the 2013 American College of Rheumatology /Association of Rheumatology Health Professionals Annual Meeting San Diego. CA Oct. 25-30, 2013.
Schildbach, Joel F., et al. "Contribution of a Single Heavy Chain Residue to Specificity of an Anti-digoxin Monoclonal Antibody." *Protein Science* 3.5 (2008): 737-749.
Schmid et al., Neutralization of IFNy defeats haemophagocytosis in LCMV-infected perforin- and Rab27a-deficient mice, 2009, EMBO Mol Med, 1, 112-124.

\* cited by examiner

METHODS OF TREATMENT USING AN INTERFERON GAMMA INHIBITOR

PRIORITY

This application is a continuation of and claims priority to U.S. patent application Ser. No. 14/862,096, filed Sep. 22, 2015 which is a continuation of U.S. Non Provisional patent application Ser. No. 13/683,684, filed Nov. 21, 2012, which claims the benefit of U.S. Provisional Application Nos. 61/563,357, filed Nov. 23, 2011, 61/616,846, filed Mar. 28, 2012, and 61/651,900 filed May 25, 2012, each of which are hereby incorporated by reference herein in their entireties.

REFERENCE TO THE SEQUENCE LISTING

The present application is being filed along with a Sequence Listing in electronic format. The Sequence Listing is provided as a file entitled A-1679-US-NP_Sequence_Listing_as_filed, created Nov. 20, 2012, which is 253 KB in size. The information in the electronic format of the Sequence Listing is incorporated herein by reference in its entirety.

FIELD

This invention is in the field of methods of patient stratification and methods treatment using an interferon gamma (IFN-γ) inhibitor, as well as uses of IFN-γ inhibitors.

BACKGROUND

IFN-γ plays an important role in regulating the immune system. It is a cytokine with pleiotropic effects and is thought to play a role in mediating various autoimmune diseases, as well as immune responses to infectious agents and cancer cells. See, e.g., Heremans et al., Develop. Biol. Standard., 71: 113-119, in Symposium on Monoclonal Antibodies for Therapy, Prevention and in vivo diagnosis of human disease, Ultrecht, The Netherlands, 1989, S. Karger, Basel, 1990. Comparatively recent analyses of RNA and protein levels have yielded detailed information concerning the identities of collections of genes that are over- and under-expressed in biological samples from patients suffering from autoimmune diseases. For example, in patients suffering from a variety of autoimmune diseases, type I (i.e., IFNα, IFNβ, IFNω, IFNε, and IFNκ) and/or type II (i.e., IFN-γ) interferon-induced genes are overexpressed. Baechler et al. (2003), Proc. Natl. Acad. Sci. 100(5): 2610-2615; Mavragani et al. (2010), Arthr. & Rheum. 62(2): 392-401; Pietrzak et al. (2008), Clinica Chimica Acta 394: 7-21; van Baarsen et al. (2006), Genes and Immunity 7: 522-531; Reynier et al. (2010), Genes and Immunity 11: 269-278; Fiorentino (2008), Arch. Dermatol. 144(10): 1379-1382. In the case of systemic lupus erythematosus (SLE), overexpression of these genes correlates with clinical and laboratory measures of disease activity. See, e.g., Bauer et al. (2006), PLoS Medicine 3(12): 2274-2284; Bauer et al. (2009), Arthr. & Rheum. 60(10): 3098-3107; Baechler et al. (2003), Proc. Natl. Acad. Sci. 100(5): 2610-2615. Type I and type II interferons affect expression of a distinct, but overlapping, set of genes, and such effects may vary depending on the tissue examined. See, e.g., van Baarsen et al. (2006), Genes and Immunity 7: 522-531 and Baechler et al. (2003), Proc. Natl. Acad. Sci. 100(5): 2610-2615.

Selection of the right patient group and dosage and assessment of patient response to a particular dosage on an ongoing basis can be key factors in the successful use of an IFN-γ inhibitor as a therapeutic for the treatment of autoimmune/inflammatory diseases. Many autoimmune/inflammatory diseases are episodic in nature and have variable clinical manifestations, and possibly also variable etiologies. Some of these diseases have long asymptomatic periods between symptoms or prior to the onset of symptoms. There is a need to determine whether a patient is a candidate for a particular treatment and/or whether an ongoing treatment is having the desired effects. Because of the biological variations between patients who are clinically diagnosed as having the same disease, it is possible that IFN-γ inhibitors may be efficacious for some patients having a particular disease and not for others. Such variations have, for example, been observed in rheumatoid arthritis patients, some of which respond to TNF inhibitors while others do not. See, e.g., Potter et al. (2010), Ann. Rheum Dis. 69: 1315-1320. Thus, it is highly desirable to distinguish patients for whom inhibition of IFN-γ is likely to be helpful from those for whom it is not. Further, the optimal dosage and nature of a particular IFN-γ inhibitor are likely to be important factors in the therapeutic suitability of a treatment, given the important role of IFN-γ in resistance to infections, among other vital functions. Thus, there is a need to assess the efficacy and safety of various doses and/or frequencies of dosing in asymptomatic, as well as symptomatic, periods of a disease. Methods provided herein utilize current technologies for assessing gene expression at the RNA and protein levels to provide more refined and effective methods of treatment using inhibitors of IFN-γ, of identifying optimal doses, and of identifying individuals who are likely to respond to treatment, and/or who are or are not responding to treatment.

SUMMARY

Described herein are methods of treatment that include administration of an IFN-γ inhibitor to a patient and determination of levels of one or more biomarkers in a biological sample from the patient before and/or after administration of the IFN-γ inhibitor so as to assess the suitability as a treatment or the biological effects of the IFN-γ inhibitor. Such methods can inform decisions as to whether to initiate or continue treatment with an IFN-γ inhibitor. Also described are methods for distinguishing patients likely to benefit from treatment with an IFN-γ inhibitor from those unlikely to benefit by assessing the levels of one or more biomarkers in a biological sample from a patient as compared to the levels of the same biomarkers in biological samples from a healthy control group. Further described herein are methods of treatment that include the use of doses of an anti-IFN-γ antibody within a specified range and/or at a specified frequency of dosing.

Herein is described a method of treating a patient suffering from an IFN-γ-mediated disease comprising administering to the patient a monoclonal anti-human interferon gamma (anti-huIFN-γ) antibody at a dose, which can be from about 15 mg (mg) to about 300 mg or from about 30, 40, 50, or 60 mg to about 80, 120, 180, 200, 250, 300 or 400 mg, wherein expression at the RNA or protein level of one or more gene(s) listed in Table 1, 2, 4, 5, and/or 6 in a biological sample from the patient taken before the antibody is administered deviates from expression of that gene(s) in a control biological sample in a direction consistent with excess IFN-γ. In addition, described herein is a use of a monoclonal anti-huIFN-γ antibody as a medicament to treat a patient suffering from an IFN-γ-mediated disease, wherein the dose of the antibody administered is from about 15, 30, 40, 50, or 60 milligrams to about 80, 120, 180, 200, 250, or 300 milligrams and wherein expression at the RNA or protein level of one or more gene(s) listed in Table 1, 2, 4, 5, and/or 6 in a biological sample taken from the patient taken before the antibody is administered deviates from expression of that gene(s) in a control biological sample in a direction consistent with excess IFN-γ. In some embodiments, the expression of at least 2, 3, 4, 5, 6, 7, 8, 9, 10, 12, 14, 16, 18, 20, 25, 30, 35, or 40 genes listed in Table 1, 2, 4, 5, and/or 6 in the biological sample from the patient deviates from the expression of those genes in the control biological sample in a direction consistent with excess IFN-γ. The biological sample from the patient can exhibit expression of one or more of the following human genes at the RNA or protein level that deviates from expression in the control biological sample in a direction consistent with excess IFN-γ: indoleamine 2,3-dioxygenase 1 (IDO1), ankyrin repeat domain 22 (ANKRD22), chemokine (C—X—C motif) ligand 9 (CXCL9), family with sequence similarity 26, member F (FAM26F), purinergic receptor P2Y, G-protein coupled, 14 (P2RY14), guanylate binding binding protein 5 (GBP5), serpin peptidase inhibitor, clade G, member 1 (SERPING1), Fc fragment of IgG, high affinity Ib, receptor (CD64), guanylate binding protein 1, interferon-inducible, 67 kDa (GBP1), chemokine (C—X—C motif) ligand 10 (CXCL10), ets variant 7 (ETV7), lymphatic vessel endothelial hyaluronan receptor 1 (LYVE1), serpin peptidase inhibitor clade B (ovalbumin), member 2 (SERPINB2), matrix metallopeptidase 19 (MMP19), radical S-adenosyl methionine domain containing 2 (RSAD2), heparin sulfate (glucosamine) 3-O-sulfotransferase 1 (HS3ST1), indoleamine 2,3-dioxygenase 2 (IDO2), programmed death ligand-1 (PD-L1), basic leucine zipper transcription factor, ATF-like 2 (BATF2), Fc fragment of IgG, high affinity Ib, receptor (FCGR1B or CD64), activating transcription factor 3 (ATF3), pyruvate dehydrogenase kinase, isozyme 4 (nuclear gene encoding mitochondrial protein; PDK4), and/or CD274. In some embodiments, the biological sample from the patient can exhibit elevated expression at the RNA or protein level of GBP1 as compared to expression in the control biological sample. The IFN-γ-mediated disease can be systemic lupus erythematosus (SLE), discoid lupus, lupus nephritis, psoriasis, or an inflammatory bowel disease, including Crohn's disease and ulcerative colitis. The dose of the anti-huIFN-γ antibody can be from about 40 mg or 60 mg to about 300 mg, from about 20 mg or 80 mg to about 200 or 250 mg, from about 60 or 100 mg to about 180 mg, or about 40, 50, 60, 70, 80, 90, 100, 120, 150, or 180 mg. The anti-huIFN-γ antibody can be administered subcutaneously or intravenously. A gluocorticoid and/or mycophenolate mofetil, azathioprine, leflunomide, methotrexate, or an antimalarial can be administered concurrently with the antibody.

In another aspect, described herein is a method for treating a patient having an IFN-γ-mediated disease, for example SLE or an inflammatory bowel disease, with an IFN-γ inhibitor comprising: (a) determining the level(s) of expression in a biological sample from the patient of one or more genes listed in Tables 1, 2, 4, 5, and/or 6 at the RNA or protein level, wherein level of expression of the same gene(s) in a control biological sample is known or determined; (b) comparing the level(s) of expression of the gene(s) in the biological sample from the patient and in the control biological sample; and (c) if the level(s) of expression of the gene(s) in the biological sample from the patient deviate from the levels of expression of the gene(s) in the control biological sample in a direction consistent with excess IFN-γ, administering to the patient a therapeutically effective dose of an IFN-γ inhibitor. In addition, described herein is a use of an IFN-γ inhibitor as a medicament to treat a patient having an IFN-γ-mediated disease, for example SLE or an inflammatory bowel disease, (a) wherein the level(s) of expression in a biological sample from the patient of one or more gene(s) listed in Tables 1, 2, 4, 5, and/or 6 at the RNA or protein level is determined, (b) wherein the level(s) of expression of the same gene(s) in a control biological sample is known or determined, (c) wherein the level(s) of expression of the same gene(s) in the biological sample from the patient and the control biological sample are compared, and (d) wherein if the level(s) of expression of the gene(s) in the biological sample from the patient deviate from the levels of expression of the gene(s) in the control biological sample in a direction consistent with excess IFN-γ, a therapeutically effective dose of the IFN-γ inhibitor is administered. The one or more genes listed in Tables 1, 2, 4, 5, and/or 6 of (a) can include at least about 2, 3, 4, 5, 6, 7, 8, 9, 10, 12, 14, 16, 18, 20, 25, 30, 35, or 40 genes. The IFN-γ inhibitor can be a human or humanized anti-huIFN-γ antibody. The dose of the anti-huIFN-γ antibody administered can be from about 15, 30, or 60 mg to about 300 mg, from about 20, 40, or 80 mg to about 250 mg, or from about 40, 50, or 60 mg to about 120, 150, 180 or 200 mg. The patient can have discoid lupus, lupus nephritis, psoriasis, ulcerative colitis, or Crohn's disease. The biological sample from the patient can exhibit expression of one or more of the following genes at the RNA or protein level that deviates from expression in the control biological sample in a direction consistent with excess IFN-γ: indoleamine 2,3-dioxygenase 1 (IDO1), ankyrin repeat domain 22 (ANKRD22), chemokine (C—X—C motif) ligand 9 (CXCL9), family with sequence similarity 26, member F (FAM26F), purinergic receptor P2Y, G-protein coupled, 14 (P2RY14), guanylate binding binding protein 5 (GBP5), serpin peptidase inhibitor, clade G, member 1 (SERPING1), Fc fragment of IgG, high affinity Ib, receptor (CD64), guanylate binding protein 1, interferon-inducible, 67 kDa (GBP1), chemokine (C—X—C motif) ligand 10 (CXCL10), ets variant 7 (ETV7), lymphatic vessel endothelial hyaluronan receptor 1 (LYVE1), serpin peptidase inhibitor clade B (ovalbumin), member 2 (SERPINB2), matrix metallopeptidase 19 (MMP19), radical S-adenosyl methionine domain containing 2 (RSAD2), heparin sulfate (glucosamine) 3-O-sulfotransferase 1 (HS3ST1), indoleamine 2,3-dioxygenase 2 (IDO2), programmed death ligand-1 (PD-L1), basic leucine zipper transcription factor, ATF-like 2 (BATF2), Fc fragment of IgG, high affinity Ib, receptor (FCGR1B or CD64), activating transcription factor 3 (ATF3), pyruvate dehydrogenase kinase, isozyme 4 (nuclear gene encoding mitochondrial protein; PDK4), and/or CD274. The IFN-γ inhibitor can be an anti-huIFN-γ antibody that has a heavy chain complementarity determining region 1 (CDR1) comprising the amino acid sequence of SEQ ID NO:34, a heavy chain complementarity determining region 2 (CDR2) comprising the amino acid sequence of SEQ ID NO:35, a heavy chain complementarity determining region 3 (CDR3) comprising the amino acid sequence of SEQ ID NO:36 or SEQ ID NO:37, a light chain CDR1 comprising the amino acid sequence of SEQ ID NO:38, SEQ ID NO:39, or SEQ ID NO:40, a light chain CDR2 comprising the amino acid sequence of SEQ ID NO:41 or SEQ ID NO:42, and a light chain CDR3 comprising the amino acid sequence of SEQ ID NO:43 or SEQ ID NO:44. A gluocorticoid and/or mycophenolate mofetil, azathioprine, leflunomide, methotrexate, or an anti-malarial can be administered concurrently with the antibody.

In another aspect, described herein is method for identifying a patient having an IFN-γ-mediated disease who can benefit from treatment with an IFN-γ inhibitor comprising: (a) determining the level(s) of expression in a biological sample from the patient of one or more of one of the genes listed in Table 1, 2, 4, 5, and/or 6 at the RNA or protein level, wherein level(s) of expression of the same gene(s) in a control biological sample is known or determined; (b) comparing the levels of expression of the gene(s) in the biological sample from the patient and in the control biological sample; and (c) if the level(s) of expression of the gene(s) in the biological sample from the patient deviate from the level(s) in the control biological sample in a direction consistent with excess IFN-γ, determining that the patient can benefit from treatment with an IFN-γ inhibitor and/or administering a therapeutically effective dose of an IFN-γ inhibitor. The one or more genes listed in Tables 1, 2, 4, 5, and/or 6 of (a) can include at least about 2, 3, 4, 5, 6, 7, 8, 9, 10, 12, 14, 16, 18, 20, 25, 30, 35, or 40 genes. The one or more genes can be from Table 1, 2, 4, 5, or 6. In addition, described herein is a use of an IFN-γ inhibitor as a medicament for treating a patient having an IFN-γ-mediated disease, wherein the level(s) of expression in a biological sample from the patient of one or more of one of the genes listed in Table 1, 2, 4, 5, and/or 6 is determined at the RNA or protein level, wherein the level(s) of expression of the same gene(s) in a control biological sample is known or determined; wherein the level(s) of expression of the gene(s) in the biological sample from the patient and in the control biological sample are compared; and wherein if the level(s) of expression of the gene(s) in the biological sample from the patient deviate from the level(s) in the control biological sample in a direction consistent with excess IFN-γ, determining that the patient can benefit from treatment with an IFN-γ inhibitor and/or administering a therapeutically effective dose of an IFN-γ inhibitor. The IFN-γ inhibitor can be an anti-human IFN-γ antibody, for example an antibody comprising the amino acid sequences of SEQ ID NOs: 6 and 8, 10 and 12, 14, and 16, 14 and 31, or 30 and 12. The therapeutically effective dose can be from 60 mg to 500 mg, from 80 mg to 400 mg, from 100 mg to 350 mg, from 60 mg to 180 mg, or from 120 mg to 300 mg. The IFN-γ-mediated disease can be SLE including discoid lupus and lupus nephritis, an inflammatory bowel disease including Crohn's disease and ulcerative colitis, or psoriasis, among other IFN$_\gamma$-mediated diseases disclosed herein. The gene(s) can include one or more of the following genes: indoleamine 2,3-dioxygenase 1 (IDO1), ankyrin repeat domain 22 (ANKRD22), chemokine (C—X—C motif) ligand 9 (CXCL9), family with sequence similarity 26, member F (FAM26F), purinergic receptor P2Y, G-protein coupled, 14 (P2RY14), guanylate binding binding protein 5 (GBP5), serpin peptidase inhibitor, clade G, member 1 (SERPING1), Fc fragment of IgG, high affinity Ib, receptor (CD64), guanylate binding protein 1, interferon-inducible, 67 kDa (GBP1), chemokine (C—X—C motif) ligand 10 (CXCL10), ets variant 7 (ETV7), lymphatic vessel endothelial hyaluronan receptor 1 (LYVE1), serpin peptidase inhibitor clade B (ovalbumin), member 2 (SERPINB2), matrix metallopeptidase 19 (MMP19), radical S-adenosyl methionine domain containing 2 (RSAD2), heparin sulfate (glucosamine) 3-O-sulfotransferase 1 (HS3ST1), indoleamine 2,3-dioxygenase 2 (INDO2), programmed death ligand-1 (PD-L1), basic leucine zipper transcription factor, ATF-like 2 (BATF2), Fc fragment of IgG, high affinity Ib, receptor (FCGR1B or CD64), activating transcription factor 3 (ATF3), pyruvate dehydrogenase kinase, isozyme 4 (nuclear gene encoding mitochondrial protein; PDK4), and/or CD274. A gluococorticoid and/or mycophenolate mofetil, azathioprine, leflunomide, methotrexate, or an anti-malarial can be administered concurrently with the antibody.

Further described herein is a method for treating a patient suffering from an IFN-γ-mediated disease comprising: (a) determining the level(s) of expression at the RNA or protein level in a biological sample from the patient of one or more of the genes in Table 1, 2, 4, 5, and/or 6; (b) then administering to the patient a pharmacodynamically effective dose of an IFN-γ inhibitor, for example an anti-huIFN-γ antibody; (c) then determining the level of expression of the gene(s) of step (a) in a biological sample from the patient; and (d) if the level(s) of expression of the gene(s) determined in step (c), as compared to the level(s) of expression determined in step (a), is modulated in a direction consistent with inhibition of IFN-γ, then continuing treatment of the patient with another pharmacodynamically effective dose of the IFN-γ inhibitor. The one or more genes listed in Tables 1, 2, 4, 5, and/or 6 of (a) can include at least about 2, 3, 4, 5, 6, 7, 8, 9, 10, 12, 14, 16, 18, 20, 25, 30, 35, or 40 genes. In addition, described herein is the use of an IFN-γ inhibitor antibody, for example an anti-huIFN-γ antibody, as a medicament for treating a patient suffering from an IFN-γ-mediated disease, wherein (a) the level of expression at the RNA or protein level in a biological sample from the patient of one or more of the genes in Table 1, 2, 4, 5, and/or 6 is determined, (b) then a pharmacodynamically effective dose of the IFN-γ inhibitor is administered to the patient, (c) then the level(s) of expression of the gene(s) of step (a) in a biological sample from the patient is determined, and (d) if the level(s) of expression of the gene(s) determined in step (c), as compared to the level(s) of expression determined in step (a), is modulated in a direction consistent with inhibition of IFN-γ, then continuing treatment of the patient with another pharmacodynamically effective dose of the IFN-γ inhibitor. For an IFN-γ inhibitor that is an anti-huIFN-γ antibody, the pharmacodynamically effective dose can be from about 15, 30, or 60 mg to about 300 mg, from about 20, 40, or 80 mg to about 250 mg, or from about 60 mg to about 180 or 220 mg. The IFN-γ-mediated disease can be selected from the group consisting of SLE, lupus nephritis, discoid lupus, psoriasis, and inflammatory bowel diseases including ulcerative colitis and Crohn's disease. The human genes whose level(s) of expression are determined in (a) and (c) can be selected from the group consisting of: indoleamine 2,3-dioxygenase 1 (IDO1), ankyrin repeat domain 22 (ANKRD22), chemokine (C—X—C motif) ligand 9 (CXCL9), family with sequence similarity 26, member F (FAM26F), purinergic receptor P2Y, G-protein coupled, 14 (P2RY14), guanylate binding binding protein 5 (GBP5), serpin peptidase inhibitor, clade G, member 1 (SERPING1), Fc fragment of IgG, high affinity Ib, receptor (CD64), guanylate binding protein 1, interferon-inducible, 67 kDa (GBP1), chemokine (C—X—C motif) ligand 10 (CXCL10), ets variant 7 (ETV7), lymphatic vessel endothelial hyaluronan receptor 1 (LYVE1), serpin peptidase inhibitor clade B (ovalbumin), member 2 (SERPINB2), matrix metallopeptidase 19 (MMP19), radical S-adenosyl methionine domain containing 2 (RSAD2), heparin sulfate (glucosamine) 3-O-sulfotransferase 1 (HS3ST1), indoleamine 2,3-dioxygenase 2 (IDO2), programmed death ligand-1 (PD-L1), basic leucine zipper transcription factor, ATF-like 2 (BATF2), Fc fragment of IgG, high affinity Ib, receptor (FCGR1B or CD64), activating transcription factor 3 (ATF3), pyruvate dehydrogenase kinase, isozyme 4 (nuclear gene encoding mitochondrial protein; PDK4), and/or CD274.

In another aspect, a method is described for treating a patient suffering from an IFN-γ-mediated disease, for example SLE, lupus nephritis, discoid lupus, psoriasis, or an inflammatory bowel disease, with an IFN-γ inhibitor, for example an anti-huIFN-γ antibody, comprising the following steps: (a) determining the level(s) of expression at the RNA or protein level of one or more genes listed in Tables 1, 2, 4, 5, and/or 6 in a biological sample from the patient; (b) thereafter administering a pharmacodynamically effective dose of the IFN-γ inhibitor to the patient; (c) thereafter determining the level(s) of expression of the gene(s) of (a) in a second biological sample from the patient; and (d) if the level(s) of expression of the gene(s) in second biological sample of (c) is substantially the same as that in the biological sample of (a) or if the level of expression of the gene(s) in second biological sample of (c) deviates from the level of expression in the biological sample of (a) in a direction that is consistent with an excess of IFN-γ, then treatment with the IFN-γ inhibitor can be discontinued. In another aspect, described herein is a use of an IFN-γ inhibitor, for example an anti-huIFN-γ antibody, as a medicament for treating a patient suffering from an IFN-γ-mediated disease, wherein (a) the level(s) of expression at the RNA or protein level of one or more genes listed in Tables 1, 2, 4, 5, and/or 6 in a biological sample from the patient can be determined; (b) thereafter a pharmacodynamically effective dose of the IFN-γ inhibitor can be administered to the patient; (c) thereafter the level(s) of expression of the gene(s) of (a) in a second biological sample from the patient can be determined; and (d) if the level(s) of expression of the gene(s) in second biological sample of (c) is substantially the same as that in the biological sample of (a) or if the level of expression of the gene(s) in second biological sample of (c) deviates from the level of expression in the biological sample of (a) in a direction that is consistent with an excess of IFN-γ, then the treatment with the IFN-γ inhibitor can be discontinued. The one or more genes listed in Tables 1, 2, 4, 5, and/or 6 of (a) can include at least about 2, 3, 4, 5, 6, 7, 8, 9, 10, 12, 14, 16, 18, 20, 25, 30, 35, or 40 genes. Where the IFN-γ inhibitor is an anti-huIFN-γ antibody, the pharmacodynamically effective dose can be from about 15, 30, or 60 mg to about 80, 100, 120, 150, 200, 250, or 300 mg, from about 20, 40, or 80 mg to about 90, 100, 120, 150, 180, or 250 mg, or from about 60 mg to about 180 or 220 mg. The patient can be suffering from systemic lupus erythematosus, lupus nephritis and/or discoid lupus. The patient can be suffering from psoriasis or an inflammatory bowel disease, including Crohn's disease or ulcerative colitis. The genes whose level(s) of expression are determined in (a) and (c) can be selected from the group consisting of: indoleamine 2,3-dioxygenase 1 (IDO1), ankyrin repeat domain 22 (ANKRD22), chemokine (C—X—C motif) ligand 9 (CXCL9), family with sequence similarity 26, member F (FAM26F), purinergic receptor P2Y, G-protein coupled, 14 (P2RY14), guanylate binding binding protein 5 (GBP5), serpin peptidase inhibitor, clade G, member 1 (SERPING1), Fc fragment of IgG, high affinity Ib, receptor (CD64), guanylate binding protein 1, interferon-inducible, 67 kDa (GBP1), chemokine (C—X—C motif) ligand 10 (CXCL10), ets variant 7 (ETV7), lymphatic vessel endothelial hyaluronan receptor 1 (LYVE1), serpin peptidase inhibitor clade B (ovalbumin), member 2 (SERPINB2), matrix metallopeptidase 19 (MMP19), radical S-adenosyl methionine domain containing 2 (RSAD2), heparin sulfate (glucosamine) 3-O-sulfotransferase 1 (HS3ST1), indoleamine 2,3-dioxygenase 2 (IDO2), programmed death ligand-1 (PD-L1), basic leucine zipper transcription factor, ATF-like 2 (BATF2), Fc fragment of IgG, high affinity Ib, receptor (FCGR1B or CD64), activating transcription factor 3 (ATF3), pyruvate dehydrogenase kinase, isozyme 4 (nuclear gene encoding mitochondrial protein; PDK4), and/or CD274. A gluococorticoid and/or mycophenolate mofetil, azathioprine, leflunomide, methotrexate, or an anti-malarial can be administered concurrently with the antibody.

Any of the methods or uses described above or below that utilize an anti-huIFN-γ antibody can utilize an anti-huIFN-γ antibody which can have a heavy chain CDR1 comprising the amino acid sequence of SEQ ID NO:34, a heavy chain CDR2 comprising the amino acid sequence of SEQ ID NO:35, a heavy chain CDR3 comprising the amino acid sequence of SEQ ID NO:36 or SEQ ID NO:37, a light chain CDR1 comprising the amino acid sequence of SEQ ID NO:38, SEQ ID NO:39, or SEQ ID NO:40, a light chain CDR2 comprising the amino acid sequence of SEQ ID NO:41 or SEQ ID NO:42, and a light chain CDR3 comprising the amino acid sequence of SEQ ID NO:43 or SEQ ID NO:44. In specific embodiments, the heavy chain CDR3 can comprise the amino acid sequence of SEQ ID NO:36, the light chain CDR1 can comprise the amino acid sequence of SEQ ID NO:38, the light chain CDR2 can comprise the amino acid sequence of SEQ ID NO:41, and the light chain CDR3 can comprise the amino acid sequence of SEQ ID NO:43. The heavy chain variable region of the antibody can comprise the amino acid sequence of SEQ ID NO:6, SEQ ID NO:10, SEQ ID NO:14, or SEQ ID NO:30, and the light chain variable region of the antibody can comprise the amino acid sequence of SEQ ID NO:8, SEQ ID NO:12, SEQ ID NO:16, or SEQ ID NO:31. The heavy chain variable region can comprise the amino acid sequence of SEQ ID NO:6, and the light chain variable region comprises the amino acid sequence of SEQ ID NO:8. The heavy chain variable region can comprise the amino acid sequence of SEQ ID NO:10, and the light chain variable region can comprise the amino acid sequence of SEQ ID NO:12. The heavy chain variable region can comprise the amino acid sequence of SEQ ID NO:14, and the light chain variable region can comprise the amino acid sequence of SEQ ID NO:16. The heavy chain variable region can comprise the amino acid sequence of SEQ ID NO:30, and the light chain variable region can comprise the amino acid sequence of SEQ ID NO:12. The heavy chain variable region can comprise the amino acid sequence of SEQ ID NO:14, and the light chain variable region can comprise the amino acid sequence of SEQ ID NO:31. The anti-huIFN-γ antibody can be a human, humanized, or chimeric antibody of the IgG, IgM, IgE, IgD, or IgA isotype. The anti-huIFN-γ antibody can be an IgG1, IgG2, IgG3, or IgG4 antibody.

In another aspect, herein is described a method for treating a patient suffering from an IFN-γ-mediated disease comprising administering to the patient a dose of an anti-IFN-γ antibody such that the concentration of total IFN-γ protein in the patient's serum is maintained at a plateau concentration for at least about two weeks following administration of the antibody, wherein the antibody comprises the amino acid sequences of SEQ ID NO:6 and SEQ ID NO:8. The dose can comprise at least about 20, 40, 60, or 80 milligrams and not more than 100, 200, 300, 400, or 500 milligrams of an anti-IFN-γ antibody. The plateau concentration can be maintained for at least about 3, 4, 5, 6, or 8 weeks after the antibody is administered. The plateau concentration of IFN-γ protein in the patient's blood can be from about 100 pg/mL to about 2000 pg/mL and/or at least about 200 or 300 pg/mL. The anti-IFN-γ antibody can comprise a heavy chain CDR1 comprising the amino acid sequence of SEQ ID NO:34, a heavy chain CDR2 comprising the amino acid sequence of SEQ ID NO:35, a heavy chain CDR3 comprising the amino acid sequence of SEQ ID NO:36 or SEQ ID NO:37, a light chain CDR1 comprising the amino acid sequence of SEQ ID NO:38, SEQ ID NO:39, or SEQ ID NO:40, a light chain CDR2 comprising the amino acid sequence of SEQ ID NO:41 or SEQ ID NO:42, and a light chain CDR3 comprising the amino acid sequence of SEQ ID NO:43 or SEQ ID NO:44. The anti-IFN-γ antibody can comprise the amino acid sequences of SEQ ID NOs: 6 and 8, SEQ ID NOs: 10 and 12, SEQ ID NOs: 14 and 16, SEQ ID NOs: 30 and 12, or SEQ ID NOs: 14 and 31. The dose of the anti-IFN-γ antibody can be at least about 20, 40, 60, 80, 100, 150, 180, 200, 220, or 250 mg and/or not more than 180, 200, 220, 240, 260, 280, 300, 350, 400, 450, or 500 mg and can be administered subcutaneously or intravenously. The level of IFN-γ in the patient's serum can remain above about 100, 200, 250, 300, or 350 picograms per milliliter for at least about 14, 16, 18, 20, 25, 30, 35, 40, 45, or 50 days subsequent to a single dose. The IFN-γ-mediated disease can be psoriasis, SLE, lupus nephritis, discoid lupus, or an inflammatory bowel disease such as Crohn's disease or ulcerative colitis. A gluocorticoid and/or mycophenolate mofetil, azathioprine, leflunomide, methotrexate, or an anti-malarial can be administered concurrently with the antibody.

Also herein is described a method for identifying a patient that can benefit from treatment with an IFN-γ inhibitor comprising the following steps: obtaining a biological sample from the patient; determining the levels of IFN-γ protein in the biological sample; and comparing the levels of IFN-γ protein in the biological sample from the patient with the levels determined in a control biological sample; wherein if the levels of total IFN-γ protein in the biological sample from the patient are higher than those in the control biological sample, then the patient is identified as a patient that may benefit from treatment with an IFN-γ inhibitor; and wherein if the levels of IFN-γ protein in the biological sample from the patient are lower than or the same as those in the control biological sample, then the patient is identified as a patient that may not benefit from treatment with an IFN-γ inhibitor. The levels of IFN-γ protein determined can be the levels of total IFN-γ protein, meaning the total of free and bound IFN-γ protein. The IFN-γ inhibitor can be an anti-IFN-γ antibody. The anti-IFN-γ antibody can comprise a heavy chain CDR1 comprising the amino acid sequence of SEQ ID NO:34, a heavy chain CDR2 comprising the amino acid sequence of SEQ ID NO:35, a heavy chain CDR3 comprising the amino acid sequence of SEQ ID NO:36 or SEQ ID NO:37, a light chain CDR1 comprising the amino acid sequence of SEQ ID NO:38, SEQ ID NO:39, or SEQ ID NO:40, a light chain CDR2 comprising the amino acid sequence of SEQ ID NO:41 or SEQ ID NO:42, and a light chain CDR3 comprising the amino acid sequence of SEQ ID NO:43 or SEQ ID NO:44. The anti-IFN-γ antibody can comprise the amino acid sequences of SEQ ID NO:6, SEQ ID NO:10, SEQ ID NO:14, or SEQ ID NO:30 and SEQ ID NO:8, SEQ ID NO:12, SEQ ID NO:16, or SEQ ID NO:31. A gluocorticoid and/or mycophenolate mofetil, azathioprine, leflunomide, methotrexate, or an anti-malarial can be administered concurrently with the antibody.

In another embodiment, herein is described a method for treating an IFN-γ-mediated disease comprising administering a dose of an IFN-γ inhibitor such that the concentration of total IFN-γ protein in serum is maintained at a plateau concentration for at least about two, three, four, five, six, seven, eight, nine, or ten weeks after administration. The plateau concentration of total IFN-γ protein in serum can be from about 200 to about 2000 picograms per milliliter (pg/mL). The plateau concentration of total IFN-γ protein in serum can be at least about 250, 300, or 350 pg/mL and/or not more than 600, 800, 1000, or 1500 pg/mL. The IFN-γ inhibitor can be a protein that binds to IFN-γ, for example, an anti-IFN-γ antibody. The anti-IFN-γ antibody can comprise a heavy chain CDR1 comprising the amino acid sequence of SEQ ID NO:34, a heavy chain CDR2 comprising the amino acid sequence of SEQ ID NO:35, a heavy chain CDR3 comprising the amino acid sequence of SEQ ID NO:36 or SEQ ID NO:37, a light chain CDR1 comprising the amino acid sequence of SEQ ID NO:38, SEQ ID NO:39, or SEQ ID NO:40, a light chain CDR2 comprising the amino acid sequence of SEQ ID NO:41 or SEQ ID NO:42, and a light chain CDR3 comprising the amino acid sequence of SEQ ID NO:43 or SEQ ID NO:44. The anti-IFN-γ antibody can comprise the amino acid sequences of SEQ ID NO:6, SEQ ID NO:10, SEQ ID NO:14, or SEQ ID NO:30 and SEQ ID NO:8, SEQ ID NO:12, SEQ ID NO:16, or SEQ ID NO:31. Further doses of the IFN-γ inhibitor can be administered at a frequency that maintains a serum concentration of total IFN-γ that is at least half of the plateau concentration. A gluocorticoid and/or mycophenolate mofetil, azathioprine, leflunomide, methotrexate, or an anti-malarial can be administered concurrently with the antibody.

In still another aspect, herein is described a method of determining a suitable dose of an IFN-γ inhibitor for a patient comprising: determining the total IFN-γ protein concentration in a biological sample from the patient before dosing; administering the IFN-γ inhibitor to the patient at a first dosage amount; and determining the total IFN-γ protein concentration in similar biological samples from the patient periodically after dosing; wherein the first dosage amount is not suitable because it is too low if a plateau concentration of total IFN-γ protein lasting at least two weeks is not achieved or wherein the first dosage amount is high enough if a plateau concentration of total IFN-γ protein lasting at least two weeks is achieved. If the first dosage amount is high enough, the patient can maintain a plateau concentration of IFN-γ protein for at least about two, three, four, five, six, seven, eight, nine, or 10 weeks after dosing. If this is the case, after the concentration of IFN-γ protein has fallen below the plateau level, a second, lower dosage amount of the IFN-γ inhibitor can be administered and total IFN-γ protein concentrations in similar biological samples from the patient can be determined periodically after dosing at the second, lower dosage amount. If the first dosage amount is too low, a second, higher dosage amount of the IFN-γ inhibitor can be subsequently administered and total IFN-γ protein concentration in similar biological samples from the patient can be determined periodically after dosing at the second, higher dosage amount. The biological samples can be serum samples or peripheral blood samples. The IFN-γ inhibitor can be a protein that binds to IFN-γ, for example an anti-IFN-γ antibody, which can be an anti-huIFN-γ antibody. Such an anti-IFN-γ antibody can comprise a heavy chain CDR1 comprising the amino acid sequence of SEQ ID NO:34, a heavy chain CDR2 comprising the amino acid sequence of SEQ ID NO:35, a heavy chain CDR3 comprising the amino acid sequence of SEQ ID NO:36 or SEQ ID NO:37, a light chain CDR1 comprising the amino acid sequence of SEQ ID NO:38, SEQ ID NO:39, or SEQ ID NO:40, a light chain CDR2 comprising the amino acid sequence of SEQ ID NO:41 or SEQ ID NO:42, and a light chain CDR3 comprising the amino acid sequence of SEQ ID NO:43 or SEQ ID NO:44. Such an anti-IFN-γ antibody can comprise the amino acid sequences of SEQ ID NO:6, SEQ ID NO:10, SEQ ID NO:14, or SEQ ID NO:30 and SEQ ID NO:8, SEQ ID NO:12, SEQ ID NO:16, or SEQ ID NO:31. The anti-IFN-γ antibody can be a human or humanized antibody. A gluococorticoid and/or mycophenolate mofetil, azathioprine, leflunomide, methotrexate, or an anti-malarial can be administered concurrently with the antibody.

In another aspect, herein is described a method of treating a patient suffering from an IFN-γ-mediated disease, the method comprising: selecting a patient, wherein expression at the RNA or protein level of one or more gene(s) listed in Table(s) 1, 2, 4, 5, and/or 6 in a biological sample taken from the patient before treating the patient deviates from expression of that gene(s) in a control biological sample in a direction consistent with excess IFN-γ pathway activation; and administering to the patient a monoclonal human anti-human interferon gamma (anti-huIFN-γ) antibody at a dose of from about 20 milligrams to about 300 milligrams, wherein the antibody is an IgG1 antibody and comprises the amino acid sequences of SEQ ID NO:6 and SEQ ID NO:8. The IFN-γ-mediated disease can be selected from the group consisting of systemic lupus erythematosus (SLE), discoid lupus, lupus nephritis, inflammatory bowel diseases including Crohn's disease and ulcerative colitis, psoriasis, alopecia areata, Sjogren's syndrome, antiphospholipid syndrome, rheumatoid arthritis, multiple sclerosis, polymyositis, dermatomyositis, type I diabetes, sarcoidosis, macrophage activation syndrome (MAS), and hemophagocytic lymphohistiocytosis (HLH). The expression of at least 2, 3, 4, 5, 6, 7, 8, 9, 10, or 50 genes listed in Table(s) 1, 2, 4, 5, and/or 6 in the biological sample from the patient can deviate from the expression of those genes in the control biological sample in a direction consistent with excess IFN-γ pathway activation. The biological sample from the patient can exhibit elevated expression at the RNA or protein level as compared to expression in the control biological sample of one or more of the following genes: indoleamine 2,3-dioxygenase 1 (IDO1), ankyrin repeat domain 22 (ANKRD22), chemokine (C—X—C motif) ligand 9 (CXCL9), family with sequence similarity 26, member F (FAM26F), purinergic receptor P2Y, G-protein coupled, 14 (P2RY14), guanylate binding binding protein 5 (GBP5), serpin peptidase inhibitor, clade G, member 1 (SERPING1), Fc fragment of IgG, high affinity Ib, receptor (CD64), guanylate binding protein 1, interferon-inducible, 67 kDa (GBP1), chemokine (C—X—C motif) ligand 10 (CXCL10), ets variant 7 (ETV7), and/or programmed death ligand-1 (PD-L1). The dose can be from about 20 milligrams to about 300 milligrams, from about 80 milligrams to about 200, 250, or 300 milligrams, or from about 20 milligrams to about 60, 70, or 80 milligrams. The antibody can comprise the amino acid sequences of SEQ ID NO:17 and SEQ ID NO:18 and can be administered subcutaneously or intravenously. A gluococorticoid and/or mycophenolate mofetil, azathioprine, leflunomide, methotrexate, or an anti-malarial can be administered concurrently with the antibody.

In another embodiment, herein is described a method for treating a patient having an IFN-γ-mediated disease with a human anti-huIFN-γ antibody comprising: (a) taking a biological sample from the patient before treatment, wherein level(s) of expression of one or more genes listed in Table(s) 1, 2, 4, 5, and/or 6 at the RNA or protein level in the biological sample is determined and wherein level(s) of expression of the same gene(s) in a control biological sample is known or determined; (b) comparing the levels of expression of the gene(s) in the biological sample from the patient and in the control biological sample; and (c) if the level(s) of expression of the gene(s) in the biological sample from the patient deviate from the level(s) of expression of the gene(s) in the control biological sample in a direction consistent with excess IFN-γ pathway activation, administering to the patient a therapeutically effective dose of the antibody at a dose of from about 30, 40, 50, 60, or 70 mg to about 80, 100, 120, 150, 180, 250, or 300 mg, wherein the antibody comprises the amino acid sequences of SEQ ID NO:6 and SEQ ID NO:8. The IFN-γ-mediated disease can be selected from the group consisting of systemic lupus erythematosus (SLE), discoid lupus, lupus nephritis, inflammatory bowel diseases including Crohn's disease and ulcerative colitis, psoriasis, alopecia areata, Sjogren's syndrome, antiphospholipid syndrome, rheumatoid arthritis, multiple sclerosis, polymyositis, dermatomyositis, type I diabetes, sarcoidosis, macrophage activation syndrome (MAS), and hemophagocytic lymphohistiocytosis (HLH). The levels of expression of at least 2, 3, 4, 5, 6, 7, 8, 9, 10, or 50 genes from Table 5 or 6 deviate from the levels of expression of the genes in the control biological sample in a direction consistent with excess IFN-γ pathway activation. The biological sample from the patient can exhibit elevated expression at the RNA or protein level as compared to expression in the control biological sample of one or more of the following genes: indoleamine 2,3-dioxygenase 1 (IDO1), ankyrin repeat domain 22 (ANKRD22), chemokine (C—X—C motif) ligand 9 (CXCL9), family with sequence similarity 26, member F (FAM26F), purinergic receptor P2Y, G-protein coupled, 14 (P2RY14), guanylate binding binding protein 5 (GBP5), serpin peptidase inhibitor, clade G, member 1 (SERPING1), Fc fragment of IgG, high affinity Ib, receptor (CD64), guanylate binding protein 1, interferon-inducible, 67 kDa (GBP1), chemokine (C—X—C motif) ligand 10 (CXCL10), ets variant 7 (ETV7), programmed death ligand-1 (PD-L1), basic leucine zipper transcription factor, ATF-like 2 (BATF2), Fc fragment of IgG, high affinity Ib, receptor (FCGR1B or CD64), activating transcription factor 3 (ATF3), pyruvate dehydrogenase kinase, isozyme 4 (nuclear gene encoding mitochondrial protein; PDK4), and/or CD274. The dose administered can be from about 5, 10, 20, or 30 mg to about 60, 70, or 80 mg or can be from about 60, 70, 80, 90, 100, or 120 mg to about 150, 180, 200, or 250 mg. A gluococorticoid and/or mycophenolate mofetil, azathioprine, leflunomide, methotrexate, or an anti-malarial can be administered concurrently with the antibody.

In a further aspect, herein is described a method for treating a patient suffering from an IFN-γ-mediated disease comprising: (a) taking a biological sample from the patient before administering a human anti-huIFN-γ antibody in step (b), wherein the level(s) of expression at the RNA or protein level in the biological sample from the patient of one or more of the genes in Table(s) 1, 2, 4, 5, and/or 6 is determined; (b) administering to the patient a pharmacodynamically effective dose of the human anti-huIFN-γ antibody, wherein the antibody has a heavy chain CDR1 comprising the amino acid sequence of SEQ ID NO:34, a heavy chain CDR2 comprising the amino acid sequence of SEQ ID NO:35, a heavy chain CDR3 comprising the amino acid sequence of SEQ ID NO:36 or SEQ ID NO:37, a light chain CDR1 comprising the amino acid sequence of SEQ ID NO:38, SEQ ID NO:39, or SEQ ID NO:40, a light chain CDR2 comprising the amino acid sequence of SEQ ID NO:41 or SEQ ID NO:42, and a light chain CDR3 comprising the amino acid sequence of SEQ ID NO:43 or SEQ ID NO:44; (c) taking a second biological sample taken from the patient after administration of the antibody, wherein the level(s) of expression of the gene(s) of step (a) in the second biological sample are determined; and (d) if the level(s) of expression of the gene(s) determined in step (c), as compared to the level(s) of expression determined in step (a), is modulated in a direction consistent with inhibition of IFN-γ, then continuing treatment of the patient with another pharmacodynamically effective dose of the antibody. The IFN-γ-mediated disease can be selected from the group consisting of systemic lupus erythematosus (SLE), discoid lupus, lupus nephritis, inflammatory bowel diseases including Crohn's disease and ulcerative colitis, psoriasis, alopecia areata, Sjogren's syndrome, antiphospholipid syndrome, rheumatoid arthritis, multiple sclerosis, polymyositis, dermatomyositis, type I diabetes, sarcoidosis, macrophage activation syndrome (MAS), and hemophagocytic lymphohistiocytosis (HLH). The pharmacodynamically effective dose can be from about 5, 10, 20, 30, 40, 50, or 60 mg to about 60, 70, 80, 90, or 100 mg or from about 60, 70, 80, 90, or 100 mg to about 120, 150, 180, 200, or 250 mg. The heavy chain CDR3 can comprise the amino acid sequence of SEQ ID NO:36, the light chain CDR1 comprises the amino acid sequence of SEQ ID NO:38, the light chain CDR2 comprises the amino acid sequence of SEQ ID NO:41, and the light chain CDR3 comprises the amino acid sequence of SEQ ID NO:43. The heavy chain variable region of the antibody can comprise the amino acid sequence of SEQ ID NO:6, SEQ ID NO:10, SEQ ID NO:14, or SEQ ID NO:30, and the light chain variable region of the antibody can comprise the amino acid sequence of SEQ ID NO:8, SEQ ID NO:12, SEQ ID NO:16, or SEQ ID NO:31. The antibody can comprise the amino acid sequences of SEQ ID NOs:6 and 8, 10 and 12, 14 and 16, 30 and 12, or 14 and 31. The level(s) of expression of one or more of the following genes at the protein or RNA level can be determined in steps (a) and (c): indoleamine 2,3-dioxygenase 1 (IDO1), ankyrin repeat domain 22 (ANKRD22), chemokine (C—X—C motif) ligand 9 (CXCL9), family with sequence similarity 26, member F (FAM26F), purinergic receptor P2Y, G-protein coupled, 14 (P2RY14), guanylate binding binding protein 5 (GBP5), serpin peptidase inhibitor, clade G, member 1 (SERPING1), Fc fragment of IgG, high affinity Ib, receptor (CD64), guanylate binding protein 1, interferon-inducible, 67 kDa (GBP1), chemokine (C—X—C motif) ligand 10 (CXCL10), ets variant 7 (ETV7), programmed death ligand-1 (PD-L1), basic leucine zipper transcription factor, ATF-like 2 (BATF2), Fc fragment of IgG, high affinity Ib, receptor (FCGR1B or CD64), activating transcription factor 3 (ATF3), pyruvate dehydrogenase kinase, isozyme 4 (nuclear gene encoding mitochondrial protein; PDK4), and/or CD274. A glucocorticoid and/or mycophenolate mofetil, azathioprine, leflunomide, methotrexate, or an anti-malarial can be administered concurrently with the antibody.

In still a further aspect, provided is method for treating a patient suffering from an IFN-γ-mediated disease with a human anti-huIFN-γ antibody comprising the following steps: (a) taking a biological sample from the patient before administering a human anti-huIFN-γ antibody in step (b), wherein the level(s) of expression at the RNA or protein level of one or more genes listed in Table(s) 1, 2, 3, 5 and/or 6 in the biological sample are determined; (b) administering to the patient the human anti-human IFN-γ antibody, wherein the antibody has a heavy chain CDR1 comprising the amino acid sequence of SEQ ID NO:34, a heavy chain CDR2 comprising the amino acid sequence of SEQ ID NO:35, a heavy chain CDR3 comprising the amino acid sequence of SEQ ID NO:36 or SEQ ID NO:37, a light chain CDR1 comprising the amino acid sequence of SEQ ID NO:38, SEQ ID NO:39, or SEQ ID NO:40, a light chain CDR2 comprising the amino acid sequence of SEQ ID NO:41 or SEQ ID NO:42, and a light chain CDR3 comprising the amino acid sequence of SEQ ID NO:43 or SEQ ID NO:44; (c) taking a second biological sample taken from the patient taken after administration of the antibody, wherein the level(s) of expression of the gene(s) of (a) are determined in the second biological sample; and (d) if the level(s) of expression of the gene(s) in second biological sample of (c): (i) is modulated in a direction consistent with inhibition of IFN-γ as compared to the level(s) of expression in the biological sample determined in (a), then continuing treatment of the patient with another pharmacodynamically effective dose of the antibody; or (ii) is substantially the same as that in the biological sample of (a) or deviates from the level of expression in the biological sample of (a) in a direction that is consistent with an excess of IFN-γ, then treatment with the anti-human IFN-γ antibody is discontinued. The anti-human IFN-γ antibody can be a human or humanized IgG1 antibody. The dose of the antibody administered in (b) can be from about 20, 30, 40, 60, 80, or 100 mg to about 120, 150, 180, 200, 250, or 300 mg or from about 10, 20, or 30 mg to about 80 mg. The dose can be about 30, 40, 50, 60, 70, 80, 100, 120, 150, or 180 mg. The IFN-γ-mediated disease can be selected from the group consisting of systemic lupus erythematosus (SLE), discoid lupus, lupus nephritis, inflammatory bowel diseases including Crohn's disease and ulcerative colitis, psoriasis, alopecia areata, Sjogren's syndrome, antiphospholipid syndrome, rheumatoid arthritis, multiple sclerosis, polymyositis, dermatomyositis, type I diabetes, sarcoidosis, macrophage activation syndrome (MAS), and hemophagocytic lymphohistiocytosis (HLH). A gluococorticoid and/or mycophenolate mofetil, azathioprine, leflunomide, methotrexate, or an anti-malarial can be administered concurrently with the antibody.

In still a further aspect, herein is described a method for treating a patient suffering from SLE, lupus nephritis, discoid lupus, psoriasis, or an inflammatory bowel disease comprising administering to the patient a dose of at least about 15, 20, 30, 40, 50, 60, or 100 milligrams and not more than about 80, 90, 100, 120, 150, 180, 200, 250, or 300 milligrams of an anti-human IFN-γ antibody, wherein the anti-human IFN-γ antibody comprises a heavy chain CDR1 comprising the amino acid sequence of SEQ ID NO:34, a heavy chain CDR2 comprising the amino acid sequence of SEQ ID NO:35, a heavy chain CDR3 comprising the amino acid sequence of SEQ ID NO:36 or SEQ ID NO:37, a light chain CDR1 comprising the amino acid sequence of SEQ ID NO:38, SEQ ID NO:39, or SEQ ID NO:40, a light chain CDR2 comprising the amino acid sequence of SEQ ID NO:41 or SEQ ID NO:42, and a light chain CDR3 comprising the amino acid sequence of SEQ ID NO:43 or SEQ ID NO:44. The anti-IFN-γ antibody can comprise the heavy and light chain variable region amino acid sequences of SEQ ID NOs: 6 and 8, SEQ ID NOs: 10 and 12, SEQ ID NOs: 14 and 16, SEQ ID NOs: 30 and 12, or SEQ ID NOs: 14 and 31. Levels of expression of at least 5 genes listed in Table(s) 1, 2, 4, 5, and/or 6 in a biological sample taken from the patient after administration of the antibody can deviate from levels of these genes in a similar biological sample taken from the patient taken at baseline in a direction consistent with inhibition of IFN-γ. The dose of the anti-IFN-γ antibody can be from about 5, 10, 20, 30, or 40 milligrams to about 60, 70, 80, 90, or 100 milligrams or from about 60, 70, 80, 90, 100, or 120 milligrams to about 125, 150, 180, 200, or 250 milligrams. The dose can be administered subcutaneously or intravenously. The level of total IFN-γ protein in the patient's serum can remain above about 200 pg/mL for at least about 2 weeks subsequent to a single dose. A gluococorticoid, optionally prednisone, and/or mycophenolate mofetil, azathioprine, leflunomide, methotrexate, or an anti-malarial can be administered concurrently with the antibody.

In another embodiment, herein is described a method for identifying SLE, psoriasis, or inflammatory bowel disease patients that can benefit from treatment with a human anti-human IFN-γ antibody and treating such patients comprising the following steps: (a) obtaining a biological sample from the patient before administration of the antibody, wherein the level of total IFN-γ protein in the biological sample is determined; (b) administering to the patient a dose of the antibody; (c) obtaining a second biological sample from the patient after administration of the antibody, wherein the level of total IFN-γ protein in the second biological sample is determined; and (d) if the level of total IFN-γ protein determined in (c) is higher than the level determined in (a), then continuing treatment with the antibody; wherein the antibody is an IgG1 antibody and comprises the amino acid sequences of SEQ ID NO:6, SEQ ID NO:10, SEQ ID NO:14, or SEQ ID NO:30 and SEQ ID NO:8, SEQ ID NO:12, SEQ ID NO:16, or SEQ ID NO:31. The antibody can comprise the amino acid sequences of SEQ ID NO:6 and SEQ ID NO:8.

In another aspect, provided herein is a method for treating an IFN-γ-mediated disease comprising administering to a patient in need thereof a dose of a human anti-human IFN-γ antibody comprising the amino acid sequences of SEQ ID NO:6 and SEQ ID NO:8 such that the concentration of total IFN-γ protein in the patient's serum is maintained at a plateau concentration for at least about two, three, four, five, or six weeks following administration. The plateau concentration of total IFN-γ protein in serum can be from about 100, 200, or 300 pg/mL to about 2000 pg/mL.

DETAILED DESCRIPTION

Figure 1:
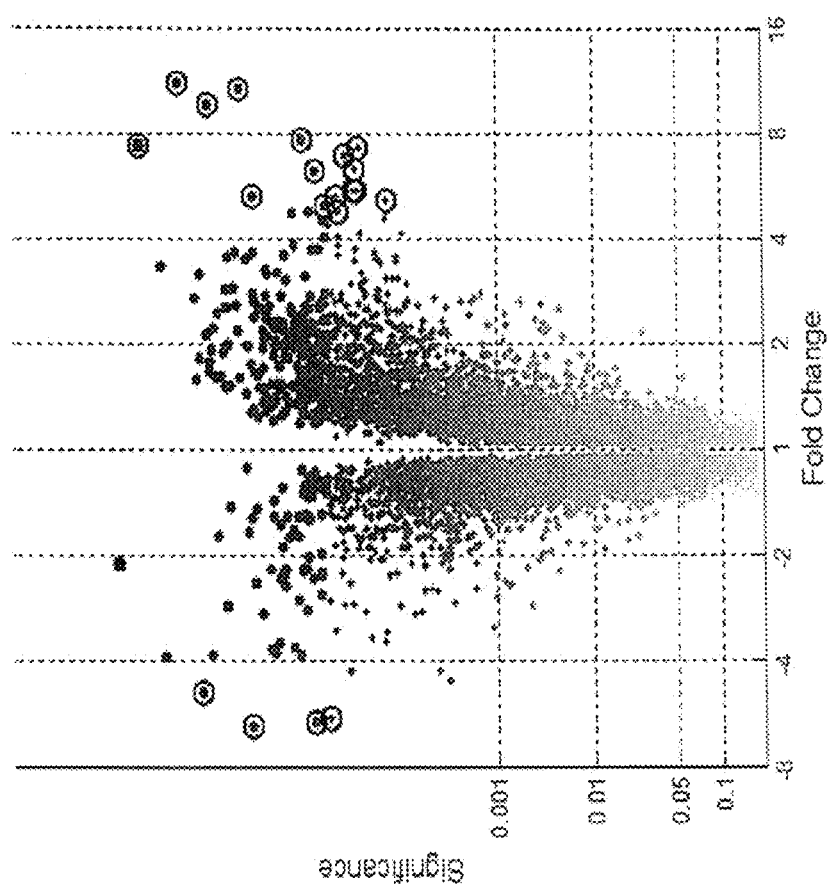
FIG. 1: Volcano plot of expression of an array of genes post- vs. pre-IFN-γ stimulation of whole blood from healthy volunteers. The average fold change in RNA expression for each gene is plotted with the associated p-value from an analysis of variance (ANOVA). The circled points have been designated as the top 20 IFN-γ regulated genes, which are those with the largest absolute fold change and that have a p-value less than 0.001.

Provided herein are methods of treatment using IFN-γ inhibitors, methods for identifying patients likely to benefit from such treatment, and methods for determining suitable dosages. The methods utilize techniques for determining levels of proteins and/or RNA transcripts in a biological sample. Using such techniques, overlapping sets of transcripts, the expression of which is modulated by IFN-γ ex vivo and by AMG 811 in vivo, have been defined. Similarly, it has been found that a particular set of transcripts and at least one serum protein is downregulated by an IFN-γ inhibitor in human patients in vivo, thus making it possible to determine dosages at which these effects are observable and to determine which transcripts in blood cells are regulated by IFN-γ in vivo. Dosages determined by such methods can be used to treat patients. Similarly, assay of these sets of transcripts can be used to predict which patients are likely to respond to treatment, i.e., those that overexpress genes whose expression can be downregulated by the IFN-γ inhibitor and/or those that are up- or down-regulated by activation of the IFN-γ pathway. Similarly, these techniques can be used to determine whether a particular dosage of an IFN-γ inhibitor is having a biological effect, especially in patients suffering from an episodic disease in which changes in symptoms may not be readily apparent. Further, if an IFN-γ inhibitor is not having a biological effect as measured by expression of such biomarkers, treatment with the IFN-γ inhibitor can be discontinued and, optionally, a new treatment can be initiated. Alternatively, if an IFN-γ inhibitor is having a biological effect as measured by biomarker expression, treatment with the IFN-γ inhibitor can be continued.

Definitions

An "antibody," as meant herein, can be a full length antibody containing two full length heavy chains (containing a heavy chain variable region ($V_H$), a first constant domain ($C_H1$), a second constant domain ($C_H2$) and a third constant domain ($C_H3$)) and two full length light chains (containing a light chain variable region ($V_L$) and a light chain constant region ($C_L$)). Alternatively, an antibody can contain only a single $V_H$ region or $V_L$ region, such as the single variable domain antibodies described in, e.g., U.S. Pat. No. 7,563,443. The portions of this reference describing such antibodies are incorporated herein by reference. An antibody can also be a fragment of a full length antibody that binds to the target antigen, which may also contain other sequences. For example, an antibody can be an a single chain antibody that comprises $V_H$ and $V_L$ regions joined by a peptide linker (i.e., an scFv), a Fab fragment, which may or may not include the hinge region, an scFv-Fc, among many other possible formats. The term "antibody" comprises any protein that includes at least one $V_H$ or $V_L$ region.

"Baseline," as meant herein, is a timepoint before dosing begins in a clinical trial that can typically be up to about a month before dosing with a test drug or placebo begins.

A "biological sample," as meant herein, is a sample of a liquid, such as blood or cerebrospinal fluid, or a solid piece of tissue, such as a skin biopsy or an excised tumor, taken from a patient. Two biological samples are said to be "similar" if they are taken from similar tissue. For example, two whole blood samples from different patients are similar, as meant herein. Further, two skin biopsies taken from lesions from different patients are also similar as meant herein.

A drug or treatment is "concurrently" administered with another drug or treatment, as meant herein, if it is administered in the same general time frame as the other drug, optionally, on an ongoing basis. For example, if a patient is taking Drug A once a week on an ongoing basis and Drug B once every six months on an ongoing basis, Drugs A and B are concurrently administered whether or not they are ever administered on the same day. Similarly, if Drug A is taken once per week on an ongoing basis and Drug B is administered only once or a few times on a daily basis, Drugs A and B are concurrently administered as meant herein. Similarly, if both Drugs A and B are administered for short periods of time either once or multiple times within a one month period, they are administered concurrently as meant herein as long as both drugs are administered within the same month.

A "control group," as meant herein, is a group of healthy people to which a patient having a particular disease is compared in some way. For example, expression of certain genes at the protein or RNA level in a biological sample from a patient can be compared to expression of those genes in one or more similar biological samples from people in a control group. In some situations, normal ranges for levels of expression for particular genes can be established by analysis of biological samples from members of a control group. In such a situation, expression levels in a given sample from a patient having a disease can be compared to these established normal ranges to determine whether expression in the sample from the patient is normal or above or below normal.

A "control biological sample," as meant herein, is (a) a group of biological samples from a "control group" that is compared to a similar biological sample from a patient or (b) a biological sample from non-diseased tissue from a patient that is compared to a biological sample from diseased tissue from the same patient. For example, a skin biopsy from non-lesional tissue from a discoid lupus patient can be a "control biological sample" for a skin biopsy from lesional tissue from the same discoid lupus patient. Alternatively, a group of skin biopsies from a healthy "control group" can be a "control biological sample" to which a skin biopsy from a discoid lupus patient can be compared. Alternatively, a group of blood samples from healthy people can be a "control biological sample" to which to compare a blood sample from an SLE patient.

"Determining the level of expression," as meant herein, refers to determining the amount of expression of a gene in a biological sample at either the protein or RNA level. Such levels can be determined in biological samples from patients suffering from an IFN-γ-mediated disease and in control biological samples from healthy people or from non-diseased tissue from the patient (for example in a skin sample not having psoriatic plaques in a psoriasis patient). The comparison between a patient's biological sample from diseased tissue (or blood in a systemic disease) and a control biological sample can provide information as to whether the biomarkers in question are expressed at normal, elevated, or lowered levels. To assay for protein levels in liquid samples, enzyme-linked immunosorbent assay (ELISA) can be used. See, e.g., Berzofsky et al., Antigen-Antibody Interactions and Monoclonal Antibodies, Chapter 12 in FUNDAMENTAL IMMUNOLOGY, THIRD EDITION, Paul, ed., Raven Press, New York, 1993, pp. 421-466, at pp. 438-440. Many such assays are commercially available. For solid biological samples, such as, for example, skin samples, immunohistochemistry or immunofluorescence can be used to determine whether and where a particular protein is expressed. Such techniques are well known in the art. See, e.g., Antigen Retrieval Techniques: Immunohistochemistry and Molecular Morphology, Shi et al., eds. Eaton Publishing, Natick, Mass., 2000. The portions of this reference that describe techniques of immunohistochemistry and immunofluorescence are incorporated herein by reference. To assay for RNA levels, real time quantitative PCR (for example using a Tagman® kit available from Invitrogen (Carlsbad, Calif.)) or microarrays (such as described, for example, in Chen et al. (1998), Genomics 51: 313-324) are generally used.

An "IFN-γ inhibitor," as meant herein, is a molecule, which can be a protein or a small molecule, that can inhibit the activity of IFN-γ as assayed by the A549 bioassay, which can be performed as follows.

One of the established properties of IFN-γ is its anti-proliferative effect on a variety of cell populations. See e.g. Aune and Pogue (1989), J. Clin. Invest. 84: 863-875. The human lung cell line A549 has been used frequently in publications describing the bioactivity of IFN-γ. See e.g. Aune and Pogue, supra; Hill et al. (1993), Immunology 79: 236-240. In general, the activity of an inhibitor is tested at a concentration of a stimulating substance, in this case IFN-γ, that falls within a part of the dose-response curve where a small change in dose will result in a change in response. One of skill in the art will realize that if an excessive dose of the stimulating substance is used, a very large dose of an inhibitor may be required to observe a change in response. Commonly used concentrations for a stimulating substance are $EC_{80}$ and $EC_{90}$ (the concentrations at which 80% or 90%, respectively, of the maximum response is achieved).

An IFN-γ dose-response curve can be generated to determine the $EC_{90}$ for the lung epithelial carcinoma cell line A549. In subsequent experiments, different concentrations of an IFN-γ-inhibitor can be mixed with a fixed dose of IFN-γ, and the ability of the IFN-γ-inhibitor to inhibit the biological activity of the anti-proliferative effect of IFN-γ can be determined. The assay can be performed for 5 days, and proliferation can be measured by determining fluorescence generated by the reduction of ALAMARBLUE™ (AccuMed International, Inc., Chicago, Ill.), a dye used to indicate cell growth, by metabolically active, i.e., proliferating, cells. See e.g., de Fries and Mitsuhashi, 1995, J. Clin. Lab. Analysis 9(2): 89-95; Ahmed et al., 1994, J. Immunol. Methods 170(2): 211-24.

An "IFN-γ-mediated disease," as meant herein, is a disease in which evidence from an in vitro or a non-human model system or from human patients indicates IFN-γ is likely to play a role in driving the course of the disease. Diseases that are included among "IFN-γ-mediated diseases" include, for example, diseases in which patient samples display elevated levels of a type I or II IFN or a type I-related "IFN signature" pattern of gene expression. See, e.g., Baechler et al. (2003), Proc. Natl. Acad. Sci. 100(5): 2610-2615; Bennett et al. (2003), J. Exp. Med. 197(6): 711-723. The portions of these references that describe the IFN signature pattern of gene expression are incorporated herein by reference. IFN-γ-mediated diseases include, for example, SLE, discoid lupus, lupus nephritis, alopecia areata, Graves'disease, Sjogren's syndrome, antiphospholipid syndrome, rheumatoid arthritis, juvenile idiopathic arthritis, psoriasis, psoriatic arthritis, dermatomyositis, polimyositis, bacterial septicemia, antigen/antibody complex diseases (Arthus-like syndromes), anaphylactic shock, multiple sclerosis (MS), type I diabetes, thyroiditis, graft versus host disease, transplant rejection, atherosclerosis, immune-mediated hepatic lesions, autoimmune hepatitis, inflammatory bowel diseases such as Crohn's disease and ulcerative colitis, giant cell arteritis, uveitis, macrophage activation syndrome (MAS), hemophagocytic lymphohistiocytosis (HLH), macrophage activation syndrome (MAS), sarcoidosis, and scleroderma.

The term "interferon signature" refers to the characteristic pattern of over- and under-expression of genes observed in response to type 1 interferons. See, e.g., Bennett et al. (2003), J. Exp. Med. 197(6): 711-723; Baechler et al. (2003), Proc. Natl. Acad. Sci 100(5): 2610-2615, the relevant portions of which are incorporated herein by reference.

The expression of a particular gene in a biological sample from a patient is said to "deviate" from the expression of that gene in a control biological sample or in a biological sample from the patient taken at a different time "in a direction consistent with excess IFN-γ" or "in a direction consistent with excess IFN-γ pathway activation" when it is found to be up- or down-modulated at the RNA or protein level in the same direction as noted in Table 1 below for blood samples stimulated with IFN-γ. Table 1 lists the group of genes that are up- or down-regulated in human whole blood from healthy volunteers in response to stimulation with IFN-γ ex vivo. Thus, for a gene to "deviate" from the expression of that gene in a control biological sample or in a biological sample from the patient taken at a different time "in a direction consistent with excess IFN-γ", it must be listed in Table 1.

Similarly, the expression of a gene can be "modulated in a direction consistent with inhibition of IFN-γ" or "modulated in a direction consistent with IFN-γ pathway inhibition." This means that the expression of the gene is decreased if the expression of that gene is up-regulated in response to ex vivo stimulation with IFN-γ as noted in Table 1, and that the expression is increased if the expression of that gene is down-regulated in response to ex vivo stimulation with IFN-γ as noted in Table 1.

A "monoclonal antibody," as meant herein, is an antibody that specifically binds to an antigen at an epitope, wherein a preparation of the antibody contains substantially only antibodies having the same amino acid sequence, although there may be certain low levels of antibodies that include one or more alteration of certain amino acids or internal, amino-terminal, or carboxyterminal cleavages of the amino acid chain. Such minor alterations may occur during the production of the antibodies or during storage. In contrast, a preparation of a "polyclonal" antibody contains antibodies having many different amino acid sequences that bind to different epitopes on the same antigen. The term "monoclonal antibody" includes, without limitation, the following kinds of molecules: tetrameric antibodies comprising two heavy and two light chains such as an IgG, IgA, IgD, IgM, or IgE antibody; single chain antibodies (scFv's) containing a $V_H$ and a $V_L$ region joined by a peptide linker; variable domain antibodies as described in, for example, U.S. Pat. No. 7,563,443, the relevant portions of which are incorporated herein by reference, that comprise one or more single variable domains, each of which can, by itself, bind specifically to antigen; Fab, Fab', or Fab $(ab')_2$ fragments; humanized or chimeric antibodies; various kinds of monovalent antibodies, including those described in U.S. Patent Application Publication 2007/0105199, the relevant portions of which are incorporated by reference herein; and bispecific antibodies, including those with mutationally altered constant regions such as those described in, e.g., U.S. Patent Application Publication 2010/0286374 or U.S. Patent Application Publication 2007/0014794; and scFv-Fc molecules.

A "pharmacodynamically effective dose," as meant herein, is a dose of an IFN-γ inhibitor that can modulate the expression of a gene "in a direction consistent with inhibition of IFN-γ," as defined herein. Genes regulated by IFN-γ ex vivo are listed in Table I.

A "plateau concentration," as meant herein, is a concentration of total IFN-γ that is observed in a biological sample, such as peripheral blood or serum, taken from a patient after dosing with an IFN-γ inhibitor. The plateau concentration is higher than the concentration of total IFN-γ protein in a similar biological sample taken from the same patient at baseline, and once it is attained, it is "substantially maintained" for at least about 2, 3, 4, 5, 6, 7, 8, 9, or 10 weeks. A concentration is considered to be substantially maintained if it varies by no more than ±50% of its total value.

A "therapeutically effective dose," as meant herein, is a dose that is effective to decrease one or more observable symptoms of a disease or to delay onset or mitigate the symptoms of a more serious condition that often follows after the condition that a patient is currently experiencing. A therapeutically effective dose may, but need not necessarily, completely eliminate all symptoms of the disease. For example, in lupus nephritis, a lowering of the degree of proteinuria and lowering or stabilization of serum concentration of creatinine would indicate an improvement in kidney function and, thus, an improvement in a symptom of the disease. Hence, a dose of an IFN-γ inhibitor that could cause a decrease in proteinuria and lower or stabilize serum creatinine concentration would be both a therapeutically effective dose and a phamacodynamically effective dose.

Interferons, IFN-γ-Mediated Diseases, and Biomarkers

Interferons were first recognized for their ability to impede viral infections and are now known to also play important roles in mediating host defense against infection by bacteria and other pathogens, as well as in integrating early, innate immune responses and later adaptive immune responses. Decker et al. (2002), J. Clin. Invest. 109(10): 1271-1277. There are at least two types of human and murine interferons: the type I interferons, including primarily a number of IFNα subtypes and IFNβ, plus IFNω, IFNε, IFNδ, IFNτ, and IFNκ; and type II interferon, a class of one member, that is, IFN-γ. Sozzani et al. (2010), Autoimmunity 43(3): 196-203. Type I interferons are produced by most cell types under appropriate conditions and are known to play a role in resisting viral infection, whereas IFN-γ is produced by limited cell types, such as NK cells and activated Th1 cells, and is known to strengthen immune responses to unicellular microorganisms, intracellular pathogens, and viruses. In humans, type I and type II interferons bind to distinct receptors, which are, respectively, the interferon alpha/beta receptor (IFNAR, containing IFNAR1 and IFNAR2 chains) and the interferon gamma receptor (IFNGR, containing IFNGR1 and IFNGR2 chains). Both of these receptors are associated with Janus kinases which, along with other intracellular proteins, mediate the transcriptional activation of genes having interferon-stimulated response elements (IFNAR only) and genes having IFN-γ-activated site elements (both IFNAR and IFNGR). Decker et al. (2002), J. Clin. Invest. 109(10): 1271-1277; Trinchieri (2010), J. Exp. Med. 207(10): 2053-2063. Thus, although the sets of genes activated by type I and II interferons differ, there is considerable overlap in the two sets. See, e.g., Baechler et al. (2003), Proc. Natl. Acad. Sci. 100(5): 2610-2615; van Baarsen et al. (2006), Genes and Immunity 7: 522-531. Some differences may be related to different magnitudes of response of a particular gene to a given dose of type I or II interferon. Kariuki et al. (2009), J. Immunol. 182: 34-38

The relationship between the biological activities of type I and II interferons is complex and intertwined and dependent on the expression of other genes. Thus, different cell types can have differing responses to the IFNs. IFN-γ is a more potent activator of phagocytic cell and antigen-presenting cell function than type I interferons. Trinchieri (2010), J. Exp. Med. 207(10): 2053-2063. Both type I and II interferons can be produced in the course of an immune response. In some situations, type I interferons can inhibit production of IFN-γ, and in other situations, for example, in the absence of STAT1, type I interferons can increase IFN-γ production. Nguyen et al. (2000), Nature Immunol. 1(1): 70-76; Brinkman et al. (1993), J. Exp. Med. 178: 1655-1663; Trinchieri (2010), J. Exp. Med. 207(10): 2053-2063. Further, low levels of type I IFN produced during stimulation of dendritic cells are essential for production of IL-12 heterodimer, which induces production of IFN-γ. However, in the presence of high levels of type I IFN, production of IL-12 p40 is suppressed, thus limiting the production of IL-12 heterodimer. Thus, the relationship between type I and II interferons is already known to be complex and may be even more complex in vivo than is currently understood.

A number of diseases have been associated with changes in gene expression patterns that are thought to reflect elevated activity of IFNs. Some investigators refer to such a gene expression pattern as an "interferon signature," which includes somewhat different groups of genes depending on exactly how the signature is defined. See, e.g., Baehler et al. (2003), Proc. Natl. Acad. Sci. 100(5): 2610-2615; Bennett et al. (2003), J. Exp. Med. 197(6): 711-723. Since IFN-γ- and type I IFN-activated genes are overlapping sets, an elevated interferon signature score could implicate elevated activity of IFN-γ and/or a type I IFN. In a number of autoimmune and/or inflammatory diseases, many of which characterized by extremely heterogeneous and episodic symptoms, it has been found that a substantial proportion of patients or persons at increased risk of disease have a gene expression pattern reflecting elevated IFN activity and/or have elevated levels of an IFN or a protein whose expression is known to be induced by type I IFN. These diseases include, for example, SLE (Bauer et al. (2006), PLoS Med. 2(12): 2274-2284; Armananzas et al. (2009), IEEE Transactions on Inform. Tech. in Biomed. 13(3): 341-350), systemic sclerosis (Sozzani et al. (2010), Autoimmunity 43(3): 196-203), alopecia areata (Ghoreishi et al. (2010), Br. J. Dermatol. 163: 57-62), Graves' disease (Ruiz-Riol et al. (2011), J. Autoimmunity 36: 189-200), Sjogren's syndrome (Sozzani et al. (2010), Autoimmunity 43(3): 196-203; Emamian et al. (2009), Genes Immun. 10: 285-296), antiphospholipid syndrome (Armananzas et al. (2009), IEEE Transactions on Inform. Tech. in Biomed. 13(3): 341-350), inflammatory bowel diseases including Crohn's disease and ulcerative colitis (see, e.g., U.S. Pat. No. 6,558,661), rheumatoid arthritis (Dawidowicz et al. (2011), Ann. Rheum. Dis. 70: 117-121), psoriasis (Pietrzak et al. (2008), Clin. Chim. Acta 394: 7-21), multiple sclerosis (van Baarsen et al. (2006), Genes and Immunity 7: 522-531), dermatomyositis (Somani et al. (2008), Arch. Dermatol. 145(4): 1341-1349), polymyositis (Sozzani et al. (2010), Autoimmunity 43(3): 196-203), type I diabetes (Reynier et al. (2010), Genes Immun. 11: 269-278), sarcoidosis (Lee et al. 2011, Ann. Dermatol. 23(2): 239-241; Kriegova et al. (2011), Eur. Respir. J. 38: 1136-1144), and hemophagocytic lymphohistiocytosis (HLH; Schmid et al. (2009), EMBO Molec. Med. 1(2): 112-124).

Elevated expression of genes whose expression is induced by IFNs is found in about half of adult SLE patients and the majority of pediatric SLE patients. Baechler et al. (2003), Proc. Natl. Acad. Sci. U.S.A.; 100: 2610-2615; Bennett et al. (2003), J. Exp. Med. 197: 711-723; Kirou et al. (2004), Arthr. & Rheum. 50: 3958-3967. Overexpression of some of these gene products at the protein level, such as CXCL10 (IP-10), CCL2 (MCP-1), and chemokine (C—C motif) ligand 19 (CCL19; also known as (MIP-3B), correlates with disease severity and is predictive of disease flares within a year. Bauer et al. (2009), Arthr. & Rheum 60(10): 3098-3107; Bauer et al. (2006), PLoS. Med. 3: e491; Lit et al. (2006), Ann. Rheum. Dis. 65: 209-215; Narumi et al. (2000), Cytokine 12: 1561-1565; Baechler et al. (2003), Proc. Natl. Acad. Sci 100(5): 2610-2615. Specifically, CXCL10 has been shown to be a major contributor to the overall association of disease with IFN signature and an independent predictor of future disease flare. Bauer et al. (2009), Arthritis & Rheum. 60: 3098-3107; Bauer et al. (2009), Arthritis Rheum. 60:S209.

A variety of other data suggest a pathogenic role for IFN-γ in SLE. Studies involving murine models of SLE consistently support the role of IFN-γ in the pathogenesis of disease. Balomenos et al. (1998), J. Clin. Invest. 101: 364-371; Jacob et al. (1987), J. Exp. Med. 166: 798-803; Peng et al. (1997), J. Clin. Invest 99: 1936-1946; Hron and Peng (2004), J. Immunol 173: 2134-2142; Seery et al. (1997), J. Exp. Med. 186: 1451-1459. In addition, lupus-like syndromes have been observed in patients treated for a variety of diseases with IFN-γ and/or IFN-α. Wandl et al. (1992), Clin. Immunol. Immunopathol. 65(1): 70-74; Graninger et al. (1991), J. Rheumatol. 18: 1621-1622. A correlation between severity of disease activity and amounts of IFN-γ secreted by a patient's peripheral blood mononuclear cells in response to stimulation by lipopolysaccharide and phytohaemagglutinin has been observed. Viallard et al. (1999), Clin. Exp. Immunol. 115: 189-195. Similarly, peripheral blood T cells from SLE patients expressed significantly more IFN-γ in response to CD28 costimulation than did T cells from normal controls. Harigai et al. (2008), J. Immunol. 181: 2211-2219. Thus, many different kinds of evidence indicate that IFN-γ is likely to play a role in mediating SLE.

SLE is an autoimmune disease of unknown etiology marked by autoreactivity to nuclear self antigens. Its clinical manifestations are so diverse that it is questionable whether it is truly a single disease or a group of related conditions. Kotzin, B. L. 1996. Systemic lupus erythematosus. *Cell* 85:303-306; Rahman, A., and Isenberg, D. A. 2008. Systemic lupus erythematosus. *N. Engl. J. Med.* 358:929-939. Symptoms can include the following: constitutional symptoms such as malaise, fatigue, fevers, anorexia, and weight loss; diverse skin symptoms including acute, transient facial rashes in adults, bullous disease, and chronic and disfiguring rashes of the head and neck; arthritis; muscle pain and/or weakness; cardiovascular symptoms such as mitral valve thickening, vegetations, regurgitation, stenosis, pericarditis, and ischemic heart disease, some of which can culminate in stroke, embolic disease, heart failure, infectious endocarditis, or valve failure; nephritis, which is a major cause of morbidity in SLE; neurological symptoms including cognitive dysfunction, depression, psychosis, coma, seizure disorders, migraine, and other headache syndromes, aseptic meningitis, chorea, stroke, and cranial neuropathies; hemotologic symptoms including leucopenia, thrombocytopenia, serositis, anemia, coagulation abnormalities, splenomegaly, and lymphadenopathy; and various gastrointestinal abnormalities. Id; Vratsanos et al., "Systemic Lupus Erythematosus," Chapter 39 in Samter's Immunological Diseases, 6$^{th}$ Edition, Austen et al., eds., Lippincott Williams & Wilkins, Phiiladelphia, Pa., 2001.

Severity of symptoms varies widely, as does the course of the disease. SLE can be deadly. The disease activity of SLE patients can be rated using an instrument such as the Systemic Lupus Erythrmatosus Disease Activity Index (SLEDAI), which provides a score for disease activity that takes into consideration the following symptoms, which are weighted according to severity: seizure, psychosis, organic brain syndrome, visual disturbance, cranial nerve disorder, lupus headache, vasculitis, arthritis, myositis, urinary casts, hematuria, proteinuria, pyuria, new rash, alopecia, mucosal ulcers, pleurisy, pericarditis, low complement, increased DNA binding, fever, thrombocytopenia, and leucopenia. Bombardier et al. (1992), Arthr. & Rheum. 35(6): 630-640, the relevant portions of which are incorporated herein by reference. The treatments described herein can be useful in lessening or eliminating symptoms of SLE as measured by SLEDAI.

Another method for assessing disease activity in SLE is the British Isles Lupus Assessment Group (BILAG) index, which is a disease activity assessment system for SLE patients based on the principle of the physician's intention to treat. Stoll et al. (1996), Ann. Rheum Dis. 55: 756-760; Hay et al. (1993), Q. J. Med. 86: 447-458. The portions of these references describing the BILAG are incorporated herein by reference. A BILAG score is assigned by giving separate numeric or alphabetic disease activity scores in each of eight organ-based systems, general (such as fever and fatigue), mucocutaneous (such as rash and alopecia, among many other symptoms), neurological (such as seizures, migraine headaches, and psychosis, among many other symptoms), musculoskeletal (such as arthritis), cardiorespiratory (such as cardiac failure and decreased pulmonary function), vasculitis and thrombosis, renal (such as nephritis), and hematological. Id. The treatments described herein can be useful in lessening or eliminating symptoms of SLE as measured by the BILAG index.

Discoid lupus is a particular form of chronic cutaneous lupus in which the patient has circular lesions that occur most commonly in sun-exposed areas. The lesions can leave disfiguring scars. Up to about 25% of SLE patients develop discoid lupus lesions at some point in the course of their disease. These lesions may occur in patients that have no other symptoms of SLE. The symptoms that relate specifically to skin in cutaneous forms of lupus can be scored using the Cutaneous Lupus Erythematosus Disease Area and Severity Index (CLASI), which takes into consideration both disease activity (including erythema, scaling, and hypertrophy of the skin in various areas, as well as mucus membrane lesions and alopecia) and disease-related damage (including dyspigmentation, scarring, atrophy, and panniculitis of the skin as well as scarring of the scalp). Such symptoms can be affected by a treatment for discoid lupus such as an IFN-γ inhibitor. The CLASI is described in detail by Albrecht et al. (2005), J. Invest. Dermatol. 125: 889-894. The portions of this article that describe what the CLASI is, what symptoms are included in it, and how to use it are incorporated herein by reference. The treatments described herein can be useful for lessening or eliminating symptoms of discoid lupus as measured by the CLASI.

Another cutaneous disease that can be mediated by IFN-γ is psoriasis. Symptoms of psoriasis include itchy, dry skin that can be pink/red in color, thickened and covered with flakes. It is a common condition and is episodic in nature, that is, patients can experience flares and periods of remission. There are five type of psoriasis, erythrodermic, guttate, inverse, plaque, and pustular. Plaque psoriasis is the most common type. Clinical studies with an anti-human IFN-γ antibody indicate that inhibition of IFN-γ can lessen symptoms of psoriasis as measured by a Psoriasis Area and Severity Index (PASI) score, thus demonstrating that IFN-γ plays a role in mediating psoriasis, at least in some patients. International Application Publication WO 2003/097083.

The severity of disease in psoriasis patients can be measured in a variety of ways. One way disease activity is commonly measured in clinical trials the PASI score. A PASI score can range from 0 to 72, with 72 being the most severe disease. For purposes of PASI assessment, the body is considered to consist of four sections, legs, torso (that is, stomach, chest, back, etc.), arms, and head, which are considered to have 40%, 30%, 20%, and 10% of a person's skin, respectively. For each section, the percent of the area of skin affected is estimated and transformed into a grade of from 0 to 6, with 0 being no affected skin and 6 being 90-100% of the skin of the body section in question being affected. The severity of disease is scored by separately considering three features of the affected skin, redness (erythema), scaling, and thickness, and assigning a severity score of from 0 to 4 for each feature for each body section. The sum of the severity scores for all three features for each body section is calculated, and this sum is multiplied by the weight of the respective section as determined by how much of the total skin that body section contains and by the percent of the body section affected. After this number is calculated for each body section, these numbers are added to yield the PASI score. Thus, the PASI score can be expressed as follows:

PASI=0.1(score for percent of the head affected) (sum of 3 severity scores for the head)+0.2 (score for percent of the arms affected)(sum of 3 severity scores for the arms)+0.3(score for percent of the torso affected)(sum of 3 severity scores for the torso)+0.4(score for percent of the legs affected)(sum of 3 severity scores for the legs)

The descriptions of PASI scores in the following two references are incorporated by reference herein: Feldman and Krueger (2005), Ann. Rheum. Dis. 64: 65-68, Langley and Ellis (2004), J. Am. Acad. Dermatol. 51(4): 563-69.

Many clinical trials refer to changes in PASI score over the course of the study. For example, a PASI 75 at a particular time point in a clinical trial means that the PASI score of a patient has decreased by 75% as compared to that patient's PASI score at baseline. Similarly a PASI 50 or a PASI 90 denotes a 50% or 90% reduction in PASI score.

Another commonly used measure of psoriasis severity in clinical trials is the static Physicians Global Assessment (sPGA). The sPGA is typically a six category scale rating ranging from 0=none to 5=severe. ENBREL® (etanercept), Package Insert, 2008. A sPGA score of "clear" or "minimal" (sometimes alternately referred to as "almost clear") requires no or minimal elevation of plaques, no or only very faint redness, and no scaling or minimal scaling over <5% of the area of the plaques. ENBREL® (etanercept), Package Insert, 2008. The individual elements of psoriasis plaque morphology or degree of body surface area involvement are not quantified. Nonetheless, sPGA scores correlate to some extent with PASI scores. Langley and Ellis (2004), J. Am. Acad. Dermatol. 51(4): 563-69. The methods described herein lessen or eliminate psoriasis symptoms as measured by a PASI or an sPGA score.

Multiple sclerosis (MS) is an autoimmune disease characterized by damage to the myelin sheath that surrounds nerves, which leads to inhibition or total blockage of nerve impulses. The disease is very heterogeneous in clinical presentation, and there is a wide variation in response to treatment as well. van Baarsen et al. (2006), Genes and Immunity 7: 522-531. Environmental factors, possibly viral infection, as well as genetic susceptibility, are thought to play a role in causing MS. Id. Symptoms can include loss of balance, muscle spasms, tremors, weakness, loss of ability to walk, loss of coordination, various bowel and bladder problems, numbness, pain, tingling, slurred speech, difficulty chewing and swallowing, double vision, loss of vision, uncontrollable eye movements, and depression, among many other possible symptoms. In many patients episodes in which symptoms occur are interspersed with long periods of remission. A subset of MS patients exhibit a pattern of gene expression consistent with high type I IFN activity, although a correlation between this pattern of gene expression and disease severity has not been demonstrated. Id. The methods described herein can lessen or eliminate one or more symptoms of MS.

Type I diabetes is an autoimmune disease resulting in the destruction of insulin-producing β-cells in the pancreas, which leads to a lack of insulin. Antibodies against β-cell epitopes are detected in the sera of pre-diabetic patients, suggesting that there is an autoimmune process in progress during a long asymptomatic period that precedes the onset of clinical symptoms. Reynier et al. (2010), Genes and Immunity 11: 269-278. The lack of insulin leads to high glucose levels in the blood and urine causing a variety of symptoms including frequent urination, increased hunger and thirst, fatigue, and weight loss. It is generally treated with insulin, a treatment that must be continued indefinitely. The causes of type I diabetes are not completely clear, but are thought to include a genetic component. About thirty percent of non-diabetic siblings of diabetic patients are found to express high levels of RNAs encoded by a group genes activated by type I interferon, although diabetic patients do not overexpress these RNAs. Reynier et al. (2010), Genes and Immunity 11: 269-278. Such overexpression may be an indication of future disease. Since various strategies for inhibiting the progress of the disease are known and may be discovered in the future, it is useful to detect the disease before the onset of clinical symptoms. The methods described herein may be useful to detect and/or treat type I diabetes before and/or after the onset of clinical symptoms.

Inflammatory bowel diseases (IBDs) such as Crohn's disease and ulcerative colitis are also IFN-γ-mediated diseases as meant herein. Crohn's disease is chronic and debilitating inflammatory bowel disease that is thought to reflect a overly-active $T_H1$-mediated immune response to the flora of the gut. The lesions of Crohn's disease can appear anywhere in the bowel and occasionally elsewhere in the gastrointestinal tract. Ulcerative colitis lesions, on the other hand, usually appear in the colon. The nature of the lesions is also different, but the diseases are sufficiently similar that is sometimes difficult to distinguish them clinically. See, e.g., U.S. Pat. No. 6,558,661.

A variety of evidence indicates that IFN-γ plays a role in inflammatory bowel diseases. Results from a clinical study using an anti-human IFN-γ antibody in patients with Crohn's disease indicated that the antibody produced dose dependent, though somewhat marginal, improvements in Crohn's Disease Activity Index (CDAI) scores. International Application Publication WO 2003/097082. The CDAI is described in Best et al. (1976), Gastroenterology 70: 439-444. The portions of this reference that describe the CDAI and how to use it are incorporated herein by reference. In addition, data from model systems for inflammatory bowel disease indicate that IFN-γ inhibition can be effective in reducing the symptoms of inflammatory bowel diseases. See, e.g., U.S. Pat. No. 6,558,661, the relevant portions of which are incorporated herein by reference. The methods described herein may be useful for selecting IBD patients to treat, for treating IBD patients, and/or for reducing or eliminating symptoms of IBD.

Sarcoidosis is a systemic granulomatous disease that can affect essentially any tissue, but it primarily affects the lung and lymphatic systems. It is characterized by the presence of noncaseating epithelioid cell granulomas in more than one organ system. Most commonly the granulomas are found in lung, lymph nodes, skin, liver, and/or spleen, among other possible sites. It can be fatal. For example, fibrosis of the lungs can lead to fatality. Increases in IFN-γ levels have been observed in sarcoidosis. Carter and Hunninghake, "Sarcoidosis," Chapter 47 in Samter's Immunological Diseases, 6$^{th}$ Edition, Austen et al., eds., Lippincott Williams & Wilkins, Phiiladelphia, Pa., 2001. IFN-γ plays a crucial role in the pathogenesis of sarcoidosis. See, e.g., Kriegova et al. (2011), Eur. Respir. J. 38: 1136-1143. The methods described herein may be useful for selecting sarcoidosis patients to treat, for treating sarcoidosis patients, and/or for reducing or eliminating symptoms of sarcoidosis.

Hemophagocytic lymphohistiocytosis (HLH) is a rare and often fatal disease having clinical manifestations including fever, hepatosplenomegaly, lymphadenopathy, jaundice and rash. Laboratory findings associated with HLH include lymphocytosis and histiocytosis and the pathologic finding of hemophagocytosis. Pancytopenia, elevated serum ferritin levels, and abnormal liver enzymes are also frequently present. IFN-γ has been clearly implicated in driving the disease process in a murine model for hemophagocytic anemia. Zoller et al. (2011), J. Exp. Med. 208(6): 1203-1214. The methods described herein may be useful for selecting HLH patients to treat, for treating HLH patients, and/or for reducing or eliminating symptoms of HLH.

For any IFN-γ-mediated disease, it would be valuable to have a test to identify patients likely to benefit from a particular treatment. Due to the episodic nature of symptoms in many such diseases, it would also be desirable to be able to evaluate the biological effects of a given treatment without having to wait for the recurrence of symptoms, or lack thereof. Thus, in the methods described herein, expression of one or more biomarkers listed in Table 1, 2, 4, 5, and/or 6 can be measured before treatment begins as a method for determining whether genes regulated by IFN-γ are dysregulated in the patient. If so, an IFN-γ inhibitor may be an effective treatment. Expression of biomarkers (such as those in Table 1, 2, 4, 5, and/or 6) can also be measured after treatment has begun to determine whether the dosage of the IFN-γ inhibitor is having a biological effect. Such information can inform treatment decisions and may be correlated with clinical signs and symptoms of the disease. For example, if the IFN-γ inhibitor is not having a biological effect, treatment can be discontinued or a different dosage can be administered. If the IFN-γ inhibitor is having a biological effect, then the treatment can be continued. Such information can also be used to determine what doses are having a phamacodynamic effect, i.e., are modulating the expression of a gene or genes whose expression is regulated by IFN-γ.

Interferon Gamma Inhibitors

Appropriate for use in the methods described herein are inhibitors of human IFN-γ, which can be proteins, small molecules, or proteins conjugated to non-protein moieties, such as, for example, a pegylated protein. The capacity of a particular small molecule or protein to inhibit the activity of human IFN-γ can be measured by the A549 bioassay described above.

Numerous proteins that are IFN-γ inhibitors are known. For example, anti-IFN-γ antibodies can inhibit IFN-γ. These can be human, humanized, or chimeric antibodies that bind to human IFN-γ and/or other mammalian homologs such a rhesus, cynomolgus monkey, chimpanzee, mouse, rabbit, rat, baboon, gorilla, and/or marmoset IFN-γ. They can be of the IgG, IgE, IgM, IgA, or IgD isotypes. They can be IgG1, IgG2, IgG3, or IgG4 antibodies. In some embodiments, these antibodies that contain the following pairs of heavy and light chain variable regions: SEQ ID NOs:6 and 8; SEQ ID NOs:10 and 12; SEQ ID NOs: 14 and 16; SEQ ID NOs:14 and 31; and SEQ ID NOs:30 and 12. Further, these antibodies can contain the following pairs of heavy and light chain amino acid sequences: SEQ ID NO:19 and SEQ ID NO:20; SEQ ID NO:17 and SEQ ID NO:18; SEQ ID NO:21 and SEQ ID NO:22; SEQ ID NO:32 and SEQ ID NO:20; or SEQ ID NO:21 and SEQ ID NO:33. These antibodies, which include an antibody called AMG 811 that is used in the clinical trials described in the Examples below, are described in detail in U.S. Pat. No. 7,335,743. The portions of U.S. Pat. No. 7,335,743 that describe these antibodies are incorporated herein by reference. These antibodies can contain a heavy chain CDR1 comprising SEQ ID NO:34, a heavy chain CDR2 comprising SEQ ID NO:35, a heavy chain CDR3 comprising SEQ ID NO:36 or SEQ ID NO:37, a light chain CDR1 comprising SEQ ID NO:38. SEQ ID NO:39, or SEQ ID NO:40, a light chain CDR2 comprising SEQ ID NO:41 or SEQ ID NO:42, and a light chain CDR3 comprising SEQ ID NO:43 or SEQ ID NO:44. In particular embodiments, the antibody can include the following heavy chain CDR1, CDR2, and CDR3 and light chain CDR1, CDR2, and CDR3, respectively: a) SEQ ID NO:34, SEQ ID NO:35, SEQ ID NO:37, SEQ ID NO:39, SEQ ID NO:41, and SEQ ID NO:43; b) SEQ ID NO:34, SEQ ID NO:35, SEQ ID NO:36, SEQ ID NO:38, SEQ ID NO:41, and SEQ ID NO:43; c) SEQ ID NO:34, SEQ ID NO:35, SEQ ID NO:37, SEQ ID NO:38, SEQ ID NO:41, and SEQ ID NO:43; or d) SEQ ID NO:34, SEQ ID NO:35, SEQ ID NO:37, SEQ ID NO:40, SEQ ID NO:42, and SEQ ID NO:44.

Other IFN-γ inhibitors are also contemplated. Any monoclonal anti-IFN-γ antibody capable of inhibiting the activity of human IFN-γ can be used. Among these are the humanized anti-IFN-γ antibody fontolizumab (HUZAF® PDL Biopharma, Inc.). The sequences of the heavy and light chain variable regions of this antibody are reported in U.S. Patent Application Publication 2002/0091240 as SEQ ID NOs:6 and 8, respectively. These sequences and any other description of this antibody included in U.S. Patent Application Publication 2002/0091240 are incorporated herein by reference. The IFN-γ inhibitors described in U.S. Pat. No. 5,451,658 (the relevant portions of which, including the amino acid sequences of the inhibitors, are incorporated herein by reference) are among the IFN-γ inhibitors that can be used to perform the methods described herein. Similarly, IFN-γ inhibitors comprising a portion of a naturally occurring human IFN-γ receptor, the sequence of which is reported in Aguet et al. (1988), Cell 55: 273-280 (the relevant portions of which are incorporated herein by reference), can be used to practice the methods described herein. One such IFN-γ inhibitor is a fusion protein comprising the extracellular region of the human IFN-γ receptor fused to a human IgG1 Fc region, which is described in U.S. Pat. No. 6,558,661, the relevant portions of which are incorporated herein by reference. Other such IFN-γ inhibitors are the fusion proteins containing part or all of the extracellular regions of IFN-γ receptor α and IFN-γ receptor β, as described is U.S. Patent Application Publication 2007/0020283, the relevant portions of which are incorporated herein by reference. Another IFN-γ inhibitor is the cytokine which is a specific antagonist of IFN-γ, which is described in U.S. Pat. No. 5,612,195, the relevant portions of which are incorporated herein by reference. Still other IFN-γ inhibitors are the genetically modified, inactivated protein derivatives of human IFN-γ described in U.S. Patent Application Publication 2010/0158865, the relevant portions of which are incorporated herein by reference. Further, a BCRF1 protein, which inhibits production of IFN-γ, is an IFN-γ inhibitor that can be used to practice the methods described herein. U.S. Pat. No. 5,736,390 describes such BCRF1 proteins, and the portions of U.S. Pat. No. 5,736,390 that describe these proteins and how to make them are incorporated herein by reference.

In addition, various chemical compounds (which are not proteins) are known to inhibit the synthesis of IFN-γ and are considered to be IFN-γ inhibitors, as meant herein. Among these are the bis phenol or phenoxy compounds and derivatives thereof described in U.S. Pat. No. 5,880,146. The portions of U.S. Pat. No. 5,880,146 that describes such compounds and how to make them are incorporated herein by reference. Similarly, the compounds described in U.S. Pat. No. 5,985,863 that inhibit production of IFN-γ by inhibiting production of IFN-γ inducing factor or inhibiting interleukin-1β converting enzyme are IFN-γ inhibitors that can be used to practice the methods described herein.

Methods of Making IFN-γ Inhibitors

With regard to protein inhibitors of IFN-γ, these can be made by methods well known in the art. Antibodies, for example, can be made by introducing hybridoma cells that produce the antibody into the peritoneal cavity of a live mouse, a so-called ascites preparation. Hybridoma cells producing an antibody can also be cultured in vitro. Other in vivo methods of protein production include, for example, protein production in hen eggs, tobacco leaves, and milk. Protein inhibitors of IFN-γ can also be made in prokaryotic or eukaryotic host cells, including bacteria such as *Escherichia coli*, various yeasts including *Saccharomyces cerevisiae* and *Pichia pastoris*, and various kinds of mammalian cells including, without limitation, human cells, baby hamster kidney (BHK) cells, Chinese hamster ovary (CHO) cells, VERO, BHK, HeLa, CV1 (including Cos), MDCK, 293, 3T3, myeloma cell lines (e.g., NSO, NS1), PC12, and WI38 cells. Such host cells, into which nucleic acids encoding the desired protein have been introduced, can be cultured in appropriate culture medium, many of which are known in the art, and the desired protein can be recovered from the cell mass or the cell culture medium.

CHO cells are widely used for the production of complex recombinant proteins, e.g. cytokines, clotting factors, and antibodies (Brasel et al. (1996), Blood 88:2004-2012; Kaufman et al (1988), J. Biol. Chem. 263:6352-6362; McKinnon et al (1991), J. Mol. Endocrinol. 6:231-239; Wood et al. (1990), J. Immunol. 145:3011-3016). The dihydrofolate reductase (DHFR)-deficient mutant cell lines (Urlaub et al. (1980), Proc. Natl. Acad. Sci. U.S.A. 77: 4216-4220, which is incorporated by reference), DX811 and DG-44, are desirable CHO host cell lines because the efficient DHFR selectable and amplifiable gene expression system allows high level recombinant protein expression in these cells (Kaufman R. J. (1990), Meth. Enzymol. 185:537-566, which is incorporated by reference). In addition, these cells are easy to manipulate as adherent or suspension cultures and exhibit relatively good genetic stability. CHO cells and recombinant proteins expressed in them have been extensively characterized and have been approved for use in clinical commercial manufacturing by regulatory agencies. The methods of the invention can also be practiced using hybridoma cell lines that produce an antibody. Methods for making hybridoma lines are well known in the art. See e.g. Berzofsky et al. in Paul, ed., *Fundamental Immunology, Second Edition*, pp. 315-356, at 347-350, Raven Press Ltd., New York (1989). Cell lines derived from the above-mentioned lines are also suitable for making IFN-γ inhibitor proteins.

Determining Dosage Using Biomarkers

Described herein are methods for determining a pharmacodynamically effective dosage of an IFN-γ inhibitor for treating an IFN-γ mediated disease, as well as methods of treatment using such dosages. The method includes assaying for the expression of one or more genes at either the protein or RNA level both before and after administering an IFN-γ inhibitor. The gene(s) can be selected from the genes listed in Table 1 (genes whose expression is modulated in human blood by stimulation with IFN-γ ex vivo), Table 2 (twenty genes whose expression is modulated in human blood to the greatest extent by IFN-γ stimulation ex vivo), Table 3 (ten genes whose expression is modulated to the greatest extent by administration of AMG 811 in vivo), Table 5 (genes whose expression is modulated by a neutralizing human anti-human IFN-γ antibody in vivo), and/or Table 6 (genes whose expression is modulated in human blood by stimulation with IFN-γ ex vivo and whose expression is modulated by a neutralizing human anti-human IFN-γ antibody in vivo). Those doses that modulate the expression of one or more of these genes in a direction consistent with inhibition of IFN-γ can be used to treat an IFN-γ mediated disease.

Alternatively or in addition, a pharmacodynamically effective dosage and/or dosing frequency of an IFN-γ inhibitor can be determined by the effect of an IFN-γ inhibitor on the serum concentration of total IFN-γ protein. For example, some doses of an IFN-γ inhibitor, for example an IFN-γ binding protein such as AMG 811, can cause elevation of the serum levels of total IFN-γ. See FIGS. 6A and 6B below. Presumably, this effect results from protection of IFN-γ that is bound by the IFN-γ inhibitor from degradation or more rapid clearance. If patients receiving a higher dose of an IFN-γ inhibitor (for example, 180 mg SC of AMG 811 in FIG. 6A) reach about the same levels of total IFN-γ as those attained by patients receiving a somewhat lower dose (for example, 60 mg SC of AMG 811 in FIG. 6A), it may be that all available IFN-γ is protected at the lower dose. A desirable dose of an IFN-γ binding protein, for example AMG 811, would be one that causes patients to achieve a higher-than-baseline level of total IFN-γ and to maintain this "plateau" concentration for a time period of, for example, at least about 2, 3, 4, 5, 6, 7, or 8 weeks and/or at least about 1, 2, 3, or 4 months. Based on the data in FIGS. 6A and 6B for AMG 811, a desirable dose can be greater than about 20 mg SC, at least about 60 mg SC, at least about 180 mg SC, and/or at least about 60 mg IV. Further, using a dose of an IFN-γ inhibitor such that the levels of total IFN-γ reach and maintain a higher-than-baseline plateau concentration for at least about 2 weeks, dosing frequency can be adjusted such that the levels of total IFN-γ do not fall below about 25%, 50%, 60%, 70%, or 80% of this plateau value. Thus, at a lower dose of an IFN-γ inhibitor where a plateau value is maintained for a shorter period, dosing can be more frequent, whereas at a higher dose of an IFN-γ inhibitor where a plateau value is maintained for a longer period, dosing can be less frequent. For example, based on the data in FIGS. 6A and 6B, at a dose of 60 mg SC of AMG 811, doses can be administered approximately every 2, 3, 4, or 5 weeks. Similarly, at a dose of AMG 811 of 180 mg SC or 60 mg IV, doses can be administered approximately every 6, 7, 8, 9, 10, 11, or 12 weeks.

In a particular embodiment, at least the lower end of dosage ranges for treating patients having SLE and/or lupus nephritis with a human anti-human IFN-γ antibody called AMG 811 have been clarified. See Examples 3 and 4 and FIGS. 4, 6-9, and 12-14. In that data, the lowest dose at which a clear biological effect was observed was a dose of 20 milligrams, although clearer effects were observed in some cases at a dose of 60 mg.

For any IFN-γ inhibitor that contains a protein, for example an anti-huIFN-γ antibody such as AMG 811, the dose can be at least about 10, 15, 20, 25, 30, 35, 40, 50, 60, 70, 80, 90, 100, 110, 120, 130, 140, 150, 160, 170, 180, 190, 200, 210, 220, 230, 240, or 250 mg and/or may not exceed 180, 200, 250, 300, 350, 400, 450, 500, 600, 700, 800, 900, 1000, or 2000 mg. For example, a per-treatment dose of about 15-500, 20-400, 30-300, 60-180, 80-200, or 100-200 milligrams of the antibody can be used to treat an IFN-γ-mediated disease. Alternatively, a per-treatment dose of about 10, 15, 20, 30, 40, 50, 60, 70, 80, 90, 100, 110, 120, 130, 140, 150, 160, 170, 180, 190, 200, 220, 240, 260, 270, 290, 300, 350, or 400 milligrams can be used.

Alternatively, a dose can be gauged on the basis of a patient's body weight. For example, a dose of at least about 0.1, 0.15, 0.2. 0.25, 0.3, 0.35, 0.4, 0.5, 0.6, 0.7, 0.8, 0.9, 1.0, 1.2, 1.4, 1.6, 1.8, 2.0, 2.2, 2.4, 2.6, 2.8, 3.0, 3.2, 3.4, 3.6, 3.8, 4.0, 4.2, 4.4, 4.6, 4.8, or 5.0 milligrams per kilogram (mg/kg) and/or not more than about 3.0, 3.5, 4.0, 4.5, 5.0, 5.5, 6.0, 6.5, 7.0, 7.5, 8.0, 8.5, 9.0, 9.5, or 10 mg/kg can be administered. In some embodiments, the dose can be from about 0.2 mg/kg to about 10 mg/kg, from about 0.25 mg/kg to about 8 mg/kg, from about 0.5 mg/kg to about 5 mg/kg, from about 1 mg/kg to about 2 mg/kg, from about 1 mg/kg to about 3 mg/kg, or from about 3 mg/kg to about 5 mg/kg.

Alternatively, a dose can be administered on the basis of the calculated body surface area of a patient. For example, a dose of at least about 4, 6, 8, 12, 24, 36, 48, 60, 72, 84, 96, 108, 120, 130, 140, 150, 160, 170, 180, or 190 milligrams per square millimeter (mg/mm$^2$) and/or not more than 200, 220, 240, 260, 280, 300, 320, 340, 360, or 380 mg/mm$^2$ can be administered. In some embodiments the dose can be from about 8 mg/mm$^2$ to about 380 mg/mm$^2$, from about 10 mg/mm$^2$ to about 300 mg/mm$^2$, from about 20 mg/mm$^2$ to about 190 mg/mm$^2$, from about 40 mg/mm$^2$ to about 80 mg/mm$^2$, from about 80 mg/mm$^2$ to about 200 mg/mm$^2$.

Since many IFN-γ-mediated diseases are chronic and/or recurrent, repeated doses of the IFN-γ inhibitor, optionally an anti-huIFN-γ antibody, may be required. Repeated doses can be administered, for example, twice per week, once a week, every two, three, four, five, six, seven, eight, nine, ten, eleven, or twelve weeks, or once every one, two, three, four, five, six, seven, eight, nine, ten, eleven, or twelve months.

It is always advantageous for clinicians and patients to be able to predict whether a given treatment will be effective for a particular patient. This is particularly true where the disease commonly includes long asymptomic periods, either alternating with symptomic periods or before the onset of symptoms. Provided herein are methods for determining which patients are likely to be successfully treated with an IFN-γ inhibitor. As discussed above, there are a number of IFN-γ mediated diseases. These include various autoimmune and inflammatory diseases including SLE, including discoid lupus and lupus nephritis, rheumatoid arthritis, type I diabetes, multiple sclerosis, psoriasis, dermatomyositis, sarcoidosis, HLH, and IBDs including Crohn's disease and ulcerative colitis, among a number of others. In the Examples below, it is shown that some genes whose expression was found to be upregulated by IFN-γ ex vivo are downregulated by an anti-human IFN-γ antibody in vivo. These genes are listed in Table 6 below.

Provided are methods for identifying patients suffering from an IFN-γ mediated disease likely to benefit from treatment with an IFN-γ inhibitor comprising determining whether the expression of one or more genes listed in Tables 1, 2, 4, 5, and/or 6 in a biological sample from the patient deviates from the expression of that gene(s) in a control biological sample in a direction consistent with excess IFN-γ. If the level of expression of one or more genes mentioned above in the biological sample from the patient deviates from the levels of expression in the control biological sample in a direction consistent with excess IFN-γ, it can indicate that the patient is a candidate for treatment with an IFN-γ inhibitor. The IFN-γ inhibitor can be an anti-huIFN-γ antibody or an IFN-γ receptor.

In another aspect, patients likely to benefit from treatment with an IFN-γ inhibitor can be identified by determining the levels of total IFN-γ in a biological sample from the patient as, for example, described in Example 3. Patients with undetectable or very low levels of total IFN-γ may not benefit from therapy with an IFN-γ inhibitor, for example an IFN-γ binding protein such an antibody. On the other hand, patients whose biological samples have total IFN-γ levels that are substantially higher than those detected in a control biological sample can benefit from therapy with an IFN-γ inhibitor, for example an IFN-γ binding protein such as an antibody. Thus, determination of total IFN-γ levels in a biological sample from a patient can be used to identify patients likely to benefit from therapy with an IFN-γ inhibitor, for example an IFN-γ binding protein such as an anti-IFN-γ antibody.

Methods for Determining Treatment Efficacy

The methods provided herein can be useful for patients and clinicians in deciding whether to continue a treatment with an IFN-γ inhibitor in a particular patient. In the clinical studies reported in the Examples below, it is reported that the expression of a number of genes is modulated in a statistically significant manner in response to treatment with an anti-huIFN-γ antibody. In a variable and episodic disease such as, for example, SLE or MS, it may be impossible to tell from clinical signs and symptoms whether a treatment is having an effect within a given time period, such as, for example, 1, 2, or 3 weeks or 1, 2, 3, 4, 5, or 6 months. If, however, the expression of a biomarker listed in Table 1, 2, 4, 5, and/or 6 is modulated in a direction consistent with inhibition of IFN-γ, then it can be known that the treatment is having a biological effect, even though the patient might not show immediate changes in signs and symptoms. In such a case, according to the judgment of a clinician, it can be reasonable to continue treatment. However, if the expression of a biomarker listed in Table 1, 2, 4, 5, and/or 6 is not modulated by the IFN-γ inhibitor or is modulated in a direction consistent with an excess of IFN-γ, and there is not a change in signs and symptoms, it could be reasonably concluded that the patient is not responding to treatment. In such a situation, according to a clinician's judgment, treatment with an IFN-γ inhibitor could be discontinued, and a different treatment could be initiated.

Provided are methods for determining the efficacy of an IFN-γ inhibitor such as an anti-huIFN-γ antibody. Such an anti-huIFN-γ antibody can comprise the amino acid sequence of SEQ ID NO: 6, 10, 14, or 30 and SEQ ID NO: 8, 12, 16, or 31 and/or can comprise a light chain CDR1 comprising SEQ ID NO:38, 39, or 40, a light chain CDR2 comprising SEQ ID NO:41 or 42, a light chain CDR3 comprising SEQ ID NO:43 or 44, a heavy chain CDR1 comprising SEQ ID NO:34, a heavy chain CDR2 comprising SEQ ID NO:35, and a heavy chain CDR3 comprising SEQ ID NO:36 or 37. A method for determining the efficacy of an IFN-γ inhibitor as a treatment for an IFN-γ-mediated disease can comprise the following steps: 1) determining the level of expression of one or more of the genes listed in Table 1, 2, 4, 5, and/or 6 in a biological sample from a patient at the protein or RNA level; 2) determining the level of expression of the same gene(s) in a biological sample from the patient after administration of the drug; 3) comparing the expression of the gene(s) in biological samples from the patient before and after administration of the drug; 4) determining that the drug has shown evidence of efficacy if the level of expression of the gene(s) in the biological sample taken after administration of the drug has been modulated in a direction consistent with inhibition of IFN-γ; and 5) continuing treatment with the drug if it is determined that the drug has shown evidence of efficacy and discontinuing treatment with the drug if it is determined that the drug has not shown evidence of efficacy.

Combination Therapies

Treatments exist for most IFN-γ-mediated diseases, even though many of these treatments are relatively ineffective, effective for only a subset of patients, and/or have substantial toxicities that limit patient tolerance of treatment. The IFN-γ inhibitors described herein can be combined with other existing therapies for IFN-γ-mediated diseases.

In particular, an SLE patient can be treated concurrently with another therapy for SLE plus an IFN-γ inhibitor such as an anti-IFN-γ antibody comprising SEQ ID NO:6 and SEQ ID NO:8 and/or comprising a light chain CDR1 comprising SEQ ID NO:38, a light chain CDR2 comprising SEQ ID NO:41, a light chain CDR3 comprising SEQ ID NO:43, a heavy chain CDR1 comprising SEQ ID NO:34, a heavy chain CDR2 comprising SEQ ID NO:35, and a heavy chain CDR3 comprising SEQ ID NO:36. Existing therapies for SLE include glucocorticoids such as prednisone, prednisolone, and methylprednisolone, antimalarials such as hydroxychloroquine, quinacrine, and chloroquine, retinoic acid, aspirin and other nonsteroidal anti-inflammatory drugs (NSAIDs), cyclophosphamide, dehydroepiandrosterone, mycophenolate mofetil, azathioprine, chlorambucil, methotrexate, tacrolimus, dapsone, thalidomide, leflunomide, cyclosporine, anti-CD20 antibodies such as rituximab, BLyS inhibitors such as belimumab, and fusion proteins such as abatacept. Methods of patient stratification and biomarker monitoring concurrently with treatment, as described herein, can be used in patients receiving such combination drug treatments.

In other embodiments a patient suffering from an inflammatory bowel disease (IBD), such as Crohn's disease or ulcerative colitis, can be concurrently treated with a therapy for IBD plus an IFN-γ inhibitor, such as an anti-huIFN-γ antibody comprising SEQ ID NO:6 and SEQ ID NO:8 and/or comprising a light chain CDR1 comprising SEQ ID NO:38, a light chain CDR2 comprising SEQ ID NO:41, a light chain CDR3 comprising SEQ ID NO:43, a heavy chain CDR1 comprising SEQ ID NO:34, a heavy chain CDR2 comprising SEQ ID NO:35, and a heavy chain CDR3 comprising SEQ ID NO:36. Existing therapies for IBD include sulfasalazine, 5-aminosalicylic acid and its derivatives (such as olsalazine, balsalazide, and mesalamine), anti-TNF antibodies (including infliximab, adalimumab, golimumab, and certolizumab pegol), corticosteroids for oral or parenteral administration (including prednisone, methylprednisone, budesonide, or hydrocortisone), adrenocorticotropic hormone, antibiotics (including metronidazole, ciprofloxacin, or rifaximin), azathioprine, 6-mercaptopurine, methotrexate, cyclosporine, tacrolimus, and thalidomide. Methods of patient stratification and biomarker monitoring concurrently with treatment, as described herein, can be used in patients receiving such combination drug treatments.

In other embodiments, a patient suffering from rheumatoid arthritis can be concurrently treated with a drug used for RA therapy plus an IFN-γ inhibitor, such as an anti-huIFN-γ antibody comprising SEQ ID NO:6 and SEQ ID NO:8 and/or comprising a light chain CDR1 comprising SEQ ID NO:38, a light chain CDR2 comprising SEQ ID NO:41, a light chain CDR3 comprising SEQ ID NO:43, a heavy chain CDR1 comprising SEQ ID NO:34, a heavy chain CDR2 comprising SEQ ID NO:35, and a heavy chain CDR3 comprising SEQ ID NO:36. Therapies for rheumatoid arthritis (RA) include non-steroidal anti-inflammatory drugs (NSAIDs) (such aspirin and cyclooxygenase-2 (COX-2) inhibitors), disease modifying anti-inflammatory drugs (DMARDs)(such as methotrexate, leflunomide, and sulfasalazine), anti-malarials (such as hydroxychloroquine), cyclophosphamide, D-penicillamine, azathioprine, gold salts, tumor necrosis factor inhibitors (such as etanercept, infliximab, adalimumab, golimumab, and certolizumab pegol), CD20 inhibitors such as rituximab, IL-1 antagonists such as anakinra, IL-6 inhibitors such as tocilizumab, inhibitors of Janus kinases (JAK)(such as tofacitinib), abatacept, and glucocorticoids, among others. Methods of patient stratification and biomarker monitoring concurrently with treatment, as described herein, can be used in patients receiving such combination drug treatments.

In another embodiment, a patient suffering from sarcoidosis can be concurrently treated with a drug used for sarcoidosis therapy plus an IFN-γ inhibitor, such as an anti-huIFN-γ antibody comprising SEQ ID NO:6 and SEQ ID NO:8 and/or comprising a light chain CDR1 comprising SEQ ID NO:38, a light chain CDR2 comprising SEQ ID NO:41, a light chain CDR3 comprising SEQ ID NO:43, a heavy chain CDR1 comprising SEQ ID NO:34, a heavy chain CDR2 comprising SEQ ID NO:35, and a heavy chain CDR3 comprising SEQ ID NO:36. Therapies for sarcoidosis include corticosteroids (may be topical or parenteral, depending on symptoms), salicylates (such as aspirin), and colchicine. Methotrexate, cyclophosphamide, azathioprine, and nonsteroidal anti-inflammatory drugs have also been used in sarcoidosis. Various other treatment strategies can be helpful for some of the many different symptoms of sarcoidosis. For example, heart arrhythmias can be treated with antiarrhythmics or a pacemaker. Hypercalcemia can be treated with hydration, reduction in calcium and vitamin D intake, avoidance of sunlight, or ketoconazole. Skin lesions can be treated with chloroquine, hydroxychloroquine, methotrexate, or thalidomide. Methods of patient stratification and biomarker monitoring concurrently with treatment, as described herein, can be used in patients receiving such a combination treatment including an IFN-γ inhibitor plus an existing treatment for sarcoidosis.

In another embodiment, a patient suffering from HLH can be concurrently treated with a drug used for HLH therapy plus an IFN-γ inhibitor such as an anti-huIFN-γ antibody comprising SEQ ID NO:6 and SEQ ID NO:8 and/or comprising a light chain CDR1 comprising SEQ ID NO:38, a light chain CDR2 comprising SEQ ID NO:41, a light chain CDR3 comprising SEQ ID NO:43, a heavy chain CDR1 comprising SEQ ID NO:34, a heavy chain CDR2 comprising SEQ ID NO:35, and a heavy chain CDR3 comprising SEQ ID NO:36. Therapies for HLH include corticosteroids, intravenous immunoglobulin, IL-1 inhibiting agents such as anakinra, VP-16, etoposide, cyclosporine A, dexamethasone, various other chemotherapeutics, bone marrow transplant or stem cell transplant, and antiviral and/or antibacterial agents. Any one or more of these therapies can be combined with an anti-huIFN-γ treatment. Further, methods of patient stratification and biomarker monitoring concurrently with treatment, as described herein, can be used in patients receiving such a combination treatment including an IFN-γ inhibitor plus an existing treatment for HLH.

Methods of Administration

The IFN-γ inhibitors and the other disease treatments described herein can be administered by any feasible method. Therapeutics that comprise a protein will ordinarily be administered by injection since oral administration, in the absence of some special formulation or circumstance, would lead to hydrolysis of the protein in the acid environment of the stomach. Subcutaneous, intramuscular, intravenous, intraarterial, intralesional, or peritoneal injection are possible routes of administration. Topical administration is also possible, especially for diseases involving the skin. Alternatively, IFN-γ inhibitors, and/or other therapeutics comprising a protein, can be administered through contact with a mucus membrane, for example by intra-nasal, sublingual, vaginal, or rectal administration or as an inhalant. Therapeutics that are small molecules can be administered orally, although the routes of administration mentioned above are also possible.

Having described the invention in general terms above, the following examples are offered by way of illustration and not limitation.

EXAMPLES

Example 1

Determining the Identity of Genes Whose Expression in Blood is Modulated by IFN-γ Ex Vivo To define a group of genes regulated by IFN-γ, blood from healthy volunteers was collected into sodium heparin tubes, and then incubated at 37° C., 5% $CO_2$ with or without 294 pM recombinant human IFN-γ for 0, 24, or 48 hours. After incubation, the blood was added to PAXGENE® whole blood tubes (Becton Dickenson Catalog #762165) and processed for RNA purification.

Total RNA was isolated from the PAXGENE® whole blood tubes using the PAXGENE® RNA Kit (Qiagen Catalog #762164) on the QIACUBE® automated sample prep system. Samples were labeled using the AGILENT® Low RNA Input Linear Amplification Kit PLUS, Two-Color (Agilent Catalog #5188-5340) per manufacturer's instructions. Briefly, double-stranded cDNA was reverse transcribed from about 300 nanograms of total RNA and acted as template for T7 RNA polymerase in an in vitro transcription reaction in which the target material was simultaneously amplified and labeled with cyanine 3- or cyanine 5-CTPs. The resulting fluorescent complementary RNA was hybridized to AGILENT® human whole genome 4×44K (Cat #G4112F) oligonucleotide microarrays per manufacturer's instructions.

Extracted feature intensities for each channel on each array were processed separately by subtracting the lower $0.1^{th}$ percentile from all intensities and then taking the log base 2. The transformed intensities were mapped using a non-linear function to ensure the distribution of the intensities were comparable between arrays and channels. Arrays were hybridized using a loop-design that allowed estimation and removal of technical bias when averaging the technical repeats.

Samples were processed in batches that roughly corresponded to samples from individual cohorts but with a small number of samples repeated between batches to allow estimation and removal of batch effects. Finally, replicates of any identical sequences on the array were averaged to produce a value we called gene intensities.

In additional to the above processing, a pre-filtering step was applied. Reporters with low levels of expression were removed if 90% of the values fell below the limit of detection, defined as 1.96 standard deviations above mean background. Background was determined by a set of sequences on the array that are specifically designed to not hybridize with human sequences. Reporters with small dispersion are unlikely to be meaningfully changed, and so, to reduce noise, these were removed. They were defined as those where the fold change between the $5^{th}$ and $95^{th}$ percentile was less than 1.5.

Statistical analysis of the data to identify genes regulated ex vivo by IFN-γ was performed using a fixed-effects regression model containing factors for donor, time, treatment and all pair wise interactions terms. The treatment effect was similar at the two post-treatment times of 24 and 48 hours (data not shown), so these data were considered a single group to display the treatment effect. The significance threshold was defined at a false discovery rate of 5% and a fold change of 1.72. See Storey, J. D. 2002. A direct approach to false discovery rates. J. R. Statist. Soc. B. 64: 479-498, the relevant portions of which are incorporated herein by reference. The fold change was selected because we expected about 90% power to detect this fold change at a significance level of 0.001 assuming a standard deviation of 0.38. The results from this analysis are shown in FIG. 1.

In FIG. 1 each dot represents the average fold change in expression of an individual gene at the RNA level in blood from a healthy volunteer stimulated ex vivo with IFN-γ as compared to the same blood pre-stimulation. The x-axis reflects the fold change, and the y-axis represents the p-value of the difference in gene expression in post-stimulation blood as compared to pre-stimulation blood. Generally, a p-value of 0.05 or less would be considered to indicate statistical significance. The circled dots in FIG. 1 correspond to the twenty genes that showed the greatest fold change in expression upon stimulation with IFN-γ, where the change had a nominal significance level of 0.001 or less. These data show that a large number of genes are up- and down-regulated by IFN-γ. Table 1 below lists genes that were found to be up- or down-regulated by ex vivo stimulation with IFN-γ. The criteria applied to select these genes from among the tens of thousands of genes on the array were a false discovery rate of <0.001, powered at 90% to detect an alpha of 0.001.

TABLE 1

Genes whose expression is modulated by IFN-γ

| AGILENT ® Probe Name | Sequence Listing number of AGILENT ® Probe Sequence | Symbol of Gene | NCBI Accession Number of Gene Sequence | Gene Name | Direction of modulation by IFN-γ |
|---|---|---|---|---|---|
| A_23_P112026 | SEQ ID NO: 350 | INDO | NM_002164 | indoleamine-pyrrole 2,3 dioxygenase | up |
| A_23_P161428 | SEQ ID NO: 72 | ANKRD22 | NM_144590 | ankyrin repeat domain 22 | up |
| A_23_P18452 | SEQ ID NO: 109 | CXCL9 | NM_002416 | chemokine (C-X-C motif) ligand 9 | up |
| A_23_P7827 | SEQ ID NO: 83 | RP1-93H18.5 | NM_001010919 | hypothetical protein LOC441168 | up |
| A_24_P28722 | SEQ ID NO: 351 | RSAD2 | NM_080657 | radical 5-adenosyl methionine domain containing 2 | up |
| A_23_P150457 | SEQ ID NO: 352 | XLKD1 | NM_006691 | extracellular link domain containing 1 | down |
| A_24_P165864 | SEQ ID NO: 300 | P2RY14 | NM_014879 | purinergic receptor P2Y, G-protein coupled, 14 | up |
| A_23_P74290 | SEQ ID NO: 79 | GBP5 | NM_052942 | guanylate binding protein 5 | up |
| A_23_P63390 | SEQ ID NO: 73 | FCGR1B | NM_001017986 | Fc fragment of IgG, high affinity Ib, receptor (CD64) | up |
| A_24_P245379 | SEQ ID NO: 353 | SERPINB2 | NM_002575 | serpin peptidase inhibitor, clade B (ovalbumin), member 2 | down |
| A_24_P316965 | SEQ ID NO: 354 | RSAD2 | NM_080657 | radical 5-adenosyl methionine domain containing 2 | up |
| A_24_P561165 | SEQ ID NO: 322 | A_24_P561165 | A_24_P561165 | Unknown | up |
| A_23_P121657 | SEQ ID NO: 355 | HS3ST1 | NM_005114 | heparan sulfate (glucosamine) 3-O-sulfotransferase 1 | down |
| A_23_P203882 | SEQ ID NO: 356 | MMP19 | NM_002429 | matrix metallopeptidase 19 | down |
| A_24_P303091 | SEQ ID NO: 311 | CXCL10 | NM_001565 | chemokine (C-X-C motif) ligand 10 (IP-10) | up |
| A_32_P107372 | SEQ ID NO: 76 | GBP1 | NM_002053 | guanylate binding protein 1, interferon-inducible, 67 kDa | up |
| A_23_P62890 | SEQ ID NO: 74 | GBP1 | NM_002053 | guanylate binding protein 1, interferon-inducible, 67 kDa | up |
| A_23_P256487 | SEQ ID NO: 78 | CD274 | ENST00000381577 | CD274 molecule | up |
| A_23_P65651 | SEQ ID NO: 278 | WARS | NM_004184 | tryptophanyl-tRNA synthetase | up |
| A_23_P18604 | SEQ ID NO: 232 | LAP3 | NM_015907 | leucine aminopeptidase 3 | up |
| A_24_P12690 | SEQ ID NO: 357 | INDOL1 | AK128691 | indoleamine-pyrrole 2,3 dioxygenase-like 1 | up |
| A_23_P48513 | SEQ ID NO: 269 | IFI27 | NM_005532 | interferon, alpha-inducible protein 27 | up |
| A_24_P478940 | SEQ ID NO: 358 | A_24_P478940 | THC2668815 | Low quality annotation—Q4TBH3_TETNG (Q4TBH3) Chromosome 13 SCAF7124, whole genome shotgun sequence, partial (3%) [THC2668815] | down |

TABLE 1-continued

Genes whose expression is modulated by IFN-γ

| AGILENT ® Probe Name | Sequence Listing number of AGILENT ® Probe Sequence | Symbol of Gene | NCBI Accession Number of Gene Sequence | Gene Name | Direction of modulation by IFN-γ |
|---|---|---|---|---|---|
| A_23_P103496 | SEQ ID NO: 196 | GBP4 | NM_052941 | guanylate binding protein 4 | up |
| A_23_P42353 | SEQ ID NO: 77 | ETV7 | NM_016135 | ets variant gene 7 (TEL2 oncogene) | up |
| A_23_P62115 | SEQ ID NO: 359 | TIMP1 | NM_003254 | TIMP metallopeptidase inhibitor 1 | down |
| A_24_P270460 | SEQ ID NO: 309 | IFI27 | NM_005532 | interferon, alpha-inducible protein 27 | up |
| A_23_P74609 | SEQ ID NO: 360 | G0S2 | NM_015714 | G0/G1switch 2 | up |
| A_23_P39840 | SEQ ID NO: 163 | VAMP5 | NM_006634 | vesicle-associated membrane protein 5 (myobrevin) | up |
| A_23_P27306 | SEQ ID NO: 361 | COLEC12 | NM_030781 | collectin sub-family member 12 | down |
| A_24_P45446 | SEQ ID NO: 108 | GBP4 | NM_052941 | guanylate binding protein 4 | up |
| A_23_P76386 | SEQ ID NO: 362 | SLC6A12 | NM_003044 | solute carrier family 6 (neurotransmitter transporter, betaine/GABA), member 12 | up |
| A_23_P121253 | SEQ ID NO: 110 | TNFSF10 | NM_003810 | tumor necrosis factor (ligand) superfamily, member 10 | up |
| A_23_P91390 | SEQ ID NO: 363 | THBD | NM_000361 | thrombomodulin | down |
| A_24_P167642 | SEQ ID NO: 301 | GCH1 | NM_000161 | GTP cyclohydrolase 1 (dopa-responsive dystonia) | up |
| A_23_P338479 | SEQ ID NO: 75 | CD274 | NM_014143 | CD274 molecule | up |
| A_23_P21485 | SEQ ID NO: 364 | FLJ20701 | NM_017933 | hypothetical protein FLJ20701 | down |
| A_23_P33723 | SEQ ID NO: 365 | CD163 | NM_004244 | CD163 molecule | down |
| A_23_P420196 | SEQ ID NO: 366 | SOCS1 | NM_003745 | suppressor of cytokine signaling 1 | up |
| A_23_P165624 | SEQ ID NO: 226 | TNFAIP6 | NM_007115 | tumor necrosis factor, alpha-induced protein 6 | up |
| A_24_P912985 | SEQ ID NO: 326 | A_24_P912985 | A_24_P912985 | Unknown | up |
| A_24_P15702 | SEQ ID NO: 298 | LOC389386 | XR_017251 | similar to leucine aminopeptidase 3 | up |
| A_23_P156687 | SEQ ID NO: 221 | CFB | NM_001710 | complement factor B | up |
| A_23_P137366 | SEQ ID NO: 367 | SEQ ID NO: 100C1QB | NM_000491 | complement component 1, q subcomponent, B chain | up |
| A_23_P139123 | SEQ ID NO: 210 | SERPING1 | NM_000062 | serpin peptidase inhibitor, clade G (C1 inhibitor), member 1, (angioedema, hereditary) | up |
| A_23_P384355 | SEQ ID NO: 368 | A_23_P384355 | BG547557 | Low quality annotation—BG547557 602575410F1 NH_MGC_77 Homo sapiens cDNA clone IMAGE: 4703546 5', mRNA sequence [BG547557] | up |
| A_23_P55356 | SEQ ID NO: 369 | VMO1 | NM_182566 | vitellne membrane outer layer 1 homolog (chicken) | down |
| A_23_P32500 | SEQ ID NO: 370 | STAB1 | NM_015136 | stabilin 1 | down |
| A_32_P171061 | SEQ ID NO: 371 | ASCL2 | NM_005170 | achaete-scute complex homolog 2 (Drosophila) | up |
| A_23_P210763 | SEQ ID NO: 238 | JAG1 | NM_000214 | jagged 1 (Alagille syndrome) | up |
| A_24_P48204 | SEQ ID NO: 320 | SECTM1 | NM_003004 | secreted and transmembrane 1 | up |
| A_23_P354387 | SEQ ID NO: 257 | FER1L3 | NM_013451 | fer-1-like 3, myoferlin (C. elegans) | up |
| A_24_P353638 | SEQ ID NO: 372 | SLAMF7 | NM_021181 | SLAM family member 7 | up |
| A_23_P53891 | SEQ ID NO: 270 | KLF5 | NM_001730 | Kruppel-like factor 5 (intestinal) | up |
| A_32_P44394 | SEQ ID NO: 87 | AIM2 | NM_004833 | absent in melanoma 2 | up |
| A_23_P153185 | SEQ ID NO: 373 | SERPINB2 | ENST00000299502 | serpin peptidase inhibitor, clade B (ovalbumin), member 2 | down |
| A_23_P200138 | SEQ ID NO: 374 | SLAMF8 | NM_020125 | SLAM family member 8 | up |
| A_23_P207456 | SEQ ID NO: 375 | CCL8 | NM_005623 | chemokine (C-C motif) ligand 8 | up |
| A_24_P380734 | SEQ ID NO: 376 | SDC2 | NM_002998 | syndecan 2 (heparan sulfate proteoglycan 1, cell surface-associated, fibroglycan) | down |
| A_23_P370682 | SEQ ID NO: 80 | BATF2 | NM_138456 | basic leucine zipper transcription factor, ATF-like 2 | up |
| A_23_P329261 | SEQ ID NO: 251 | KCNJ2 | NM_000891 | potassium inwardly-rectifying channel, subfamily J, member 2 | up |
| A_24_P383523 | SEQ ID NO: 317 | SAMD4A | NM_015589 | sterile alpha motif domain containing 4A | up |
| A_23_P167328 | SEQ ID NO: 377 | CD38 | NM_001775 | CD38 molecule | up |
| A_23_P209625 | SEQ ID NO: 236 | CYP1B1 | NM_000104 | cytochrome P450, family 1, subfamily B, polypeptide 1 | down |
| A_23_P335661 | SEQ ID NO: 253 | SAMD4A | AB028976 | sterile alpha motif domain containing 4A | up |
| A_23_P159325 | SEQ ID NO: 378 | ANGPTL4 | NM_139314 | angiopoietin-like 4 | down |
| A_23_P2831 | SEQ ID NO: 379 | EDNRB | NM_003991 | endothelin receptor type B | down |
| A_23_P35412 | SEQ ID NO: 256 | IFIT3 | NM_001549 | interferon-induced protein with tetratricopeptide repeats 3 | up |
| A_23_P29773 | SEQ ID NO: 380 | LAMP3 | NM_014398 | lysosomal-associated membrane protein 3 | up |
| A_23_P101992 | SEQ ID NO: 381 | MARCO | NM_006770 | macrophage receptor with collagenous structure | down |
| A_23_P105794 | SEQ ID NO: 197 | EPSTI1 | NM_033255 | epithelial stromal interaction 1 (breast) | up |
| A_23_P207507 | SEQ ID NO: 382 | ABCC3 | NM_003786 | ATP-binding cassette, sub-family C (CFTR/MRP), member 3 | down |
| A_23_P45871 | SEQ ID NO: 383 | IFI44L | NM_006820 | interferon-induced protein 44-like | up |
| A_23_P75430 | SEQ ID NO: 285 | C11ORF75 | NM_020179 | chromosome 11 open reading frame 75 | up |

TABLE 1-continued

Genes whose expression is modulated by IFN-γ

| AGILENT ® Probe Name | Sequence Listing number of AGILENT ® Probe Sequence | Symbol of Gene | NCBI Accession Number of Gene Sequence | Gene Name | Direction of modulation by IFN-γ |
|---|---|---|---|---|---|
| A_24_P350686 | SEQ ID NO: 106 | TIFA | NM_052864 | TRAF-interacting protein with a forkhead-associated domain | up |
| A_23_P57709 | SEQ ID NO: 384 | PCOLCE2 | NM_013363 | procollagen C-endopeptidase enhancer 2 | down |
| A_23_P70095 | SEQ ID NO: 385 | CD74 | NM_001025158 | CD74 molecule, major histocompatibility complex, class II invariant chain | up |
| A_32_P56001 | SEQ ID NO: 386 | CD93 | NM_012072 | CD93 molecule | down |
| A_24_P943205 | SEQ ID NO: 332 | EPSTI1 | ENST00000313624 | epithelial stromal interaction 1 (breast) | up |
| A_24_P305067 | SEQ ID NO: 387 | HOXB4 | NM_024015 | homeobox B4 | up |
| A_23_P347541 | SEQ ID NO: 99 | GRIN3A | NM_133445 | glutamate receptor, ionotropic, N-methyl-D-aspartate 3A | up |
| A_32_P162183 | SEQ ID NO: 338 | C2 | NM_000063 | complement component 2 | up |
| A_23_P30913 | SEQ ID NO: 388 | HLA-DPA1 | NM_033554 | major histocompatibility complex, class II, DP alpha 1 | up |
| A_23_P211445 | SEQ ID NO: 240 | LIMK2 | NM_016733 | LIM domain kinase 2 | up |
| A_23_P207905 | SEQ ID NO: 389 | SECTM1 | NM_003004 | secreted and transmembrane 1 | up |
| A_23_P128050 | SEQ ID NO: 390 | BCL2L14 | NM_030766 | BCL2-like 14 (apoptosis facilitator) | up |
| A_23_P41765 | SEQ ID NO: 261 | IRF1 | NM_002198 | interferon regulatory factor 1 | up |
| A_24_P245815 | SEQ ID NO: 306 | ASPHD2 | AK097157 | aspartate beta-hydroxylase domain containing 2 | up |
| A_23_P86682 | SEQ ID NO: 391 | FER1L3 | NM_013451 | fer-1-like 3, myoferlin (C. elegans) | up |
| A_23_P58390 | SEQ ID NO: 392 | C4ORF32 | NM_152400 | chromosome 4 open reading frame 32 | up |
| A_23_P56630 | SEQ ID NO: 89 | STAT1 | NM_007315 | signal transducer and activator of transcription 1, 91 kDa | up |
| A_23_P25354 | SEQ ID NO: 393 | P2RX7 | NM_002562 | purinergic receptor P2X, ligand-gated ion channel, 7 | up |
| A_23_P358709 | SEQ ID NO: 394 | AHRR | NM_020731 | aryl-hydrocarbon receptor repressor | down |
| A_23_P207003 | SEQ ID NO: 395 | 40790 | NM_004574 | septin 4 | up |
| A_24_P170136 | SEQ ID NO: 396 | A_24_P170136 | ENST00000383097 | Low quality annotation—similar to HLA class II histocompatibility antigen, DP alpha chain precursor (HLA-SB alpha chain) (MHC class II DP3-alpha) (DP(W3)) (DP(W4)) (LOC642043), mRNA [Source: RefSeq_dna; Acc: XR_018078] [ENST00000383097] | up |
| A_23_P144959 | SEQ ID NO: 397 | CSPG2 | NM_004385 | chondroitin sulfate proteoglycan 2 (versican) | down |
| A_23_P163079 | SEQ ID NO: 225 | GCH1 | NM_000161 | GTP cyclohydrolase 1 (dopa-responsive dystonia) | up |
| A_23_P134176 | SEQ ID NO: 398 | SOD2 | NM_001024465 | superoxide dismutase 2, mitochondrial | up |
| A_24_P852756 | SEQ ID NO: 399 | HLA-DQA2 | NM_020056 | major histocompatibility complex, class II, DQ alpha 2 | up |
| A_24_P165423 | SEQ ID NO: 400 | RBP7 | NM_052960 | retinol binding protein 7, cellular | down |
| A_32_P9543 | SEQ ID NO: 348 | APOBEC3A | NM_145699 | apolipoprotein B mRNA editing enzyme, catalytic polypeptide-like 3A | up |
| A_32_P15169 | SEQ ID NO: 336 | A_32_P15169 | A_32_P15169 | Unknown | up |
| A_24_P7040 | SEQ ID NO: 401 | LOC123862 | XR_017225 | similar to Interferon-induced transmembrane protein 3 (Interferon-inducible protein 1-8U) | up |
| A_24_P378019 | SEQ ID NO: 402 | IRF7 | NM_004031 | interferon regulatory factor 7 | up |
| A_23_P59005 | SEQ ID NO: 113 | TAP1 | NM_000593 | transporter 1, ATP-binding cassette, sub-family B (MDR/TAP) | up |
| A_23_P331928 | SEQ ID NO: 403 | CD109 | NM_133493 | CD109 molecule | down |
| A_23_P218928 | SEQ ID NO: 243 | C4ORF18 | NM_016613 | chromosome 4 open reading frame 18 | down |
| A_23_P8513 | SEQ ID NO: 290 | SNX10 | NM_013322 | sorting nexin 10 | up |
| A_24_P54863 | SEQ ID NO: 142 | C4ORF32 | NM_152400 | chromosome 4 open reading frame 32 | up |
| A_23_P17837 | SEQ ID NO: 231 | APOL1 | NM_145343 | apolipoprotein L, 1 | up |
| A_23_P65427 | SEQ ID NO: 277 | PSME2 | NM_002818 | proteasome (prosome, macropain) activator subunit 2 (PA28 beta) | up |
| A_32_P30004 | SEQ ID NO: 342 | A_32_P30004 | AF086044 | Low quality annotation—Homo sapiens full length insert cDNA clone YX74D05. [AF086044] | up |
| A_23_P421423 | SEQ ID NO: 263 | TNFAIP2 | NM_006291 | tumor necrosis factor, alpha-induced protein 2 | up |
| A_23_P14174 | SEQ ID NO: 213 | TNFSF13B | NM_006573 | tumor necrosis factor (ligand) superfamily, member 13b | up |
| A_23_P29237 | SEQ ID NO: 404 | APOL3 | NM_145641 | apolipoprotein L, 3 | up |
| A_23_P64721 | SEQ ID NO: 276 | GPR109B | NM_006018 | G protein-coupled receptor 109B | up |
| A_23_P166633 | SEQ ID NO: 405 | ITGB5 | NM_002213 | integrin, beta 5 | down |
| A_24_P98109 | SEQ ID NO: 334 | SNX10 | NM_013322 | sorting nexin 10 | up |
| A_24_P243528 | SEQ ID NO: 406 | HLA-DPA1 | NM_033554 | major histocompatibility complex, class II, DP alpha 1 | up |
| A_23_P83098 | SEQ ID NO: 289 | ALDH1A1 | NM_000689 | aldehyde dehydrogenase 1 family, member A1 | up |
| A_23_P166797 | SEQ ID NO: 228 | RTP4 | NM_022147 | receptor (chemosensory) transporter protein 4 | up |

TABLE 1-continued

Genes whose expression is modulated by IFN-γ

| AGILENT ® Probe Name | Sequence Listing number of AGILENT ® Probe Sequence | Symbol of Gene | NCBI Accession Number of Gene Sequence | Gene Name | Direction of modulation by IFN-γ |
|---|---|---|---|---|---|
| A_23_P214821 | SEQ ID NO: 407 | EDN1 | NM_001955 | endothelin 1 | up |
| A_23_P123608 | SEQ ID NO: 107 | JAK2 | NM_004972 | Janus kinase 2 (a protein tyrosine kinase) | up |
| A_23_P11543 | SEQ ID NO: 408 | FUCA1 | NM_000147 | fucosidase, alpha-L-1, tissue | down |
| A_23_P259901 | SEQ ID NO: 409 | TKTL1 | NM_012253 | transketolase-like 1 | down |
| A_23_P145874 | SEQ ID NO: 215 | SAMD9L | NM_152703 | sterile alpha motif domain containing 9-like | up |
| A_23_P217269 | SEQ ID NO: 410 | VSIG4 | NM_007268 | V-set and immunoglobulin domain containing 4 | down |
| A_23_P33384 | SEQ ID NO: 411 | CIITA | NM_000246 | class II, major histocompatibility complex, transactivator | up |
| A_23_P85783 | SEQ ID NO: 412 | PHGDH | NM_006623 | phosphoglycerate dehydrogenase | up |
| A_32_P166272 | SEQ ID NO: 96 | A_32_P166272 | THC2650457 | Low quality annotation—ALU6_HUMAN (P39193) Alu subfamily SP sequence contamination warning entry, partial (12%) [THC2650457] | up |
| A_23_P150768 | SEQ ID NO: 413 | SLCO2B1 | NM_007256 | solute carrier organic anion transporter family, member 2B1 | down |
| A_24_P319113 | SEQ ID NO: 414 | P2RX7 | NM_002562 | purinergic receptor P2X, ligand-gated ion channel, 7 | up |
| A_23_P206212 | SEQ ID NO: 415 | THBS1 | NM_003246 | thrombospondin 1 | down |
| A_24_P239731 | SEQ ID NO: 416 | B4GALT5 | NM_004776 | UDP-Gal: betaGlcNAc beta 1,4-galactosyltransferase, polypeptide 5 | up |
| A_24_P98210 | SEQ ID NO: 335 | TFEC | NM_012252 | transcription factor EC | up |
| A_32_P87697 | SEQ ID NO: 417 | HLA-DRA | NM_019111 | major histocompatibility complex, class II, DR alpha | up |
| A_23_P417383 | SEQ ID NO: 418 | SASP | NM_152792 | skin aspartic protease | up |
| A_23_P45099 | SEQ ID NO: 419 | HLA-DRB5 | NM_002125 | major histocompatibility complex, class II, DR beta 5 | up |
| A_23_P3014 | SEQ ID NO: 420 | RNASE6 | NM_005615 | ribonuclease, RNase A family, k6 | down |
| A_24_P868905 | SEQ ID NO: 421 | LOC391020 | XR_018907 | similar to Interferon-induced transmembrane protein 3 (Interferon-inducible protein 1-8U) | up |
| A_24_P557479 | SEQ ID NO: 422 | BIRC4BP | NM_017523 | XIAP associated factor-1 | up |
| A_24_P196827 | SEQ ID NO: 423 | HLA-DQA1 | NM_002122 | major histocompatibility complex, class II, DQ alpha 1 | up |
| A_24_P365469 | SEQ ID NO: 424 | B4GALT5 | NM_004776 | UDP-Gal: betaGlcNAc beta 1,4-galactosyltransferase, polypeptide 5 | up |
| A_23_P72737 | SEQ ID NO: 283 | IFITM1 | NM_003641 | interferon induced transmembrane protein 1 (9-27) | up |
| A_23_P8108 | SEQ ID NO: 425 | HLA-DQB1 | NM_002123 | major histocompatibility complex, class II, DQ beta 1 | up |
| A_24_P322353 | SEQ ID NO: 91 | PSTPIP2 | NM_024430 | proline-serine-threonine phosphatase interacting protein 2 | up |
| A_23_P209995 | SEQ ID NO: 426 | IL1RN | NM_173842 | interleukin 1 receptor antagonist | up |
| A_23_P23074 | SEQ ID NO: 427 | IFI44 | NM_006417 | interferon-induced protein 44 | up |
| A_23_P73837 | SEQ ID NO: 428 | TLR8 | NM_016610 | toll-like receptor 8 | up |
| A_23_P160720 | SEQ ID NO: 224 | SNFT | NM_018664 | Jun dimerization protein p21SNFT | up |
| A_32_P184394 | SEQ ID NO: 339 | TFEC | NM_012252 | transcription factor EC | up |
| A_23_P87545 | SEQ ID NO: 429 | IFITM3 | NM_021034 | interferon induced transmembrane protein 3 (1-8U) | up |
| A_23_P48414 | SEQ ID NO: 430 | CCNA1 | NM_003914 | cyclin A1 | up |
| A_23_P258769 | SEQ ID NO: 431 | HLA-DPB1 | NM_002121 | major histocompatibility complex, class II, DP beta 1 | up |
| A_23_P96556 | SEQ ID NO: 94 | GK | NM_203391 | glycerol kinase | up |
| A_23_P63209 | SEQ ID NO: 432 | HSD11B1 | NM_181755 | hydroxysteroid (11-beta) dehydrogenase 1 | up |
| A_23_P31006 | SEQ ID NO: 433 | HLA-DRB5 | NM_002125 | major histocompatibility complex, class II, DR beta 5 | up |
| A_23_P120316 | SEQ ID NO: 434 | MTHFD2 | NM_001040409 | methylenetetrahydrofolate dehydrogenase (NADP+ dependent) 2, methenyltetrahydrofolate cyclohydrolase | up |
| A_23_P63896 | SEQ ID NO: 92 | FAS | NM_000043 | Fas (TNF receptor superfamily, member 6) | up |
| A_24_P845223 | SEQ ID NO: 435 | A_24_P845223 | M27126 | Low quality annotation—Human lymphocyte antigen (DRw8) mRNA. [M27126] | up |
| A_23_P81898 | SEQ ID NO: 288 | UBD | NM_006398 | ubiquitin D | up |
| A_23_P153320 | SEQ ID NO: 217 | ICAM1 | NM_000201 | intercellular adhesion molecule 1 (CD54), human rhinovirus receptor | up |
| A_23_P213102 | SEQ ID NO: 436 | PALLD | NM_016081 | palladin, cytoskeletal associated protein | down |
| A_23_P819 | SEQ ID NO: 437 | ISG15 | NM_005101 | ISG15 ubiquitin-like modifier | up |
| A_23_P202029 | SEQ ID NO: 438 | SPFH1 | NM_006459 | SPFH domain family, member 1 | up |
| A_23_P170719 | SEQ ID NO: 439 | A_23_P170719 | A_23_P170719 | Unknown | down |
| A_24_P367576 | SEQ ID NO: 440 | RCBTB2 | AK125170 | regulator of chromosome condensation (RCC1) and BTB (POZ) domain containing protein 2 | down |

TABLE 1-continued

Genes whose expression is modulated by IFN-γ

| AGILENT ® Probe Name | Sequence Listing number of AGILENT ® Probe Sequence | Symbol of Gene | NCBI Accession Number of Gene Sequence | Gene Name | Direction of modulation by IFN-γ |
|---|---|---|---|---|---|
| A_23_P69109 | SEQ ID NO: 281 | PLSCR1 | NM_021105 | phospholipid scramblase 1 | up |
| A_23_P19510 | SEQ ID NO: 441 | HLA-DQB2 | NM_182549 | major histocompatibility complex, class II, DQ beta 2 | up |
| A_24_P100387 | SEQ ID NO: 85 | GK | NM_203391 | glycerol kinase | up |
| A_23_P4283 | SEQ ID NO: 442 | BIRC4BP | NM_017523 | XIAP associated factor-1 | up |
| A_24_P288836 | SEQ ID NO: 443 | HLA-DPB2 | NR_001435 | major histocompatibility complex, class II, DP beta 2 (pseudogene) | up |
| A_24_P66027 | SEQ ID NO: 324 | APOBEC3B | NM_004900 | apolipoprotein B mRNA editing enzyme, catalytic polypeptide-like 3B | up |
| A_23_P157136 | SEQ ID NO: 444 | SCIN | NM_033128 | scinderin | up |
| A_24_P274270 | SEQ ID NO: 88 | STAT1 | NM_139266 | signal transducer and activator of transcription 1, 91 kDa | up |
| A_23_P306148 | SEQ ID NO: 445 | PML | NM_002675 | promyelocytic leukemia | up |
| A_24_P370472 | SEQ ID NO: 446 | HLA-DRB4 | NM_021983 | major histocompatibility complex, class II, DR beta 4 | up |
| A_23_P218549 | SEQ ID NO: 447 | EMR3 | NM_032571 | egf-like module containing, mucin-like, hormone receptor-like 3 | down |
| A_24_P246626 | SEQ ID NO: 448 | A_24_P246626 | ENST00000308384 | Low quality annotation—similar to HLA class II histocompatibility antigen, DP alpha chain precursor (HLA-SB alpha chain) (MHC class II DP3-alpha) (DP(W3)) (DP(W4)) (LOC642074), mRNA [Source: RefSeq_dna; Acc: XR_018081] [ENST00000308384] | up |
| A_23_P358944 | SEQ ID NO: 449 | PML | NM_033244 | promyelocytic leukemia | up |
| A_23_P69383 | SEQ ID NO: 101 | PARP9 | NM_031458 | poly (ADP-ribose) polymerase family, member 9 | up |
| A_24_P343929 | SEQ ID NO: 450 | OAS2 | NM_016817 | 2'-5'-oligoadenylate synthetase 2, 69/71 kDa | up |
| A_24_P354800 | SEQ ID NO: 451 | HLA-DOA | NM_002119 | major histocompatibility complex, class II, DO alpha | up |
| A_32_P209960 | SEQ ID NO: 452 | CIITA | NM_000246 | class II, major histocompatibility complex, transactivator | up |
| A_24_P118892 | SEQ ID NO: 453 | IRF7 | NM_004029 | interferon regulatory factor 7 | up |
| A_24_P222655 | SEQ ID NO: 305 | C1QA | NM_015991 | complement component 1, q subcomponent, A chain | up |
| A_24_P119745 | SEQ ID NO: 454 | FN1 | NM_212482 | fibronectin 1 | down |
| A_23_P34835 | SEQ ID NO: 455 | LMNA | NM_005572 | lamin NC | down |
| A_24_P578437 | SEQ ID NO: 456 | A_24_P578437 | BE926212 | Low quality annotation—BE926212 RCS-BN0193-310800-034-A04 BN0193 Homo sapiens cDNA, mRNA sequence [BE926212] | up |
| A_23_P47955 | SEQ ID NO: 457 | OAS3 | NM_006187 | 2'-5'-oligoadenylate synthetase 3, 100 kDa | up |
| A_24_P169013 | SEQ ID NO: 458 | HLA-DRB6 | NR_001298 | major histocompatibility complex, class II, DR beta 6 (pseudogene) | up |
| A_23_P76450 | SEQ ID NO: 459 | PHLDA1 | NM_007350 | pleckstrin homology-like domain, family A, member 1 | down |
| A_23_P328740 | SEQ ID NO: 460 | LINCR | BC012317 | likely ortholog of mouse lung-inducible Neutralized-related C3HC4 RING domain protein | up |
| A_23_P380857 | SEQ ID NO: 259 | APOL4 | NM_030643 | apolipoprotein L, 4 | up |
| A_24_P299318 | SEQ ID NO: 461 | FAM101B | NM_182705 | family with sequence similarity 101, member B | down |
| A_32_P13337 | SEQ ID NO: 462 | A_32_P13337 | THC2645080 | Unknown | down |
| A_23_P4773 | SEQ ID NO: 463 | LILRB5 | NM_006840 | leukocyte immunoglobulin-like receptor, subfamily B (with TM and ITIM domains), member 5 | down |
| A_32_P108254 | SEQ ID NO: 464 | FAM20A | NM_017565 | family with sequence similarity 20, member A | up |
| A_24_P343233 | SEQ ID NO: 465 | HLA-DRB1 | NM_002124 | major histocompatibility complex, class II, DR beta 1 | up |
| A_32_P351968 | SEQ ID NO: 466 | HLA-DMB | NM_002118 | major histocompatibility complex, class II, DM beta | up |
| A_23_P145336 | SEQ ID NO: 467 | HLA-DRB3 | BC106057 | major histocompatibility complex, class II, DR beta 3 | up |
| A_24_P325520 | SEQ ID NO: 468 | SORT1 | NM_002959 | sortilin 1 | up |
| A_32_P75264 | SEQ ID NO: 469 | TMEM26 | NM_178505 | transmembrane protein 26 | down |
| A_23_P39364 | SEQ ID NO: 470 | HOMER3 | NM_004838 | homer homolog 3 (Drosophila) | down |
| A_24_P402222 | SEQ ID NO: 471 | HLA-DRB3 | NM_022555 | major histocompatibility complex, class II, DR beta 3 | up |

TABLE 1-continued

Genes whose expression is modulated by IFN-γ

| AGILENT ® Probe Name | Sequence Listing number of AGILENT ® Probe Sequence | Symbol of Gene | NCBI Accession Number of Gene Sequence | Gene Name | Direction of modulation by IFN-γ |
|---|---|---|---|---|---|
| A_24_P353300 | SEQ ID NO: 472 | LIMK2 | NM_001031801 | LIM domain kinase 2 | up |
| A_32_P167592 | SEQ ID NO: 473 | A_32_P167592 | ENST00000339867 | Low quality annotation—similar to Interferon-induced transmembrane protein 3 (Interferon-inducible protein 1-8U) (LOC650205), mRNA [Source: RefSeq_dna; Acc: XR_018421] [ENST00000339867] | up |
| A_24_P100382 | SEQ ID NO: 474 | GK | NM_203391 | glycerol kinase | up |
| A_23_P255444 | SEQ ID NO: 100 | DAPP1 | NM_014395 | dual adaptor of phosphotyrosine and 3-phosphoinositides | up |
| A_23_P359245 | SEQ ID NO: 475 | MET | NM_000245 | met proto-oncogene (hepatocyte growth factor receptor) | down |
| A_32_P78121 | SEQ ID NO: 476 | A_32_P78121 | CD743044 | Low quality annotation—CD743044 UI-H-FT1-bjx-e-03-0-UI.s1 NCI_CGAP_FT1 *Homo sapiens* cDNA clone UI-H-FT1-bjx-e-03-0-UI 3', mRNA sequence [CD743044] | up |
| A_23_P252106 | SEQ ID NO: 166 | RIPK2 | NM_003821 | receptor-interacting serine-threonine kinase 2 | up |
| A_23_P120883 | SEQ ID NO: 477 | HMOX1 | NM_002133 | heme oxygenase (decycling) 1 | down |
| A_23_P97064 | SEQ ID NO: 296 | FBXO6 | NM_018438 | F-box protein 6 | up |
| A_24_P416997 | SEQ ID NO: 478 | APOL3 | NM_145641 | apolipoprotein L, 3 | up |
| A_23_P68155 | SEQ ID NO: 279 | IFIH1 | NM_022168 | interferon induced with helicase C domain 1 | up |
| A_23_P149476 | SEQ ID NO: 216 | EFCAB2 | NM_032328 | EF-hand calcium binding domain 2 | up |
| A_24_P172481 | SEQ ID NO: 302 | TRIM22 | NM_006074 | tripartite motif-containing 22 | up |
| A_23_P51487 | SEQ ID NO: 93 | GBP3 | NM_018284 | guanylate binding protein 3 | up |
| A_23_P30900 | SEQ ID NO: 479 | HLA-DQA1 | BC008585 | major histocompatibility complex, class II, DQ alpha 1 | up |
| A_24_P323148 | SEQ ID NO: 313 | LYPD5 | NM_182573 | LY6/PLAUR domain containing 5 | up |
| A_24_P928052 | SEQ ID NO: 327 | NRP1 | NM_003873 | neuropilin 1 | down |
| A_24_P166443 | SEQ ID NO: 480 | HLA-DPB1 | NM_002121 | major histocompatibility complex, class II, DP beta 1 | up |
| A_24_P16124 | SEQ ID NO: 481 | IFITM4P | NR_001590 | interferon induced transmembrane protein 4 pseudogene | up |
| A_23_P136683 | SEQ ID NO: 482 | HLA-DQB1 | M20432 | major histocompatibility complex, class II, DQ beta 1 | up |
| A_24_P278126 | SEQ ID NO: 310 | NBN | NM_001024688 | nibrin | up |
| A_23_P203498 | SEQ ID NO: 233 | TRIM22 | NM_006074 | tripartite motif-containing 22 | up |
| A_23_P125278 | SEQ ID NO: 202 | CXCL11 | NM_005409 | chemokine (C-X-C motif) ligand 11 | up |
| A_23_P79518 | SEQ ID NO: 287 | IL1B | NM_000576 | interleukin 1, beta | down |
| A_24_P923271 | SEQ ID NO: 483 | A_24_P923271 | M15073 | Low quality annotation—Human MHC class II HLA-DR-beta-1 chain mRNA (DR4, Dw14), 3' end, clone BIN40c30. [M15073] | up |
| A_23_P209678 | SEQ ID NO: 237 | PLEK | NM_002664 | pleckstrin | up |
| A_23_P258493 | SEQ ID NO: 247 | LMNB1 | NM_005573 | lamin B1 | up |
| A_23_P146943 | SEQ ID NO: 484 | ATP1B1 | NM_001677 | ATPase, Na+/K+ transporting, beta 1 polypeptide | up |
| A_23_P208119 | SEQ ID NO: 84 | PSTPIP2 | NM_024430 | proline-serine-threonine phosphatase interacting protein 2 | up |
| A_24_P915692 | SEQ ID NO: 485 | PHLDA1 | NM_007350 | pleckstrin homology-like domain, family A, member 1 | down |
| A_23_P259561 | SEQ ID NO: 486 | A_23_P259561 | THC2632039 | Low quality annotation—Q8SPE4_9PRIM (Q8SPE4) Major histocompatibility complex (Fragment), partial (85%) [THC2632039] | up |
| A_24_P361896 | SEQ ID NO: 487 | MT2A | NM_005953 | metallothionein 2A | up |
| A_23_P106844 | SEQ ID NO: 488 | MT2A | NM_005953 | metallothionein 2A | up |
| A_24_P370702 | SEQ ID NO: 126 | GBP3 | NM_018284 | guanylate binding protein 3 | up |
| A_23_P132388 | SEQ ID NO: 205 | SCO2 | NM_005138 | SCO cytochrome oxidase deficient homolog 2 (yeast) | up |
| A_23_P25155 | SEQ ID NO: 489 | GPR84 | NM_020370 | G protein-coupled receptor 84 | up |
| A_23_P64343 | SEQ ID NO: 275 | TIMM10 | NM_012456 | translocase of inner mitochondrial membrane 10 homolog (yeast) | up |
| A_24_P97405 | SEQ ID NO: 490 | CCRL2 | NM_003965 | chemokine (C-C motif) receptor-like 2 | up |
| A_24_P190472 | SEQ ID NO: 491 | SLPI | NM_003064 | secretory leukocyte peptidase inhibitor | up |
| A_23_P207058 | SEQ ID NO: 492 | SOCS3 | NM_003955 | suppressor of cytokine signaling 3 | up |
| A_24_P52168 | SEQ ID NO: 493 | A_24_P52168 | A_24_P52168 | Unknown | up |
| A_23_P29953 | SEQ ID NO: 248 | IL15 | NM_172174 | interleukin 15 | up |
| A_32_P72351 | SEQ ID NO: 494 | A_32_P72351 | AK026140 | Low quality annotation—*Homo sapiens* cDNA: FLJ22487 fis, clone HRC10931. [AK026140] | down |
| A_23_P35912 | SEQ ID NO: 129 | CASP4 | NM_033306 | caspase 4, apoptosis-related cysteine peptidase | up |

TABLE 1-continued

Genes whose expression is modulated by IFN-γ

| AGILENT ® Probe Name | Sequence Listing number of AGILENT ® Probe Sequence | Symbol of Gene | NCBI Accession Number of Gene Sequence | Gene Name | Direction of modulation by IFN-γ |
|---|---|---|---|---|---|
| A_23_P252413 | SEQ ID NO: 495 | MT2A | ENST00000245185 | metallothionein 2A | up |
| A_32_P118013 | SEQ ID NO: 496 | A_32_P118013 | THC2657593 | Low quality annotation—ALU1_HUMAN (P39188) Alu subfamily J sequence contamination warning entry, partial (7%) [THC2657593] | up |
| A_23_P201587 | SEQ ID NO: 497 | SORT1 | NM_002959 | sortilin 1 | up |
| A_23_P347040 | SEQ ID NO: 255 | DTX3L | NM_138287 | deltex 3-like (Drosophila) | up |
| A_23_P47304 | SEQ ID NO: 267 | CASP5 | NM_004347 | caspase 5, apoptosis-related cysteine peptidase | up |
| A_23_P133916 | SEQ ID NO: 208 | C2 | NM_000063 | complement component 2 | up |
| A_23_P94412 | SEQ ID NO: 295 | PDCD1LG | NM_025239 | programmed cell death 1 ligand 2 2 | up |
| A_24_P662177 | SEQ ID NO: 498 | A_24_P662177 | THC2666469 | Unknown | up |
| A_23_P85693 | SEQ ID NO: 90 | GBP2 | NM_004120 | guanylate binding protein 2, interferon-inducible | up |
| A_24_P48014 | SEQ ID NO: 499 | SOCS1 | NM_003745 | suppressor of cytokine signaling 1 | up |
| A_32_P56249 | SEQ ID NO: 500 | A_32_P56249 | THC2670291 | Low quality annotation—UBP30_HUMAN (Q70CQ3) Ubiquitin carboxyl-terminal hydrolase 30 (Ubiquitin thioesterase 30) (Ubiquitin-specific-processing protease 30) (Deubiquitinating enzyme 30), partial (5%) [THC2670291] | up |
| A_32_P56759 | SEQ ID NO: 344 | PARP14 | NM_017554 | poly (ADP-ribose) polymerase family, member 14 | up |
| A_23_P154235 | SEQ ID NO: 102 | NMI | NM_004688 | N-myc (and STAT) interactor | up |
| A_24_P397817 | SEQ ID NO: 501 | LEP | NM_000230 | leptin (obesity homolog, mouse) | down |
| A_24_P62530 | SEQ ID NO: 502 | RHOU | NM_021205 | ras homolog gene family, member U | up |
| A_23_P156788 | SEQ ID NO: 222 | STX11 | NM_003764 | syntaxin 11 | up |
| A_24_P925314 | SEQ ID NO: 503 | GM2A | AK127910 | GM2 ganglioside activator | up |
| A_23_P64828 | SEQ ID NO: 504 | OAS1 | NM_002534 | 2',5'-oligoadenylate synthetase 1, 40/46 kDa | up |
| A_23_P128541 | SEQ ID NO: 505 | TRAFD1 | NM_006700 | TRAF-type zinc finger domain containing 1 | up |
| A_23_P42718 | SEQ ID NO: 506 | NFE2L3 | NM_004289 | nuclear factor (erythroid-derived 2)-like 3 | up |
| A_24_P89457 | SEQ ID NO: 507 | CDKN1A | NM_078467 | cyclin-dependent kinase inhibitor 1A (p21, Cip1) | up |
| A_23_P14754 | SEQ ID NO: 508 | HAPLN3 | NM_178232 | hyaluronan and proteoglycan link protein 3 | up |
| A_23_P103398 | SEQ ID NO: 509 | PSEN2 | NM_000447 | presenilin 2 (Alzheimer disease 4) | up |
| A_23_P75741 | SEQ ID NO: 286 | UBE2L6 | NM_198183 | ubiquitin-conjugating enzyme E2L 6 | up |
| A_23_P101434 | SEQ ID NO: 510 | NLRP12 | NM_033297 | NLR family, pyrin domain containing 12 | down |
| A_23_P141362 | SEQ ID NO: 511 | FZD2 | NM_001466 | frizzled homolog 2 (Drosophila) | up |
| A_24_P287043 | SEQ ID NO: 512 | IFITM2 | NM_006435 | interferon induced transmembrane protein 2 (1-8D) | up |
| A_24_P207139 | SEQ ID NO: 513 | PML | NM_033238 | promyelocytic leukemia | up |
| A_23_P121716 | SEQ ID NO: 201 | ANXA3 | NM_005139 | annexin A3 | up |
| A_23_P120002 | SEQ ID NO: 514 | SP110 | NM_004510 | SP110 nuclear body protein | up |
| A_23_P111000 | SEQ ID NO: 119 | PSMB9 | NM_002800 | proteasome (prosome, macropain) subunit, beta type, 9 (large multifunctional peptidase 2) | up |
| A_32_P356316 | SEQ ID NO: 515 | HLA-DOA | NM_002119 | major histocompatibility complex, class II, DO alpha | up |
| A_23_P69310 | SEQ ID NO: 282 | CCRL2 | NM_003965 | chemokine (C-C motif) receptor-like 2 | up |
| A_24_P254933 | SEQ ID NO: 516 | A_24_P254933 | ENST00000270031 | Low quality annotation—interferon induced transmembrane protein 3 (1-8U) (IFITM3), mRNA [Source: RefSeq_dna; Acc: NM_021034] [ENST00000270031] | up |
| A_23_P85240 | SEQ ID NO: 517 | TLR7 | NM_016562 | toll-like receptor 7 | up |
| A_24_P36898 | SEQ ID NO: 86 | GBP2 | ENST00000294663 | guanylate binding protein 2, interferon-inducible | up |
| A_23_P210811 | SEQ ID NO: 518 | CD93 | NM_012072 | CD93 molecule | down |
| A_23_P133142 | SEQ ID NO: 207 | ALPK1 | NM_025144 | alpha-kinase 1 | up |
| A_23_P210465 | SEQ ID NO: 519 | PI3 | NM_002638 | peptidase inhibitor 3, skin-derived (SKALP) | up |
| A_23_P24004 | SEQ ID NO: 244 | IFIT2 | NM_001547 | interferon-induced protein with tetratricopeptide repeats 2 | up |
| A_24_P48898 | SEQ ID NO: 321 | APOL2 | NM_145637 | apolipoprotein L, 2 | up |
| A_23_P82449 | SEQ ID NO: 520 | DFNA5 | NM_004403 | deafness, autosomal dominant 5 | down |
| A_23_P128447 | SEQ ID NO: 203 | LRRK2 | NM_198578 | leucine-rich repeat kinase 2 | up |
| A_23_P416894 | SEQ ID NO: 521 | LOC54103 | AK126364 | hypothetical protein LOC54103 | up |
| A_23_P57036 | SEQ ID NO: 522 | CD40 | NM_001250 | CD40 molecule, TNF receptor superfamily member 5 | up |
| A_24_P403959 | SEQ ID NO: 523 | RNASE1 | NM_198232 | ribonuclease, RNase A family, 1 (pancreatic) | down |
| A_23_P110196 | SEQ ID NO: 524 | HERC5 | NM_016323 | hect domain and RLD 5 | up |
| A_23_P1962 | SEQ ID NO: 525 | RARRES3 | NM_004585 | retinoic acid receptor responder (tazarotene induced) 3 | up |

TABLE 1-continued

Genes whose expression is modulated by IFN-γ

| AGILENT® Probe Name | Sequence Listing number of AGILENT® Probe Sequence | Symbol of Gene | NCBI Accession Number of Gene Sequence | Gene Name | Direction of modulation by IFN-γ |
|---|---|---|---|---|---|
| A_23_P500614 | SEQ ID NO: 526 | TNFRSF8 | NM_001243 | tumor necrosis factor receptor superfamily, member 8 | down |
| A_23_P11201 | SEQ ID NO: 527 | GPR34 | NM_001033513 | G protein-coupled receptor 34 | down |
| A_23_P217258 | SEQ ID NO: 528 | CYBB | NM_000397 | cytochrome b-245, beta polypeptide (chronic granulomatous disease) | up |
| A_32_P71710 | SEQ ID NO: 529 | A_32_P71710 | AI094165 | Low quality annotation —AI094165 qa29a01.s1 Soares_NhHMPu_S1 Homo sapiens cDNA clone IMAGE: 1688136 3' similar to gb: X64532_rna1 INTERLEUKIN-1 RECEPTOR ANTAGONIST PROTEIN PRECURSOR (HUMAN);, mRNA sequence [AI094165] | up |
| A_24_P935652 | SEQ ID NO: 530 | NUB1 | CR606629 | negative regulator of ubiquitin-like proteins 1 | up |
| A_24_P851254 | SEQ ID NO: 531 | A_24_P851254 | AK026267 | Low quality annotation—Homo sapiens cDNA: FLJ22614 fis, clone HSI05089. [AK026267] | down |
| A_23_P116414 | SEQ ID NO: 532 | HRASLS3 | NM_007069 | HRAS-like suppressor 3 | up |
| A_23_P59210 | SEQ ID NO: 533 | CDKN1A | NM_000389 | cyclin-dependent kinase inhibitor 1A (p21, Cip1) | up |
| A_23_P42969 | SEQ ID NO: 266 | FGL2 | NM_006682 | fibrinogen-like 2 | up |
| A_24_P403417 | SEQ ID NO: 534 | PTGES | NM_004878 | prostaglandin E synthase | down |
| A_23_P17655 | SEQ ID NO: 230 | KCNJ15 | NM_170736 | potassium inwardly-rectifying channel, subfamily J, member 15 | up |
| A_23_P91230 | SEQ ID NO: 535 | SLPI | NM_003064 | secretory leukocyte peptidase inhibitor | up |
| A_23_P152234 | SEQ ID NO: 536 | CMTM2 | NM_144673 | CKLF-like MARVEL transmembrane domain containing 2 | down |
| A_23_P62932 | SEQ ID NO: 537 | ATP1B1 | NM_001677 | ATPase, Na+/K+ transporting, beta 1 polypeptide | up |
| A_24_P161018 | SEQ ID NO: 299 | PARP14 | NM_017554 | poly (ADP-ribose) polymerase family, member 14 | up |
| A_23_P42306 | SEQ ID NO: 538 | HLA-DMA | NM_006120 | major histocompatibility complex, class II, DM alpha | up |
| A_23_P144872 | SEQ ID NO: 539 | GM2A | NM_000405 | GM2 ganglioside activator | up |
| A_32_P115555 | SEQ ID NO: 540 | A_32_P115555 | AA991488 | Low quality annotation—os91h09.s1 NCI_CGAP_GC3 Homo sapiens cDNA clone IMAGE: 1612769 3' similar to gb: J00194 HLA CLASS II HISTOCOMPATIBILITY ANTIGEN, DR ALPHA CHAIN (HUMAN);, mRNA sequence [M991488] | up |
| A_23_P91640 | SEQ ID NO: 541 | ASPHD2 | NM_020437 | aspartate beta-hydroxylase domain containing 2 | up |
| A_23_P140807 | SEQ ID NO: 211 | PSMB10 | NM_002801 | proteasome (prosome, macropain) subunit, beta type, 10 | up |
| A_23_P378588 | SEQ ID NO: 542 | ARL5B | NM_178815 | ADP-ribosylation factor-like 5B | up |
| A_23_P104493 | SEQ ID NO: 543 | PAPSS2 | NM_001015880 | 3'-phosphoadenosine 5'-phosphosulfate synthase 2 | down |
| A_23_P87709 | SEQ ID NO: 293 | FLJ22662 | NM_024829 | hypothetical protein FLJ22662 | up |
| A_23_P111804 | SEQ ID NO: 544 | PARP12 | NM_022750 | poly (ADP-ribose) polymerase family, member 12 | up |
| A_23_P129486 | SEQ ID NO: 545 | SEPX1 | NM_016332 | selenoprotein X, 1 | up |
| A_23_P9232 | SEQ ID NO: 294 | GCNT1 | NM_001490 | glucosaminyl (N-acetyl) transferase 1, core 2 (beta-1,6-N-acetylglucosaminyltransferase) | up |
| A_24_P15502 | SEQ ID NO: 546 | A_24_P15502 | A_24_P15502 | Unknown | up |
| A_23_P55998 | SEQ ID NO: 547 | SLC1A5 | NM_005628 | solute carrier family 1 (neutral amino acid transporter), member 5 | up |
| A_23_P15414 | SEQ ID NO: 218 | SCARF1 | NM_145351 | scavenger receptor class F, member 1 | up |
| A_23_P100711 | SEQ ID NO: 548 | PMP22 | NM_000304 | peripheral myelin protein 22 | down |
| A_24_P11142 | SEQ ID NO: 549 | KIAA0040 | NM_014656 | KIAA0040 | up |
| A_23_P3221 | SEQ ID NO: 250 | SQRDL | NM_021199 | sulfide quinone reductase-like (yeast) | up |
| A_23_P39237 | SEQ ID NO: 550 | ZFP36 | NM_003407 | zinc finger protein 36, C3H type, homolog (mouse) | up |
| A_23_P353717 | SEQ ID NO: 551 | C16ORF75 | NM_152308 | chromosome 16 open reading frame 75 | up |
| A_24_P382319 | SEQ ID NO: 316 | CEACAM1 | NM_001712 | carcinoembryonic antigen-related cell adhesion molecule 1 (biliary glycoprotein) | up |
| A_24_P141214 | SEQ ID NO: 552 | STOM | NM_198194 | stomatin | up |
| A_23_P252062 | SEQ ID NO: 553 | PPARG | NM_138711 | peroxisome proliferator-activated receptor gamma | down |
| A_24_P53051 | SEQ ID NO: 128 | LACTB | NM_171846 | lactamase, beta | up |
| A_32_P108277 | SEQ ID NO: 554 | A_32_P108277 | BQ130147 | Low quality annotation—BQ130147 ij85d08.x1 Human insulinoma Homo sapiens cDNA clone IMAGE: 5778111 3', mRNA sequence [BQ130147] | up |

TABLE 1-continued

Genes whose expression is modulated by IFN-γ

| AGILENT ® Probe Name | Sequence Listing number of AGILENT ® Probe Sequence | Symbol of Gene | NCBI Accession Number of Gene Sequence | Gene Name | Direction of modulation by IFN-γ |
|---|---|---|---|---|---|
| A_32_P95082 | SEQ ID NO: 347 | C9ORF39 | NM_017738 | chromosome 9 open reading frame 39 | up |
| A_23_P211488 | SEQ ID NO: 241 | APOL2 | NM_145637 | apolipoprotein L, 2 | up |
| A_23_P56746 | SEQ ID NO: 271 | FAP | NM_004460 | fibroblast activation protein, alpha | up |
| A_24_P935819 | SEQ ID NO: 328 | SOD2 | BC016934 | superoxide dismutase 2, mitochondrial | up |
| A_23_P329870 | SEQ ID NO: 252 | RHBDF2 | NM_024599 | rhomboid 5 homolog 2 (Drosophila) | up |
| A_23_P4821 | SEQ ID NO: 268 | JUNB | NM_002229 | Jun B proto-oncogene | up |
| A_23_P95172 | SEQ ID NO: 555 | C17ORF27 | NM_020914 | chromosome 17 open reading frame 27 | up |
| A_23_P93442 | SEQ ID NO: 556 | SASH1 | NM_015278 | SAM and SH3 domain containing 1 | up |
| A_23_P112260 | SEQ ID NO: 200 | GNG10 | NM_001017998 | guanine nucleotide binding protein (G protein), gamma 10 | up |
| A_24_P260101 | SEQ ID NO: 557 | MME | NM_007289 | membrane metallo-endopeptidase (neutral endopeptidase, enkephalinase) | down |
| A_23_P20814 | SEQ ID NO: 235 | DDX58 | NM_014314 | DEAD (Asp-Glu-Ala-Asp) box polypeptide 58 (SEQ ID NO: 697) | up |
| A_24_P98047 | SEQ ID NO: 558 | SLC16A10 | NM_018593 | solute carrier family 16, member 10 (aromatic amino acid transporter) | down |
| A_23_P401106 | SEQ ID NO: 260 | PDE2A | NM_002599 | phosphodiesterase 2A, cGMP-stimulated | down |
| A_23_P142424 | SEQ ID NO: 214 | TMEM149 | NM_024660 | transmembrane protein 149 | up |
| A_23_P216225 | SEQ ID NO: 559 | EGR3 | NM_004430 | early growth response 3 | up |
| A_23_P17663 | SEQ ID NO: 560 | MX1 | NM_002462 | myxovirus (influenza virus) resistance 1, interferon-inducible protein p78 (mouse) | up |
| A_23_P26024 | SEQ ID NO: 561 | C15ORF48 | NM_032413 | chromosome 15 open reading frame 48 | up |
| A_23_P4286 | SEQ ID NO: 562 | BIRC4BP | NM_017523 | XIAP associated factor-1 | up |
| A_23_P364024 | SEQ ID NO: 563 | GLIPR1 | NM_006851 | GLI pathogenesis-related 1 (glioma) | down |
| A_23_P166408 | SEQ ID NO: 227 | OSM | NM_020530 | oncostatin M | up |
| A_23_P155049 | SEQ ID NO: 219 | APOL6 | NM_030641 | apolipoprotein L, 6 | up |
| A_23_P141021 | SEQ ID NO: 564 | AYTL1 | NM_017839 | acyltransferase like 1 | up |
| A_24_P47329 | SEQ ID NO: 319 | A_24_P47329 | BC063641 | Low quality annotation—Homo sapiens cDNA clone IMAGE: 4745832, partial cds. [BC063641] | up |
| A_23_P44836 | SEQ ID NO: 565 | NT5DC2 | NM_022908 | 5'-nucleotidase domain containing 2 | down |
| A_23_P68106 | SEQ ID NO: 566 | TMSB10 | NM_021103 | thymosin, beta 10 | up |
| A_23_P2793 | SEQ ID NO: 567 | ALOX5AP | NM_001629 | arachidonate 5-lipoxygenase-activating protein | down |
| A_24_P481844 | SEQ ID NO: 568 | HLA-DMB | BC035650 | major histocompatibility complex, class II, DM beta | up |
| A_23_P133133 | SEQ ID NO: 206 | ALPK1 | NM_025144 | alpha-kinase 1 | up |
| A_24_P315405 | SEQ ID NO: 569 | A_24_P315405 | A_24_P315405 | Unknown | up |
| A_23_P251480 | SEQ ID NO: 245 | NBN | NM_001024688 | nibrin | up |
| A_23_P402892 | SEQ ID NO: 164 | NLRC5 | NM_032206 | NLR family, CARD domain containing 5 | up |
| A_23_P427703 | SEQ ID NO: 570 | MT1L | X97261 | metallothionein 1L (pseudogene) | up |
| A_23_P112251 | SEQ ID NO: 199 | GNG10 | NM_001017998 | guanine nucleotide binding protein (G protein), gamma 10 | up |
| A_23_P34142 | SEQ ID NO: 571 | WBP5 | NM_016303 | WW domain binding protein 5 | down |
| A_23_P76823 | SEQ ID NO: 572 | ADSSL1 | NM_199165 | adenylosuccinate synthase like 1 | down |
| A_23_P161338 | SEQ ID NO: 573 | PPA1 | NM_021129 | pyrophosphatase (inorganic) 1 | up |
| A_32_P156746 | SEQ ID NO: 337 | A_32_P156746 | BE825944 | Low quality annotation—BE825944 CM2-EN0014-310500-207-g07 EN0014 Homo sapiens cDNA, mRNA sequence [BE825944] | up |
| A_24_P198598 | SEQ ID NO: 574 | PML | NM_002675 | promyelocytic leukemia | up |
| A_23_P137856 | SEQ ID NO: 575 | MUC1 | NM_002456 | mucin 1, cell surface associated | up |
| A_24_P940166 | SEQ ID NO: 576 | PAPSS2 | NM_001015880 | 3'-phosphoadenosine 5'-phosphosulfate synthase 2 | down |
| A_23_P103765 | SEQ ID NO: 577 | FCER1A | NM_002001 | Fc fragment of IgE, high affinity I, receptor for; alpha polypeptide | down |
| A_23_P26583 | SEQ ID NO: 158 | NLRC5 | NM_032206 | NLR family, CARD domain containing 5 | up |
| A_23_P259692 | SEQ ID NO: 578 | PSAT1 | NM_058179 | phosphoserine aminotransferase 1 | up |
| A_23_P111583 | SEQ ID NO: 579 | CD36 | NM_001001547 | CD36 molecule (thrombospondin receptor) | down |
| A_24_P943597 | SEQ ID NO: 580 | PHLDA1 | NM_007350 | pleckstrin homology-like domain, family A, member 1 | down |
| A_24_P49199 | SEQ ID NO: 581 | GLDN | NM_181789 | gliomedin | up |
| A_24_P941912 | SEQ ID NO: 331 | DTX3L | NM_138287 | deltex 3-like (Drosophila) | up |
| A_23_P142697 | SEQ ID NO: 582 | TTLL4 | NM_014640 | tubulin tyrosine ligase-like family, member 4 | down |
| A_23_P256445 | SEQ ID NO: 138 | VCPIP1 | NM_025054 | valosin containing protein (p97)/p47 complex interacting protein 1 | up |
| A_23_P129492 | SEQ ID NO: 204 | SEPX1 | NM_016332 | selenoprotein X, 1 | up |
| A_23_P78037 | SEQ ID NO: 583 | CCL7 | NM_006273 | chemokine (C-C motif) ligand 7 | down |
| A_23_P119789 | SEQ ID NO: 584 | FAM11B | NR_000034 | family with sequence similarity 11, member B | up |
| A_23_P168828 | SEQ ID NO: 229 | KLF10 | NM_005655 | Kruppel-like factor 10 | up |
| A_24_P273716 | SEQ ID NO: 585 | ZBTB24 | NM_014797 | zinc finger and BTB domain containing 24 | up |
| A_23_P137931 | SEQ ID NO: 586 | ADORA3 | NM_000677 | adenosine A3 receptor | down |
| A_23_P255263 | SEQ ID NO: 587 | STOM | NM_198194 | stomatin | up |
| A_24_P210406 | SEQ ID NO: 588 | KLF5 | NM_001730 | Kruppel-like factor 5 (intestinal) | up |

TABLE 1-continued

Genes whose expression is modulated by IFN-γ

| AGILENT ® Probe Name | Sequence Listing number of AGILENT ® Probe Sequence | Symbol of Gene | NCBI Accession Number of Gene Sequence | Gene Name | Direction of modulation by IFN-γ |
|---|---|---|---|---|---|
| A_32_P91773 | SEQ ID NO: 345 | A_32_P91773 | THC2544236 | Low quality annotation—ALU1_HUMAN (P39188) Alu subfamily J sequence contamination warning entry, partial (10%) [THC2530569] | up |
| A_24_P183150 | SEQ ID NO: 589 | CXCL3 | NM_002090 | chemokine (C-X-C motif) ligand 3 | down |
| A_24_P84198 | SEQ ID NO: 590 | LOC441849 | XR_019057 | similar to Methionine-R-sulfoxide reductase (Selenoprotein X 1) | up |
| A_24_P88690 | SEQ ID NO: 591 | SLC11A1 | NM_000578 | solute carrier family 11 (proton-coupled divalent metal ion transporters), member 1 | down |
| A_32_P92415 | SEQ ID NO: 346 | A_32_P92415 | THC2526269 | Low quality annotation—ALU5_HUMAN (P39192) Alu subfamily SC sequence contamination warning entry, partial (14%) [THC2526269] | up |
| A_23_P68851 | SEQ ID NO: 280 | KREMEN1 | NM_001039570 | kringle containing transmembrane protein 1 | up |
| A_24_P50245 | SEQ ID NO: 592 | HLA-DMA | NM_006120 | major histocompatibility complex, class II, DM alpha | up |
| A_24_P935986 | SEQ ID NO: 329 | BCAT1 | NM_005504 | branched chain aminotransferase 1, cytosolic | down |
| A_24_P201360 | SEQ ID NO: 593 | ACSL5 | NM_203380 | acyl-CoA synthetase long-chain family member 5 | up |
| A_24_P124624 | SEQ ID NO: 594 | OLR1 | NM_002543 | oxidized low density lipoprotein (lectin-like) receptor 1 | down |
| A_23_P253145 | SEQ ID NO: 595 | TAGAP | NM_054114 | T-cell activation GTPase activating protein | up |
| A_24_P354724 | SEQ ID NO: 596 | TAGAP | NM_054114 | T-cell activation GTPase activating protein | up |
| A_23_P160025 | SEQ ID NO: 597 | IFI16 | NM_005531 | interferon, gamma-inducible protein 16 | up |
| A_23_P161647 | SEQ ID NO: 598 | PC | NM_001040716 | pyruvate carboxylase | down |
| A_23_P8812 | SEQ ID NO: 599 | A_23_P8812 | W60781 | Low quality annotation—W60781 zd26f05.r1 Soares_fetal_heart_NbHH19W Homo sapiens cDNA clone IMAGE: 341793 5' similar to gb: J02874 FATTY ACID-BINDING PROTEIN, ADIPOCYTE (HUMAN);, mRNA sequence [W60781] | down |
| A_23_P250245 | SEQ ID NO: 600 | CD72 | NM_001782 | CD72 molecule | up |
| A_23_P502520 | SEQ ID NO: 601 | IL4I1 | NM_172374 | interleukin 4 induced 1 | up |
| A_23_P153390 | SEQ ID NO: 602 | CLEC4G | NM_198492 | C-type lectin superfamily 4, member G | up |
| A_24_P941167 | SEQ ID NO: 330 | APOL6 | NM_030641 | apolipoprotein L, 6 | up |
| A_23_P138680 | SEQ ID NO: 209 | IL15RA | NM_172200 | interleukin 15 receptor, alpha | up |
| A_32_P191417 | SEQ ID NO: 340 | A_32_P191417 | AI439246 | Low quality annotation—AI439246 ti59a08.x1 NCI_CGAP_Lym12 Homo sapiens cDNA clone IMAGE: 2134742 3' similar to gb: M81141 HLA CLASS II HISTOCOMPATIBILITY ANTIGEN, DQ(1) BETA CHAIN (HUMAN);, mRNA sequence [AI439246] | up |
| A_23_P202978 | SEQ ID NO: 603 | CASP1 | NM_033292 | caspase 1, apoptosis-related cysteine peptidase (interleukin 1, beta, convertase) | up |
| A_23_P97990 | SEQ ID NO: 604 | HTRA1 | NM_002775 | HtrA serine peptidase 1 | down |
| A_24_P334361 | SEQ ID NO: 314 | FLJ20035 | NM_017631 | hypothetical protein FLJ20035 | up |
| A_23_P114814 | SEQ ID NO: 605 | RHOU | NM_021205 | ras homolog gene family, member U | up |
| A_23_P122924 | SEQ ID NO: 606 | INHBA | NM_002192 | inhibin, beta A (activin A, activin AB alpha polypeptide) | up |
| A_23_P152782 | SEQ ID NO: 607 | IFI35 | NM_005533 | interferon-induced protein 35 | up |
| A_24_P212481 | SEQ ID NO: 304 | MCTP1 | NM_024717 | multiple C2 domains, transmembrane 1 | up |
| A_23_P145965 | SEQ ID NO: 608 | TPST1 | NM_003596 | tyrosylprotein sulfotransferase 1 | down |
| A_24_P77008 | SEQ ID NO: 609 | PTGS2 | NM_000963 | prostaglandin-endoperoxide synthase 2 (prostaglandin G/H synthase and cyclooxygenase) | up |
| A_23_P37983 | SEQ ID NO: 610 | MT1B | NM_005947 | metallothionein 1B (functional) | up |
| A_23_P253791 | SEQ ID NO: 611 | CAMP | NM_004345 | cathelicidin antimicrobial peptide | down |
| A_23_P5273 | SEQ ID NO: 612 | SBNO2 | NM_014963 | strawberry notch homolog 2 (Drosophila) | up |
| A_23_P91802 | SEQ ID NO: 613 | ECGF1 | NM_001953 | endothelial cell growth factor 1 (platelet-derived) | up |
| A_23_P152548 | SEQ ID NO: 614 | SCPEP1 | NM_021626 | serine carboxypeptidase 1 | up |
| A_23_P4662 | SEQ ID NO: 615 | BCL3 | NM_005178 | B-cell CLL/lymphoma 3 | up |
| A_32_P222250 | SEQ ID NO: 341 | A_32_P222250 | AF119908 | Low quality annotation—Homo sapiens PRO2955 mRNA, complete cds. [AF119908] | up |
| A_23_P256724 | SEQ ID NO: 616 | TNFRSF10C | NM_003841 | tumor necrosis factor receptor superfamily, member 10c, decoy without an intracellular domain | down |
| A_23_P205489 | SEQ ID NO: 617 | SLC7A8 | NM_182728 | solute carrier family 7 (cationic amino acid transporter, y+ system), member 8 | down |
| A_24_P243749 | SEQ ID NO: 618 | PDK4 | NM_002612 | pyruvate dehydrogenase kinase, isozyme 4 | down |
| A_24_P272389 | SEQ ID NO: 619 | LOC285216 | AK092228 | hypothetical protein LOC285216 | up |

TABLE 1-continued

Genes whose expression is modulated by IFN-γ

| AGILENT ® Probe Name | Sequence Listing number of AGILENT ® Probe Sequence | Symbol of Gene | NCBI Accession Number of Gene Sequence | Gene Name | Direction of modulation by IFN-γ |
|---|---|---|---|---|---|
| A_23_P161125 | SEQ ID NO: 620 | MOV10 | NM_020963 | Mov10, Moloney leukemia virus 10, homolog (mouse) | up |
| A_24_P659202 | SEQ ID NO: 323 | A_24_P659202 | THC2527772 | Low quality annotation—HUMC4AA2 complement component C4A {Homo sapiens} (exp = −1; wgp = 0; cg = 0), partial (6%) [THC2527772] | up |
| A_24_P914519 | SEQ ID NO: 621 | CYBB | S67289 | cytochrome b-245, beta polypeptide (chronic granulomatous disease) | up |
| A_24_P304071 | SEQ ID NO: 622 | IFIT2 | NM_001547 | interferon-induced protein with tetratricopeptide repeats 2 | up |
| A_23_P214176 | SEQ ID NO: 623 | CD109 | NM_133493 | CD109 molecule | down |
| A_23_P127663 | SEQ ID NO: 624 | PRRG4 | NM_024081 | proline rich Gla (G-carboxyglutamic acid) 4 (transmembrane) | up |
| A_23_P215566 | SEQ ID NO: 625 | AHR | NM_001621 | aryl hydrocarbon receptor | down |
| A_24_P398130 | SEQ ID NO: 626 | USP6NL | ENST00000277575 | USP6 N-terminal like | up |
| A_24_P42264 | SEQ ID NO: 627 | LYZ | NM_000239 | lysozyme (renal amyloidosis) | up |
| A_23_P397293 | SEQ ID NO: 628 | LY6K | NM_017527 | lymphocyte antigen 6 complex, locus K | down |
| A_23_P30243 | SEQ ID NO: 629 | LRAP | NM_022350 | leukocyte-derived arginine aminopeptidase | up |
| A_24_P133542 | SEQ ID NO: 630 | PML | NM_002675 | promyelocytic leukemia | up |
| A_24_P211106 | SEQ ID NO: 631 | A_24_P211106 | ENST00000382790 | Low quality annotation—Tumor necrosis factor receptor superfamily member 11A precursor (Receptor activator of NF-KB) (Osteoclast differentiation factor receptor) (ODFR) (CD265 antigen). [Source: Uniprot/SWISSPROT; Acc: Q9Y6Q6] [ENST00000382790] | down |
| A_24_P7322 | SEQ ID NO: 632 | A_24_P7322 | A_24_P7322 | Unknown | up |
| A_23_P343837 | SEQ ID NO: 254 | PARP11 | NM_020367 | poly (ADP-ribose) polymerase family, member 11 | up |
| A_23_P90041 | SEQ ID NO: 633 | NLRP12 | NM_033297 | NLR family, pyrin domain containing 12 | down |
| A_32_P121978 | SEQ ID NO: 634 | A_32_P121978 | A_32_P121978 | Unknown | up |
| A_23_P202837 | SEQ ID NO: 635 | CCND1 | NM_053056 | cyclin D1 | up |
| A_24_P136866 | SEQ ID NO: 636 | SLC8A1 | NM_021097 | solute carrier family 8 (sodium/calcium exchanger), member 1 | up |
| A_24_P97342 | SEQ ID NO: 333 | PROK2 | NM_021935 | prokineticin 2 | down |
| A_24_P352952 | SEQ ID NO: 637 | FAM20A | NM_017565 | family with sequence similarity 20, member A | up |
| A_23_P32233 | SEQ ID NO: 638 | KLF4 | NM_004235 | Kruppel-like factor 4 (gut) | up |
| A_23_P156327 | SEQ ID NO: 639 | TGFBI | NM_000358 | transforming growth factor, beta-induced, 68 kDa | down |
| A_23_P60933 | SEQ ID NO: 640 | MT1G | NM_005950 | metallothionein 1G | up |
| A_32_P199462 | SEQ ID NO: 641 | LOC389073 | ENST00000341287 | similar to RI KEN cDNA D630023F18 | up |
| A_24_P835388 | SEQ ID NO: 642 | A_24_P835388 | A_24_P835388 | Unknown | down |
| A_23_P217428 | SEQ ID NO: 643 | ARHGAP6 | NM_001174 | Rho GTPase activating protein 6 | down |
| A_23_P571 | SEQ ID NO: 272 | SLC2A1 | NM_006516 | solute carrier family 2 (facilitated glucose transporter), member 1 | down |
| A_23_P30069 | SEQ ID NO: 249 | FLJ31033 | AK023743 | hypothetical protein FLJ31033 | up |
| A_23_P52219 | SEQ ID NO: 644 | SPFH1 | NM_006459 | SPFH domain family, member 1 | up |
| A_23_P53763 | SEQ ID NO: 645 | C13ORF18 | NM_025113 | chromosome 13 open reading frame 18 | down |
| A_23_P42302 | SEQ ID NO: 265 | HLA-DQA2 | NM_020056 | major histocompatibility complex, class II, DQ alpha 2 | up |
| A_23_P42282 | SEQ ID NO: 264 | C4B | NM_001002029 | complement component 4B (Childo blood group) | up |
| A_23_P329353 | SEQ ID NO: 646 | C2ORF32 | NM_015463 | chromosome 2 open reading frame 32 | down |
| A_23_P46936 | SEQ ID NO: 647 | EGR2 | NM_000399 | early growth response 2 (Krox-20 homolog, Drosophila) | up |
| A_23_P74001 | SEQ ID NO: 284 | S100A12 | NM_005621 | S100 calcium binding protein A12 | down |
| A_23_P206724 | SEQ ID NO: 648 | MT1E | NM_175617 | metallothionein 1E (functional) | up |
| A_32_P118010 | SEQ ID NO: 649 | A_32_P118010 | THC2657593 | Low quality annotation—ALU1_HUMAN (P39188) Alu subfamily J sequence contamination warning entry, partial (7%) [THC2657593] | up |
| A_23_P502312 | SEQ ID NO: 650 | CD97 | NM_078481 | CD97 molecule | up |
| A_24_P135322 | SEQ ID NO: 651 | NRP1 | NM_001024629 | neuropilin 1 | down |
| A_23_P368484 | SEQ ID NO: 652 | C17ORF76 | NM_207387 | chromosome 17 open reading frame 76 | down |
| A_24_P335656 | SEQ ID NO: 653 | SECTM1 | NM_003004 | secreted and transmembrane 1 | up |
| A_23_P139066 | SEQ ID NO: 654 | RNF141 | NM_016422 | ring finger protein 141 | down |
| A_23_P138426 | SEQ ID NO: 655 | USP6NL | BC042943 | USP6 N-terminal like | up |
| A_23_P116286 | SEQ ID NO: 656 | AMPD3 | NM_001025390 | adenosine monophosphate deaminase (isoform E) | down |
| A_24_P85539 | SEQ ID NO: 657 | FN1 | NM_212482 | fibronectin 1 | down |
| A_24_P304154 | SEQ ID NO: 312 | AMPD3 | NM_001025390 | adenosine monophosphate deaminase (isoform E) | down |

TABLE 1-continued

Genes whose expression is modulated by IFN-γ

| AGILENT ® Probe Name | Sequence Listing number of AGILENT ® Probe Sequence | Symbol of Gene | NCBI Accession Number of Gene Sequence | Gene Name | Direction of modulation by IFN-γ |
|---|---|---|---|---|---|
| A_23_P41424 | SEQ ID NO: 658 | SLC39A8 | NM_022154 | solute carrier family 39 (zinc transporter), member 8 | down |
| A_24_P125096 | SEQ ID NO: 659 | MT1X | NM_005952 | metallothionein 1X | up |
| A_23_P138541 | SEQ ID NO: 660 | AKR1C3 | NM_003739 | aldo-keto reductase family 1, member C3 (3-alpha hydroxysteroid dehydrogenase, type II) | down |
| A_24_P372625 | SEQ ID NO: 315 | RNF141 | NM_016422 | ring finger protein 141 | down |
| A_32_P2605 | SEQ ID NO: 661 | A_32_P2605 | AV756170 | Low quality annotation—AV756170 BM Homo sapiens cDNA clone BMFBGA09 5', mRNA sequence [AV756170] | up |
| A_23_P378288 | SEQ ID NO: 662 | IKZF4 | BX647761 | IKAROS family zinc finger 4 (Eos) | up |
| A_23_P434919 | SEQ ID NO: 663 | RAB42 | NM_152304 | RAB42, member RAS oncogene family | down |
| A_23_P55738 | SEQ ID NO: 664 | CEACAM1 | NM_001024912 | carcinoembryonic antigen-related cell adhesion molecule 1 (biliary glycoprotein) | up |
| A_23_P414343 | SEQ ID NO: 665 | MT1H | NM_005951 | metallothionein 1H | up |
| A_24_P924010 | SEQ ID NO: 666 | A_24_P924010 | AW275876 | Low quality annotation—xq40c08.x1 NCI_CGAP_Lu28 Homo sapiens cDNA clone IMAGE: 2753102 3'similar to gb: X57352 INTERFERON-INDUCIBLE PROTEIN 1-8U (HUMAN);, mRNA sequence [AW275876] | up |
| A_32_P117016 | SEQ ID NO: 667 | A_32_P117016 | AK094088 | Low quality annotation—Homo sapiens cDNA FLJ36769 fis, clone ADIP52000245. [AK094088] | up |
| A_23_P303242 | SEQ ID NO: 668 | MT1X | NM_005952 | metallothionein 1X | up |
| A_24_P156490 | SEQ ID NO: 133 | KCNMA1 | NM_002247 | potassium large conductance calcium-activated channel, subfamily M, alpha member | up 1 |
| A_32_P103695 | SEQ ID NO: 669 | FAM92A1 | CR627475 | family with sequence similarity 92, member A1 | up |
| A_24_P335305 | SEQ ID NO: 670 | OA53 | NM_006187 | 2'-5'-oligoadenylate synthetase 3, 100 kDa | up |
| A_23_P52266 | SEQ ID NO: 671 | IFIT1 | NM_001548 | interferon-induced protein with tetratricopeptide repeats 1 | up |
| A_23_P24104 | SEQ ID NO: 672 | PLAU | NM_002658 | plasminogen activator, urokinase | up |
| A_23_P161837 | SEQ ID NO: 673 | MRVI1 | NM_130385 | murine retrovirus integration site 1 homolog | down |
| A_32_P133090 | SEQ ID NO: 674 | A_32_P133090 | BG216262 | Low quality annotation—R5T35951 Athersys RAGE Library Homo sapiens cDNA, mRNA sequence [BG216262] | up |
| A_24_P306810 | SEQ ID NO: 675 | KIAA1618 | ENST00000319902 | KIAA1618 | up |
| A_32_P200724 | SEQ ID NO: 676 | A_32_P200724 | AK128013 | Low quality annotation—Homo sapiens cDNA FLJ46132 fis, clone TESTI2051627. [AK128013] | up |
| A_23_P87879 | SEQ ID NO: 677 | CD69 | NM_001781 | CD69 molecule | up |
| A_23_P41344 | SEQ ID NO: 678 | EREG | NM_001432 | epiregulin | down |
| A_23_P48596 | SEQ ID NO: 679 | RNASE1 | NM_198232 | ribonuclease, RNase A family, 1 (pancreatic) | down |
| A_23_P135755 | SEQ ID NO: 680 | IL8RB | NM_001557 | interleukin 8 receptor, beta | down |
| A_23_P132822 | SEQ ID NO: 115 | XRN1 | NM_019001 | 5'-3' exoribonuclease 1 | up |
| A_23_P213014 | SEQ ID NO: 681 | SLC2A9 | NM_001001290 | solute carrier family 2 (facilitated glucose transporter), member 9 | up |
| A_32_P399546 | SEQ ID NO: 343 | ARNTL2 | AF256215 | aryl hydrocarbon receptor nuclear translocator-like 2 | up |
| A_24_P62521 | SEQ ID NO: 682 | PSEN2 | NM_000447 | presenilin 2 (Alzheimer disease 4) | up |
| A_24_P277367 | SEQ ID NO: 683 | CXCL5 | NM_002994 | chemokine (C-X-C motif) ligand 5 | down |
| A_23_P39925 | SEQ ID NO: 684 | DYSF | NM_003494 | dysferlin, limb girdle muscular dystrophy 2B (autosomal recessive) | up |
| A_24_P250922 | SEQ ID NO: 307 | PTGS2 | NM_000963 | prostaglandin-endoperoxide synthase 2 (prostaglandin G/H synthase and cyclooxygenase) | up |
| A_23_P163782 | SEQ ID NO: 685 | LOC645745 | NM_001039954 | metallothionein 1H-like protein | up |
| A_23_P216712 | SEQ ID NO: 686 | TRPM6 | NM_017662 | transient receptor potential cation channel, subfamily M, member 6 | down |
| A_23_P69171 | SEQ ID NO: 687 | SUCNR1 | NM_033050 | succinate receptor 1 | up |
| A_24_P7594 | SEQ ID NO: 688 | APOL6 | NM_030641 | apolipoprotein L, 6 | up |
| A_23_P373017 | SEQ ID NO: 689 | CCL3 | NM_002983 | chemokine (C-C motif) ligand 3 | up |
| A_23_P205200 | SEQ ID NO: 234 | DHRS12 | NM_024705 | dehydrogenase/reductase (SDR family) member 12 | up |
| A_23_P304356 | SEQ ID NO: 690 | CLEC5A | NM_013252 | C-type lectin domain family 5, member A | down |
| A_23_P217049 | SEQ ID NO: 691 | FREQ | NM_014286 | frequenin homolog (Drosophila) | down |
| A_23_P157527 | SEQ ID NO: 692 | LRRCC1 | NM_033402 | leucine rich repeat and coiled-coil domain containing 1 | up |

TABLE 1-continued

Genes whose expression is modulated by IFN-γ

| AGILENT® Probe Name | Sequence Listing number of AGILENT® Probe Sequence | Symbol of Gene | NCBI Accession Number of Gene Sequence | Gene Name | Direction of modulation by IFN-γ |
|---|---|---|---|---|---|
| A_23_P206707 | SEQ ID NO: 693 | MT1G | NM_005950 | metallothionein 1G | up |
| A_32_P138348 | SEQ ID NO: 694 | LY6K | NM_017527 | lymphocyte antigen 6 complex, locus K | down |
| A_23_P110204 | SEQ ID NO: 695 | CXCL5 | NM_002994 | chemokine (C-X-C motif) ligand 5 | down |
| A_23_P113212 | SEQ ID NO: 696 | TMEM45A | NM_018004 | transmembrane protein 45A | up |

Amino acid and nucleotide sequences included in publicly available database entries corresponding to the National Center for Biotechnology Information (NCBI) accession numbers listed in Table 1 above are incorporated herein by reference. Similarly, the sequences of the Agilent® probes are publicly available in the Gene Expression Omnibus (GEO) Database of NCBI. In particular, these sequences are among those disclosed for the Agilent-026652 Whole Human Genome Microarray 4×44K v2 and are incorporated herein by reference.

Example 2

Serum Levels of Selected Proteins in Lupus and Lupus Nephritis Patients Compared to Healthy Volunteers Gene dysregulation in SLE was initially examined in a study of 19 healthy volunteers and 39 lupus subjects, which included patients from the clinical trial described in Example 3 as well as other lupus patients. Further, these studies were extended to include patients participating in the clinical trial described in Example 4 below, which included lupus nephritis patients as well as patients having SLE without nephritis. Peripheral blood samples from healthy volunteers and from lupus patients (before dosing) were collected in serum separator tubes (red/black marble top) and processed for serum. Serum CXCL10, CCL2, C—C motif chemokine 5 (CCL5; also known as RANTES), and IL-18 concentrations were determined with commercially available ELISAs according to the manufacturers' instructions (R&D Systems, Minneapolis, Minn. and Medical & Biological Laboratories Co, Ltd, Des Plaines, Ill.). Samples were analyzed in triplicate and levels were quantified by interpolation from a standard curve run in parallel on each micro-titer plate. Log ratio of gene expression in lupus subjects relative to healthy subjects along with 95% confidence intervals were estimated using linear regression and expressed as fold change. See Kackar, R. N., and Harville, D. A. 1984. Approximations for Standard Errors of Estimators of Fixed and Random Effects in Mixed Linear-Models. *Journal of the American Statistical Association* 79: 853-862, the relevant portions of which are incorporated herein by reference.

Figure 2:
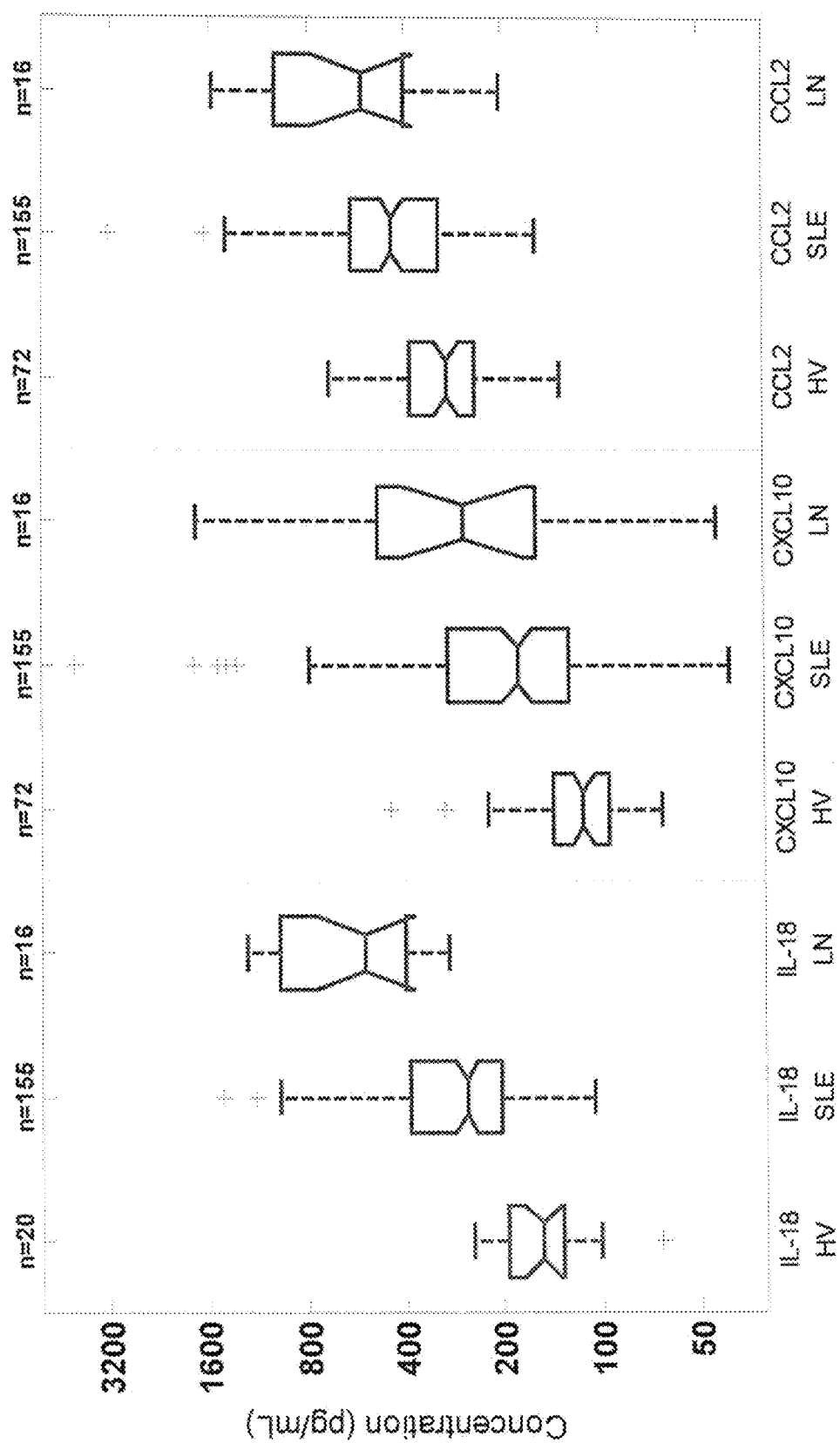
FIG. 2: Analysis of serum protein levels. Top: Boxplot of interleukin-18 (IL-18), chemokine (C—X—C motif) ligand 10 (CXCL10; also known as interferon gamma inducible protein 10 (IP10)), and chemokine (C—C motif) ligand 2 (CCL2; also known as MCP-1) protein levels in healthy volunteers (HV), SLE, and lupus nephritis (LN) subjects. The y-axis is log-scaled. The horizontal lines are the group medians and the boxes represent the $25^{th}$ and $75^{th}$ percentiles. The whiskers represent the most extreme data point within 1.5 times the inter-quartile range away from the boxes. The black crosses are points outside the whiskers. The numbers above each boxplot, e.g., "n=155," refer to the number of samples from individual subjects that the boxplot represents.

The results are shown in FIG. 2. These data indicate that median serum levels of CXCL10, IL-18, and CCL2 were elevated in SLE and lupus nephritis subjects compared to healthy volunteers. Further, median levels observed in lupus nephritis patients were at least numerically higher than levels observed in SLE patients, though differences were statistically significant only for IL-18 expression. No difference in levels of RANTES could be demonstrated (data not shown). As will be shown below, expression of CXCL10 at the RNA and protein levels is decreased in vivo in human lupus and lupus nephritis patients in response to treatment with the anti-huIFN-γ antibody AMG 811.

Similarly, gene dysregulation in SLE compared to healthy subjects at the RNA level was investigated using microarray analysis performed essentially as described in Example 1 except that the pre-filtering step was omitted. These results are reported in part in Table 2 below. Like the results displayed in FIG. 2, data in Table 2 indicate that levels of expression of some genes at the RNA level differ in SLE patients as compared to healthy volunteers.

Example 3

Single Dose Escalation Study of a Neutralizing Anti-huIFN-γ Antibody

Described below is a phase 1, randomized, double-blind, placebo-controlled, single dose escalation study of an anti-huIFN-γ antibody (AMG 811) in subjects with mild, stable SLE. Anti-huIFN-γ antibodies, including AMG 811, are described herein (above under the heading "Interferon Gamma Inhibitors") and in U.S. Pat. No. 7,335,743, the relevant portions of which are incorporated herein by reference. Adults aged 18 to 65 with a diagnosis of SLE (as defined by the American College of Rheumatology classification criteria) of at least 6 months duration were enrolled. Anti-malarials, leflunomide, or methotrexate, and up to 20 mg/day of prednisone (or equivalent) were permitted as concomitant therapies. The subjects had stable disease, that is, symptoms that were constant with no change in therapy for at least 30 days prior to randomization.

Twenty-six subjects with mild, stable SLE were enrolled in this Phase 1, single dose, double blind, randomized, placebo controlled, clinical trial. There were three subjects treated with active drug in each cohort (total of eighteen subjects) and eight subjects in the combined placebo group. The mean age was 43.3 years in the active group and 44.1 in the placebo group. The subjects were predominantly female (92%) and Caucasian (62%). The mean Systemic Lupus Erythematosus Disease Activity Index (SLEDAI; see Bombardier et al. (1992), Arthritis & Rheum. 35(6): 630-640, the relevant portions of which are incorporated herein by reference) score was low (2.3 and 3.8 for placebo and AMG 811 groups, respectively). Fifty percent of placebo subjects and 28% of the subjects receiving AMG 811 were on corticosteroids, receiving mean doses of 10 mg/day and 13.5 mg/day, respectively. Seventy five percent of placebo subjects and 100% of the subjects receiving AMG 811 were on anti-malarials, while a single subject in the AMG 811 group was on an immunosuppressant (methotrexate).

Each subject was treated with a single dose of AMG 811 (2 milligrams (mg) subcutaneous (SC), 6 mg SC, 20 mg SC, 60 mg SC, 180 mg SC, or 60 mg intravenous (IV)) or placebo (vehicle control) on day 1 of the study. The end of study (EOS) ranged from day 84 to day 196 depending on the dose level. Serum tube and PAXgene® blood RNA tube samples were collected from all cohorts at baseline, that is, on day 1 prior to dosing and at days 15, 56, and EOS after treatment. All samples were collected and included for analysis with the exception of one placebo EOS sample, one EOS sample from the 6 mg treated cohort, and two day 15 samples from the 20 mg cohort. One sample at the day 15 time point (60 mg IV) was subsequently determined to be from an unscheduled day 8 visit. As an actual day 15 sample was not available from this patient, and the expected drug exposure was not anticipated to be very different between day 8 and day 15, this sample was included with the day 15 results.

Total RNA was isolated from each sample and processed and analyzed by hybridization to a microarray as described in Example 1 above, except that the pre-filtering step to remove genes having low levels of expression was not performed.

Figure 3:
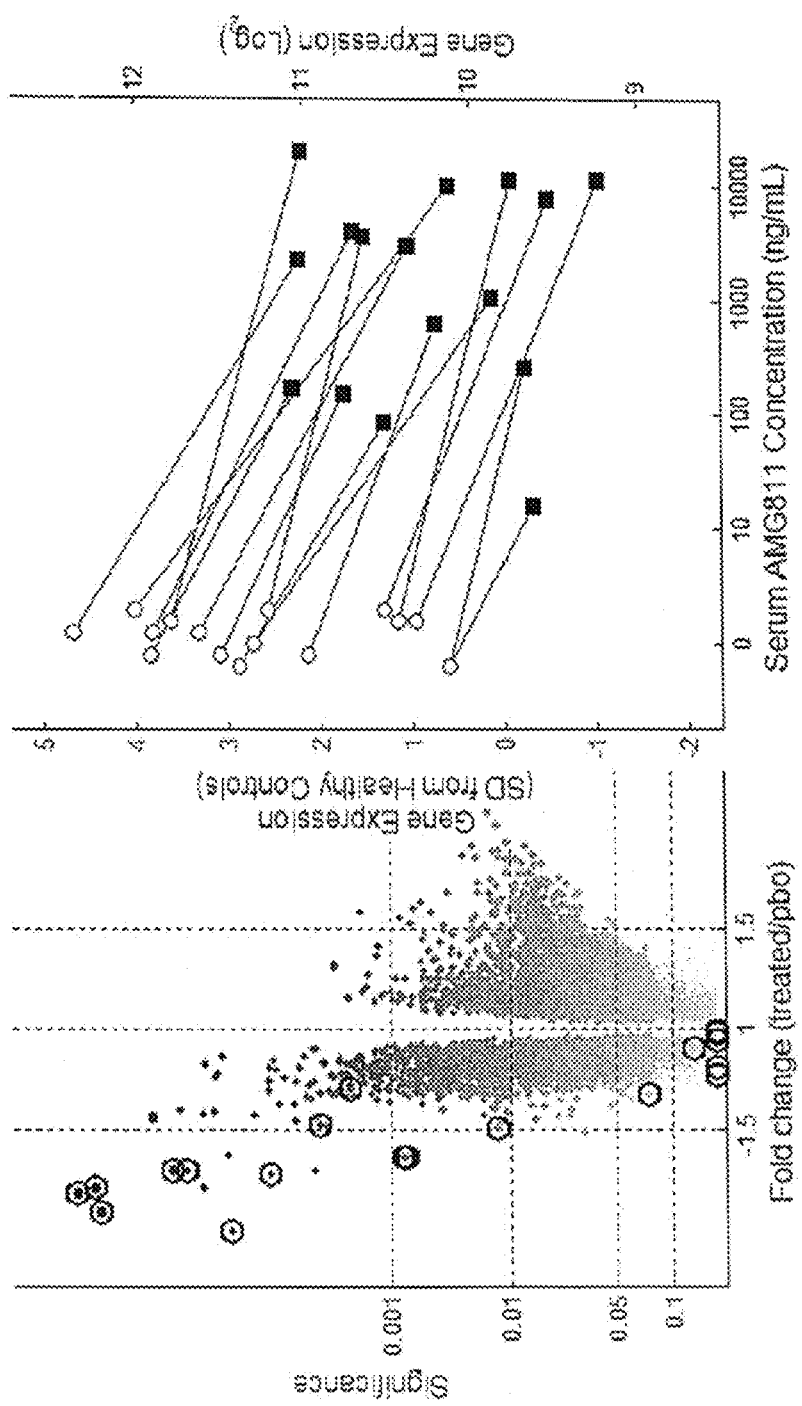
FIG. 3: IFN-related gene expression in SLE patients treated with AMG 811 compared to patients treated with a placebo. Left: Volcano plot of RNA expression of an array of genes in biological samples from treated subjects at day 15 (described in Example 3) versus samples from untreated/placebo treated subjects. The average fold difference in RNA expression for each gene is plotted with the associated p-value. The top 20 IFN-γ signature genes (see FIG. 1) are circled. Right: Relationship between AMG 811 serum concentration and guanylate binding protein 1 (GBP1) transcript expression in SLE patients. Samples were taken on Day −1 (pre-dosing; Q and Day 15 (■) in the clinical trial described in Example 3. The x axis indicates the serum concentration of AMG 811, and the y axis indicates the fold difference in guanylate binding protein 1 (GBP1) RNA expression from that seen in a control group of healthy people.

These results are shown in the left panel of FIG. 3, which shows the fold difference in expression of individual genes at the RNA level in day 15 blood samples from patients treated with AMG 811 and baseline or placebo-treated subjects. As in FIG. 1, dots represent data from a particular gene sequence. The x-axis shows the fold difference in RNA expression in samples from patients treated with AMG 811 versus in samples from patients treated with placebo. Dots representing the same twenty genes that were circled in FIG. 1 are also circled here.

More detailed data on these twenty genes from this experiment, as well as from the ex vivo stimulation experiment described in Example 1 and the comparison of healthy vs. SLE subjects described in Example 2, is shown in Table 2 below.

TABLE 2

Data from the top 20 IFN-γ regulated genes

| Agilent ® Probe Designation | Sequence Listing Number of the probe sequence | Symbol, Product (NCBI accession number of cDNA sequence) | Sequene Listing Number of cDNA sequence | IFN-γ-Stim Fold change (95% CI) | Lupus v. healthy Fold change (95% CI) | D15 treatment effect Fold change (95% CI) | P-value for treatment effect (treated at day 15 vs. baseline) |
|---|---|---|---|---|---|---|---|
| A_23_P112026 | SEQ ID NO: 350 | INDO1, indoleamine 2,3-dioxygenase 1 (NM_002164) | SEQ ID NO: 50 | 11.3 (10.0, 12.8) | 1.1 (−1.2, 1.4) | −1.4 (−2.0, 1.0) | 0.076 |
| A_23_P161428 | SEQ ID NO: 72 | ANKRD22, ankyrin repeat domain 22 (NM_144590) | SEQ ID NO: 51 | 10.8 (8.8, 13.2) | 1.3 (−1.0, 1.7) | −2.2 (−3.0, −1.6) | <0.001 |
| A_23_P18452 | SEQ ID NO: 109 | CXCL9, chemokine (C—X—C motif) ligand 9 (NM_002416) | SEQ ID NO: 52 | 9.8 (8.4, 11.4) | 1.3 (1.1, 1.5) | −1.3 (−1.6, −1.2) | <0.001 |
| A_24_P28722 | SEQ ID NO: 351 | RSAD2, radical S-adenosyl methionine domain containing 2 (NM_080657) | SEQ ID NO: 53 | 7.7 (5.9, 10.1) | 5.2 (2.3, 11.5) | −1.3 (−1.8, 1.1) | 0.184 |
| A_23_P7827 | SEQ ID NO: 83 | FAM26F, family with sequence similarity 26, member F (NM_001010919) | SEQ ID NO: 54 | 7.4 (6.9, 8.0) | 1.2 (−1.0, 1.5) | −1.6 (−1.9, −1.3) | <0.001 |
| A_24_P165864 | SEQ ID NO: 300 | P2RY14, purinergic receptor P2Y, G-protein coupled, 14 (NM_001081455) | SEQ ID NO: 55 | 7.3 (5.0, 10.7) | −1.1 (−1.5, 1.2) | −1.7 (−2.4, −1.3) | 0.001 |
| A_23_P74290 | SEQ ID NO: 79 | GBP5, guanylate binding protein 5 (NM_052942) | SEQ ID NO: 56 | 7.0 (5.0, 9.8) | 1.3 (1.0, 1.7) | −1.8 (−2.3, −1.5) | <0.001 |
| A_24_P561165 | SEQ ID NO: 322 | SERPING1, serpin peptidase inhibitor, clade G, member 1 (NM_000062) | SEQ ID NO: 57 | 6.4 (4.5, 8.9) | 2.5 (1.7, 3.8) | −1.7 (−2.4, −1.3) | 0.001 |
| A_23_P63390 | SEQ ID NO: 73 | FCGR1B or CD64Fc fragment of IgG, high affinity Ib, receptor (NM_001017986)) | SEQ ID NO: 58 | 6.3 (4.8, 8.2) | 1.2 (−1.1, 1.6) | −2.1 (−2.6, −1.6) | <0.001 |
| A_23_P150457 | SEQ ID NO: 352 | LYVE1, lymphatic vessel endothelial hyaluronan receptor 1 (NM_006691) | SEQ ID NO: 59 | −6.0 (−7.1, 5.1) | −1.0 (−1.2, 1.1) | −1.1 (−1.2, 1.1) | 0.367 |
| A_24_P245379 | SEQ ID NO: 353 | SERPINB2, serpin peptidase inhibitor, clade B (ovalbumin), member 2 (NM_001143818) | SEQ ID NO: 60 | −5.9 (−7.6, 4.6) | 1.0 (−1.2, 1.2) | −1.1 (−1.3, 1.1) | 0.536 |
| A_23_P203882 | SEQ ID NO: 356 | MMP19, matrix metallopeptidase 19 (NM_002429) | SEQ ID NO: 61 | −5.8 (−7.6, −4.4) | 1.2 (1.0, 1.4) | −1.0 (−1.2, 1.1) | 0.699 |
| A_23_P62890 | SEQ ID NO: 74 | GBP1, guanylate binding protein 1, interferon-inducible, 67 kDa (NM_002053) | SEQ ID NO: 62 | 5.6 (4.0, 7.7) | 1.6 (1.1, 2.2) | −2.0 (−2.4, −1.6) | <0.001 |

TABLE 2-continued

Data from the top 20 IFN-γ regulated genes

| Agilent ® Probe Designation | Sequence Listing Number of the probe sequence | Symbol, Product (NCBI accession number of cDNA sequence) | Sequene Listing Number of cDNA sequence | IFN-γ-Stim Fold change (95% CI) | Lupus v. healthy Fold change (95% CI) | D15 treatment effect Fold change (95% CI) | P-value for treatment effect (treated at day 15 vs. baseline) |
|---|---|---|---|---|---|---|---|
| A_32_P107372 | SEQ ID NO: 76 | GBP1, guanylate binding protein 1, interferon-inducible, 67 kDa (NM_002053) | SEQ ID NO: 62 | 5.6 (4.1, 7.6) | 1.6 (1.2, 2.1) | −1.9 (−2.4, −1.5) | <0.001 |
| A_24_P303091 | SEQ ID NO: 311 | CXCL10, chemokine (C—X—C motif) ligand 10 (NM_001565) | SEQ ID NO: 63 | 5.4 (4.1, 7.1) | 1.3 (−1.0, 1.8) | −1.6 (−2.2, −1.1) | 0.008 |
| A_24_P316965 | SEQ ID NO: 354 | RSAD2, radical S-adenosyl methionine domain containing 2 (NM_080657) | SEQ ID NO: 53 | 5.4 (4.6, 6.3) | 3.6 (2.1, 6.2) | −1.2 (−1.7, 1.1) | 0.235 |
| A_23_P42353 | SEQ ID NO: 77 | ETV7, ets variant 7 (NM_016135) | SEQ ID NO: 64 | 5.2 (3.6, 7.5) | 1.8 (1.3, 2.6) | −1.8 (−2.4, −1.4) | <0.001 |
| A_23_P256487 | SEQ ID NO: 78 | PD-L1, Programmed Death Ligand-1 (AY254342) | SEQ ID NO: 65 | 5.0 (3.9, 6.4) | 1.2 (1.1, 1.4) | −1.8 (−2.3, −1.4) | <0.001 |
| A_23_P121657 | SEQ ID NO: 355 | HS3ST1, heparan sulfate (glucosamine) 3-O-sulfotransferase 1 (NM_005114) | SEQ ID NO: 66 | −4.9 (−5.4, 4.4) | 1.0 (−1.3, 1.3) | −1.0 (−1.2, 1.1) | 0.892 |
| A_24_P12690 | SEQ ID NO: 357 | INDO2, indoleamine 2,3-dioxygenase 2 (BC113498) | SEQ ID NO: 67 | 4.8 (3.7, 6.2) | 1.0 (−1.1, 1.2) | −1.1 (−1.3, 1.0) | 0.126 |

Many of the transcripts that were most impacted by treatment with IFN-γ ex vivo, which are circled in FIG. 1 and the left panel of FIG. 3, are downregulated by treatment with AMG 811 in vivo. These data provide strong evidence that AMG 811 can inhibit IFN-γ-regulated gene expression in vivo in SLE patients. These data are also reported in more detail Table 5 (described in more detail below) which names a broader set of genes whose expression is modulated by AMG 811 in vivo.

An example of the in vivo effect of AMG 811 on gene expression at the RNA level is provided by guanylate binding protein 1 (GBP1). Levels of GBP1 RNA observed in individual patients before dosing with AMG 811 on Day −1 and on Day 15 of the study (after dosing) are shown in the right panel of FIG. 3. The gene expression levels for the GBP1 transcript were standardized against levels seen in healthy volunteers (y-axis of the figure) and plotted against the serum levels of AMG 811 observed at days −1 and 15, which, of course, varied according to dosage. GBP1 RNA expression decreased at day 15 as compared to day −1 in each patient treated with AMG 811. In samples from patients treated with placebo, considerable change in GBP1 expression was also observed, but the direction of change was not consistent, and the expression was, on average, not different between study days (p=0.54, data not shown). Since GBP-1 is one of the genes whose expression is upregulated by IFN-γ stimulation of blood of healthy volunteers ex vivo, these results suggest that inhibition of IFN-γ is occurring in every patient treated with AMG 811 in this study.

Figure 4:
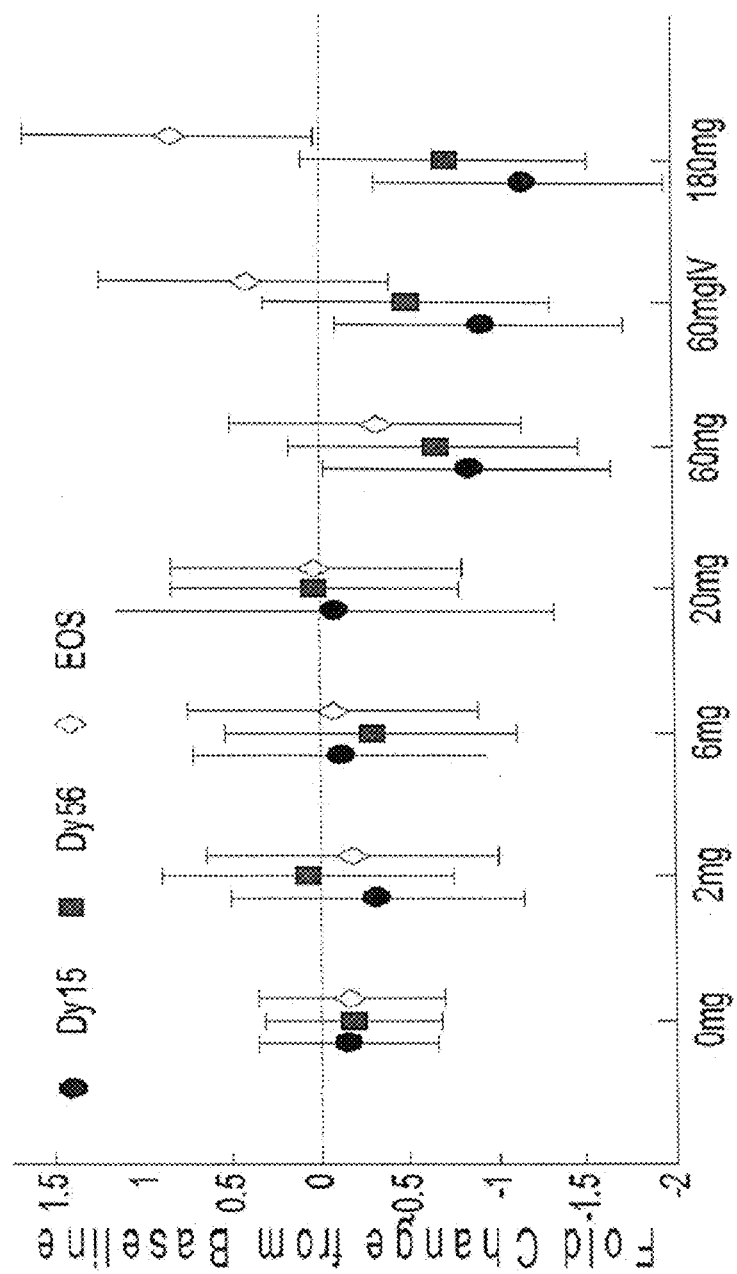
FIG. 4: Dose dependent decrease in CXCL10 protein level in response to AMG 811 administration. Symbols are average change from baseline in CXCL10 levels for each dose group by study day of the study described in Example 3. The error bars reflect the 95% confidence interval around the mean. Time points are indicated as follows: ●, day 15 (Dy15) of the study; ■, day 56 (Dy56) of the study; and ◇, end of study (EOS).

To determine the effects of various doses of AMG 811 on CXCL10 protein expression, peripheral blood samples were taken and processed for serum, and CXCL10 protein concentrations were determined by ELISA assay. Differences between levels of protein expression at baseline and after a single dose of AMG 811 were estimated by a fixed-effects regression model containing factors for visit and dose, a random factor for subject, and an interaction term for visit and dose. FIG. 4 shows the fold change in CXCL10 protein levels at Days 15 and 56 and at the end of study (EOS) as compared to baseline CXCL10 protein levels, with error bars showing the 95% confidence intervals using small sample size correction. Kackar, R. N., and Harville, D. A. 1984. Approximations for Standard Errors of Estimators of Fixed and Random Effects in Mixed Linear-Models. *Journal of the American Statistical Association* 79:853-862. These data indicate that a single dose of AMG 811 greater than 20 mg, that is, 60 mg or 180 mg, decreased levels of serum CXCL10 protein in vivo in SLE patients.

Figure 5:
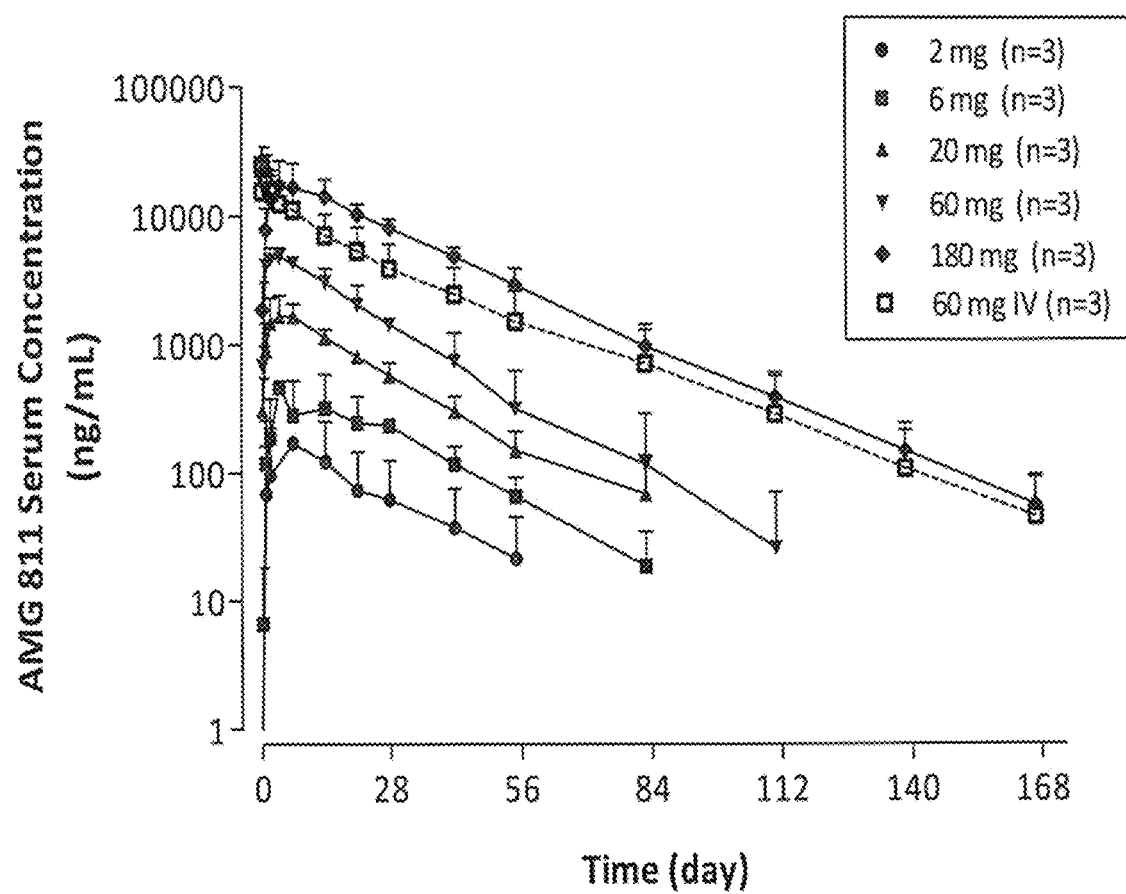
FIG. 5: Mean AMG 811 serum concentration-time profiles following a single subcutaneous or intravenous dose of AMG 811 in systemic lupus erythematosus patients. The x axis indicates the time post-injection, and the y axis indicates the serum concentration of AMG 811 in nanograms per milliliter (ng/ml). The doses represented by the various symbols and the number of patients dosed (n) are indicated in the legend in the figure.

Levels of AMG 811 in serum were determined using a validated sandwich immunoassay at Amgen Inc., Thousand Oaks, Calif. Study samples were added to a plate coated with a mouse anti-AMG 811 monoclonal antibody. After capture of AMG 811 with the immobilized antibody, unbound materials were removed by a wash step. Biotin conjugated rabbit anti-AMG 811 polyclonal antibody (Amgen Inc., CA) was added to detect the captured AMG 811. After another incubation step with streptavidin-HRP, a tetramethylbenzidine (TMB) peroxide substrate solution (KPL Inc., MD) was added to produce a colorimetric signal, which was proportional to the amount of AMG 811 bound by the capture reagent. The color development was stopped by addition of $H_2SO_4$, and the optical density (OD) signal was measured at 450 nm with reference to 650 nm. The absorbance versus concentration relationship was regressed according to a four-parameter logistic (auto-estimate) regression model with a weighting factor of 1/Y. The lower limit of quantification (LLOQ) was 15.2 ng/mL. Results from the single-dose escalation study are shown in FIG. 5. AMG 811 exhibited linear pharmacokinetics (PK), with a mean terminal half-life ($t_{1/2,z}$) ranging from 12 to 21 days. Following a single 60 mg IV dose, the mean area under the curve (AUC) value was approximately 3-fold higher than for the 60 mg SC dose, indicating an approximate 30% bioavailability. Mean AMG 811 PK parameters are presented in Table 3.

TABLE 3

Serum PK Parameters for AMG 811

| | | AMG 811 PK Parameters | | | |
|---|---|---|---|---|---|
| Route | Dose (mg) | $t_{max}$[b] (day) | $C_{max}$[c] (µg/mL) | $AUC_{last}$[d] (µg · day/mL) | $t_{1/2, z}$[e] (day) |
| SC | 2[a] | 7.1 (7.1-13) | 0.143 (0.161) | 6.25 (NA) | 21.0 (NA) |
| | 6 | 14 (14-14) | 0.323 (0.275) | 11.6 (7.61) | 17.0 (2.97) |
| | 20 | 4.0 (4.0-7.0) | 1.81 (0.541) | 45.0 (9.72) | 15.2 (3.01) |
| | 60 | 4.0 (1.2-7.2) | 4.93 (0.705) | 117 (38.6) | 12.3 (4.75) |
| | 180 | 4.0 (4.0-14) | 17.6 (9.14) | 595 (121) | 19.3 (0.667) |
| IV | 60 | 0.04 (0.02, 0.04) | 25.6 (10.0) | 369 (188) | 18.6 (4.61) |

[a] One subject in cohort 1 (receiving a dose of 2 mg) had only 2 measurable AMG 811 concentrations (data included where applicable)
[b] Time to maximum observed concentration ($t_{max}$) are presented as median (range of values observed)
[c] Mean (standard deviation) maximum serum concentration achieved.
[d] Mean (standard deviation) area under the curve value to last measured time point.
[e] Mean (standard deviation) serum terminal half life.

Levels of total IFN-γ protein in patients dosed with AMG 811 were also determined. The total IFN-γ concentration in human serum was measured using a validated sandwich immunoassay at Amgen Inc., Thousand Oaks, Calif. Specifically, study samples were incubated with 25 µg/mL of AMG 811 at 37° C. to form IFN-γ-AMG 811 complexes prior to being added to a plate coated with a mouse anti-IFN-γ monoclonal antibody (Hycult Biotechnology, Uden, Netherlands). After capture of IFN-γ-AMG 811 complex with the immobilized anti-IFN-γ monoclonal antibody, unbound materials were removed by a wash step. Biotin conjugated rabbit anti-AMG 811 polyclonal antibody (Amgen Inc., CA) was added for detection of the captured IFNγ-AMG 811 complex. After another incubation step with streptavidin-HRP, a tetramethylbenzidine (TMB) peroxide substrate solution (KPL Inc., MD) was added to produce a colorimetric signal, which was proportional to the amount of IFNγ bound by the capture reagent. The color development was stopped by addition of $H_2SO_4$, and the optical density (OD) signal was measured at 450 nm with reference to 650 nm. The absorbance versus concentration relationship was regressed according to a four-parameter logistic (auto-estimate) regression model with a weighting factor of 1/Y. The LLOQ of the method was 50 pg/mL.

Figure 6A:
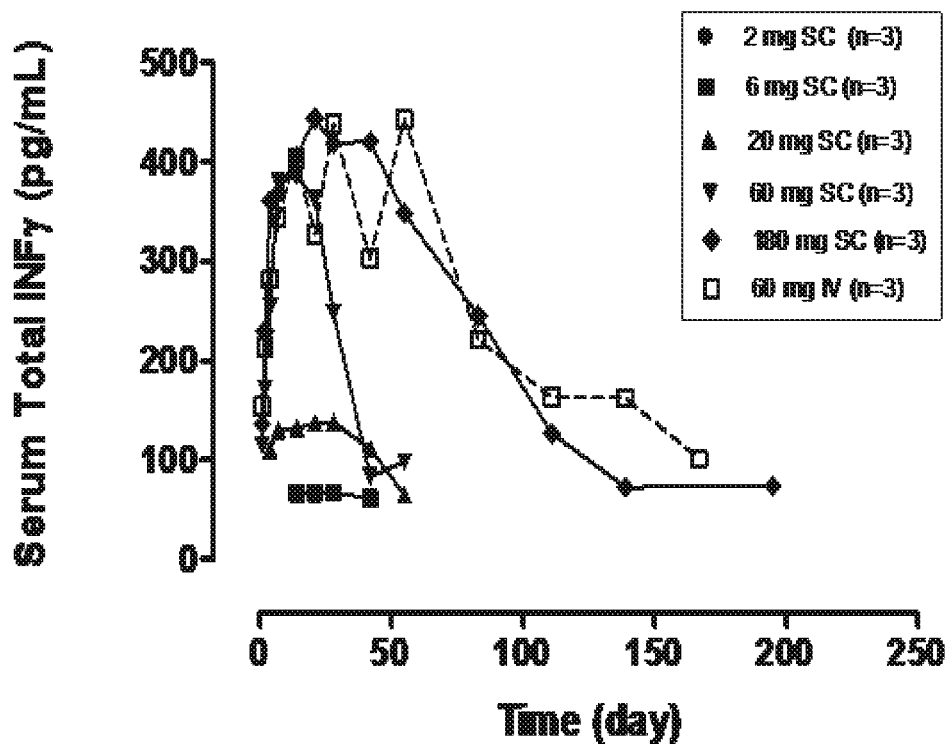
FIGS. 6A and 6B: Median (6A) and mean (6B) serum total IFN-γ protein concentration-time profiles following a single subcutaneous or intravenous dose of AMG 811 in systemic lupus erythematosus patients. The x axis indicates time post-injection, and they axis indicates the median or mean serum concentration of IFN-γ. The doses represented by the various symbols and the number of patients dosed (n) are indicated in the legend in the figure.
Figure 6B:
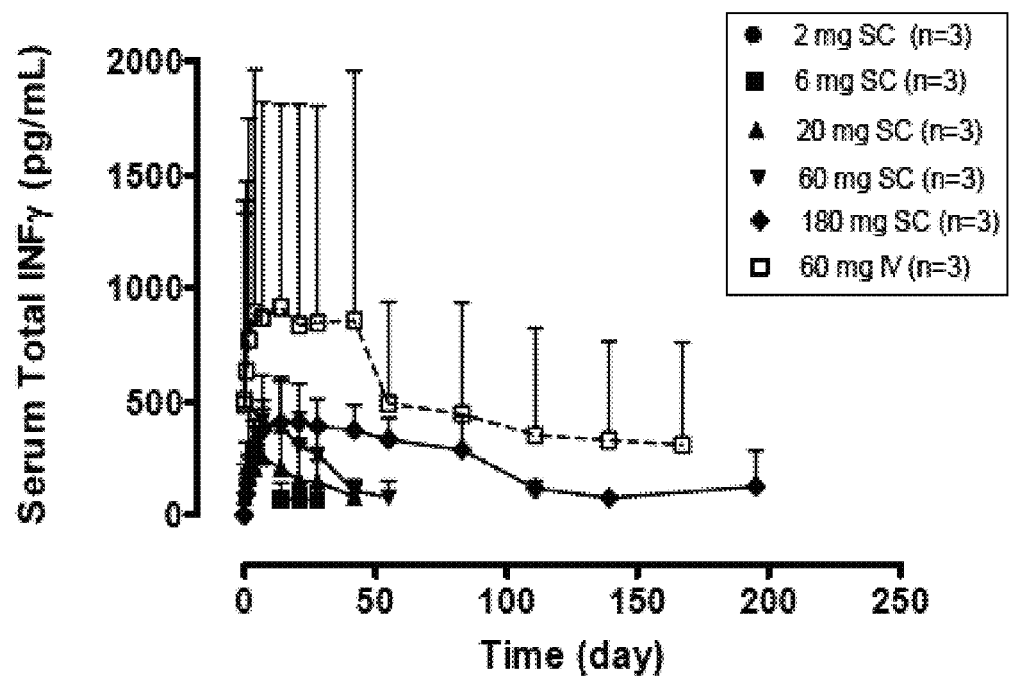

The total IFN-γ concentration represents both bound and free endogenous levels. Free IFN-γ levels were not assessed separately. An amount of AMG 811 sufficient to saturate all IFN-γ was added to the serum samples, and the resulting AMG 811:IFN-γ complexes were detected by means of the sandwich immunoassay, as described above. These results are shown in FIGS. 6A (median levels) and 6B (mean levels). Total IFN-γ median levels increased in a dose-dependent manner, then returned to baseline by approximately 6 to 7 months postdose. FIG. 6A. The plateau in $C_{max}$ values at doses of 60 and 180 mg SC and 60 mg IV may indirectly reflect the saturation of circulating, IFN-γ levels by AMG 811. These data suggest that 60 mg SC was the lowest dose tested that saturated the available IFN-γ in patients. At doses of 180 mg SC or 60 mg IV, the data suggest that this saturation of available IFN-γ was maintained for a longer period of time.

In addition, these data suggest that dosing frequency can be adjusted so as to maintain levels of total IFN-γ at or near the plateau concentrations observed at the higher doses. For example, at a dose of 60 mg SC, a level of total IFN-γ of almost 400 pg/ml is achieved at early timepoints, which starts to drop off at about three or four weeks post-dosing. Dosing repeated about every 3, 4, 5, or 6 weeks could be beneficial at a dose of 60 mg SC. Similarly, at doses of 60 mg IV or 180 SC, levels of total IFN-γ of around 400 pg/ml are achieved, but start to drop off at about 8, 9, 10, 11, or 12 weeks post dosing. Dosing repeated about every 4, 6, 8, 9, 10, 11, 12, 13, or 14 weeks could be beneficial at doses of 180 mg SC or 60 mg IV.

These data also have surprising implications about the production and turnover of IFN-γ. Generally, IFN-γ is undetectable or detectable at only low levels in peripheral blood. The comparatively high levels of total IFN-γ detected upon dosing with AMG 811 indicate that IFN-γ is likely produced at much higher levels than are generally appreciated and rapidly clearly from circulation. The relatively high levels of IFN-γ detected in the presence of AMG 811 may be due to protection of the IFN-γ from degradation and/or reduced clearance by binding to AMG 811. This assay allows for a better determination of the total production of IFN-γ in an individual and can be useful for determination of dose, dosing frequency, and stratification purposes.

Additionally, although mean total IFN-γ levels observed in the 60 mg IV dose group were significantly higher than in other groups (FIG. 6B), this may be attributed to one subject with very high baseline levels of total IFN-γ. Median profiles (FIG. 6A) indicate that the 60 mg IV dose group had similar to IFN-γ levels to those observed in the 180 mg SC dose group.

Example 4

Multi-Dose Clinical Trial in SLE Patients with and without Lupus Nephritis

In addition to the single dose clinical trial described in Example 3, a multi-dose trial was initiated to determine the safety and tolerability of multiple subcutaneous doses of AMG 811 in SLE patients with or without lupus nephritis. Part A of the study included three cohorts, 1, 2, and 3, each containing eight SLE patients without lupus nephritis. To be eligible for cohorts 1-3, a patient must have been diagnosed with SLE at least 6 months before the start of the study. Prednisone at a dose of 20 mg/day was permitted during the study, as were concurrently administered medications used for treating SLE including mycophenolate mofetil, azathioprine, leflunomide, methotrexate, and anti-malarials. Two of the eight patients in each of cohorts 1-3 received three doses of placebo administered every four weeks, and the other six received three doses AMG 811 (6, 20, or 60 mg for cohorts 1, 2, and 3, respectively) administered every four weeks, that is on days 1, 29, and 57. Part B of the study will include cohorts, 4, 5, and 6. Patients in cohorts 4-6 are required to have been diagnosed with SLE at least 6 months before the start of the study and with proliferative glomerulonephritis, as evidenced by a renal biopsy and urine protein/creatinine ratio of >1 or a 24 hour urine protein level of >1 g/day. These patients were also permitted to take prednisone at a dose of 20 mg/day and to take SLE medications including mycophenolate mofetil, azathioprine, leflunomide, methotrexate, and anti-malarials. Cohorts 4 and 5, for which dosing is now complete, contained eight and twelve SLE patients that had lupus nephritis, respectively. Cohort 6 is to contain eight lupus nephritis patients. Two of the patients in each of cohorts 4 and 6 and three of the twelve patients in cohort 5 will receive (and, in some cases, have received) three doses of placebo administered every four weeks, and the other patients will receive three doses AMG 811 (20, 60, or 120 mg for cohorts 4, 5, and 6, respectively) administered every four weeks, that is, on days 1, 29, and 57. Blood samples will be taken at baseline, i.e., one to three days before dosing, and on days, 1 (after dosing), 3, 8, 15, 29, 57, 85, 113, and 197 (which was the end of the study (EOS)) to determine levels of expression of various biomarker genes. Samples will be analyzed for RNA expression by DNA array as described above in Example 3 or for expression of selected proteins by ELISA assay. Blood samples taken at baseline and on days 1 (after dosing), 3, 5, 8, 15, 22, 29, 43, 57 (pre- and post-dosing), 59, 61, 64, 71, 78, 85, 113, 141, 169, and 197 will be analyzed to assess a number of laboratory parameters. Twenty four hour urine samples were taken at baseline and on days 15, 29 (pre-dosing), 57 (pre-dosing), 85, 113, 141, 169, and 197 (EOS). Spot urine samples were taken at baseline and on days 3, 8, 15, 22, 29 (pre-dosing), 43, 57 (pre-dosing), 71, 85, 113, 141, 169, and 197 (EOS). Urine samples were analyzed for levels of urine protein using the a dye-binding assay (pyrocatechol violet-ammonium molybdate dye), which was analyzed in a "dry-slide" format using an automated laboratory analyzer such as the Ortho-Clinical VITROS® 5.1 FS Chemistry Analyzer from Ortho Clinical Diagnostics. Creatinine levels in urine samples were assessed by a multi-step coupled enzymatic two-point rate colorimetric assay (creatinine amidohydrolase/creatine amidinohydrolase/sarcosine oxidase/peroxidase) analyzed using a dry-slide format and automated laboratory analyzer. Such an assay is described in, e.g., Guder et al. (1986), J. Clin. Chem. Clin Biochem. 24(11): 889-902.

In Table 4 below are listed the ten genes whose expression, as detected at the RNA level, was most significantly correlated with the concentration of AMG 811 in serum as assessed in the single dose clinical trial described in Example 3. Data from the multiple dose clinical trial described in Example 4 showed that the average of the expression levels of these ten genes was responsive to the dosage level of AMG 811.

TABLE 4

Ten genes whose expression is most affected by AMG 811 concentration in serum

| AGILENT® probe designation | Sequence Listing Number of Agilent Probe Sequence | Gene symbol | NCBI Accession No. of cDNA Sequence | Sequence Listing Number of cDNA Sequence |
|---|---|---|---|---|
| A_33_P3407880 | SEQ ID NO: 349 | ANKRD22 | NM_144590 | SEQ ID NO: 51 |
| A_23_P62890 | SEQ ID NO: 74 | GBP1 | NM_002053 | SEQ ID NO: 62 |
| A_23_P370682 | SEQ ID NO: 80 | BATF2 | NM_138456 | SEQ ID NO: 68 |
| A_23_P42353 | SEQ ID NO: 77 | ETV7 | NM_016135 | SEQ ID NO: 64 |
| A_23_P63390 | SEQ ID NO: 73 | FCGR1B | NM_001017986 | SEQ ID NO: 58 |
| A_23_P34915 | SEQ ID NO: 81 | ATF3 | NM_001040619 | SEQ ID NO: 69 |
| A_23_P139123 | SEQ ID NO: 210 | SERPING1 | NM_000062 | SEQ ID NO: 57 |
| A_23_P74290 | SEQ ID NO: 79 | GBP5 | NM_052942 | SEQ ID NO: 56 |
| A_24_P243749 | SEQ ID NO: 82 | PDK4 | NM_002612 | SEQ ID NO: 70 |
| A_23_P338479 | SEQ ID NO: 75 | CD274 | NM_014143 | SEQ ID NO: 71 |

Figure 7:
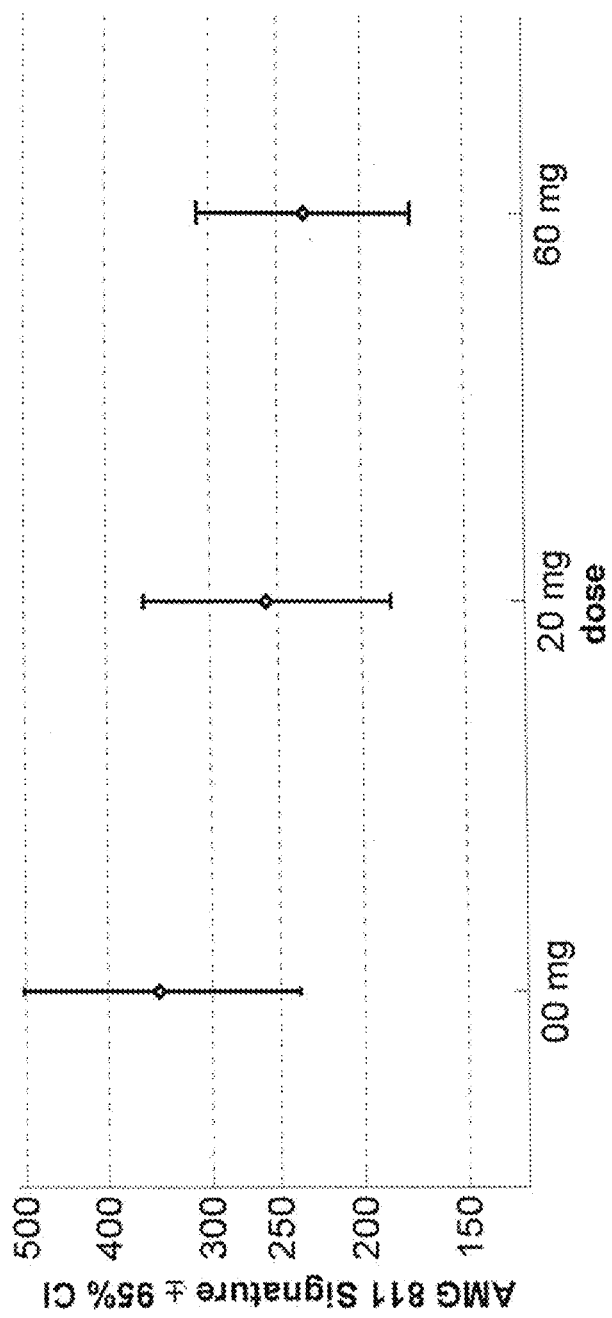
FIG. 7: Average post-dose AMG 811 score in lupus nephritis patients. An "AMG 811 score" was determined as explained in Example 4 for lupus nephritis patients. Diamonds indicate the average score for each dose while vertical lines indicate the 95% confidence interval.

Based on average RNA expression of the ten genes listed in Table 4, an "AMG 811 Score" could be assigned to each patient. FIG. 7 shows the average AMG 811 Score for the lupus nephritis patients receiving placebo or 20 or 60 mg of AMG 811. The average AMG 811 Score for patients receiving 20 mg or 60 mg was significantly less than the average score for patients receiving placebo. The amount of reduction in the AMG 811 Score was smaller than what was seen in the general SLE population (data not shown), suggesting that the 60 mg doses may not be high enough to achieve the maximal pharmacodynamic effect of AMG 811 in lupus nephritis patients.

Figure 8:
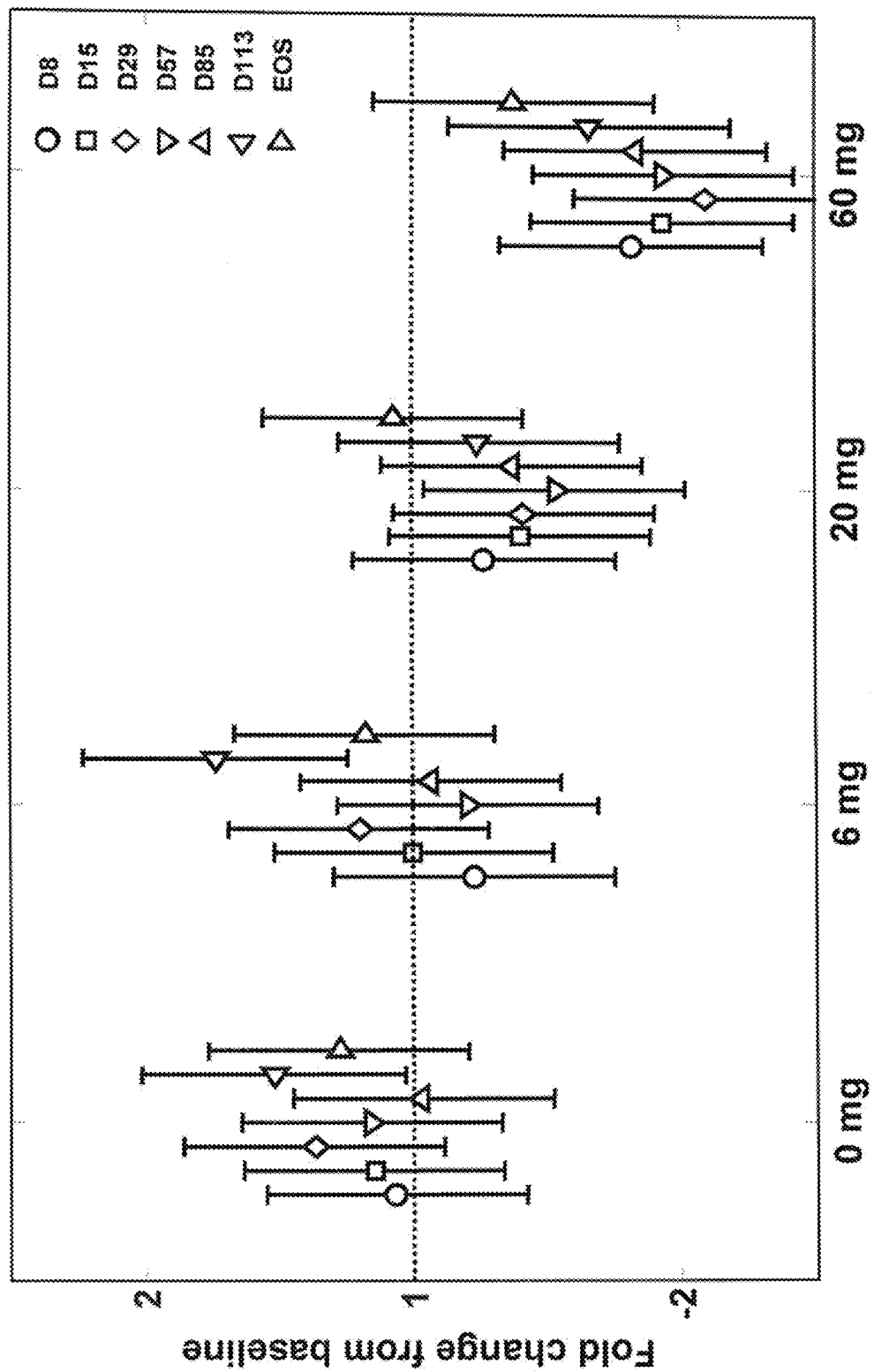
FIG. 8: Dose dependent decrease in CXCL10 protein level in response to multiple doses of AMG 811 in general SLE patients. Symbols (circles, squares, triangles, etc.) indicate the average fold change from baseline values in CXCL10 levels, and the vertical lines represent the 95% confidence interval. The data are from the study described in Example 4. Each group of seven vertical lines represents data from patient samples taken at, from left to right, day 8 (D8), 16 (D16), 29 (D29), 57 (D57), 86 (D86), 113 (D113), and end of study (EOS), as indicated. The dose of AMG 811 administered is indicated below. A dose of zero indicates that those patients received a placebo.
Figure 9:
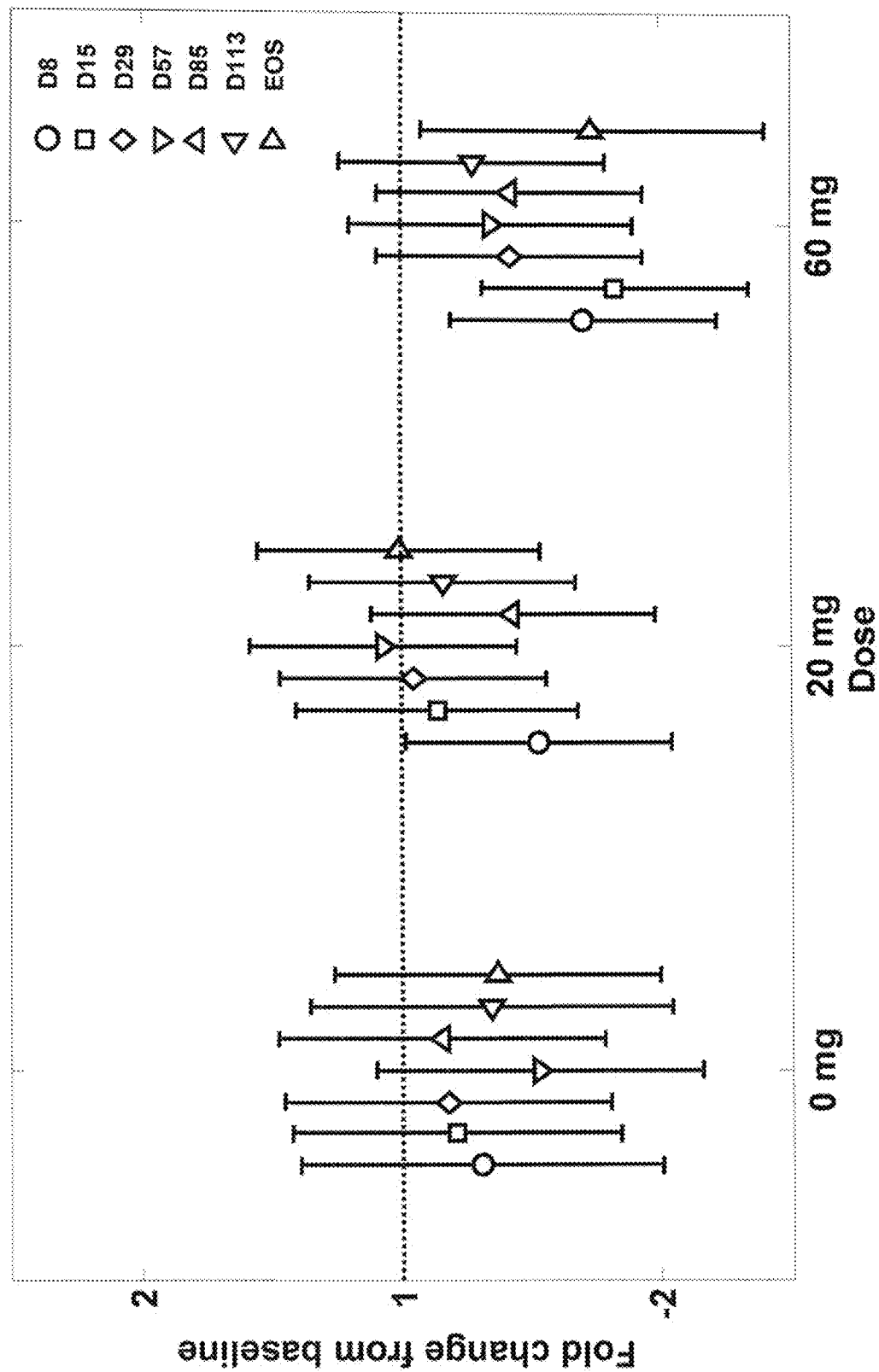
FIG. 9: Dose dependent decrease in CXCL10 (IP-10) protein level in response to multiple doses of AMG 811 in lupus nephritis patients. Symbols (circles, squares, triangles, etc.) indicate the average fold change from baseline values in CXCL10 levels, and the vertical lines represent the 95% confidence interval. Each group of seven vertical lines represents data from patient samples taken at, from left to right, day 8 (D8), 16 (D16), 29 (D29), 57 (D57), 86 (D86), 113 (D113), and end of study (EOS) of the study described in Example 4, with the dose of AMG 811 administered indicated below. A dose of zero indicates that those patients received a placebo.

Data from cohorts 1-3 was combined to create FIG. 8, which shows the fold change from baseline in the expression of CXCL10 at the protein level as measured by ELISA. FIG. 9 shows similar data from the lupus nephritis patients in cohorts 4 and 5, who received multiple doses of 20 mg and 60 mg, respectively. These data indicate that the 20 mg and 60 mg multiple dose regimes used were effective to reduce in vivo expression of CXCL10 among SLE patients, indicating that these dosage regimes are having a biological effect. These data indicate that the 60 mg multiple dose regime did reduce in vivo expression of CXCL10 in lupus nephritis patients at some early time points, although effects were not as clear as those observed in SLE patients without nephritis. Further, lupus nephritis patients dosed with 20 mg of AMG 811 did not exhibit a clear decrease in serum levels of CXCL10. This difference in apparent dosing requirements between SLE and lupus nephritis patients could reflect a generally more highly activated IFN-γ pathway in lupus nephritis patients as compared to SLE patients. More highly expressed IL-18, IP-10, and CCL2 proteins (FIG. 2) are consistent with this interpretation. Further, these data suggest that expression of biomarkers, for example, CXCL10, IL-18, CCL2, etc., could guide dose selection.

Figure 10:
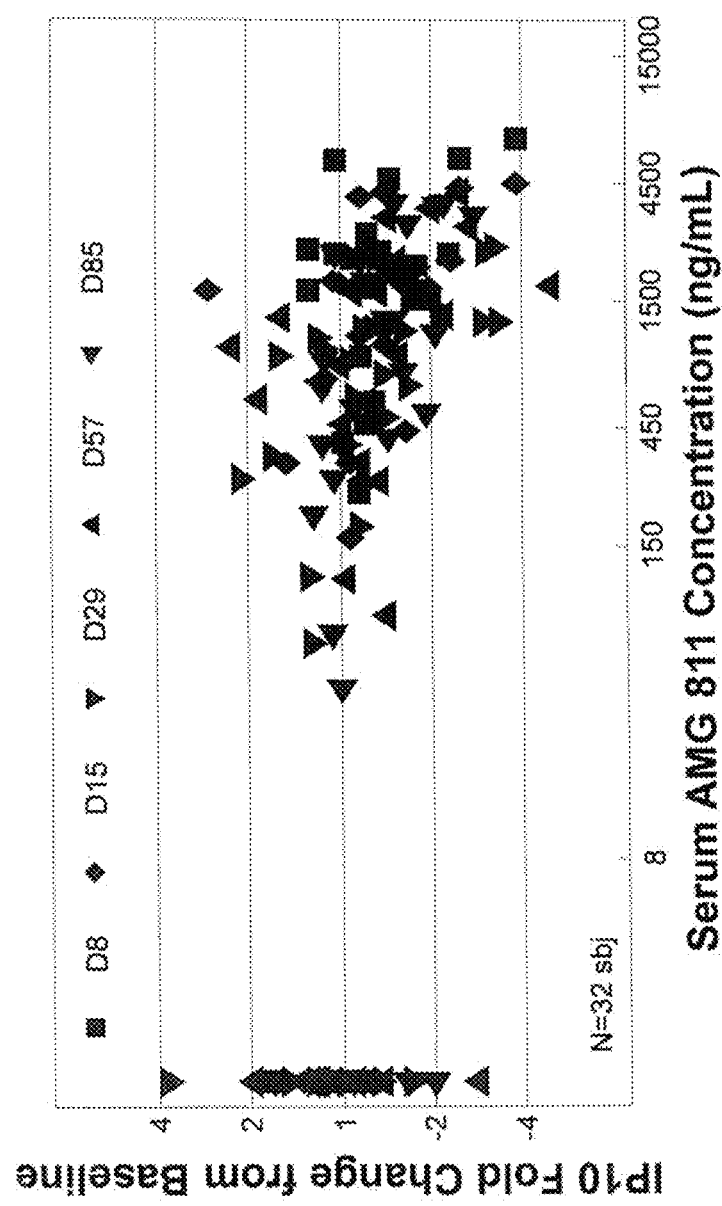
FIG. 10: Relationship between AMG 811 levels and changes in IP-10 (CXCL10) expression in SLE and lupus nephritis patients. This graph shows the AMG 811 concentration (x axis) in peripheral blood of patients plotted against the fold change in IP-10 concentration from baseline for lupus and lupus nephritis patients involved in the trial described in Example 4 at a variety of time points in the trial, as indicated.

The data in FIG. 10 shows serum CXCL10 levels as fold change from baseline plotted against serum concentration of AMG 811 in combined patients with general SLE and with lupus nephritis. Higher levels of AMG 811 correlate with further reduction in CXCL10 levels. This suggests that AMG 811 is reducing CXCL10 levels in these patients.

Data from the single dose clinical trial described above was used to compile a list of genes whose expression is significantly (with a p value<0.001) modulated (either up- or down-regulated) in vivo in SLE patients dosed with AMG 811 as compared to SLE patients dosed with placebo. This list of genes is shown in Table 5 below.

TABLE 5

Genes whose expression is modulated in vivo by AMG 811

| AGILENT ® Probe Designation | Sequence Listing Number of Agilent Probe Sequence | Gene Symbol | NCBI Accession Number of cDNA Sequence | Direction of Modulation by AMG 811 |
| --- | --- | --- | --- | --- |
| A_23_P161428 | SEQ ID NO: 72 | ANKRD22 | NM_144590 | down |
| A_23_P63390 | SEQ ID NO: 73 | FCGR1B | NM_001017986 | down |
| A_23_P62890 | SEQ ID NO: 74 | GBP1 | NM_002053 | down |
| A_23_P338479 | SEQ ID NO: 75 | CD274 | NM_014143 | down |
| A_32_P107372 | SEQ ID NO: 76 | GBP1 | NM_002053 | down |
| A_23_P42353 | SEQ ID NO: 77 | ETV7 | NM_016135 | down |
| A_23_P256487 | SEQ ID NO: 78 | A_23_P256487 | THC2651085 | down |
| A_23_P74290 | SEQ ID NO: 79 | GBP5 | NM_052942 | down |
| A_23_P370682 | SEQ ID NO: 80 | BATF2 | NM_138456 | down |
| A_23_P34915 | SEQ ID NO: 81 | ATF3 | NM_001040619 | down |
| A_24_P243749 | SEQ ID NO: 82 | PDK4 | NM_002612 | down |
| A_23_P7827 | SEQ ID NO: 83 | FAM26F | NM_001010919 | down |
| A_23_P208119 | SEQ ID NO: 84 | PSTPIP2 | NM_024430 | down |
| A_24_P100387 | SEQ ID NO: 85 | GK | NM_203391 | down |
| A_24_P36898 | SEQ ID NO: 86 | A_24_P36898 | AL832451 | down |
| A_32_P44394 | SEQ ID NO: 87 | AIM2 | NM_004833 | down |
| A_24_P274270 | SEQ ID NO: 88 | STAT1 | NM_139266 | down |
| A_23_P56630 | SEQ ID NO: 89 | STAT1 | NM_007315 | down |
| A_23_P85693 | SEQ ID NO: 90 | GBP2 | NM_004120 | down |
| A_24_P322353 | SEQ ID NO: 91 | PSTPIP2 | NM_024430 | down |
| A_23_P63896 | SEQ ID NO: 92 | FAS | NM_000043 | down |
| A_23_P51487 | SEQ ID NO: 93 | GBP3 | NM_018284 | down |
| A_23_P96556 | SEQ ID NO: 94 | GK | NM_203391 | down |
| A_23_P319792 | SEQ ID NO: 95 | XRN1 | NM_019001 | down |
| A_32_P166272 | SEQ ID NO: 96 | STX11 | NM_003764 | down |
| A_24_P196382 | SEQ ID NO: 97 | ATG3 | BC002830 | down |
| A_24_P33895 | SEQ ID NO: 98 | ATF3 | NM_001040619 | down |
| A_23_P347541 | SEQ ID NO: 99 | GRIN3A | NM_133445 | down |
| A_23_P255444 | SEQ ID NO: 100 | DAPP1 | NM_014395 | down |
| A_23_P69383 | SEQ ID NO: 101 | PARP9 | NM_031458 | down |
| A_23_P154235 | SEQ ID NO: 102 | NMI | NM_004688 | down |
| A_24_P7594 | SEQ ID NO: 103 | APOL6 | NM_030641 | down |
| A_32_P11058 | SEQ ID NO: 104 | A_32_P11058 | THC2646969 | down |
| A_23_P202978 | SEQ ID NO: 105 | CASP1 | NM_033292 | down |
| A_24_P350686 | SEQ ID NO: 106 | TIFA | NM_052864 | down |
| A_23_P123608 | SEQ ID NO: 107 | JAK2 | NM_004972 | down |
| A_24_P45446 | SEQ ID NO: 108 | GBP4 | NM_052941 | down |
| A_23_P18452 | SEQ ID NO: 109 | CXCL9 | NM_002416 | down |
| A_23_P121253 | SEQ ID NO: 110 | TNFSF10 | NM_003810 | down |
| A_24_P192805 | SEQ ID NO: 111 | CARD17 | NM_001007232 | down |
| A_24_P687326 | SEQ ID NO: 112 | C9ORF109 | NR_024366 | down |
| A_23_P59005 | SEQ ID NO: 113 | TAP1 | NM_000593 | down |
| A_32_P159254 | SEQ ID NO: 114 | A_32_P159254 | AK123584 | down |
| A_23_P132822 | SEQ ID NO: 115 | XRN1 | NM_019001 | down |
| A_23_P64173 | SEQ ID NO: 116 | CARD16 | NM_001017534 | down |
| A_23_P502797 | SEQ ID NO: 117 | WDFY1 | NM_020830 | down |
| A_32_P131401 | SEQ ID NO: 118 | A_32_P131401 | AI276257 | down |
| A_23_P111000 | SEQ ID NO: 119 | PSMB9 | NM_002800 | down |
| A_32_P34552 | SEQ ID NO: 120 | POLB | NM_002690 | down |
| A_23_P102060 | SEQ ID NO: 121 | SSFA2 | NM_006751 | down |
| A_24_P71938 | SEQ ID NO: 122 | SMAD1 | NM_005900 | down |
| A_32_P74366 | SEQ ID NO: 123 | VCPIP1 | ENST00000310421 | down |
| A_23_P213247 | SEQ ID NO: 124 | FBXL5 | NM_033535 | down |
| A_23_P202199 | SEQ ID NO: 125 | SLK | NM_014720 | down |
| A_24_P370702 | SEQ ID NO: 126 | GBP3 | NM_018284 | down |
| A_24_P937817 | SEQ ID NO: 127 | A_24_P937817 | AK026195 | down |
| A_24_P53051 | SEQ ID NO: 128 | LACTB | NM_171846 | down |
| A_23_P35912 | SEQ ID NO: 129 | CASP4 | NM_033306 | down |
| A_23_P212706 | SEQ ID NO: 130 | ATG3 | NM_022488 | down |
| A_23_P119992 | SEQ ID NO: 131 | VRK2 | NM_006296 | down |
| A_24_P707156 | SEQ ID NO: 132 | A_24_P707156 | BG623116 | down |
| A_24_P156490 | SEQ ID NO: 133 | KCNMA1 | NM_002247 | down |
| A_23_P113263 | SEQ ID NO: 134 | A_23_P113263 | A_23_P113263 | down |
| A_23_P35906 | SEQ ID NO: 135 | CASP4 | NM_033306 | down |
| A_24_P393740 | SEQ ID NO: 136 | FYB | NM_001465 | down |
| A_24_P239606 | SEQ ID NO: 137 | GADD45B | NM_015675 | down |
| A_23_P256445 | SEQ ID NO: 138 | VCPIP1 | NM_025054 | down |
| A_23_P251962 | SEQ ID NO: 139 | ZNF273 | BC019234 | down |
| A_23_P83073 | SEQ ID NO: 140 | HIATL1 | NM_032558 | down |

TABLE 5-continued

Genes whose expression is modulated in vivo by AMG 811

| AGILENT ® Probe Designation | Sequence Listing Number of Agilent Probe Sequence | Gene Symbol | NCBI Accession Number of cDNA Sequence | Direction of Modulation by AMG 811 |
|---|---|---|---|---|
| A_32_P65804 | SEQ ID NO: 141 | A_32_P65804 | THC2661836 | down |
| A_24_P54863 | SEQ ID NO: 142 | C4ORF32 | NM_152400 | down |
| A_23_P356163 | SEQ ID NO: 143 | WDR49 | NM_178824 | down |
| A_32_P35256 | SEQ ID NO: 144 | A_32_P35256 | BF436068 | down |
| A_24_P211689 | SEQ ID NO: 145 | A_24_P211689 | AK021629 | down |
| A_23_P417261 | SEQ ID NO: 146 | EFHB | NM_144715 | down |
| A_23_P407090 | SEQ ID NO: 147 | NFXL1 | NM_152995 | down |
| A_32_P164061 | SEQ ID NO: 148 | A_32_P164061 | A_32_P164061 | down |
| A_23_P102582 | SEQ ID NO: 149 | C20ORF24 | NM_018840 | down |
| A_24_P393353 | SEQ ID NO: 150 | XRN1 | NM_001042604 | down |
| A_24_P50543 | SEQ ID NO: 151 | TRIM69 | BC031266 | down |
| A_24_P920333 | SEQ ID NO: 152 | A_24_P920333 | M748674 | down |
| A_24_P101921 | SEQ ID NO: 153 | A_24_P101921 | ENST00000391612 | down |
| A_23_P382148 | SEQ ID NO: 154 | RAB1A | NM_004161 | down |
| A_24_P43391 | SEQ ID NO: 155 | TMEM165 | NM_018475 | down |
| A_24_P167473 | SEQ ID NO: 156 | ARPC3 | NM_005719 | down |
| A_23_P380901 | SEQ ID NO: 157 | PTH2R | NM_005048 | down |
| A_23_P26583 | SEQ ID NO: 158 | NLRC5 | NM_032206 | down |
| A_24_P263623 | SEQ ID NO: 159 | PTGES3 | NM_006601 | down |
| A_23_P367610 | SEQ ID NO: 160 | SESTD1 | NM_178123 | down |
| A_24_P372223 | SEQ ID NO: 161 | MSR1 | NM_138715 | down |
| A_24_P367326 | SEQ ID NO: 162 | A_24_P367326 | A_24_P367326 | down |
| A_23_P39840 | SEQ ID NO: 163 | VAMP5 | NM_006634 | down |
| A_23_P402892 | SEQ ID NO: 164 | NLRC5 | NM_032206 | down |
| A_23_P211080 | SEQ ID NO: 165 | IFNAR2 | NM_207585 | down |
| A_23_P252106 | SEQ ID NO: 166 | RIPK2 | NM_003821 | down |
| A_23_P12603 | SEQ ID NO: 167 | 40607 | NM_017824 | down |
| A_23_P259272 | SEQ ID NO: 168 | WSB2 | NM_018639 | down |
| A_23_P209805 | SEQ ID NO: 169 | NAB1 | NM_005966 | down |
| A_23_P79942 | SEQ ID NO: 170 | PANK2 | NM_153638 | down |
| A_23_P383053 | SEQ ID NO: 171 | APPBP2 | NM_006380 | down |
| A_23_P147238 | SEQ ID NO: 172 | WSB2 | NM_018639 | down |
| A_23_P90589 | SEQ ID NO: 173 | MRPL44 | NM_022915 | down |
| A_23_P250629 | SEQ ID NO: 174 | PSMB8 | NM_004159 | down |
| A_23_P200560 | SEQ ID NO: 175 | CDC42 | NM_001039802 | down |
| A_24_P390403 | SEQ ID NO: 176 | RTF1 | NM_015138 | down |
| A_24_P269619 | SEQ ID NO: 177 | DECR1 | NM_001359 | down |
| A_23_P71464 | SEQ ID NO: 178 | DECR1 | NM_001359 | down |
| A_23_P164536 | SEQ ID NO: 179 | PIK3C3 | NM_002647 | down |
| A_23_P11915 | SEQ ID NO: 180 | GDAP2 | NM_017686 | down |
| A_23_P74928 | SEQ ID NO: 181 | MR1 | NM_001531 | down |
| A_24_P206736 | SEQ ID NO: 182 | ZNF143 | NM_003442 | down |
| A_23_P12920 | SEQ ID NO: 183 | RAD9A | NM_004584 | up |
| A_23_P56188 | SEQ ID NO: 184 | UBA52 | NM_001033930 | up |
| A_24_P914134 | SEQ ID NO: 185 | PRNP | NM_001080122 | up |
| A_32_P108870 | SEQ ID NO: 186 | PMP2 | NM_002677 | up |
| A_24_P921683 | SEQ ID NO: 187 | FOXP2 | NM_014491 | up |
| A_23_P342612 | SEQ ID NO: 188 | HCN2 | NM_001194 | up |
| A_24_P227326 | SEQ ID NO: 189 | RCOR2 | NM_173587 | up |
| A_23_P111571 | SEQ ID NO: 190 | HOXA3 | NM_153631 | up |
| A_23_P55716 | SEQ ID NO: 191 | BCAM | NM_005581 | up |
| A_23_P397208 | SEQ ID NO: 192 | GSTM2 | NM_000848 | up |
| A_23_P150162 | SEQ ID NO: 193 | DRD4 | NM_000797 | up |
| A_32_P151317 | SEQ ID NO: 194 | A_32_P151317 | BI818647 | up |
| A_24_P142305 | SEQ ID NO: 195 | HBA2 | NM_000517 | up |

The amino acid and protein sequences included in the database entries having the accession numbers listed in Table 5 are incorporated herein by reference. In addition, the sequences of the AGILENT® probes are publicly available in GEO database of NCBI website as mentioned above.

These data indicate that administration of AMG 811 affects expression of many genes in vivo. Among these are a number of genes whose expression is also modulated by IFN-γ ex vivo as described in Example 1 and Table 1 above. A group of genes whose expression is modulated by IFN-γ ex vivo and by AMG 811 in vivo (in opposite directions), is listed in Table 6 below. The thresholds for being included in this list included (a) being included in Table 1 and (b) being significantly (p<0.05) modulated in vivo in patients receiving AMG 811 as compared to patients receiving placebo. This different cutoff value (as compared to p<0.001) for in vivo modulation by AMG 811 is appropriate and was used in view of the fact that this list was selected only from among the genes included in Table 1, rather than from the tens of thousands of genes represented in the array.

TABLE 6

Genes modulated by IFN-γ ex vivo and by AMG 811 in vivo

| Probe Identifier | Sequence Listing Number of Probe Sequence | Symbol | Accession No. of Sequence of cDNA | Direction of modulation by AMG 811 |
|---|---|---|---|---|
| A_23_P103496 | SEQ ID NO: 196 | GBP4 | NM_052941 | down |
| A_23_P105794 | SEQ ID NO: 197 | EPSTI1 | NM_033255 | down |
| A_23_P111000 | SEQ ID NO: 198 | PSMB9 | NM_002800 | down |
| A_23_P112251 | SEQ ID NO: 199 | GNG10 | NM_001017998 | down |
| A_23_P112260 | SEQ ID NO: 200 | GNG10 | NM_001017998 | down |
| A_23_P121253 | SEQ ID NO: 110 | TNFSF10 | NM_003810 | down |
| A_23_P121716 | SEQ ID NO: 201 | ANXA3 | NM_005139 | down |
| A_23_P123608 | SEQ ID NO: 107 | JAK2 | NM_004972 | down |
| A_23_P125278 | SEQ ID NO: 202 | CXCL11 | NM_005409 | down |
| A_23_P128447 | SEQ ID NO: 203 | LRRK2 | NM_198578 | down |
| A_23_P129492 | SEQ ID NO: 204 | SEPX1 | NM_016332 | down |
| A_23_P132388 | SEQ ID NO: 205 | SCO2 | NM_005138 | down |
| A_23_P132822 | SEQ ID NO: 115 | XRN1 | NM_019001 | down |
| A_23_P133133 | SEQ ID NO: 206 | ALPK1 | NM_025144 | down |
| A_23_P133142 | SEQ ID NO: 207 | ALPK1 | NM_025144 | down |
| A_23_P133916 | SEQ ID NO: 208 | C2 | NM_000063 | down |
| A_23_P138680 | SEQ ID NO: 209 | IL15RA | NM_172200 | down |
| A_23_P139123 | SEQ ID NO: 210 | SERPING1 | NM_000062 | down |
| A_23_P140807 | SEQ ID NO: 211 | PSMB10 | NM_002801 | down |
| A_23_P14105 | SEQ ID NO: 212 | RCBTB2 | NM_001268 | down |
| A_23_P14174 | SEQ ID NO: 213 | TNFSF13B | NM_006573 | down |
| A_23_P142424 | SEQ ID NO: 214 | TMEM149 | NM_024660 | down |
| A_23_P145874 | SEQ ID NO: 215 | SAMD9L | NM_152703 | down |
| A_23_P149476 | SEQ ID NO: 216 | EFCAB2 | NM_032328 | down |
| A_23_P153320 | SEQ ID NO: 217 | ICAM1 | NM_000201 | down |
| A_23_P15414 | SEQ ID NO: 218 | SCARF1 | NM_145351 | down |
| A_23_P154235 | SEQ ID NO: 102 | NMI | NM_004688 | down |
| A_23_P155049 | SEQ ID NO: 219 | APOL6 | NM_030641 | down |
| A_23_P155052 | SEQ ID NO: 220 | APOL6 | NM_030641 | down |
| A_23_P156687 | SEQ ID NO: 221 | CFB | NM_001710 | down |
| A_23_P156788 | SEQ ID NO: 222 | STX11 | NM_003764 | down |
| A_23_P160025 | SEQ ID NO: 223 | IFI16 | NM_005531 | down |
| A_23_P160720 | SEQ ID NO: 224 | BATF3 | NM_018664 | down |
| A_23_P161428 | SEQ ID NO: 72 | ANKRD22 | NM_144590 | down |
| A_23_P163079 | SEQ ID NO: 225 | GCH1 | NM_000161 | down |
| A_23_P165624 | SEQ ID NO: 226 | TNFAIP6 | NM_007115 | down |
| A_23_P166408 | SEQ ID NO: 227 | OSM | NM_020530 | down |
| A_23_P166797 | SEQ ID NO: 228 | RTP4 | NM_022147 | down |
| A_23_P168828 | SEQ ID NO: 229 | KLF10 | NM_005655 | down |
| A_23_P17655 | SEQ ID NO: 230 | KCNJ15 | NM_170736 | down |
| A_23_P17837 | SEQ ID NO: 231 | APOL1 | NM_145343 | down |
| A_23_P18452 | SEQ ID NO: 109 | CXCL9 | NM_002416 | down |
| A_23_P18604 | SEQ ID NO: 232 | LAP3 | NM_015907 | down |
| A_23_P202978 | SEQ ID NO: 105 | CASP1 | NM_033292 | down |
| A_23_P203498 | SEQ ID NO: 233 | TRIM22 | NM_006074 | down |
| A_23_P205200 | SEQ ID NO: 234 | DHRS12 | NM_024705 | down |
| A_23_P208119 | SEQ ID NO: 84 | PSTPIP2 | NM_024430 | down |
| A_23_P20814 | SEQ ID NO: 235 | DDX58 | NM_014314 | down |
| A_23_P209625 | SEQ ID NO: 236 | CYP1B1 | NM_000104 | down |
| A_23_P209678 | SEQ ID NO: 237 | PLEK | NM_002664 | down |
| A_23_P210763 | SEQ ID NO: 238 | JAG1 | NM_000214 | down |
| A_23_P211401 | SEQ ID NO: 239 | KREMEN1 | NM_001039570 | down |
| A_23_P211445 | SEQ ID NO: 240 | LIMK2 | NM_016733 | down |
| A_23_P211488 | SEQ ID NO: 241 | APOL2 | NM_145637 | down |
| A_23_P215154 | SEQ ID NO: 242 | NUB1 | NM_016118 | down |
| A_23_P218928 | SEQ ID NO: 243 | C4ORF18 | NM_016613 | down |
| A_23_P24004 | SEQ ID NO: 244 | IFIT2 | NM_001547 | down |
| A_23_P251480 | SEQ ID NO: 245 | NBN | NM_002485 | down |
| A_23_P252106 | SEQ ID NO: 166 | RIPK2 | NM_003821 | down |
| A_23_P255444 | SEQ ID NO: 100 | DAPP1 | NM_014395 | down |
| A_23_P256445 | SEQ ID NO: 138 | VCPIP1 | NM_025054 | down |
| A_23_P256487 | SEQ ID NO: 78 | A_23_P256487 | THC2651085 | down |
| A_23_P257087 | SEQ ID NO: 246 | PDK4 | NM_002612 | down |
| A_23_P258493 | SEQ ID NO: 247 | LMNB1 | NM_005573 | down |
| A_23_P26583 | SEQ ID NO: 158 | NLRC5 | NM_032206 | down |
| A_23_P29953 | SEQ ID NO: 248 | IL15 | NM_172174 | down |
| A_23_P30069 | SEQ ID NO: 249 | DDX60L | NM_001012967 | down |
| A_23_P3221 | SEQ ID NO: 250 | SQRDL | NM_021199 | down |
| A_23_P329261 | SEQ ID NO: 251 | KCNJ2 | NM_000891 | down |
| A_23_P329870 | SEQ ID NO: 252 | RHBDF2 | NM_024599 | down |
| A_23_P335661 | SEQ ID NO: 253 | SAMD4A | AB028976 | down |
| A_23_P338479 | SEQ ID NO: 75 | CD274 | NM_014143 | down |
| A_23_P343837 | SEQ ID NO: 254 | PARP11 | NM_020367 | down |
| A_23_P347040 | SEQ ID NO: 255 | DTX3L | NM_138287 | down |

TABLE 6-continued

Genes modulated by IFN-γ ex vivo and by AMG 811 in vivo

| Probe Identifier | Sequence Listing Number of Probe Sequence | Symbol | Accession No. of Sequence of cDNA | Direction of modulation by AMG 811 |
|---|---|---|---|---|
| A_23_P347541 | SEQ ID NO: 99 | GRIN3A | NM_133445 | down |
| A_23_P35412 | SEQ ID NO: 256 | IFIT3 | NM_001549 | down |
| A_23_P354387 | SEQ ID NO: 257 | MYOF | NM_013451 | down |
| A_23_P358904 | SEQ ID NO: 258 | IKZF4 | NM_022465 | up |
| A_23_P35906 | SEQ ID NO: 135 | CASP4 | NM_033306 | down |
| A_23_P35912 | SEQ ID NO: 129 | CASP4 | NM_033306 | down |
| A_23_P370682 | SEQ ID NO: 80 | BATF2 | NM_138456 | down |
| A_23_P380857 | SEQ ID NO: 259 | APOL4 | NM_030643 | down |
| A_23_P39840 | SEQ ID NO: 163 | VAMP5 | NM_006634 | down |
| A_23_P401106 | SEQ ID NO: 260 | PDE2A | NM_002599 | up |
| A_23_P402892 | SEQ ID NO: 164 | NLRC5 | NM_032206 | down |
| A_23_P41765 | SEQ ID NO: 261 | IRF1 | NM_002198 | down |
| A_23_P420942 | SEQ ID NO: 262 | MT1E | AF495759 | up |
| A_23_P421423 | SEQ ID NO: 263 | TNFAIP2 | NM_006291 | down |
| A_23_P42282 | SEQ ID NO: 264 | C4B | NM_001002029 | up |
| A_23_P42302 | SEQ ID NO: 265 | HLA-DQA2 | NM_020056 | up |
| A_23_P42353 | SEQ ID NO: 77 | ETV7 | NM_016135 | down |
| A_23_P42969 | SEQ ID NO: 266 | FGL2 | NM_006682 | down |
| A_23_P47304 | SEQ ID NO: 267 | CASP5 | NM_004347 | down |
| A_23_P4821 | SEQ ID NO: 268 | JUNB | NM_002229 | down |
| A_23_P48513 | SEQ ID NO: 269 | IFI27 | NM_005532 | up |
| A_23_P51487 | SEQ ID NO: 93 | GBP3 | NM_018284 | down |
| A_23_P53891 | SEQ ID NO: 270 | KLF5 | NM_001730 | down |
| A_23_P56630 | SEQ ID NO: 89 | STAT1 | NM_007315 | down |
| A_23_P56746 | SEQ ID NO: 271 | FAP | NM_004460 | down |
| A_23_P571 | SEQ ID NO: 272 | SLC2A1 | NM_006516 | up |
| A_23_P57983 | SEQ ID NO: 273 | PARP14 | AB033094 | down |
| A_23_P58390 | SEQ ID NO: 274 | C4ORF32 | NM_152400 | down |
| A_23_P59005 | SEQ ID NO: 113 | TAP1 | NM_000593 | down |
| A_23_P62890 | SEQ ID NO: 74 | GBP1 | NM_002053 | down |
| A_23_P63390 | SEQ ID NO: 73 | FCGR1B | NM_001017986 | down |
| A_23_P63896 | SEQ ID NO: 92 | FAS | NM_000043 | down |
| A_23_P64343 | SEQ ID NO: 275 | TIMM10 | NM_012456 | down |
| A_23_P64721 | SEQ ID NO: 276 | GPR109B | NM_006018 | down |
| A_23_P65427 | SEQ ID NO: 277 | PSME2 | NM_002818 | down |
| A_23_P65651 | SEQ ID NO: 278 | WARS | NM_004184 | down |
| A_23_P68155 | SEQ ID NO: 279 | IFIH1 | NM_022168 | down |
| A_23_P68851 | SEQ ID NO: 280 | KREMEN1 | NM_001039570 | down |
| A_23_P69109 | SEQ ID NO: 281 | PLSCR1 | NM_021105 | down |
| A_23_P69310 | SEQ ID NO: 282 | CCRL2 | NM_003965 | down |
| A_23_P69383 | SEQ ID NO: 101 | PARP9 | NM_031458 | down |
| A_23_P72737 | SEQ ID NO: 283 | IFITM1 | NM_003641 | down |
| A_23_P74001 | SEQ ID NO: 284 | S100A12 | NM_005621 | down |
| A_23_P74290 | SEQ ID NO: 79 | GBP5 | NM_052942 | down |
| A_23_P75430 | SEQ ID NO: 285 | C11ORF75 | NM_020179 | down |
| A_23_P75741 | SEQ ID NO: 286 | UBE2L6 | NM_198183 | down |
| A_23_P7827 | SEQ ID NO: 83 | FAM26F | NM_001010919 | down |
| A_23_P79518 | SEQ ID NO: 287 | IL1B | NM_000576 | down |
| A_23_P81898 | SEQ ID NO: 288 | UBD | NM_006398 | down |
| A_23_P83098 | SEQ ID NO: 289 | ALDH1A1 | NM_000689 | down |
| A_23_P8513 | SEQ ID NO: 290 | SNX10 | NM_013322 | down |
| A_23_P85693 | SEQ ID NO: 90 | GBP2 | NM_004120 | down |
| A_23_P85783 | SEQ ID NO: 291 | PHGDH | NM_006623 | up |
| A_23_P86390 | SEQ ID NO: 292 | NRP1 | NM_003873 | up |
| A_23_P87709 | SEQ ID NO: 293 | FLJ22662 | NM_024829 | down |
| A_23_P9232 | SEQ ID NO: 294 | GCNT1 | NM_001490 | down |
| A_23_P94412 | SEQ ID NO: 295 | PDCD1LG2 | NM_025239 | down |
| A_23_P96556 | SEQ ID NO: 94 | GK | NM_203391 | down |
| A_23_P97064 | SEQ ID NO: 296 | FBXO6 | NM_018438 | down |
| A_24_P100387 | SEQ ID NO: 85 | GK | NM_203391 | down |
| A_24_P124032 | SEQ ID NO: 297 | RIPK2 | NM_003821 | down |
| A_24_P156490 | SEQ ID NO: 133 | KCNMA1 | NM_002247 | down |
| A_24_P15702 | SEQ ID NO: 298 | LOC389386 | XR_017251 | down |
| A_24_P161018 | SEQ ID NO: 299 | PARP14 | NM_017554 | down |
| A_24_P165864 | SEQ ID NO: 300 | P2RY14 | NM_014879 | down |
| A_24_P167642 | SEQ ID NO: 301 | GCH1 | NM_000161 | down |
| A_24_P172481 | SEQ ID NO: 302 | TRIM22 | NM_006074 | down |
| A_24_P184445 | SEQ ID NO: 303 | MMP19 | NM_002429 | up |
| A_24_P212481 | SEQ ID NO: 304 | MCTP1 | NM_024717 | down |
| A_24_P222655 | SEQ ID NO: 305 | C1QA | NM_015991 | down |
| A_24_P243749 | SEQ ID NO: 82 | PDK4 | NM_002612 | down |
| A_24_P245815 | SEQ ID NO: 306 | ASPHD2 | NM_020437 | down |
| A_24_P250922 | SEQ ID NO: 307 | PTGS2 | NM_000963 | down |
| A_24_P251764 | SEQ ID NO: 308 | CXCL3 | NM_002090 | up |

TABLE 6-continued

Genes modulated by IFN-γ ex vivo and by AMG 811 in vivo

| Probe Identifier | Sequence Listing Number of Probe Sequence | Symbol | Accession No. of Sequence of cDNA | Direction of modulation by AMG 811 |
|---|---|---|---|---|
| A_24_P270460 | SEQ ID NO: 309 | IFI27 | NM_005532 | up |
| A_24_P274270 | SEQ ID NO: 88 | STAT1 | NM_139266 | down |
| A_24_P278126 | SEQ ID NO: 310 | NBN | NM_002485 | down |
| A_24_P303091 | SEQ ID NO: 311 | CXCL10 | NM_001565 | down |
| A_24_P304154 | SEQ ID NO: 312 | AMPD3 | NM_001025390 | down |
| A_24_P322353 | SEQ ID NO: 91 | PSTPIP2 | NM_024430 | down |
| A_24_P323148 | SEQ ID NO: 313 | LYPD5 | NM_182573 | down |
| A_24_P334361 | SEQ ID NO: 314 | DDX60 | NM_017631 | down |
| A_24_P350686 | SEQ ID NO: 106 | TIFA | NM_052864 | down |
| A_24_P36898 | SEQ ID NO: 86 | A_24_P36898 | AL832451 | down |
| A_24_P370702 | SEQ ID NO: 126 | GBP3 | NM_018284 | down |
| A_24_P372625 | SEQ ID NO: 315 | RNF141 | NM_016422 | down |
| A_24_P382319 | SEQ ID NO: 316 | CEACAM1 | NM_001712 | down |
| A_24_P383523 | SEQ ID NO: 317 | SAMD4A | NM_015589 | down |
| A_24_P393353 | SEQ ID NO: 318 | XRN1 | NM_001042604 | down |
| A_24_P45446 | SEQ ID NO: 108 | GBP4 | NM_052941 | down |
| A_24_P47329 | SEQ ID NO: 319 | A_24_P47329 | BC063641 | down |
| A_24_P48204 | SEQ ID NO: 320 | SECTM1 | NM_003004 | down |
| A_24_P48898 | SEQ ID NO: 321 | APOL2 | NM_145637 | down |
| A_24_P53051 | SEQ ID NO: 128 | LACTB | NM_171846 | down |
| A_24_P54863 | SEQ ID NO: 142 | C4ORF32 | NM_152400 | down |
| A_24_P561165 | SEQ ID NO: 322 | A_24_P561165 | A_24_P561165 | down |
| A_24_P659202 | SEQ ID NO: 323 | A_24_P659202 | THC2527772 | up |
| A_24_P66027 | SEQ ID NO: 324 | APOBEC3B | NM_004900 | down |
| A_24_P7594 | SEQ ID NO: 103 | APOL6 | NM_030641 | down |
| A_24_P87931 | SEQ ID NO: 325 | APOL1 | NM_145343 | down |
| A_24_P912985 | SEQ ID NO: 326 | A_24_P912985 | A_24_P912985 | down |
| A_24_P928052 | SEQ ID NO: 327 | NRP1 | NM_003873 | down |
| A_24_P935819 | SEQ ID NO: 328 | SOD2 | BC016934 | down |
| A_24_P935986 | SEQ ID NO: 329 | BCAT1 | NM_005504 | down |
| A_24_P941167 | SEQ ID NO: 330 | APOL6 | NM_030641 | down |
| A_24_P941912 | SEQ ID NO: 331 | DTX3L | NM_138287 | down |
| A_24_P943205 | SEQ ID NO: 332 | EPSTI1 | AL831953 | down |
| A_24_P97342 | SEQ ID NO: 333 | PROK2 | NM_021935 | down |
| A_24_P98109 | SEQ ID NO: 334 | SNX10 | NM_013322 | down |
| A_24_P98210 | SEQ ID NO: 335 | TFEC | NM_012252 | down |
| A_32_P107372 | SEQ ID NO: 76 | GBP1 | NM_002053 | down |
| A_32_P15169 | SEQ ID NO: 336 | A_32_P15169 | A_32_P15169 | down |
| A_32_P156746 | SEQ ID NO: 337 | A_32_P156746 | BE825944 | down |
| A_32_P162183 | SEQ ID NO: 338 | C2 | NM_000063 | down |
| A_32_P166272 | SEQ ID NO: 96 | STX11 | NM_003764 | down |
| A_32_P184394 | SEQ ID NO: 339 | TFEC | NM_012252 | down |
| A_32_P191417 | SEQ ID NO: 340 | A_32_P191417 | AW276186 | down |
| A_32_P222250 | SEQ ID NO: 341 | A_32_P222250 | AF119908 | down |
| A_32_P30004 | SEQ ID NO: 342 | A_32_P30004 | AF086044 | down |
| A_32_P399546 | SEQ ID NO: 343 | ARNTL2 | AF256215 | down |
| A_32_P44394 | SEQ ID NO: 87 | AIM2 | NM_004833 | down |
| A_32_P56759 | SEQ ID NO: 344 | PARP14 | NM_017554 | down |
| A_32_P91773 | SEQ ID NO: 345 | A_32_P91773 | THC2544236 | down |
| A_32_P92415 | SEQ ID NO: 346 | A_32_P92415 | AA455656 | down |
| A_32_P95082 | SEQ ID NO: 347 | CNTLN | NM_017738 | down |
| A_32_P9543 | SEQ ID NO: 348 | APOBEC3A | NM_145699 | down |

Assaying for levels of expression of one or more of the genes in Tables 1, 2, 4, 5, and/or 6 in a biological sample from a diseased patient, optionally an SLE patient, before treatment with an IFN-γ inhibitor, such as AMG 811, and comparison to levels of expression in a control biological sample can indicate which patients might benefit from treatment with an IFN-γ inhibitor. Patients expressing elevated levels of an RNA or protein that is downregulated in vivo by AMG 811 or decreased levels of an RNA or protein that is upregulated by AMG 811 in vivo might benefit from treatment with an IFN-γ inhibitor. Similarly, patients expressing elevated or lowered levels of an RNA or protein that is up- or down-regulated by IFN-γ could also benefit from treatment with an IFN-γ inhibitor. Further, comparison of expression levels of one or more of the genes listed in Tables 1, 2, 4, 5, and/or 6 before and after treatment with an IFN-γ inhibitor can indicate whether the IFN-γ inhibitor is having a biological effect in a particular patient in vivo. If so, continuing treatment can be advantageous for that patient. If not, treatment can be discontinued, or the IFN-γ inhibitor can be administered at a higher dose or at a greater frequency.

Figure 11:
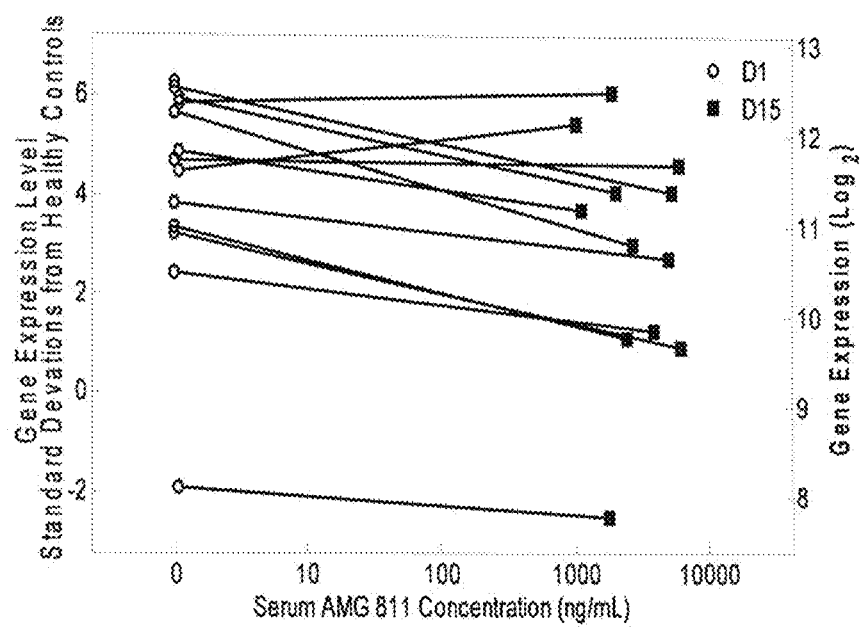
FIG. 11: Relationship between AMG 811 serum concentration and GBP1 transcript expression in lupus nephritis patients. Blood samples were taken from lupus nephritis patients at baseline and on day 15 in the multi-dose clinical trial described in Example 4. The x axis indicates the serum concentration of AMG 811, and they axis indicates the fold difference in guanylate binding protein 1 (GBP1) RNA expression from that seen in a control group of healthy people.

In FIG. 11, levels of GBP1 transcript versus AMG 811 concentration in serum on days 1 and 15 of the study in lupus nephritis patients are plotted. Comparing FIG. 11 to the right panel of FIG. 3, which contains similar data from SLE patients, a number of conclusions can be made. First, lupus nephritis patients as a group have higher levels of GBP1 expression at baseline than SLE patients as a group. Further, whereas all SLE patients exhibited a decrease in GBP1 expression upon administration of AMG 811, this was not true for lupus nephritis patients. Also, the magnitude of the decreases observed among general SLE patients was apparently greater than the decreases observed among lupus nephritis patients. Hence, these data indicate that SLE and lupus nephritis patients, as groups, have different responses to AMG 811. These differences may be related to differences in the nature and severity of disease activity in these two groups and may indicate that dosing requirements can differ between these two categories of patients. These data also suggest that expression of biomarkers such as GBP1 could inform dose selection. For example, patients having, for example, higher GBP1 expression could require higher doses of AMG 811, whereas patients with lower GBP1 expression could require lower doses of AMG 811.

Clinical parameters related to kidney function were assessed for patients in cohorts 4 and 5 in this trial. Spot urine protein, spot urine creatinine, 24 hour urine protein, 24 hour urine creatinine, serum creatinine, serum albumin, antibodies against double stranded DNA, and complement factors C3 and C4 were assessed.

Urine protein amounts were determined by a dye-binding assay (pyrocatechol violet-ammounium molybdate dye) analyzed in a "dry slide" format using an automated laboratory analyzer. Samples used were either a collection of all the patient's urine over a 24 hour period (24 hour urine protein) or a single urine sample (spot urine protein). Urine creatinine was assessed by a multi-step coupled enzymatic two-point rate colorimetric assay (creatininie amidohydrolase/creatine amidinohydrolase/sarcosine oxidase/peroxidase) analyzed using a "dry slide" format in an automated laboratory analyzer.

Figure 12:
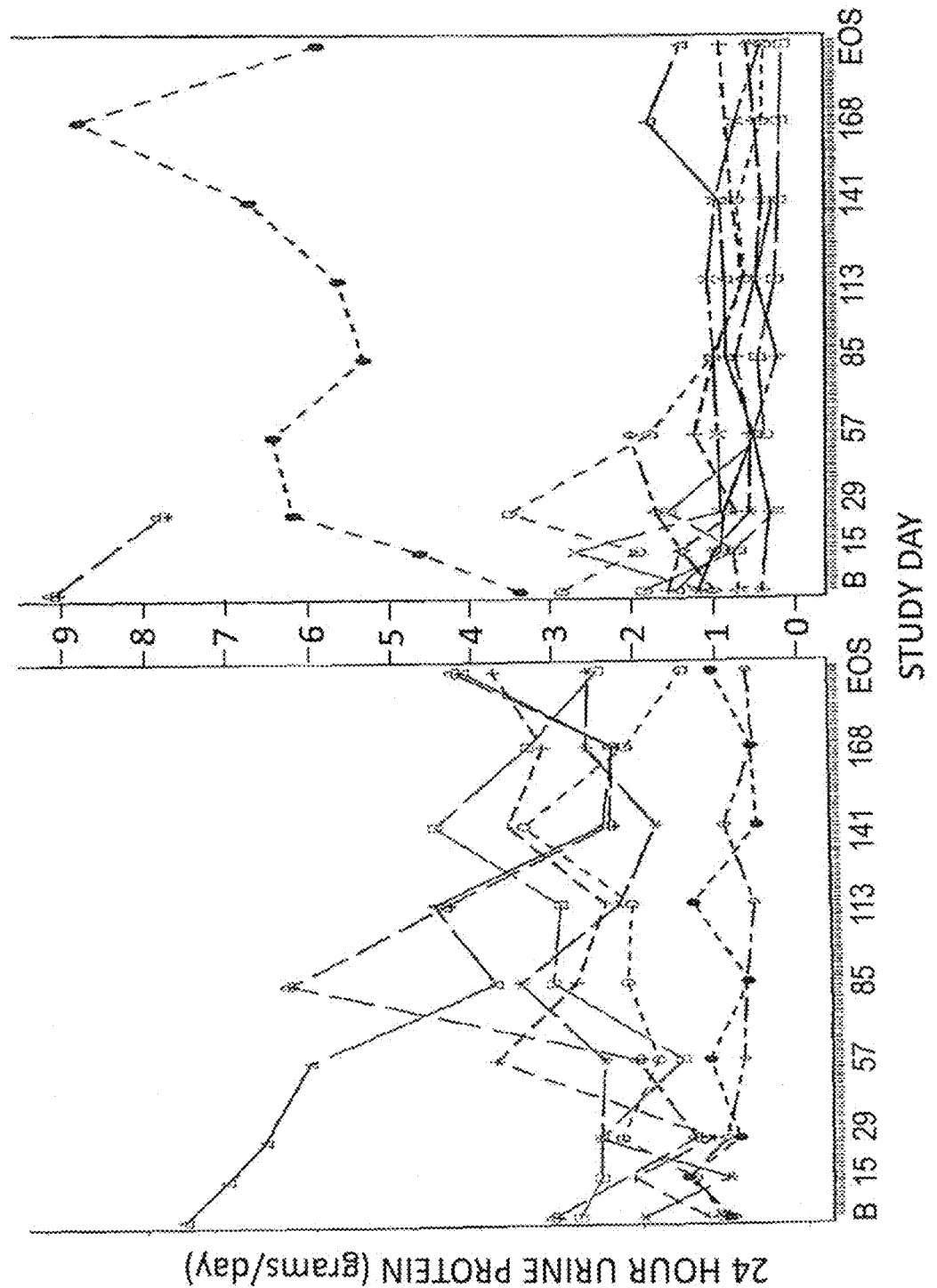
FIG. 12: Blinded data showing the amount of protein detected in 24-hour urine samples from lupus nephritis patients treated with multiple doses of AMG 811 or placebo. This graph show the levels of protein in twenty four hour urine samples from lupus nephritis patients from cohorts 4 (left panel) and 5 (right panel) of the clinical trial described in Example 4. Cohort 4 contained eight patients, two of which received placebo and six of which received 3 doses of 20 mg of AMG 811. Cohort 5 contained 12 patients, three of which received placebo and nine of which received three doses of 60 mg of AMG 811.
Figure 13:
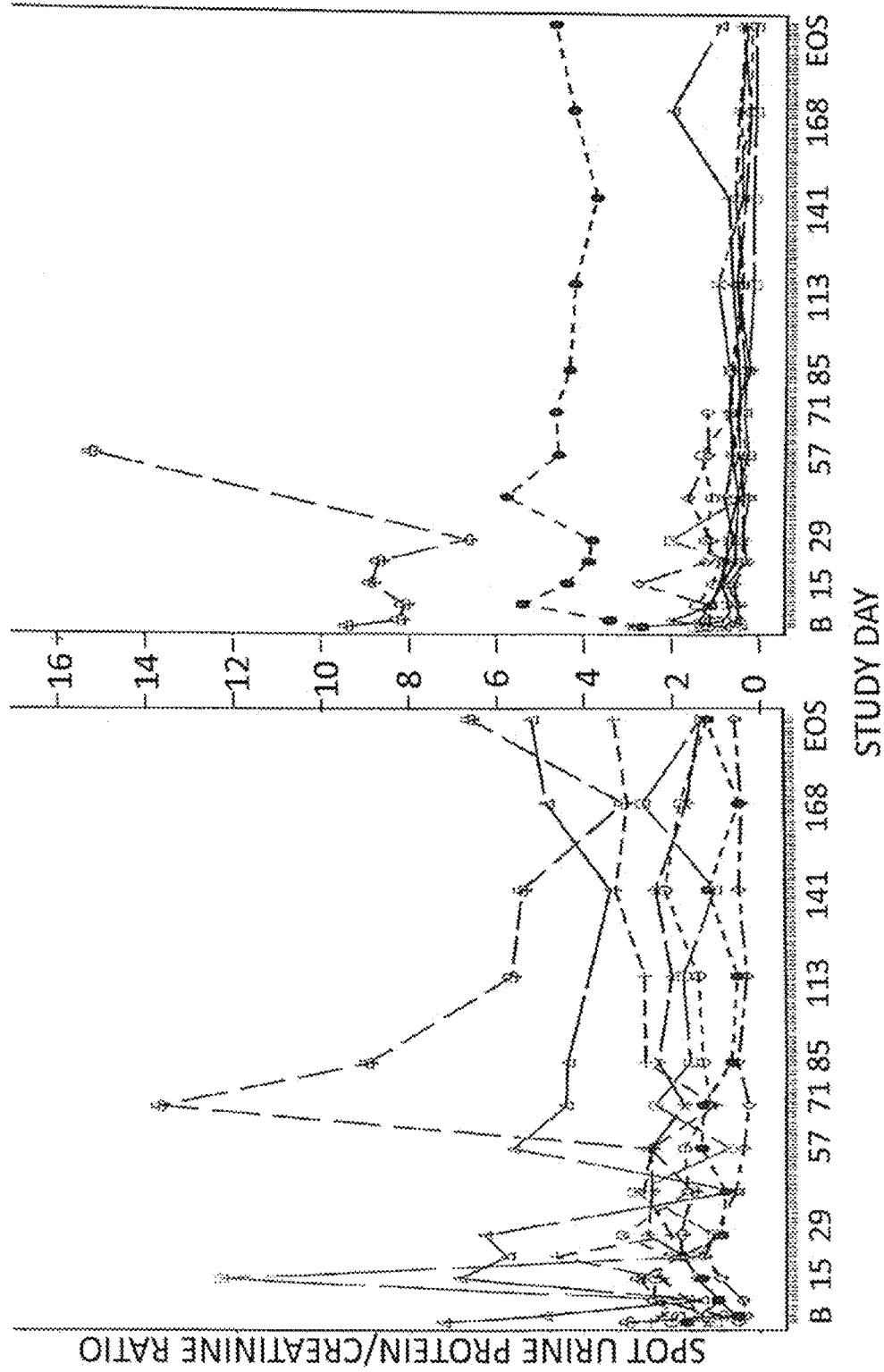
FIG. 13: Blinded spot urine protein/creatinine ratio (UPCR) in lupus nephritis patients. Blinded data showing the UPCR of patients in cohorts 4 (left panel) and 5 (right panel) at various time points during the clinical trial described in Example 4. Cohort 4 contained eight patients, two of which received placebo and six of which received three doses of 20 mg of AMG 811. Cohort 5 contained 12 patients, three of which received placebo and nine of which received three doses of 60 mg of AMG 811.

Cohorts 4 and 5 comprised lupus nephritis patients receiving doses of 20 mg or 60 mg AMG 811, respectively, or placebo. Although some results from these cohorts are now available, the results are still blinded. Since only two of eight (cohort 4) and three of twelve (cohort 5) patients received placebo, differences in clinical parameters between cohorts 4 and 5 might indicate dose-dependent responses to AMG 811. Among the various measurements made, the following tests indicated no clear difference between cohorts 4 and 5: spot urine creatinine, 24 hour urine creatinine, serum creatinine, serum albumin, complement factors C3 and C4, and anti-double stranded DNA antibodies. On the other hand, urine protein in a 24 hour urine collection and the ratio of urine protein to urine creatinine (UPCR) clearly differed between cohorts 4 and 5, as shown in FIGS. 12 and 13. High amounts of urine protein and/or high UPCR indicate impairment of kidney function. Since all but two of the patients in cohort 4 and two or three in cohort 5 received AMG 811, these data suggest that AMG 811 may have a dose-dependent effect on kidney function in lupus nephritis patients. More specifically, these results suggest that a dose of more than 20 mg of AMG 811 is necessary to have a positive effect on kidney function in lupus nephritis patients.

Example 5

Single Dose Trial in Discoid Lupus

A phase 1b single dose crossover study in discoid lupus has been enrolled. Sixteen subjects (of twenty planned subjects) with discoid lupus were dosed with a single dose of 180 milligrams of AMG 811 and a single dose of placebo, each administered subcutaneously, in one of two sequences. Per study protocol, twelve patients were to receive 180 mg SC of AMG 811 on day 1 and a dose of placebo on day 85, and eight patients were to receive a dose of placebo on day 1 and 180 mg SC of AMG 811 on day 85. However, enrollment of the study was stopped after sixteen patients had been enrolled. As primary endpoints of the study, treatment-emergent adverse events, vital signs, clinical laboratory tests, ECGs, and the incidence of binding and neutralizing antibodies to AMG 811 were monitored. Physical examinations were also to be performed.

In secondary endpoints of the study, the pharmacokinetic profile of AMG 811 is determined, and CLASI scores are determined. Expression of biomarkers in peripheral blood at the RNA level are assessed by hybridization to a DNA array as described above in samples taken at baseline (in the time period from three days prior to dosing to one day prior to dosing) and on days 15, 29, 57, 85, 99, 113, 141, 169, and 197 (which is the end of study). Analysis of selected biomarkers at the protein level by ELISA may also be performed. In addition, skin samples were taken at baseline and on days 15 and 57 for analysis of biomarker expression at the RNA level by hybridization to a DNA array. Selected biomarkers may also be assayed at the protein level in the skin samples using immunohistochemistry, immunofluorescence, or ELISA. Information available to date indicates that clinical parameters, such as improvements in the CLASI score, did not correlate clearly with dosing of AMG 811. The results of this trial are still blinded.

Example 6

Single Dose Trial in Psoriasis

A phase 1b single dose, double-blind, placebo-controlled study in psoriasis is in progress. Nine subjects) were enrolled in the study. The study is still blinded. Proceeding with a study plan that originally included ten, not nine, patients, seven or eight patients will receive drug, and one or two patients will receive placebo. Those that receive drug will receive (or have received) a single dose of 180 milligrams of AMG 811 on study day 1. As primary endpoints of the study, treatment-emergent adverse events, vital signs, clinical laboratory tests, ECGs, and the incidence of binding and neutralizing antibodies to AMG 811 were monitored. Physical examinations were also performed.

As secondary endpoints, clinicians assessed PASI scores, PGA scores, and target lesions. Photos were taken to document skin lesions. The pharmacokinetic profile of AMG 811 will also be determined. All of these primary and secondary endpoints were assessed at baseline (from three days to one day before dosing) and on days 15, 29, 43, 57, 85, and 113 (which is the end of study). Skin biopsies were taken at baseline and at baseline and on days 15 and 57 for analysis of biomarker expression at the RNA level as described above. In addition selected biomarkers may be assessed for expression at the protein level by ELISA for serum samples or by immunohistochemistry or immunofluorescence for skin biopsies.

Figure 14:
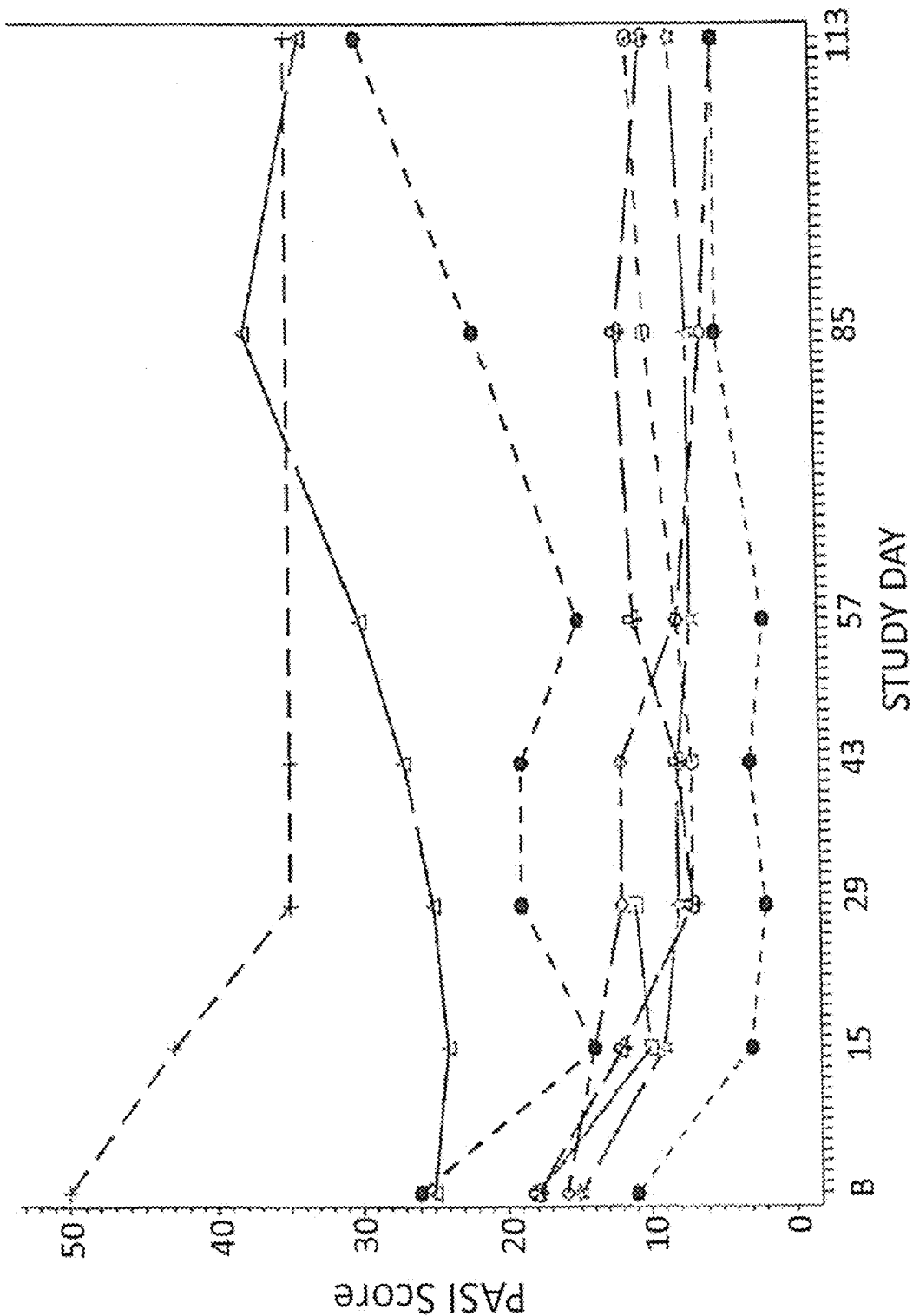
FIG. 14: Blinded data showing PASI scores of psoriasis patients treated with AMG 811 or placebo. This graph shows the PASI scores (y axis) of individual psoriasis patients treated with AMG 811 or placebo at various time points during the trial described in Example 6, as indicated along the x axis. The baseline measurement (B) was taken one to three days prior to the single dose of AMG 811 administered on day 1 of the study.

In FIG. 14, blinded data showing PASI scores for the nine patients in this trial are displayed. Given the design of the trial, one or two of these patients received placebo, and seven or eight received AMG 811. All but one of these eight patients experienced a decrease, i.e., an improvement, in PASI score at some or all post-dose time points, a result indicating that most patients receiving AMG 811 experienced at least a temporary clinical benefit. However, since the data is blinded and one or two of these patients received placebo, the effects of AMG 811 on PASI scores will be more clear when the data is unblinded.

What is claimed is:

1. A method for treating a patient suffering from an IFN-γ-mediated disease comprising administering to the patient a monoclonal anti-human interferon gamma (anti-huIFN-γ) antibody at a dose of 60 milligrams or 180 milligrams,
wherein the anti-huIFN-γ antibody has a heavy chain complementarity determining region 1 (CDR1) comprising the amino acid sequence of SEQ ID NO:34, a heavy chain complementarity determining region 2 (CDR2) comprising the amino acid sequence of SEQ ID NO:35, a heavy chain complementarity determining region 3 (CDR3) comprising the amino acid sequence of SEQ ID NO:36, a light chain CDR1 comprising the amino acid sequence of SEQ ID NO:38, a light chain CDR2 comprising the amino acid sequence of SEQ ID NO:41, and a light chain CDR3 comprising the amino acid sequence of SEQ ID NO:43.

2. The method of claim 1, wherein the heavy chain variable region of the antibody comprises the amino acid sequence of SEQ ID NO:6.

3. The method of claim 2, wherein the light chain variable region of the antibody comprises the amino acid sequence of SEQ ID NO:8.

4. The method of claim 3, wherein the heavy chain variable region and the light chain variable region comprise, respectively, SEQ ID NO:6 and SEQ ID NO:8.

5. The method of claim 1, wherein a glucocorticoid and/or mycophenolate mofetil, azathioprine, leflunomide, methotrexate, or an anti-malarial is concurrently administered to the patient.

6. The method of claim 1, wherein expression at the RNA or protein level of one or more gene(s) listed in Table 1, 2, 4, 5, and/or 6 in a biological sample from the patient taken before the antibody is administered deviates from expression of that gene(s) in a control biological sample in a direction consistent with excess IFN-γ.

7. The method of claim 6, wherein the expression of at least five genes listed in Table 5 and/or 6 in the biological sample from the patient deviates from the expression of those genes in the control biological sample in a direction consistent with excess IFN-γ.

8. The method of claim 6, wherein the biological sample from the patient exhibits elevated expression at the RNA or protein level as compared to expression in the control biological sample of one or more of the following genes: indoleamine 2,3-dioxygenase 1 (INDO1), ankyrin repeat domain 22 (ANKRD22), chemokine (C—X—C motif) ligand 9 (CXCL9), family with sequence similarity 26, member F (FAM26F), purinergic receptor P2Y, G-protein coupled, 14 (P2RY14), guanylate binding binding protein 5 (GBP5), serpin peptidase inhibitor, clade G, member 1 (SERPING1), Fc fragment of IgG, high affinity Ib, receptor (CD64), guanylate binding protein 1, interferon-inducible, 67 kDa (GBP1), chemokine (C—X—C motif) ligand 10 (CXCL10), ets variant 7 (ETV7), programmed death ligand-1 (PD-L1), basic leucine zipper transcription factor, ATF-like 2 (BATF2), Fc fragment of IgG, high affinity Ib, receptor (FCGR1B or CD64), activating transcription factor 3 (ATF3), pyruvate dehydrogenase kinase, isozyme 4 (nuclear gene encoding mitochondrial protein; PDK4), and/or CD274.

9. The method of claim 1, wherein the IFN-γ-mediated disease is selected from the group consisting of systemic lupus erythematosus (SLE), including discoid lupus and lupus nephritis, inflammatory bowel disease, Crohn's disease, ulcerative colitis, and psoriasis.

10. The method of claim 9, wherein the IFN-γ-mediated disease is SLE.

11. The method of claim 10, wherein the IFN-γ-mediated disease is lupus nephritis.

12. The method of claim 1, wherein the antibody is a human IgG1 antibody.

13. A method for treating a patient having an IFN-γ-mediated disease comprising administering to the patient a therapeutically effective dose an anti-huIFN-γ antibody,
wherein the anti-huIFN-γ antibody has a heavy chain CDR1 comprising the amino acid sequence of SEQ ID NO:34, a heavy chain CDR2 comprising the amino acid sequence of SEQ ID NO:35, a heavy chain CDR3 comprising the amino acid sequence of SEQ ID NO:36, a light chain CDR1 comprising the amino acid sequence of SEQ ID NO:38, a light chain CDR2 comprising the amino acid sequence of SEQ ID NO:41, and a light chain CDR3 comprising the amino acid sequence of SEQ ID NO:43, and wherein the level(s) of expression in a biological sample taken from the patient before administration of the antibody of one or more genes listed in Table 1, 2, 4, 5, and/or 6 at the RNA or protein level deviate from the level(s) of expression of the gene(s) in a control biological sample in a direction consistent with excess IFN-γ.

14. The method of claim 13, wherein the levels expression in the biological sample of at least 5 genes from Table 5 and/or 6 deviate from the levels of expression of the genes in the control biological sample in a direction consistent with excess IFN-γ.

15. The method of claim 13, wherein the antibody comprises the amino acid sequences of SEQ ID NO:6 and SEQ ID NO:8.

16. The method of claim 13, wherein the dose administered is 60 mg or 180 mg.

17. The method of claim 13, wherein the IFN-γ-mediated disease is SLE, an inflammatory bowel disease, or psoriasis patient.

18. The method of claim 17, wherein the IFN-γ-mediated disease is SLE.

19. The method of claim 18, wherein IFN-γ-mediated disease is lupus nephritis.

20. The method of claim 13, wherein a glucocorticoid and/or mycophenolate mofetil, azathioprine, leflunomide, methotrexate, or an anti-malarial is concurrently administered to the patient.

21. A method for treating a patient suffering from SLE, an inflammatory bowel disease, or psoriasis comprising:
  (a) taking a biological sample from the patient before administering a human anti-huIFN-γ antibody in step (b), wherein the level(s) of expression at the RNA or protein level in the biological sample from the patient of one or more of the genes in Table(s) 2, 4, 5, and/or 6 is determined;
  (b) administering to the patient a pharmacodynamically effective dose of the human anti-huIFN-γ antibody, wherein the antibody has a heavy chain complementarity determining region 1 (CDR1) comprising the amino acid sequence of SEQ ID NO:34, a heavy chain complementarity determining region 2 (CDR2) comprising the amino acid sequence of SEQ ID NO:35, a heavy chain complementarity determining region 3 (CDR3) comprising the amino acid sequence of SEQ ID NO:36, a light chain CDR1 comprising the amino acid sequence of SEQ ID NO:38, a light chain CDR2 comprising the amino acid sequence of SEQ ID NO:41, and a light chain CDR3 comprising the amino acid sequence of SEQ ID NO:43;
  (c) taking a second biological sample taken from the patient after administration of the antibody, wherein the level(s) of expression of the gene(s) of step (a) in the second biological sample are determined; and
  (d) if the level(s) of expression of the gene(s) in the second biological sample determined in step (c), as compared to the level(s) of expression in the biological sample determined in step (a)
    (i) is modulated in a direction consistent with inhibition of IFN-γ, then continuing treatment of the patient with another pharmacodynamically effective dose of the antibody or
    (ii) is substantially the same as that in the biological sample of (a) or if the level of expression of the gene(s) in second biological sample of (c) deviates from the level of expression in the biological sample of (a) in a direction that is consistent with an excess of IFN-γ, then discontinuing treatment with the anti-human IFN-γ antibody.

22. The method of claim 21, wherein the pharmacodynamically effective dose is 60 mg or 180 mg.

23. The method of claim 21, wherein the heavy chain variable region of the antibody comprises the amino acid sequence of SEQ ID NO:6 and the light chain variable region of the antibody comprises the amino acid sequence of SEQ ID NO:8.

24. The method of claim 21, wherein the patient has SLE.

25. The method of claim 24, wherein the patient has lupus nephritis.

26. The method of claim 21, wherein a glucocorticoid and/or mycophenolate mofetil, azathioprine, leflunomide, methotrexate, or an anti-malarial is concurrently administered to the patient.

27. The method of claim 21, wherein the patient has psoriasis, Crohn's disease, or ulcerative colitis.

28. The method of claim 21, wherein the level(s) of expression of one or more of the following genes at the protein or RNA level is determined in steps (a) and (c): indoleamine 2,3-dioxygenase 1 (INDO1), ankyrin repeat domain 22 (ANKRD22), chemokine (C—X—C motif) ligand 9 (CXCL9), family with sequence similarity 26, member F (FAM26F), purinergic receptor P2Y, G-protein coupled, 14 (P2RY14), guanylate binding binding protein 5 (GBP5), serpin peptidase inhibitor, clade G, member 1 (SERPING1), Fc fragment of IgG, high affinity Ib, receptor (CD64), guanylate binding protein 1, interferon-inducible, 67 kDa (GBP1), chemokine (C—X—C motif) ligand 10 (CXCL10), ets variant 7 (ETV7), programmed death ligand-1 (PD-L1), basic leucine zipper transcription factor, ATF-like 2 (BATF2), Fc fragment of IgG, high affinity Ib, receptor (FCGR1B or CD64), activating transcription factor 3 (ATF3), pyruvate dehydrogenase kinase, isozyme 4 (nuclear gene encoding mitochondrial protein; PDK4), and/or CD274.

29. The method of claim 28, wherein the level of expression of CXCL10 is determined in steps (a) and (c).

* * * * *

SEQUENCE LISTING

<160> NUMBER OF SEQ ID NOS: 697

<210> SEQ ID NO 1
<211> LENGTH: 990
<212> TYPE: DNA
<213> ORGANISM: Homo sapiens

<400> SEQUENCE: 1

| | | | | | |
|---|---|---|---|---|---|
| gcctccacca | agggcccatc | ggtcttcccc | ctggcaccct | cctccaagag | cacctctggg | 60 |
| ggcacagcgg | ccctgggctg | cctggtcaag | gactacttcc | ccgaaccggt | gacggtgtcg | 120 |
| tggaactcag | gcgccctgac | cagcggcgtg | cacaccttcc | cggctgtcct | acagtcctca | 180 |
| ggactctact | ccctcagcag | cgtggtgacc | gtgccctcca | gcagcttggg | cacccagacc | 240 |
| tacatctgca | acgtgaatca | caagcccagc | aacaccaagg | tggacaagaa | agttgagccc | 300 |
| aaatcttgtg | acaaaactca | cacatgccca | ccgtgcccag | cacctgaact | cctggggggga | 360 |
| ccgtcagtct | tcctcttccc | cccaaaaccc | aaggacaccc | tcatgatctc | ccggaccccct | 420 |
| gaggtcacat | gcgtggtggt | ggacgtgagc | cacgaagacc | ctgaggtcaa | gttcaactgg | 480 |
| tacgtggacg | gcgtggaggt | gcataatgcc | aagacaaagc | cgcgggagga | gcagtacaac | 540 |
| agcacgtacc | gtgtggtcag | cgtcctcacc | gtcctgcacc | aggactggct | gaatggcaag | 600 |
| gagtacaagt | gcaaggtctc | caacaaagcc | ctcccagccc | ccatcgagaa | aaccatctcc | 660 |
| aaagccaaag | ggcagccccg | agaaccacag | gtgtacaccc | tgcccccatc | ccgggatgag | 720 |
| ctgaccaaga | accaggtcag | cctgacctgc | ctggtcaaag | gcttctatcc | cagcgacatc | 780 |
| gccgtggagt | gggagagcaa | tgggcagccg | gagaacaact | acaagaccac | gcctcccgtg | 840 |
| ctggactccg | acggctcctt | cttcctctat | agcaagctca | ccgtggacaa | gagcaggtgg | 900 |
| cagcagggga | acgtcttctc | atgctccgtg | atgcatgagg | ctctgcacaa | ccactacacg | 960 |
| cagaagagcc | tctccctgtc | tccgggtaaa | | | | 990 |

<210> SEQ ID NO 2
<211> LENGTH: 330
<212> TYPE: PRT
<213> ORGANISM: Homo sapiens

<400> SEQUENCE: 2

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 3
<211> LENGTH: 321
<212> TYPE: DNA
<213> ORGANISM: Homo sapiens

<400> SEQUENCE: 3
cgaactgtgg ctgcaccatc tgtcttcatc ttcccgccat ctgatgagca gttgaaatct    60
ggaactgcct ctgttgtgtg cctgctgaat aacttctatc ccagagaggc caaagtacag   120
tggaaggtgg ataacgccct ccaatcgggt aactcccagg agagtgtcac agagcaggac   180
agcaaggaca gcacctacag cctcagcagc accctgacgc tgagcaaagc agactacgag   240
aaacacaaag tctacgcctg cgaagtcacc catcagggcc tgagctcgcc cgtcacaaag   300
agcttcaaca ggggagagtg t                                             321

<210> SEQ ID NO 4
<211> LENGTH: 107
<212> TYPE: PRT
<213> ORGANISM: Homo sapiens

<400> SEQUENCE: 4

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 5
<211> LENGTH: 351
<212> TYPE: DNA
<213> ORGANISM: Homo sapiens

<400> SEQUENCE: 5
gaggtgcagc tggtacagtc tggagcagag gtgaaaaagc ccggggagtc tctgaagatc      60
tcctgtaagg gttctggata caactttacc agctactgga tcggctgggt gcgccagatg     120
cccgggaaag gcctggagtt gatggggatc atctatcctg gtgactctga taccagatac     180
agcccgtcct tccaaggcca ggtcaccatc tcagccgaca gtccatcag caccgcctac      240 ctgcagtgga gcagcctgaa ggcctcggac accgccatgt attactgtgg ttcggggagc     300 tactttact cgatctctg gggccgtggc accctggtca ccgtctctag t                351

<210> SEQ ID NO 6
<211> LENGTH: 117
<212> TYPE: PRT
<213> ORGANISM: Homo sapiens

<400> SEQUENCE: 6

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Asn Phe Thr Ser Tyr
            20                  25                  30

Trp Ile Gly Trp Val Arg Gln Met Pro Gly Lys Gly Leu Glu Leu Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Gly Ser Gly Ser Tyr Phe Tyr Phe Asp Leu Trp Gly Arg Gly Thr Leu
            100                 105                 110

Val Thr Val Ser Ser
        115

<210> SEQ ID NO 7
<211> LENGTH: 324
<212> TYPE: DNA
<213> ORGANISM: Homo sapiens

<400> SEQUENCE: 7
gaaattgtgt tgacgcagtc tccaggcacc ctgtctttgt ctccagggga aagagccacc      60
ctctcctgca gggccagtca gagtgttagc agcagctact tagcctggta ccagcagaaa     120
cctggccagg ctcccaggct cctcatatat ggtgcatcca gcagggccac tggcatccca     180
gacaggttca gtggcagtgg gtctgggaca gacttcactc tcaccatcag cagactggag     240
cctgaagatt ttgcagtgta ttactgtcag cggtctggtg gctcatcatt cactttcggc     300
cctgggacca aagtggatat caaa                                             324

-continued

```
<210> SEQ ID NO 8
<211> LENGTH: 108
<212> TYPE: PRT
<213> ORGANISM: Homo sapiens

<400> SEQUENCE: 8
```

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Arg Ser Gly Gly Ser Ser
                85                  90                  95

Phe Thr Phe Gly Pro Gly Thr Lys Val Asp Ile Lys
            100                 105

```
<210> SEQ ID NO 9
<211> LENGTH: 351
<212> TYPE: DNA
<213> ORGANISM: Homo sapiens

<400> SEQUENCE: 9
```
gaggtgcagc tggtgcagtc tggagcagag gtgaaaaagc ccggggagtc tctgaagatc    60
tcctgtaagg gttctggata cagctttacc agctactgga tcggctgggt gcgccagatg   120
cccgggaaag cctggagtg gatggggatc atctatcctg gtgactctga taccagatac   180
agcccgtcct ccaaggcca ggtcaccatc tcagccgaca gtccatcag caccgcctac   240 ctgcagtgga gcagcctgaa ggcctcggac accgccatgt attactgtgg ttcggggagc   300
tactggtact cgatctctg gggccgtggc accctggtca ccgtctctag t             351

```
<210> SEQ ID NO 10
<211> LENGTH: 117
<212> TYPE: PRT
<213> ORGANISM: Homo sapiens

<400> SEQUENCE: 10
```

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Gly Ser Gly Ser Tyr Trp Tyr Phe Asp Leu Trp Gly Arg Gly Thr Leu
            100                 105                 110

Val Thr Val Ser Ser
            115

<210> SEQ ID NO 11
<211> LENGTH: 324
<212> TYPE: DNA
<213> ORGANISM: Homo sapiens

<400> SEQUENCE: 11

```
gaaattgtgt tgacgcagtc tccaggcacc ctgtctttgt ctccagggga aagagccacc      60
ctctcctgca gggccagtca gagtgttagc agcagctcct tagcctggta ccagcagaaa     120
cctggccagg ctcccaggct cctcatatat ggtgcatcca gcagggccac tggcatccca     180
gacaggttca gtggcagtgg gtctgggaca gacttcactc tcaccatcag cagactggag     240
cctgaagatt ttgcagtgta ttactgtcag cggtctggtg gctcatcatt cactttcggc     300
cctgggacca aagtggatat caaa                                            324
```

<210> SEQ ID NO 12
<211> LENGTH: 108
<212> TYPE: PRT
<213> ORGANISM: Homo sapiens

<400> SEQUENCE: 12

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Ser Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Arg Ser Gly Gly Ser Ser
                85                  90                  95

Phe Thr Phe Gly Pro Gly Thr Lys Val Asp Ile Lys
            100                 105

<210> SEQ ID NO 13
<211> LENGTH: 351
<212> TYPE: DNA
<213> ORGANISM: Homo sapiens

<400> SEQUENCE: 13

```
gaggtgcagc tggtgcagtc tggagcagag gtgaaaaagc ccggggagtc tctgaagatc      60
tcctgtaagg gttctggata caactttacc agctactgga tcggctgggt gcgccagatg     120
cccgggaaag gcctggagtt gatggggatc atctatcctg gtgactctga taccagatac     180
agcccgtcct tccaaggcca ggtcaccatc tcagccgaca gtccatcagc caccgcctac     240
ctgcagtgga gcagcctgaa ggcctcggac accgccatgt attactgtgg ttcggggagc     300
tactggtact cgatctcctg ggccgtggca accctggtca ccgtctctag t              351
```

<210> SEQ ID NO 14
<211> LENGTH: 117
<212> TYPE: PRT
<213> ORGANISM: Homo sapiens

<400> SEQUENCE: 14

Glu Val Gln Leu Val Gln Ser Gly Ala Glu Val Lys Lys Pro Gly Glu

```
                1               5                  10                  15
            Ser Leu Lys Ile Ser Cys Lys Gly Ser Gly Tyr Asn Phe Thr Ser Tyr
                            20                  25                  30

Trp Ile Gly Trp Val Arg Gln Met Pro Gly Lys Gly Leu Glu Leu Met
                        35                  40                  45

Gly Ile Ile Tyr Pro Gly Asp Ser Asp Thr Arg Tyr Ser Pro Ser Phe
                    50                  55                  60

Gln Gly Gln Val Thr Ile Ser Ala Asp Lys Ser Ile Ser Thr Ala Tyr
             65                 70                  75                  80

Leu Gln Trp Ser Ser Leu Lys Ala Ser Asp Thr Ala Met Tyr Tyr Cys
                            85                  90                  95

Gly Ser Gly Ser Tyr Trp Tyr Phe Asp Leu Trp Gly Arg Gly Thr Leu
                        100                 105                 110

Val Thr Val Ser Ser
                    115

<210> SEQ ID NO 15
<211> LENGTH: 324
<212> TYPE: DNA
<213> ORGANISM: Homo sapiens

<400> SEQUENCE: 15
gaaattgtgt tgacgcagtc tccaggcacc ctgtctttgt ctccagggga aagagccacc     60
ctctcctgca gggccagtca gagtgttagc agcagctact tagcctggta ccagcagaaa    120
cctggccagg ctcccaggct cctcatatat ggtgcatcca gcagggccac tggcatccca    180
gacaggttca gtggcagtgg gtctgggaca gacttcactc tcaccatcag cagactggag    240
cctgaagatt ttgcagtgta ttactgtcag cggtctggtg gctcatcatt cactttcggc    300
cctgggacca agtggatat caaa                                             324

<210> SEQ ID NO 16
<211> LENGTH: 108
<212> TYPE: PRT
<213> ORGANISM: Homo sapiens

<400> SEQUENCE: 16

Glu Ile Val Leu Thr Gln Ser Pro Gly Thr Leu Ser Leu Ser Pro Gly
             1               5                  10                  15

Glu Arg Ala Thr Leu Ser Cys Arg Ala Ser Gln Ser Val Ser Ser Ser
                            20                  25                  30

Tyr Leu Ala Trp Tyr Gln Gln Lys Pro Gly Gln Ala Pro Arg Leu Leu
                        35                  40                  45

Ile Tyr Gly Ala Ser Ser Arg Ala Thr Gly Ile Pro Asp Arg Phe Ser
                    50                  55                  60

Gly Ser Gly Ser Gly Thr Asp Phe Thr Leu Thr Ile Ser Arg Leu Glu
             65                 70                  75                  80

Pro Glu Asp Phe Ala Val Tyr Tyr Cys Gln Arg Ser Gly Gly Ser Ser
                            85                  90                  95

Phe Thr Phe Gly Pro Gly Thr Lys Val Asp Ile Lys
                        100                 105

<210> SEQ ID NO 17
<211> LENGTH: 447
<212> TYPE: PRT
<213> ORGANISM: Homo sapiens

<400> SEQUENCE: 17
```

-continued

| | | | | | | | | | | | |
|---|---|---|---|---|---|---|---|---|---|---|---|
| Glu<br>1 | Val | Gln | Leu | Val<br>5 | Gln | Ser | Gly | Ala | Glu<br>10 | Lys | Lys | Pro | Gly | Glu<br>15 |

Glu Val Gln Leu Val Gln Ser Gly Ala Glu Lys Lys Pro Gly Glu
1               5                   10                  15

Ser Leu Lys Ile Ser Cys Lys Gly Ser Gly Tyr Asn Phe Thr Ser Tyr
            20                  25                  30

Trp Ile Gly Trp Val Arg Gln Met Pro Gly Lys Gly Leu Glu Leu Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Gly Ser Gly Ser Tyr Phe Tyr Phe Asp Leu Trp Gly Arg Gly Thr Leu
            100                 105                 110

Val Thr Val Ser Ser Ala Ser Thr Lys Gly Pro Ser Val Phe Pro Leu
    115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
            435                 440                 445

<210> SEQ ID NO 18
<211> LENGTH: 215
<212> TYPE: PRT
<213> ORGANISM: Homo sapiens

<400> SEQUENCE: 18

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Arg Ser Gly Gly Ser Ser
                85                  90                  95

Phe Thr Phe Gly Pro Gly Thr Lys Val Asp Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 19
<211> LENGTH: 447
<212> TYPE: PRT
<213> ORGANISM: Homo sapiens

<400> SEQUENCE: 19

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

```
Leu Gln Trp Ser Ser Leu Lys Ala Ser Asp Thr Ala Met Tyr Tyr Cys
                85                  90                  95

Gly Ser Gly Ser Tyr Trp Tyr Phe Asp Leu Trp Gly Arg Gly Thr Leu
            100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445

<210> SEQ ID NO 20
<211> LENGTH: 215
<212> TYPE: PRT
<213> ORGANISM: Homo sapiens

<400> SEQUENCE: 20

Glu Ile Val Leu Thr Gln Ser Pro Gly Thr Leu Ser Leu Ser Pro Gly
1               5                   10                  15
```

```
Glu Arg Ala Thr Leu Ser Cys Arg Ala Ser Gln Ser Val Ser Ser Ser
             20                  25                  30

Ser Leu Ala Trp Tyr Gln Gln Lys Pro Gly Gln Ala Pro Arg Leu Leu
         35                  40                  45

Ile Tyr Gly Ala Ser Ser Arg Ala Thr Gly Ile Pro Asp Arg Phe Ser
     50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Arg Ser Gly Gly Ser Ser
                 85                  90                  95

Phe Thr Phe Gly Pro Gly Thr Lys Val Asp Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 21
<211> LENGTH: 447
<212> TYPE: PRT
<213> ORGANISM: Homo sapiens

<400> SEQUENCE: 21

Glu Val Gln Leu Val Gln Ser Gly Ala Glu Val Lys Lys Pro Gly Glu
 1               5                  10                  15

Ser Leu Lys Ile Ser Cys Lys Gly Ser Gly Tyr Asn Phe Thr Ser Tyr
             20                  25                  30

Trp Ile Gly Trp Val Arg Gln Met Pro Gly Lys Gly Leu Glu Trp Met
         35                  40                  45

Gly Ile Ile Tyr Pro Gly Asp Ser Asp Thr Arg Tyr Ser Pro Ser Phe
     50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Gly Ser Gly Ser Tyr Trp Tyr Phe Asp Leu Trp Gly Arg Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
```

```
                    165                 170                 175
Ser Gly Leu Tyr Ser Leu Ser Val Val Thr Val Pro Ser Ser Ser
                180                 185                 190

Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Asp Lys Thr His
        210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 22
<211> LENGTH: 215
<212> TYPE: PRT
<213> ORGANISM: Homo sapiens

<400> SEQUENCE: 22

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Arg Ser Gly Gly Ser Ser
                85                  90                  95
```

Phe Thr Phe Gly Pro Gly Thr Lys Val Asp Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (18)..(23)
<223> OTHER INFORMATION: a, c, t, g, unknown or other

<400> SEQUENCE: 23
ggccggatag gcctccannn nnnt                                          24

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ggggtcaggc tggaactgag g                                             21

<210> SEQ ID NO 25
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
tgaggacgct gaccacacg                                                19

<210> SEQ ID NO 26
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
acaacaaagc ttctagacca ccatggaaac cccagctcag cttctctt                48

<210> SEQ ID NO 27
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
cttgtcgact caacactctc ccctgttgaa gct                                  33

<210> SEQ ID NO 28
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
cagcagaagc ttctagacca ccatggggtc aaccgccatc ctcg                      44

<210> SEQ ID NO 29
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
cttggtggag gcactagaga cggtgaccag ggtgccacgg cc                        42

<210> SEQ ID NO 30
<211> LENGTH: 117
<212> TYPE: PRT
<213> ORGANISM: Homo sapiens

<400> SEQUENCE: 30

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Gly Ser Gly Ser Tyr Trp Tyr Phe Asp Leu Arg Gly Arg Gly Thr Leu
            100                 105                 110

Val Thr Val Ser Ser
        115

<210> SEQ ID NO 31
<211> LENGTH: 109
<212> TYPE: PRT
<213> ORGANISM: Homo sapiens

<400> SEQUENCE: 31

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Ile Ser Ser
            20                  25                  30

Tyr Leu Ala Trp Tyr Gln Gln Lys Pro Gly Gln Thr Pro Arg Leu Leu
        35                  40                  45

Ile Tyr Gly Val Ser Ser Arg Ala Thr Gly Ile Pro Asp Arg Phe Ser
    50                  55                  60

Gly Ser Gly Ser Gly Thr Asp Phe Thr Leu Thr Ile Thr Arg Leu Glu
65                  70                  75                  80

Pro Glu Asp Phe Ala Val Tyr Tyr Cys Gln Gln Tyr Gly Asn Ser Phe
                85                  90                  95

Met Tyr Thr Phe Gly Gln Gly Thr Lys Leu Glu Ile Lys
            100                 105

<210> SEQ ID NO 32
<211> LENGTH: 447
<212> TYPE: PRT
<213> ORGANISM: Homo sapiens

<400> SEQUENCE: 32

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Gly Ser Gly Ser Tyr Trp Tyr Phe Asp Leu Arg Gly Arg Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
```

```
                    260                 265                 270
Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 33
<211> LENGTH: 216
<212> TYPE: PRT
<213> ORGANISM: Homo sapiens

<400> SEQUENCE: 33

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Ile Ser Ser
            20                  25                  30

Tyr Leu Ala Trp Tyr Gln Gln Lys Pro Gly Gln Thr Pro Arg Leu Leu
        35                  40                  45

Ile Tyr Gly Val Ser Ser Arg Ala Thr Gly Ile Pro Asp Arg Phe Ser
    50                  55                  60

Gly Ser Gly Ser Gly Thr Asp Phe Thr Leu Thr Ile Thr Arg Leu Glu
65                  70                  75                  80

Pro Glu Asp Phe Ala Val Tyr Tyr Cys Gln Gln Tyr Gly Asn Ser Phe
                85                  90                  95

Met Tyr Thr Phe Gly Gln Gly Thr Lys Leu Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190
```

Val Tyr Ala Cys Glu Val Thr His Gln Gly Leu Ser Ser Pro Val Thr
            195                 200                 205

Lys Ser Phe Asn Arg Gly Glu Cys
    210                 215

<210> SEQ ID NO 34
<211> LENGTH: 5
<212> TYPE: PRT
<213> ORGANISM: Homo sapiens

<400> SEQUENCE: 34

Ser Tyr Trp Ile Gly
1               5

<210> SEQ ID NO 35
<211> LENGTH: 17
<212> TYPE: PRT
<213> ORGANISM: Homo sapiens

<400> SEQUENCE: 35

Ile Ile Tyr Pro Gly Asp Ser Asp Thr Arg Tyr Ser Pro Ser Phe Gln
1               5                   10                  15

Gly

<210> SEQ ID NO 36
<211> LENGTH: 8
<212> TYPE: PRT
<213> ORGANISM: Homo sapiens

<400> SEQUENCE: 36

Gly Ser Tyr Phe Tyr Phe Asp Leu
1               5

<210> SEQ ID NO 37
<211> LENGTH: 8
<212> TYPE: PRT
<213> ORGANISM: Homo sapiens

<400> SEQUENCE: 37

Gly Ser Tyr Trp Tyr Phe Asp Leu
1               5

<210> SEQ ID NO 38
<211> LENGTH: 12
<212> TYPE: PRT
<213> ORGANISM: Homo sapiens

<400> SEQUENCE: 38

Arg Ala Ser Gln Ser Val Ser Ser Ser Tyr Leu Ala
1               5                   10

<210> SEQ ID NO 39
<211> LENGTH: 12
<212> TYPE: PRT
<213> ORGANISM: Homo sapiens

<400> SEQUENCE: 39

Arg Ala Ser Gln Ser Val Ser Ser Ser Ser Leu Ala
1               5                   10

<210> SEQ ID NO 40
<211> LENGTH: 12
<212> TYPE: PRT
<213> ORGANISM: Homo sapiens

```
<400> SEQUENCE: 40

Arg Ala Ser Gln Ser Ile Ile Ser Ser Tyr Leu Ala
1               5                   10

<210> SEQ ID NO 41
<211> LENGTH: 7
<212> TYPE: PRT
<213> ORGANISM: Homo sapiens

<400> SEQUENCE: 41

Gly Ala Ser Ser Arg Ala Thr
1               5

<210> SEQ ID NO 42
<211> LENGTH: 7
<212> TYPE: PRT
<213> ORGANISM: Homo sapiens

<400> SEQUENCE: 42

Gly Val Ser Ser Arg Ala Thr
1               5

<210> SEQ ID NO 43
<211> LENGTH: 9
<212> TYPE: PRT
<213> ORGANISM: Homo sapiens

<400> SEQUENCE: 43

Gln Arg Ser Gly Gly Ser Ser Phe Thr
1               5

<210> SEQ ID NO 44
<211> LENGTH: 10
<212> TYPE: PRT
<213> ORGANISM: Homo sapiens

<400> SEQUENCE: 44

Gln Gln Tyr Gly Asn Ser Phe Met Tyr Thr
1               5                   10

<210> SEQ ID NO 45
<211> LENGTH: 24
<212> TYPE: DNA
<213> ORGANISM: Homo sapiens

<400> SEQUENCE: 45
gggagctact tttacttcga tctc                                          24

<210> SEQ ID NO 46
<211> LENGTH: 24
<212> TYPE: DNA
<213> ORGANISM: Homo sapiens

<400> SEQUENCE: 46
gggagctact ggtacttcga tctc                                          24

<210> SEQ ID NO 47
<211> LENGTH: 27
<212> TYPE: DNA
<213> ORGANISM: Homo sapiens

<400> SEQUENCE: 47
cagcggtctg gtggctcatc attcact                                       27
```

<210> SEQ ID NO 48
<211> LENGTH: 351
<212> TYPE: DNA
<213> ORGANISM: Homo sapiens

<400> SEQUENCE: 48

```
gaggtgcagc tggtgcagtc tggagcagag gtgaaaaagc ccggggagtc tctgaagatc      60
tcctgtaagg gttctggata cagctttacc agctactgga tcggctgggt gcgccagatg     120
cccgggaaag gcctggagtg gatggggatc atctatcctg gtgactctga taccagatac     180
agcccgtcct tccaaggcca ggtcaccatc tcagccgaca gtccatcagc accgcctac      240
ctgcagtgga gcagcctgaa ggcctcggac accgccatgt attactgtgg ttcggggagc     300
tactggtact cgatctccg gggccgtggc accctggtca ccgtctctag t              351
```

<210> SEQ ID NO 49
<211> LENGTH: 327
<212> TYPE: DNA
<213> ORGANISM: Homo sapiens

<400> SEQUENCE: 49

```
gaaattgtgt tgacgcagtc tccaggcacc ctgtctttgt ctccagggga aagagccacc      60
ctctcctgca gggccagtca gagtattatc agcagctact tagcctggta ccagcagaaa     120
cctggccaga ctcccaggct cctcatctat ggtgtatcca gcagggccac tggcatccca     180
gacaggttca gtggcagtgg gtctgggaca gacttcactc tcaccatcac cagactggag     240
cctgaagatt ttgcagtgta ttactgtcag cagtatggta actcatttat gtacactttt     300
ggccagggga ccaagctgga gatcaaa                                          327
```

<210> SEQ ID NO 50
<211> LENGTH: 1944
<212> TYPE: DNA
<213> ORGANISM: Homo sapiens

<400> SEQUENCE: 50

```
aatttctcac tgcccctgtg ataaactgtg gtcactggct gtggcagcaa ctattataag      60
atgctctgaa aactcttcag acactgaggg gcaccagagg agcagactac aagaatggca     120
cacgctatgg aaaactcctg acaatcagt aaagagtacc atattgatga agaagtgggc      180
tttgctctgc caaatccaca ggaaaatcta cctgattttt ataatgactg gatgttcatt     240
gctaaacatc tgcctgatct catagagtct ggccagcttc gagaaagagt tgagaagtta     300
aacatgctca gcattgatca tctcacagac acaagtcac agcgccttgc acgtctagtt      360
ctgggatgca tcaccatggc atatgtgtgg ggcaaaggtc atgagatgt ccgtaaggtc      420
ttgccaagaa atattgctgt tccttactgc caactctcca gaaactgga actgcctcct      480
attttggttt atgcagactg tgtcttggca aactggaaga aaaaggatcc taataagccc     540
ctgacttatg agaacatgga cgttttgttc tcatttcgtg atggagactg cagtaaagga     600
ttcttcctgg tctctctatt ggtggaaata gcagctgctt ctgcaatcaa agtaattcct     660
actgtattca aggcaatgca aatgcaagaa cgggacactt tgctaaaggc gctgttggaa     720
atagcttctt gcttggagaa agcccttcaa gtgtttcacc aaatccacga tcatgtgaac     780
ccaaaagcat ttttcagtgt tcttcgcata tatttgtctg gctggaaagg caaccccag     840
ctatcagacg gtctggtgta tgaagggttc tgggaagacc caaaggagtt tgcagggggc     900
```

```
agtgcaggcc aaagcagcgt ctttcagtgc tttgacgtcc tgctgggcat ccagcagact    960
gctggtggag acatgctgc tcagttcctc caggacatga aagatatat gccaccagct    1020
cacaggaact tcctgtgctc attagagtca aatccctcag tccgtgagtt tgtcctttca    1080
aaaggtgatg ctggcctgcg ggaagcttat gacgcctgtg tgaaagctct ggtctccctg    1140
aggagctacc atctgcaaat cgtgactaag tacatcctga ttcctgcaag ccagcagcca    1200
aaggagaata gacctctga agaccttca aaactggaag ccaaaggaac tggaggcact    1260
gatttaatga atttcctgaa gactgtaaga agtacaactg agaaatccct tttgaaggaa    1320
ggttaatgta acccaacaag agcacatttt atcatagcag agacatctgt atgcattcct    1380
gtcattaccc attgtaacag agccacaaac taatactatg caatgtttta ccaataatgc    1440
aatacaaaag acctcaaaat acctgtgcat ttcttgtagg aaaacaacaa aaggtaatta    1500
tgtgtaatta tactagaagt tttgtaatct gtatcttatc attggaataa aatgacattc    1560
aataaataaa aatgcataag atatattctg tcggctgggc gcggtggctc acgcctgtaa    1620
tcccagcact ttgggaggcc gaggcgggcg gatcacaagg tcaggagatc gagaccatct    1680
tggctaacac ggtgaaaccc cgtctctact aaaaatacaa aaaattagcc gggcgcggtg    1740
gcgggcacct gtagtcccag ctactcggga ggctgaggca ggagaatggc gtgaacctgg    1800
gaggcggagc ttgcagtgag ccaagattgt gccactgcaa tccggcctgg gctaaagagc    1860
gggactccgt ctcaaaaaaa aaaaaaaaaa gatatattct gtcataataa ataaaaatgc    1920
ataagatata aaaaaaaaaa aaaa                                            1944

<210> SEQ ID NO 51
<211> LENGTH: 3993
<212> TYPE: DNA
<213> ORGANISM: Homo sapiens

<400> SEQUENCE: 51
aatgtaagaa cttttcttcc tcccttaact ttgcttcctt ctttcctgca tgttaccact     60
ggcagagcaa atatgactca gaaaccggct cctcagggtt gtaacattag atgatacagg    120
cttgggtcgt tacacatgac accagtgcct ttgtttcatt gggctgggct ctctggaagg    180
tgtgctgctg cctgagctgc tggaaaagca ctgacaggtg tttgctagaa aagcactcct    240
ggagcttgcc accagcttgg acttctaggg actttcctct cagccaggaa ggattttgat    300
attcatcaga aatacctcca gaagattcaa ggagctgtag aggtgaagta agcctgtgaa    360
ggaccagcat gggaatccta tactctgagc ccatctgcca agcagcctat cagaatgact    420
ttggacaagt gtggcggtgg gtgaaagaag acagcagcta tgccaacgtt caagatggct    480
ttaatggaga cacgccctg atctgtgctt gcaggcgagg gcatgtgaga atcgtttcct    540
tcctttaag aagaaatgct aatgtcaacc tcaaaaacca gaaagagaga acctgcttgc    600
attatgctgt gaagaaaaaa tttaccttca ttgattatct actaattatc ctcttaatgc    660
ctgttctgct tattgggtat ttcctcatgg tatcaaagac aaagcagaat gaggctcttg    720
tacgaatgct acttgatgct ggcgtcgaag ttaatgctac agattgttat ggctgtaccg    780
cattacatta tgcctgtgaa atgaaaaacc agtctcttat ccctctgctc ttggaagccc    840
gtgcagaccc cacaataaag aataagcatg gtgagagctc actggatatt gcacggagat    900
taaaattttc ccagattgaa ttaatgctaa ggaaagcatt gtaatccttg tgaccacacc    960
gatggagata cagaaaaagt taacgactgg attctatctt cattttagac ttttggtctg    1020
tgggccattt aacctggatg ccaccatttt atggggataa tgatgcttac catggttaat    1080
```

```
gttttggaag agctttttat ttatagcatt gtttactcag tcaagttcac catggccgta    1140
atccttctaa gggaaacact aaagttgttg tagtctccac ttcagtcaga aactgatgtt    1200
tcagctaggc acagtggtac atgcctgtaa tcccagctac ttgggaggct gaggtgggag    1260
gatcacttga actcaggagt ttgagagcag ccagggcaac acagcgagac cctgtctcaa    1320
aaaaaaaaaa aaaaaaaaaa gccctggtgt tccaaactca gtctttcctg aagaagagga    1380
tctgagttat cttctgaaac agcgttctcc cttcccagtt gtatcactct tataaaaga    1440 ctgtccagtc tatgtcatgc cctaggagac aaactgttcc tcccagcccc ctttgagtat    1500
tgagcagaag aatcaaatta ttaaatacgt atgtttgtac agaatggtat ttgtgtatgt    1560
gtgtgggctt agagattcac aagtaaatat tcctttggtg aaggaatttc aataaaaaca    1620
tctatcaagt gtcagcggtg agtgtgttta caccacagaa attggcaaat tgacaaatca    1680
gagtttgttt ttgttttttt gttttttact ttccataaag ttcgtttacc agcataccac    1740
tagagatttc ggtttacaaa taaaagccat cttggtttga gcaagactat gcaactatga    1800
aaatgttcgt ttaaaaaaat cttcatgatc cttttgtaaa tacaaggtgg ttgccaagct    1860
tgttagtttt gtttatttta ttgatagatg taaaatatta ttgtaactta tttggataaa    1920
gttcttcaaa agaaacagag ctatacaatg aggtaggatc tggattattt gtctaagtga    1980
gagattgcga atatcaaaat atctgtctca cttcttctgt gaatgacaca gagtagaaat    2040
aaattcactt taaaaatatg actgaatttt gaaaatcaag actgaatctc acatagctgc    2100
agacaggaac taagccagcc tctttgtatg tggtaacaag tacagtataa gaatgaaaga    2160
tttaccatcc ttgaaagctc taatgaaaat caaatccagc aatatatatt caactgtgta    2220
caggatttaa gaaacttatt ttatgaagga agtaatagtg tgtagatata gattctgaag    2280
tctttaaacg tgtcttaata aattaagatt cactggcatt gagctgagct accaggtgac    2340
ccttggggac aaaaaacccca cacaagtgaa tttcacacac cagtatacct tcaacaatat    2400
acttttgaca cacacaaacc tttgatttgg tttcagagat tttgcaaaat agtaccaatg    2460
taatttacaa ctgtcatctt tgaaattgtg taaaagtgga ataattttct gaagaaataa    2520
atcatggttt gtcaatgagt tgcagagact gtctgacatt aactttgtca agattaaagg    2580
ataaagtata tgacaatttg tttcatcatg ctcatgacat tatgcaattt ctccctagc    2640 ttttaattt tggaggcaga aaattgagcc agaaattttt agtcattagg tctcctagca    2700
acaagctgta aaccttccaa caagcttgga ctagaatcta gacactgaaa tgcacataca    2760
tgctttatgt aatgcagaat gcattttattg gagaactcat aaacatccta taaaattttc    2820
ttccctgaga tgcaactata aaacttggcc ttattctgag aatgcttaac atagatttca    2880
tccatactgt aacactgatt tgttgttgt tgtccttaaa gcagctcagc ttcctgaggt    2940
agtgttatgt ctctgtggca acaaggtgaa aatgtctagc ttattttgtc aaagtcaaca    3000
ataatccaca gactccagac ctcaatatct gtcccaattt gccatttttac tttagtgctc    3060 caaaaatatg gcttatagaa aaaacaatag gtgttttaaa gagatttacc tgaatgatat    3120
agagaatgtc tagatatttt ctggctatca ggtaaaacct accccttcaag atggtagaat    3180 atataatagc atacaaaacc tctatttacc taataagtac tttaatttac agaaaaaaaa    3240
tgtaaatgta agtgtcggat ttagtgccaa gtgcagggaa tctgaaaaat gtatactagg    3300
tctctgctct ccgtaattct gccttcatgg gtcctagccc catccctcag gaggttgtcc    3360
taagatcgtc agtgtcagat gcttcacaat acggcctcac accgtccctg ggaaaggttg    3420
```

```
gtctcctcct gctgcatcag atggatgatt tcattgtaca tacggtgagg agcatccaaa    3480
ccccagatga atccacgtg agcccattca ggaatattct tatggtagat gaggttggtc    3540
acctcagaga gcagcatttt cacgtcttct ggatttgaaa gccagtcctg acctcctgtc    3600
cacattgctg tagggaccgt catatctctg actctgtacc ttacaggagt tggctagaga    3660
aaaggaatag ttcttaactc taggtaacat ttggactttc aggctcataa tttatgtttc    3720
aaatagacat aataaacatg ccatctgttg tggtgaaggg tacatgggtg ttagagccac    3780
acaactctgt taagaatttc tgttcccgcc cttactttaa ggtaaaatta cttaacatta    3840
ttgaacctca gtttcttctt ctgtgactgg ggataatatc tgtaataact tgctagatca    3900
aatgacaaaa cacataaaaa catgtaatgc cttgtatttc tttttcttc ctattaaata     3960 ttttgtaaat aaattgtttt taaaaaaaaa aaa                                 3993

<210> SEQ ID NO 52
<211> LENGTH: 2545
<212> TYPE: DNA
<213> ORGANISM: Homo sapiens

<400> SEQUENCE: 52
atccaataca ggagtgactt ggaactccat tctatcacta tgaagaaaag tggtgttctt      60
ttcctcttgg gcatcatctt gctggttctg attggagtgc aaggaacccc agtagtgaga     120
aagggtcgct gttcctgcat cagcaccaac caagggacta ccacctaca atccttgaaa      180 gaccttaaac aatttgcccc aagcccttcc tgcgagaaaa ttgaaatcat tgctacactg     240
aagaatggag ttcaaacatg tctaaaccca gattcagcag atgtgaagga actgattaaa     300
aagtgggaga acaggtcag ccaaaagaaa aagcaaaaga tgggaaaaa acatcaaaaa       360 aagaaagttc tgaaagttcg aaaatctcaa cgttctcgtc aaaagaagac tacataagag     420
accacttcac caataagtat tctgtgttaa aaatgttcta ttttaattat accgctatca     480
ttccaaagga ggatggcata taatacaaag gcttattaat ttgactagaa aatttaaaac     540
attactctga aattgtaact aaagttagaa agttgatttt aagaatccaa acgttaagaa     600
ttgttaaagg ctatgattgt cttgttcctt ctaccaccca ccagttgaat ttcatcatgc     660
ttaaggccat gattttagca atacccatgt ctacacagat gttcacccaa ccacatccca     720
ctcacaacag ctgcctggaa gagcagccct aggcttccac gtactgcagc tccagagag     780 tatctgaggc acatgtcagc aagtcctaag cctgttagca tgctggtgag ccaagcagtt    840
tgaaattgag ctggacctca ccaagctgct gtggccatca acctctgtat ttgaatcagc    900
ctacaggcct cacacacaat gtgtctgaga gattcatgct gattgttatt gggtatcacc    960
actggagatc accagtgtgt ggctttcaga gcctcctttc tggctttgga agccatgtga   1020
ttccatcttg cccgctcagg ctgaccactt tatttctttt tgttcccctt tgcttcattc   1080
aagtcagctc ttctccatcc taccacaatg cagtgccttt cttctctcca gtgcacctgt   1140
catatgctct gatttatctg agtcaactcc tttctcatct tgtccccaac accccacaga   1200
agtgctttct tctcccaatt catcctcact cagtccagct tagttcaagt cctgcctctt   1260
aaataaacct ttttgacac acaaattatc ttaaaactcc tgtttcactt ggttcagtac     1320
cacatgggtg aacactcaat ggttaactaa ttcttgggtg tttatcctat ctctccaacc    1380
agattgtcag ctccttgagg gcaagagcca cagtatattt ccctgtttct tccacagtgc    1440 ctaataaatac tgtggaacta ggttttaata atttttttaat tgatgttgtt atgggcagga   1500
tggcaaccag accattgtct cagagcaggt gctggctctt tcctggctac tccatgttgg   1560
```

| | |
|---|---|
| ctagcctctg gtaacctctt acttattatc ttcaggacac tcactacagg gaccagggat | 1620 |
| gatgcaacat ccttgtcttt ttatgacagg atgtttgctc agcttctcca acaataagaa | 1680 |
| gcacgtggta aaacacttgc ggatattctg gactgttttt aaaaaatata cagtttaccg | 1740 |
| aaaatcatat aatcttacaa tgaaaaggac tttatagatc agccagtgac caaccttttc | 1800 |
| ccaaccatac aaaaattcct tttcccgaag gaaaagggct ttctcaataa gcctcagctt | 1860 |
| tctaagatct aacaagatag ccaccgagat ccttatcgaa actcatttta ggcaaatatg | 1920 |
| agttttattg tccgtttact tgtttcagag tttgtattgt gattatcaat taccacacca | 1980 |
| tctcccatga agaagggaa cggtgaagta ctaagcgcta gaggaagcag ccaagtcggt | 2040 |
| tagtggaagc atgattggtg cccagttagc ctctgcagga tgtggaaacc tccttccagg | 2100 |
| ggaggttcag tgaattgtgt aggagaggtt gtctgtggcc agaatttaaa cctatactca | 2160 |
| ctttcccaaa ttgaatcact gctcacactg ctgatgattt agagtgctgt ccggtggaga | 2220 |
| tcccacccga acgtcttatc taatcatgaa actccctagt tccttcatgt aacttccctg | 2280 |
| aaaaatctaa gtgtttcata aatttgagag tctgtgaccc acttaccttg catctcacag | 2340 |
| gtagacagta taactaac aaccaaagac tacatattgt cactgacaca cacgttataa | 2400 |
| tcatttatca tatatataca tacatgcata cactctcaaa gcaaataatt tttcacttca | 2460 |
| aaacagtatt gacttgtata ccttgtaatt tgaaatattt tctttgttaa aatagaatgg | 2520 |
| tatcaataaa tagaccatta atcag | 2545 |

<210> SEQ ID NO 53
<211> LENGTH: 3512
<212> TYPE: DNA
<213> ORGANISM: Homo sapiens

<400> SEQUENCE: 53

| | |
|---|---|
| aactcagctg agtgttagtc aaagaaggtg tgtcctgctc cccaatgaca ggttgctcag | 60 |
| agactgctga tttccatccc tatataaaga gagtccctgg catacagaga ctgctctgct | 120 |
| ccaggcatct gccacaatgt gggtgcttac acctgctgct tttgctggga agctcttgag | 180 |
| tgtgttcagg caacctctga gctctctgtg gaggagcctg gtcccgctgt tctgctggct | 240 |
| gagggcaacc ttctggctgc tagctaccaa gaggagaaag cagcagctgg tcctgagagg | 300 |
| gccagatgag accaaagagg aggaagagga ccctcctctg cccaccaccc caaccagcgt | 360 |
| caactatcac ttcactcgcc agtgcaacta caaatgcggc ttctgtttcc acacagccaa | 420 |
| aacatccttt gtgctgcccc ttgaggaagc aaagagagga ttgcttttgc ttaaggaagc | 480 |
| tggtatggag aagatcaact tttcaggtgg agagccattt cttcaagacc ggggagaata | 540 |
| cctgggcaag ttggtgaggt tctgcaaagt agagttgcgg ctgcccagcg tgagcatcgt | 600 |
| gagcaatgga agcctgatcc gggagaggtg gttccagaat tatggtgagt atttggacat | 660 |
| tctcgctatc tcctgtgaca gctttgacga ggaagtcaat gtccttattg gccgtggcca | 720 |
| aggaaagaag aaccatgtgg aaaaccttca aaagctgagg aggtggtgta gggattatag | 780 |
| agtcgctttc aagataaaatt ctgtcattaa tcgtttcaac gtggaagagg acatgacgga | 840 |
| acagatcaaa gcactaaacc ctgtccgctg gaaagtgttc cagtgcctct taattgaggg | 900 |
| tgagaattgt ggagaagatg ctctaagaga agcagaaaga tttgttattg gtgatgaaga | 960 |
| atttgaaaga ttcttggagc gccacaaaga agtgtcctgc ttggtgcctg aatctaacca | 1020 |
| gaagatgaaa gactcctacc ttattctgga tgaatatatg cgctttctga actgtagaaa | 1080 |

```
gggacggaag gacccttcca agtccatcct ggatgttggt gtagaagaag ctataaaatt    1140
cagtggattt tgatgaaaaga tgtttctgaa gcgaggagga aaatacatat ggagtaaggc    1200
tgatctgaag ctggattggt agagcggaaa gtggaacgag acttcaacac accagtggga    1260
aaactcctag agtaactgcc attgtctgca atactatccc gttggtattt cccagtggct    1320
gaaaacctga ttttctgctg cacgtggcat ctgattacct gtggtcactg aacacacgaa    1380
taacttggat agcaaatcct gagacaatgg aaaaccatta actttacttc attggcttat    1440
aaccttgttg ttattgaaac agcacttctg tttttgagtt tgttttagct aaaaagaagg    1500
aatacacaca ggaataatga ccccaaaaat gcttagataa ggcccctata cacaggacct    1560
gacatttagc tcaatgatgc gtttgtaaga aataagctct agtgatatct gtggggcaa     1620 aatttaattt ggatttgatt ttttaaaaca atgtttactg cgatttctat atttccattt    1680
tgaaactatt tcttgttcca ggtttgttca tttgacagag tcagtatttt ttgccaaata    1740
tccagataac cagttttcac atctgagaca ttacaaagta tctgcctcaa ttatttctgc    1800
tggttataat gctttttttt ttttgccttt atgccattgc agtcttgtac ttttttactgt   1860 gatgtacaga aatagtcaac agatgttttcc aagaacatat gatatgataa tcctaccaat   1920
tttcaagaag tctctagaaa gagataacac atggaaagac ggtgtggtgc agcccagccc    1980
acggtggctg ttccatgaat gctggctacc tatgtgtgtg gtacctgttg tgtccctttc    2040
tcttcaaaga tcctgagcaa aacaaagata cgctttccat ttgatgatgg agttgacatg    2100
gaggcagtgc ttgcattgct ttgttcgcct atcatctggc cacatgaggc tgtcaagcaa    2160
aagaatagga gtgtagttga gtagctggtt ggccctacat ctctgagaag tgacggcaca    2220
ctgggttggc ataagatatc ctaaaatcac gctggaacct tgggcaagga agaatgtgag    2280
caagagtaga gagagtgcct ggatttcatg tcagtgaagc caagtcacca tatcatattt    2340
ttgaatgaac tctgagtcag ttgaaatagg gtaccatcta ggtcagttta agaagagtca    2400
gctcagagaa agcaagcata agggaaaatg tcacgtaaac tagatcaggg aacaaaatcc    2460
tctccttgtg gaaatatccc atgcagtttg ttgatacaac ttagtatctt attgcctaaa    2520
aaaaaatttc ttatcattgt ttcaaaaaag caaaatcatg gaaaattttt gttgtccagg    2580
caaataaaag gtcattttaa tttagctgca atttcagtgt tcctcactag gtggcattta    2640
aatgtcgcct gatgtcatta agcaccatcc aaaaagtctg cttcataatc tattttcaag    2700
acttggtgat tctgaaagtt ttggttttttg tgactttgtt tctcaggaaa aaaaatattc    2760
ctacttaaat tttaagtcta taattcaatt taaatatgtg tgtgtctcat ccaggatagg    2820
ataggttgtc ttctattttc cattttacct atttactttt tttgtaagaa aagagaaaaa    2880
tgaattctaa agatgttccc catgggtttt gattgtgtct aagctatgat gaccttcata    2940
taatcagcat aaacataaaa caaattttttt acttaacatg agtgcacttt actaatcctc    3000
atggcacagt ggctcacgcc tgtaatccca gcacttggga ggacaatgtg ggtggatcac    3060
gaggtcagga gttcgagaac agcctggcca acatggtgaa accccgtctc cactaaaaat    3120
acaaaaatta gccaggcatg gtggcgtaca cttgtaattc cagctactca agaggctgag    3180
gcaggaggat tgcttgaacc ctgaaggcag aggttacaga gccaagatag cgccactgca    3240
ctccagcctg gatgacagag caagactccg tctcaaaaaa aaaaaaaaaa aaaagcaaga    3300
gagttcaact aagaaaggtc acatatgtga aagcccaagg acactgtttg atatacagca    3360
ggtattcaat cagtgttatt tgaaaccaaa tctgaatttg aagtttgaat cttctgagtt    3420
ggaatgaatt ttttctagc tgagggaaac tgtattttc tttccccaaa gaggaatgta     3480
```

```
atgtaaagtg aaataaaact ataagctatg tt                                  3512
```

<210> SEQ ID NO 54
<211> LENGTH: 1109
<212> TYPE: DNA
<213> ORGANISM: Homo sapiens

<400> SEQUENCE: 54

```
agaggaacca gaaatttgtc cttgaataat gtttcccgac aacgaagagg cagaaggatc     60
tgggcctgtg cgcgacgccc cgggggacga ggctcatgga gaagtttcgg gcggtgctgg    120
acctgcacgt caagcaccac agcgccttgg gctacggcct ggtgaccctg ctgacggcgg    180
gcggggagcg catcttctcc gccgtggcat ccagtgccc gtgcagcgcc gcctggaacc    240
tgccctacgg cctggtcttc ttgctggtgc cggcgctcgc gctcttcctc ctgggctacg    300
tgctgagcgc acgcacgtgg cgcctgctca ccggatgctg ctccagcgcc cgcgcgagtt    360
gcggatcggc gctgcgcggc tccctggtgt gcacgcaaat cagcgcggcc gccgcgctcg    420
cgcccctcac ctgggtggcc gtggcgctgc tcggggcgc cttttacgag tgcgcggcca    480
ccggagcgcg ggccttcgcg cagcgcctgt gcctcggccg caaccgcagc tgcgccgcgg    540
agctgccgct ggtgccgtgc aaccaggcca aggcgtcgga cgtgcaggac ctcctgaagg    600
atctgaaggc tcagtcgcag gtgttgggct ggatcttgat agcagttgtt atcatcattc    660
ttctgatttt tacatctgtc acccgatgcc tatctccagt tagttttctg cagctgaaat    720
tctgaaaaat ctatttggaa caggagcagc agatccttaa aagtaaagcc acagagcatg    780
caactgaatt ggcaaaagag aatattaaat gtttctttga gggctcgcat ccaaaagaat    840
ataacactcc aagcatgaaa gagtggcagc aaatttcatc actgtatact ttcaatccga    900
agggccagta ctacagcatg ttgcacaaat atgtcaacag aaaagagaag actcacagta    960
tcaggtctac tgaaggagat acggtgattc ctgttcttgg ctttgtagat tcatctggta   1020
taaacagcac tcctgagtta tgaccttttg aatgagtaga aaaaaaaatt gttttgaatt   1080
attgctttat taaaaaataa acattggta                                     1109
```

<210> SEQ ID NO 55
<211> LENGTH: 2694
<212> TYPE: DNA
<213> ORGANISM: Homo sapiens

<400> SEQUENCE: 55

```
tctcccttt cacagctggt ttcatactat ttactatttg gtcaagccgt gctaatctgt     60
aaccctaagc aaatccaaat caggtccaac ttatgcaagc atatattaga gctgggctcc    120
aaagaatact ggacatctgt agtacctgac attcaagcat ttggcgagat gtcaatattt    180
cagagagcac tttaaatgtt ttgatttgaa agctaatgca gtgtttccca ctggtcaaca    240
cgagcagtcc agcagagagc aaaatctatt tccctcaaca tcaaatgcta cactcagttg    300
ctgatcctat cttgcctaca gagaacctaa aagactggaa aaattggatc tttaatgaaa    360
aaacacttgg gccacttcaa gacgacaaac gctcactggg caaaacacct tcactgaaaa    420
gagacctcat attatgcaaa aaaaatctta aaaggcctct gccttcagaa gttacaagat    480
gatcaattca acctccacac agcctccaga tgaatcctgc tctcagaacc tcctgatcac    540
tcagcagatc attcctgtgc tgtactgtat ggtcttcatt gcaggaatcc tactcaatgg    600
agtgtcagga tggatattct tttacgtgcc cagctctaag agtttcatca tctatctcaa    660
```

| | |
|---|---|
| gaacattgtt attgctgact tgtgatgag cctgactttt cctttcaaga tccttggtga | 720 |
| ctcaggcctt ggtccctggc agctgaacgt gtttgtgtgc agggtctctg ccgtgctctt | 780 |
| ctacgtcaac atgtacgtca gcattgtgtt ctttgggctc atcagctttg acagatatta | 840 |
| taaaattgta aagcctcttt ggacttcttt catccagtca gtgagttaca gcaaacttct | 900 |
| gtcagtgata gtatggatgc tcatgctcct ccttgctgtt ccaaatatta ttctcaccaa | 960 |
| ccagagtgtt agggaggtta cacaaataaa atgtatagaa ctgaaaagtg aactgggacg | 1020 |
| gaagtggcac aaagcatcaa actacatctt cgtggccatc ttctggattg tgtttctttt | 1080 |
| gttaatcgtt ttctatactg ctatcacaaa gaaaatcttt aagtcccacc ttaagtcaag | 1140 |
| tcggaattcc acttcggtca aaagaaatc tagccgcaac atattcagca tcgtgtttgt | 1200 |
| gttttttgtc tgttttgtac cttaccatat tgccagaatc ccctacacaa agagtcagac | 1260 |
| cgaagctcat tacagctgcc agtcaaaaga aatcttgcgg tatatgaaag aattcactct | 1320 |
| gctactatct gctgcaaatg tatgcttgga ccctattatt tatttctttc tatgccagcc | 1380 |
| gtttagggaa atcttatgta agaaattgca cattccatta aaagctcaga atgacctaga | 1440 |
| catttccaga atcaaaagag gaaatacaac acttgaaagc acagatactt tgtgagttcc | 1500 |
| taccctcttc caagaaaga ccacgtgtgc atgttgtcat cttcaattac ataacagaaa | 1560 |
| tcaataagat atgtgccctc atcataaata tcatctctag cactgccatc caatttagtt | 1620 |
| caataaaatt caaatataag tttccatgct tttttgtaac atcaaagaaa acatacccat | 1680 |
| cagtaatttc tctaatactg acctttctat tctctattaa taaaaatta atacatacaa | 1740 |
| ttattcaatt ctattatatt aaaataagtt aaagtttata accactagtc tggtcagtta | 1800 |
| atgtagaaat ttaaatagta aataaaacac aacataatca aagacaactc actcaggcat | 1860 |
| cttctttctc taaataccag aatctagtat gtaattgttt tcaacactgt ccttaaagac | 1920 |
| taacttgaaa gcaggcacag tttgatgaag ggctagagag ctgtttgcaa taaaagtca | 1980 |
| ggttttttc ctgatttgaa gaagcaggaa aagctgacac ccagacaatc acttaagaaa | 2040 |
| ccccttattg atgtatttca tggcactgca aaggaagagg aatattaatt gtatacttag | 2100 |
| caagaaaatt ttttttttct gatagcactt tgaggatatt agatacatgc taaatatgtt | 2160 |
| ttctacaaag acttacgtca tttaatgagc ctggggttct ggtgttagaa tatttttaag | 2220 |
| taggctttac tgagagaaac taaatattgg catacgttat cagcaacttc ccctgttcaa | 2280 |
| tagtatggga aaaataagat gactgggaaa aagacacacc cacaccgtag aacatatatt | 2340 |
| aatctactgg cgaatgggaa aggagaccat tttcttagaa agcaaataaa cttgattttt | 2400 |
| ttaaatctaa aatttacatt aatgagtgca aaataacaca taaaatgaaa attcacacat | 2460 |
| cacatttttc tggaaaacag acggatttta cttctggaga catggcatac ggttactgac | 2520 |
| ttatgagcta ccaaaactaa attctttctc tgctattaac tggctagaag acattcatct | 2580 |
| atttttcaaa tgttctttca aaacattttt ataagtaatg tttgtatcta tttcatgctt | 2640 |
| tactgtctat atactaataa agaaatgttt taatactgaa aaaaaaaaa aaaa | 2694 |

<210> SEQ ID NO 56
<211> LENGTH: 4065
<212> TYPE: DNA
<213> ORGANISM: Homo sapiens

<400> SEQUENCE: 56

| | |
|---|---|
| cactgaggtc accctccagg ctgtggaacc tttgttcttt cactctttgc aataaatctt | 60 |
| gctgctgctc actctttggg tccacactgc ctttatgagc tgtaacactc actgggaatg | 120 |

```
tctgcagctt cactcctgaa gccagcgaga ccacgaaccc accaggagga acaaacaact    180
ccagacgcgc agccttaaga gctgtaacac tcaccgcgaa ggtctgcagc ttcactcctg    240
agccagccag accacgaacc caccagaagg aagaaactcc aaacacatcc gaacatcaga    300
aggagcaaac tcctgacacg ccaccttta gaaccgtgac actcaacgct agggtccgcg    360
gcttcattct tgaagtcagt gagaccaaga acccaccaat tccggacacg ctaattgttg    420
tagatcatca cttcaaggtg cccatatctt tctagtggaa aaattattct ggcctccgct    480
gcatacaaat caggcaacca gaattctaca tatataaggc aaagtaacat cctagacatg    540
gctttagaga tccacatgtc agaccccatg tgcctcatcg agaactttaa tgagcagctg    600
aaggttaatc aggaagcttt ggagatcctg tctgccatta cgcaacctgt agttgtggta    660
gcgattgtgg gcctctatcg cactggcaaa tcctacctga tgaacaagct ggctgggaag    720
aacaagggct tctctgttgc atctacggtg cagtctcaca ccaagggaat tggatatgg    780 tgtgtgcctc atcccaactg gccaaatcac acattagttc tgcttgacac cgagggcctg    840
ggagatgtag agaaggctga caacaagaat gatatccaga tctttgcact ggcactctta    900
ctgagcagca cctttgtgta caatactgtg aacaaaattg atcagggtgc tatcgaccta    960
ctgcacaatg tgacagaact gacagatctg ctcaaggcaa gaaactcacc cgaccttgac    1020
agggttgaag atcctgctga ctctgcgagc ttcttcccag acttagtgtg gactctgaga    1080
gatttctgct taggcctgga aatagatggg caacttgtca caccagatga atacctggag    1140
aattccctaa ggccaaagca aggtagtgat caaagagttc aaaatttcaa tttgccccgt    1200
ctgtgtatac agaagttctt tccaaaaaag aaatgcttta tctttgactt acctgctcac    1260 caaaaaagc ttgcccaact tgaaacactg cctgatgatg agctagagcc tgaatttgtg    1320
caacaagtga cagaattctg ttcctacatc tttagccatt ctatgaccaa gactcttcca    1380
ggtggcatca tggtcaatgg atctcgtcta aagaacctgg tgctgaccta tgtcaatgcc    1440
atcagcagtg gggatctgcc ttgcatagag aatgcagtcc tggccttggc tcagagagag    1500
aactcagctg cagtgcaaaa ggccattgcc cactatgacc agcaaatggg ccagaaagtg    1560
cagctgccca tggaaaccct ccaggagctg ctggacctgc acaggaccag tgagagggag    1620
gccattgaag tcttcatgaa aaactctttc aaggatgtag accaaagttt ccagaaagaa    1680
ttggagactc tactagatgc aaaacagaat gacatttgta acggaacct ggaagcatcc    1740 tcggattatt gctcggcttt acttaaggat atttttggtc ctctagaaga agcagtgaag    1800
cagggaattt attctaagcc aggaggccat aatctcttca ttcagaaaac agaagaactg    1860
aaggcaaagt actatcggga gcctcggaaa ggaatacagg ctgaagaagt tctgcagaaa    1920
tatttaaagt ccaaggagtc tgtgagtcat gcaatattac agactgacca ggctctcaca    1980
gagacggaaa aaagaagaa agaggcacaa gtgaaagcag aagctgaaaa ggctgaagcg    2040
caaaggttgg cggcgattca aaggcagaac gagcaaatga tgcaggagag ggagagactc    2100
catcaggaac aagtgagaca atggagata gccaaacaaa attggctggc agagcaacag    2160
aaaatgcagg aacaacagat gcaggaacag gctgcacagc tcagcacaac attccaagct    2220
caaaatagaa gccttctcag tgagctccag cacgcccaga ggactgttaa taacgatgat    2280
ccatgtgttt tactctaaag tgctaaatat gggagtttcc ttttttttact ctttgtcact    2340 gatgacacaa cagaaaagaa actgtagacc ttgggacaat caacatttaa ataaacttta    2400
taattatttt ttcaaacttt catatagagt tataagatta tgatgctggt atctggtaaa    2460
```

| | |
|---|---|
| atgtacatcc cagtagtcca atagtttaaa tgtttattgc ttcctttaag agattataaa | 2520 |
| ttgtataagg gacattgtat cactgccttc atttatgcgt gatattggga tggtttcatc | 2580 |
| aggagatgct ttccttgcat ctcaatgtca tctgtctaat ttctcataag gggattatgt | 2640 |
| tacctagagc agggcttccc aaccctcagg ccatagacta gctctgatct gtggcctctt | 2700 |
| aggaacccgg ccacacagca ggaggtgagc agcaggtaag tgagcattac agcctgagct | 2760 |
| ccacctcctg tcagatcagc agtgacatta gattctcaca ggagtgggaa ccctattgtg | 2820 |
| aactgtgcat gcaaaagatc taggttgtgt gatccttgtg gaacaatata aaccagaaac | 2880 |
| caataacgcc accccacctc caaccccgc caaccctg tggaaaaatt accttccacg | 2940 |
| aaactggtcc ctgatgccaa ataggttggg ggaccgctga cctagaggga gttatgcaca | 3000 |
| tgggcttata aggttagcca agagaaagga caagaagacc caaagtcggc aagcaaattt | 3060 |
| attaacctgc tgggctgctc tacagaaatc tgaggaggca gacaccgggc ttacaggcta | 3120 |
| aggggtataa gtaggtctgc aggggttttg tgtgtgtgtg cgggggtgtc ggggggggcaa | 3180 |
| ggccatttgt ggagactttt cctcccagta tggccacatc ctgcagtttg tcagttttttg | 3240 |
| cccccgcctg gctcagggta ccaggatgtg gtttagctta ggggtggtta tagtggcacc | 3300 |
| taagttctgg gaacttgcgg tgggggcgac cttttggacg aaaaataagc tgcagggcag | 3360 |
| ctaggggagg gggcttgtta tattcctctg ggggcagggt gtccctaact gggctcagtc | 3420 |
| ggaaggaact tgaccaaagt ctgggctcag ttgggcatca ctcaggctaa tggtcgtgtg | 3480 |
| ctggatgcca tcagagggaa gtaccaatgg taaagtggaa acaatgtgca gctttcaact | 3540 |
| gggtggaggc tgctattctg tggacagtga gatgtttcct tggcactgtc aatagacaat | 3600 |
| ctgcgtagag aaattccaag ctgaaagcca ataatgttat aataaaatag agattcttca | 3660 |
| gaagatgaaa ggaattacca gcatggaaat tgtgtcatag gcttaagggc taaagaagaa | 3720 |
| gccttttctt ttctgttcac cctcaccaag agcacaactt aaataggca ttttataacc | 3780 |
| tgaacacaat ttatattgga cttaattatt atgtgtaata tgtttataat cctttagatc | 3840 |
| ttataaatat gtggtataag gaatgccata taatgtgcca aaaatctgag tgcatttaat | 3900 |
| ttaatgcttg cttatagtgc taaagttaaa tgatcttaat tctttgcaat tatatatgaa | 3960 |
| aaatgactga tttttcttaa aatatgtaac ttatataaat atatctgttt gtacagattt | 4020 |
| taaccataaa aacatttttg gaaaaccata aaaaaaaaaa aaaaa | 4065 |

<210> SEQ ID NO 57
<211> LENGTH: 1984
<212> TYPE: DNA
<213> ORGANISM: Homo sapiens

<400> SEQUENCE: 57

| | |
|---|---|
| ctgatttaca ggaactcaca ccagcgatca atcttcctta atttgtaact gggcagtgtc | 60 |
| ccgggccagc caatagctaa gactgccccc cccgcacccc accctccctg acctggggg | 120 |
| actctctact cagtctgcac tggagctgcc tggtgaccag aagtttggag tccgctgacg | 180 |
| tcgccgccca gatggcctcc aggctgaccc tgctgaccct cctgctgctg ctgctggctg | 240 |
| gggatagagc ctcctcaaat ccaaatgcta ccagctccag ctcccaggat ccagagagtt | 300 |
| tgcaagacag aggcgaaggg aaggtcgcaa caacagttat ctccaagatg ctattcgttg | 360 |
| aacccatcct ggaggtttcc agcttgccga caaccaactc aacaaccaat tcagccacca | 420 |
| aaataacagc taataccact gatgaaccca ccacacaacc caccacagag cccaccaccc | 480 |
| aacccaccat ccaacccacc caaccaacta cccagctccc aacagattct cctacccagc | 540 |

```
ccactactgg gtccttctgc ccaggacctg ttactctctg ctctgacttg gagagtcatt      600
caacagaggc cgtgttgggg gatgctttgg tagatttctc cctgaagctc taccacgcct      660
tctcagcaat gaagaaggtg gagaccaaca tggccttttc cccattcagc atcgccagcc      720
tccttaccca ggtcctgctc ggggctgggg agaacaccaa aacaaacctg gagagcatcc      780
tctcttaccc caaggacttc acctgtgtcc accaggccct gaagggcttc acgaccaaag      840
gtgtcacctc agtctctcag atcttccaca gcccagacct ggccataagg gacacctttg      900
tgaatgcctc tcggaccctg tacagcagca gccccagagt cctaagcaac aacagtgacg      960
ccaacttgga gctcatcaac acctgggtgg ccaagaacac caacaacaag atcagccggc     1020
tgctagacag tctgccctcc gatacccgcc ttgtcctcct caatgctatc tacctgagtg     1080
ccaagtggaa gacaacattt gatcccaaga aaaccagaat ggaacccttt cacttcaaaa     1140
actcagttat aaaagtgccc atgatgaata gcaagaagta ccctgtggcc catttcattg     1200
accaaacttt gaaagccaag gtggggcagc tgcagctctc ccacaatctg agtttggtga     1260
tcctggtacc ccagaacctg aaacatcgtc ttgaagacat ggaacaggct ctcagccctt     1320
ctgttttcaa ggccatcatg gagaaactgg agatgtccaa gttccagccc actctcctaa     1380
cactaccccg catcaaagtg acgaccagcc aggatatgct ctcaatcatg gagaaattgg     1440
aattcttcga tttttcttat gaccttaacc tgtgtgggct gacagaggac ccagatcttc     1500
aggtttctgc gatgcagcac cagacagtgc tggaactgac agagactggg gtggaggcgg     1560
ctgcagcctc cgccatctct gtggcccgca ccctgctggt cttttgaagtg cagcagccct     1620 tcctcttcgt gctctgggac cagcagcaca agttccctgt cttcatgggg cgagtatatg     1680
accccagggc ctgagacctg caggatcagg ttagggcgag cgctacctct ccagcctcag     1740
ctctcagttg cagccctgct gctgcctgcc tggacttggc ccctgccacc tcctgcctca     1800
ggtgtccgct atccaccaaa agggctccct gagggtctgg gcaagggacc tgcttctatt     1860
agcccttctc catggccctg ccatgctctc caaaccactt tttgcagctt tctctagttc     1920
aagttcacca gactctataa ataaaacctg acagaccatg actttcaaaa aaaaaaaaa     1980 aaaa                                                                 1984

<210> SEQ ID NO 58
<211> LENGTH: 1917
<212> TYPE: DNA
<213> ORGANISM: Homo sapiens

<400> SEQUENCE: 58
aatatcttgc atgttacaga tttcactact cccaccagct tggagacaac atgtggttct       60
tgacaactct gctcctttgg gttccagttg atgggcaagt ggacaccaca aaggcagtga      120
tcactttgca gcctccatgg gtcagcgtgt tccaagagga aaccgtaacc ttgcactgtg      180
aggtgctcca tctgcctggg agcagctcca cacagtggtt tctcaatggc acagccactc      240
agacctcgac ccccagctac agaatcacct ctgccagtgt caatgacagt ggtgaataca      300
ggtgccagag aggtctctca gggcgaagtg accccataca gctggaaatc cacagaggct      360
ggctactact gcaggtctcc agcagagtct tcatggaagg agaacctctg gccttgaggt      420
gtcatgcgtg gaaggataag ctggtgtaca atgtgcttta ctatcgaaat ggcaaagcct      480
ttaagttttt ccactggaat tctaacctca ccattctgaa aaccaacata agtcacaatg      540
gcacctacca ttgctcaggc atgggaaagc atcgctacac atcagcagga atatcacaat      600
```

```
acactgtgaa aggcctccag ttaccaactc ctgtctggtt tcatgtcctt ttctatctgg      660
cagtgggaat aatgttttta gtgaacactg ttctctgggt gacaatacgt aaagaactga      720
aaagaaagaa aaagtggaat ttagaaatct ctttggattc tggtcatgag aagaaggtaa      780
tttccagcct tcaagaagac agacatttag aagaagagct gaaatgtcag gaacaaaaag      840
aagaacagct gcaggaaggg gtgcaccgga aggagcccca gggggccacg tagcagcggc      900
tcagttggtg gccatcgatc tggaccgtcc cctgcccact tgctcccgt gagcactgcg       960
tacaaacatc caaaagttca acaaccagaa actgtgtgt ctcatggtat ataactctta      1020
aagcaaataa atgaactgac ttcaactggg atacatttgg aaatgtggtc atcaaagatg     1080
acttgaaatg aggcctactc taaagaattc ttgaaaaact tacaagtcaa gcctagcctg     1140
ataatcctat tacatagttt gaaaaatagt attttatttc tcagaacaag gtaaaaaggt     1200
gagtgggtgc atatgtacag aagattaaga cagagaaaca gacagaaaga gacacacaca     1260
cagccaggag tgggtagatt tcagggagac aagagggaat agtatagaca ataaggaagg     1320
aaatagtact tacaaatgac tcctaaggga ctgtgagact gagagggctc acgcctctgt     1380
gttcaggata cttagttcat ggcttttctc tttgacttta ctaaaagaga atgtctccat     1440
acgcgttcta ggcatacaag ggggtaactc atgatgagaa atggatgtgt tattcttgcc     1500
ctctcttttg aggctctctc ataacccctc tatttctaga gacaacaaaa atgttgccag     1560
tcctaggccc ctgccctgta ggaaggcaga atgtaactgt tctttttgtt taacgattaa     1620
gtccaaatct ccaagtgcgg cactgcaaag agacgcttca agtggggaga agcggcgata     1680
tcatagagtc cagatcttgc ctccagagat ttgctttacc ttcctgattt tctggttact     1740
aattagcttc aggatacgct gctctcatac ttgggctgta gtttggagac aaaatatttt     1800
cctgccactg tgtaacatag ctgaggtaaa aactgaacta tgtaaatgac tctactaaaa     1860
gtttagggaa aaaaacagg aggagtatga cacacacagc aaaaaaaaaa aaaaaaa        1917
```

<210> SEQ ID NO 59
<211> LENGTH: 2518
<212> TYPE: DNA
<213> ORGANISM: Homo sapiens

<400> SEQUENCE: 59

```
ctcatttgtg tgttttctga gtcagcatta gctaaatttt ccagaaggcc atccacaaag       60
tacagcctgg gcgttcaagg gacgtcattc atttccccca gtgaccttga caagtcagaa      120
gcttgaaagc agggaaatcc ggatgtctcg gttatgaagt ggagcagtga gtgtgagcct      180
caacatagtt ccagaactct ccatccggac tagttattga gcatctgcct ctcatatcac      240
cagtggccat ctgaggtgtt tccctggctc tgaaggggta ggcacgatgg ccaggtgctt      300
cagcctggtg ttgcttctca cttccatctg gaccacgagg ctcctggtcc aaggctcttt      360
gcgtgcagaa gagcttttcca tccaggtgtc atgcagaatt atgggatca cccttgtgag      420
caaaaaggcg aaccagcagc tgaatttcac agaagctaag gaggcctgta ggctgctggg      480
actaagtttg gccggcaagg accaagttga aacagccttg aaagctagct ttgaaacttg      540
cagctatggc tgggttggag atggattcgt ggtcatctct aggattagcc caaaccccaa      600
gtgtgggaaa atgggtgg gtgtcctgat ttggaaggtt ccagtgagcc gacagtttgc        660
agcctattgt tacaactcat ctgatacttg gactaactcg tgcattccag aaattatcac      720
caccaaagat cccatattca acactcaaac tgcaacacaa acaacagaat ttattgtcag      780
tgacagtacc tactcggtgg catccctta ctctacaata cctgccccta ctactactcc      840
```

-continued

| | |
|---|---|
| tcctgctcca gcttccactt ctattccacg gagaaaaaaa ttgatttgtg tcacagaagt | 900 |
| ttttatggaa actagcacca tgtctacaga aactgaacca tttgttgaaa ataaagcagc | 960 |
| attcaagaat gaagctgctg ggtttggagg tgtccccacg gctctgctag tgcttgctct | 1020 |
| cctcttcttt ggtgctgcag ctggtcttgg attttgctat gtcaaaaggt atgtgaaggc | 1080 |
| cttccctttt acaaacaaga atcagcagaa ggaaatgatc gaaaccaaag tagtaaagga | 1140 |
| ggagaaggcc aatgatagca accctaatga ggaatcaaag aaaactgata aaacccaga | 1200 |
| agagtccaag agtccaagca aaactaccgt gcgatgcctg gaagctgaag tttagatgag | 1260 |
| acagaaatga ggagacacac ctgaggctgg tttctttcat gctccttacc ctgccccagc | 1320 |
| tggggaaatc aaaagggcca agaaccaaa gaagaaagtc cacccttggt tcctaactgg | 1380 |
| aatcagctca ggactgccat tggactatgg agtgcaccaa agagaatgcc cttctcctta | 1440 |
| ttgtaaccct gtctggatcc tatcctccta cctccaaagc ttcccacggc ctttctagcc | 1500 |
| tggctatgtc ctaataatat cccactggga gaaggagtt ttgcaaagtg caaggaccta | 1560 |
| aaacatctca tcagtatcca gtggtaaaaa ggcctcctgg ctgtctgagg ctaggtgggt | 1620 |
| tgaaagccaa ggagtcactg agaccaaggc tttctctact gattccgcag ctcagaccct | 1680 |
| ttcttcagct ctgaaagaga aacacgtatc ccacctgaca tgtccttctg agcccggtaa | 1740 |
| gagcaaaaga atggcagaaa agtttagccc ctgaaagcca tggagattct cataacttga | 1800 |
| gacctaatct ctgtaaagct aaaataaaga aatagaacaa ggctgaggat acgacagtac | 1860 |
| actgtcagca gggactgtaa acacagacag ggtcaaagtg ttttctctga acacattgag | 1920 |
| ttggaatcac tgtttagaac acacacactt acttttctg gtctctacca ctgctgatat | 1980 |
| tttctctagg aaatatactt ttacaagtaa caaaaataaa aactcttata aatttctatt | 2040 |
| tttatctgag ttacagaaat gattactaag gaagattact cagtaatttg tttaaaaagt | 2100 |
| aataaaattc aacaaacatt tgctgaatag ctactatatg tcaagtgctg tgcaaggtat | 2160 |
| tacactctgt aattgaatat tattcctcaa aaaattgcac atagtagaac gctatctggg | 2220 |
| aagctatttt tttcagtttt gatatttcta gcttatctac ttccaaacta attttatt | 2280 |
| ttgctgagac taatcttatt cattttctct aatatggcaa ccattataac cttaatttat | 2340 |
| tattaacata cctaagaagt acattgttac ctctatatac caaagcacat tttaaagtg | 2400 |
| ccattaacaa atgtatcact agccctcctt ttccaacaa gaagggactg agagatgcag | 2460 |
| aaatatttgt gacaaaaaat taaagcattt agaaaacttc aaaaaaaaaa aaaaaaa | 2518 |

<210> SEQ ID NO 60
<211> LENGTH: 2180
<212> TYPE: DNA
<213> ORGANISM: Homo sapiens

<400> SEQUENCE: 60

| | |
|---|---|
| gtaacaactc tcagaggagc attgcccgtc agacagcaac tcagagaata accagagaac | 60 |
| aaccagcatt tcttgcacta caacttgctt aagctcttac acttcatagt gaagctatgc | 120 |
| accaccgagt gaagcgatgt ggaacattgg aaagagtggg cttccttaga cagacctggg | 180 |
| cttgaatccc tgctccacta cctaccagct gtgtgaccct atacaagtta cttaatgttt | 240 |
| ctgagcatca ggatataatc tataaaatag ggagaatcac ctctacctca tacagattct | 300 |
| gcaaagatta acgaggaga ggagattgaa acaatggagg atctttgtgt ggcaaacaca | 360 |
| ctctttgccc tcaatttatt caagcatctg gcaaaagcaa gccccaccca gaacctcttc | 420 |

| | |
|---|---|
| ctctccccat ggagcatctc gtccaccatg ccatggtct acatgggctc caggggcagc | 480 |
| accgaagacc agatggccaa ggtgcttcag tttaatgaag tgggagccaa tgcagttacc | 540 |
| cccatgactc cagagaactt taccagctgt gggttcatgc agcagatcca aagggtagt | 600 |
| tatcctgatg cgattttgca ggcacaagct gcagataaaa tccattcatc cttccgctct | 660 |
| ctcagctctg caatcaatgc atccacaggg aattatttac tggaaagtgt caataagctg | 720 |
| tttggtgaga agtctgcgag cttccgggaa gaatatattc gactctgtca gaaatattac | 780 |
| tcctcagaac cccaggcagt agacttccta gaatgtgcag aagaagctag aaaaaagatt | 840 |
| aattcctggg tcaagactca aaccaaaggc aaaatcccaa acttgttacc tgaaggttct | 900 |
| gtagatgggg ataccaggat ggtcctggtg aatgctgtct acttcaaagg aaagtggaaa | 960 |
| actccatttg agaagaaact aaatgggctt tatcctttcc gtgtaaactc ggctcagcgc | 1020 |
| acacctgtac agatgatgta cttgcgtgaa aagctaaaca ttggatacat agaagaccta | 1080 |
| aaggctcaga ttctagaact cccatatgct ggagatgtta gcatgttctt gttgcttcca | 1140 |
| gatgaaattg ccgatgtgtc cactggcttg gagctgctgg aaagtgaaat aacctatgac | 1200 |
| aaactcaaca gtggaccag caaagacaaa atggctgaag atgaagttga ggtatacata | 1260 |
| ccccagttca aattagaaga gcattatgaa ctcagatcca ttctgagaag catgggcatg | 1320 |
| gaggacgcct tcaacaaggg acgggccaat ttctcaggga tgtcggagag gaatgacctg | 1380 |
| tttctttctg aagtgttcca ccaagccatg gtggatgtga atgaggaggg cactgaagca | 1440 |
| gccgctggca caggaggtgt tatgacaggg agaactggac atggaggccc acagtttgtg | 1500 |
| gcagatcatc cttttctttt tcttattatg cataagataa ccaactgcat tttattttc | 1560 |
| ggcagatttt cctcacccta aaactaagcg tgctgcttct gcaaaagatt tttgtagatg | 1620 |
| agctgtgtgc ctcagaattg ctatttcaaa ttgccaaaaa tttagagatg ttttctacat | 1680 |
| atttctgctc ttctgaacaa cttctgctac ccactaaata aaaacacaga ataattaga | 1740 |
| caattgtcta ttataacatg acaaccctat taatcatttg gtcttctaaa atgggatcat | 1800 |
| gcccatttag attttcctta ctatcagttt attttttataa cattaacttt tactttgtta | 1860 |
| tttattattt tatataatgg tgagttttta aattattgct cactgcctat ttaatgtagc | 1920 |
| taataaagtt atagaagcag atgatctgtt aatttcctat ctaataaatg ccttaattg | 1980 |
| ttctcataat gaagaataag taggtatccc tccatgccct tctgtaataa atatctggaa | 2040 |
| aaaacattaa acaataggca aatatatgtt atgtgcattt ctagaaatac ataacacata | 2100 |
| tatatgtctg tatcttatat tcaattgcaa gtatataata aataaacctg cttccaaaca | 2160 |
| acaataaaaa aaaaaaaaa | 2180 |

<210> SEQ ID NO 61
<211> LENGTH: 3262
<212> TYPE: DNA
<213> ORGANISM: Homo sapiens

<400> SEQUENCE: 61

| | |
|---|---|
| ggctggagag taaaagaac tgggggtaag agcccctctg cctagcactg ctcccccaag | 60 |
| gctcccagaa atctcaggtc agaggcacgg acagcctctg gagctctcgt ctggtgggac | 120 |
| catgaactgc cagcagctgt ggctgggctt cctactcccc atgacagtct caggccgggt | 180 |
| cctggggctt gcagaggtgg cgcccgtgga ctacctgtca caatatgggt acctacagaa | 240 |
| gcctctagaa ggatctaata acttcaagcc agaagatatc accgaggctc tgagagcttt | 300 |
| tcaggaagca tctgaacttc cagtctcagg tcagctggat gatgccacaa gggcccgcat | 360 |

```
gaggcagcct cgttgtggcc tagaggatcc cttcaaccag aagacccctta aatacctgtt    420
gctgggccgc tggagaaaga agcacctgac tttccgcatc ttgaacctgc cctccaccct    480
tccaccccac acagcccggg cagccctgcg tcaagccttc caggactgga gcaatgtggc    540
tcccttgacc ttccaagagg tgcaggctgg tgcggctgac atccgcctct ccttccatgg    600
ccgccaaagc tcgtactgtt ccaatacttt tgatgggcct gggagagtcc tggcccatgc    660
cgacatccca gagctgggca gtgtgcactt cgacgaagac gagttctgga ctgaggggac    720
ctaccgtggg gtgaacctgc gcatcattgc agcccatgaa gtgggccatg ctctggggct    780
tgggcactcc cgatattccc aggccctcat ggccccagtc tacgagggct accggcccca    840
ctttaagctg cacccagatg atgtggcagg gatccaggct ctctatggca agaagagtcc    900
agtgataagg gatgaggaag aagaagagac agagctgccc actgtgcccc cagtgccac     960
agaacccagt cccatgccag acccttgcag tagtgaactg gatgccatga tgctggggcc   1020
ccgtgggaag acctatgctt tcaagggggga ctatgtgtgg actgtatcag attcaggacc   1080
gggccccttg ttccgagtgt ctgccctttg ggaggggctc cccggaaacc tggatgctgc   1140
tgtctactcg cctcgaacac aatggattca cttctttaag ggagacaagg tgtggcgcta   1200
cattaatttc aagatgtctc ctggcttccc caagaagctg aatagggtag aacctaacct   1260
ggatgcagct ctctattggc ctctcaacca aaaggtgttc ctctttaagg gctccgggta   1320
ctggcagtgg gacgagctag cccgaactga cttcagcagc taccccaaac caatcaaggg   1380
tttgtttacg ggagtgccaa accagccctc ggctgctatg agttggcaag atggccgagt   1440
ctacttcttc aagggcaaag tctactggcg cctcaaccag cagcttcgag tagagaaagg   1500
ctatcccaga aatatttccc acaactggat gcactgtcgt ccccggacta tagacactac   1560
cccatcaggt gggaatacca ctccctcagg tacgggcata accttggata ccactctctc   1620
agccacagaa accacgtttg aatactgact gctcacccac agacacaatc ttggacatta   1680
accctgagg ctccaccacc caccctttca tttccccccc agaagcctaa ggctaatag    1740
ctgaatgaaa tacctgtctg ctcagtagaa ccttgcaggt gctgtagcag gcgcaagacc   1800
gtagatctca ggcctctaac acttccaact ccagccacca ctttcctgtg cattttcact   1860
cctgagaagt gctcccctaa ctcagatccc ctaacttaga tttggccccc aactccattt   1920
cctgtctgtc ttagacagcc cttccaactg tgtcatctct tctctggagg tcaatggtgg   1980
agggagatgc ctgggtcctg ttcttcctac ataaaatgca agaaaacagc atggccagta   2040
aactgagcaa gggccttgga atccttgaga atcacattta tgtgcttatg attacgggca   2100
agctaattaa ccttgttgaa tctcagattc cccatttgca acattaggtt aagaccagta   2160
ctgcaggatt gttgcactaa atgaaatact gtatgtgaag tgcctggcac agtgtctggt   2220
acatttgtgt ttaataaaag ctaactccat gttcataaga gaggactgaa cagctcttcc   2280
tctagctgtc tggctgtata actcttacag tagtctgtat aataagggca tctctattag   2340
atctttaggg gacagaggat tgtcaagat ggttagctct ttgttttggg gtgcagagaa    2400
agaaaagagc agcaacagca gaggctggac tccctggttc agtatttaat gccatttat    2460
tcacatgctc ccatgttctc cctccctccc attgtagcct tgctgcccag gggagggata   2520
tgtcttcctt tatgcatctg ggaaaccagg aacagaccct gcgcaggaga gtcagagggg   2580
gaagagttag aatgggtcag tggctggaac aaagttctgg ttaaggagga aattagtgcc   2640
acccacggtg agaagcagag aaggcacttg catcctatgc agccctgaag accaggctcc   2700
```

```
tttgggcaaa aggcaagact ctggcaggtg ggtcaatgct ctctccttgg agcaagaagc   2760
cagcttttgg ggaaggcagg tcctgaggca ggcactgccc tgtggtcttc cccaggttga   2820
ggagagaagt ggaagcccca tggaagacag tgctcccagc tgaggtagga ggcggaggtg   2880
ggggtggggg tagtttaagc ctatggggcc caggggaaa ggccaaacag aaacccaact    2940
accccctaat gaagggcctg gaggttgggg tatcttggag ctcctcagag cccttcttcc   3000
catcaaaaag gtatcaaatg ccttggaagc tccctgatcc tacaaaacaa aaaaatgctt   3060 attttttacca ctgtgaggca agctgaggtg aacatttaaa aggctatttc aagacgaggt   3120
gcggtggcta taatcctagc actttgggag gctgaagcag gaggatcact tgagcccagg   3180
agttcaagac cagcttgggc aacatgggga gaccctgtct ctgcaaaaaa ataaaaacga   3240
atacataaaa attaaaaaaa aa                                            3262

<210> SEQ ID NO 62
<211> LENGTH: 3050
<212> TYPE: DNA
<213> ORGANISM: Homo sapiens

<400> SEQUENCE: 62
ggagtcagtg atttgaacga agtactttca gtttcatatt actctaaatc cattacaaat     60
ctgcttagct tctaaatatt tcatcaatga ggaaatccca gccctacaac ttcggaacag    120
tgaaatatta gtccagggat ccagtgagag acacagaagt gctagaagcc agtgctcgtg    180
aactaaggag aaaaagaaca gacaagggaa cagcctggac atggcatcag agatccacat    240
gacaggccca atgtgcctca ttgagaacac taatgggcga ctgatggcga atccagaagc    300
tctgaagatc ctttctgcca ttacacagcc tatggtggtg gtggcaattg tgggcctcta    360
ccgcacaggc aaatcctacc tgatgaacaa gctggctgga agaaaaaagg gcttctctct    420
gggctccacg gtgcagtctc acactaaagg aatctggatg tggtgtgtgc cccaccccaa    480
gaagccaggc cacatcctag ttctgctgga caccgagggt ctgggagatg tagagaaggg    540
tgacaaccag aatgactcct ggatcttcgc cctggccgtc ctcctgagca gcaccttcgt    600
gtacaatagc ataggaacca tcaaccagca ggctatggac caactgtact atgtgacaga    660
gctgacacat agaatccgat caaaatcctc acctgatgag aatgagaatg aggttgagga    720
ttcagctgac tttgtgagct tcttcccaga cttgtgtgg acactgagag atttctccct     780
ggacttggaa gcagatggac aacccctcac accagatgag tacctgacat actccctgaa    840
gctgaagaaa ggtaccagtc aaaaagatga aacttttaac ctgcccagac tctgtatccg    900
gaaattcttc ccaaagaaaa atgctttgt ctttgatcgg cccgttcacc gcaggaagct    960
tgcccagctc gagaaactac aagatgaaga gctggacccc gaatttgtgc aacaagtagc   1020
agacttctgt tcctacatct ttagtaattc caaaactaaa actcttttcag gaggcatcca   1080 ggtcaacggg cctcgtctag agagcctggt gctgacctac gtcaatgcca tcagcagtgg   1140
ggatctgccg tgcatggaga acgcagtcct ggccttggcc cagatagaga actcagctgc   1200
agtgcaaaag gctattgccc actatgaaca gcagatgggc cagaaggtgc agctgcccac   1260
agaaaccctc caggagctgc tggacctgca cagggacagt gagagagagg ccattgaagt   1320
cttcatcagg agttccttca aagatgtgga ccatctattt caaaaggagt tagcggccca   1380 gctagaaaaaa aagcgggatg actttttgtaa acagaatcag gaagcatcat cagatcgttg   1440
ctcagcttta cttcaggtca ttttcagtcc tctagaagaa gaagtgaagg cgggaattta   1500
ttcgaaacca gggggctatc gtctctttgt tcagaagcta caagacctga gaaaaagta   1560
```

```
ctatgaggaa ccgaggaagg ggatacaggc tgaagagatt ctgcagacat acttgaaatc      1620
caaggagtct atgactgatg caattctcca gacagaccag actctcacag aaaaagaaaa      1680
ggagattgaa gtggaacgtg tgaaagctga gtctgcacag gcttcagcaa aaatgttgca      1740
ggaaatgcaa agaaagaatg agcagatgat ggaacagaag gagaggagtt atcaggaaca      1800
cttgaaacaa ctgactgaga agatggagaa cgacagggtc cagttgctga agagcaaga      1860 gaggaccctc gctcttaaac ttcaggaaca ggagcaacta ctaaaagagg gatttcaaaa      1920
agaaagcaga ataatgaaaa atgagataca ggatctccag acgaaaatga gacgacgaaa      1980
ggcatgtacc ataagctaaa gaccagagcc ttcctgtcac ccctaaccaa ggcataattg      2040
aaacaatttt agaatttgga caagcgtca ctacatttga taataattag atcttgcatc       2100
ataacaccaa aagtttataa aggcatgtgg tacaatgatc aaaatcatgt ttttctttaa      2160
aaaaaaaaaa agactgtaaa ttgtgcaaca agatgcatt tacctctgta tcaactcagg       2220
aaatctcata agctggtacc actcaggaga agtttattct tccagatgac cagcagtaga      2280
caaatggata ctgagcagag tcttaggtaa aagtcttggg aaatatttgg gcattggtct      2340
ggccaagtct acaatgtccc aatatcaagg acaaccaccc tagcttctta gtgaagacaa      2400
tgtacagtta tccgttagat caagactaca cggtctatga gcaataatgt gatttctgga      2460
cattgcccat gtataatcct cactgatgat ttcaagctaa agcaaaccac cttatacaga      2520
gatctagaat ctctttatgt tctccagagg aaggtggaag aaaccatggg caggagtagg      2580
aattgagtga taaacaattg ggctaatgaa gaaaacttct cttattgttc agttcatcca      2640
gattataact tcaatgggac actttagacc attagacaat tgacactgga ttaaacaaat      2700
tcacataatg ccaaatacac aatgtattta tagcaacgta taatttgcaa agatggactt      2760 taaagatgc tgtgtaacta aactgaaata attcaattac ttattattta gaatgttaaa       2820
gcttatgata gtcttttcta actcttaaca ctcatacttg aaaactttct gagtttcccc      2880
agaagagaat atgggatttt ttttgacatt tttgactcat ttaataatgc tcttgtgttt      2940
acctagtata tgtagacttt gtcttatgtg tgaaaagtcc taggaaagtg gttgatgttt      3000
cttatagcaa ttaaaaatta ttttttgaact gaaaatacaa tgtatttcac                3050
```

<210> SEQ ID NO 63
<211> LENGTH: 1227
<212> TYPE: DNA
<213> ORGANISM: Homo sapiens

<400> SEQUENCE: 63

```
ctttgcagat aaatatggca cactagcccc acgttttctg agacattcct caattgctta        60
gacatattct gagcctacag cagaggaacc tccagtctca gcaccatgaa tcaaactgcc       120
attctgattt gctgccttat ctttctgact ctaagtggca ttcaaggagt acctctctct       180
agaactgtac gctgtacctg catcagcatt agtaatcaac ctgttaatcc aaggtctttat      240 gaaaaacttg aaattattcc tgcaagccaa ttttgtccac gtgttgagat cattgctaca       300
atgaaaaaga agggtgagaa gagatgtctg aatccagaat cgaaggccat caagaattta       360
ctgaaagcag ttagcaagga aaggtctaaa agatctcctt aaaaccagag gggagcaaaa       420
tcgatgcagt gcttccaagg atggaccaca cagaggctgc ctctcccatc acttccctac       480
atggagtata tgtcaagcca taattgttct tagtttgcag ttacactaaa aggtgaccaa       540
tgatggtcac caaatcagct gctactactc ctgtaggaag gttaatgttc atcatcctaa       600
```

```
gctattcagt aataactcta ccctggcact ataatgtaag ctctactgag gtgctatgtt         660
cttagtggat gttctgaccc tgcttcaaat atttccctca cctttcccat cttccaaggg         720
tactaaggaa tctttctgct ttggggttta tcagaattct cagaatctca ataactaaa         780 aggtatgcaa tcaaatctgc tttttaaaga atgctcttta cttcatggac ttccactgcc         840
atcctcccaa ggggcccaaa ttctttcagt ggctacctac atacaattcc aaacacatac         900
aggaaggtag aaatatctga aaatgtatgt gtaagtattc ttatttaatg aaagactgta         960
caaagtagaa gtcttagatg tatatatttc ctatattgtt ttcagtgtac atggaataac        1020
atgtaattaa gtactatgta tcaatgagta acaggaaaat tttaaaaata cagatagata        1080
tatgctctgc atgttacata agataaatgt gctgaatggt tttcaaaata aaaatgaggt        1140
actctcctgg aaatattaag aaagactatc taaatgttga aagatcaaaa ggttaataaa        1200
gtaattataa ctaagaaaaa aaaaaaa                                            1227

<210> SEQ ID NO 64
<211> LENGTH: 1761
<212> TYPE: DNA
<213> ORGANISM: Homo sapiens

<400> SEQUENCE: 64
cccgctcttt cgttttcgtt tcccggaagg atagcgatta ccggagcgcc tcgcgcgcct          60
gcccgcctgc ggaggacccg ggcgcacacg ccttggcgct tctcgaaaga gatttcctcc         120
cacgcgacct tccagttctc ggagccaggt taggggtttg gcggaggagg actgcggggc         180
gcgggcctag ggccccagca gccacagcca ggggagcgct caagacagaa agccggtggc         240
ttcctcacct ccacctgtaa tgcaggaggg agaattggct atttctccta taagccctgt         300
ggcagccatg cctcccctag gcacccacgt gcaagccaga tgtgaagctc aaattaacct         360
gctgggtgaa gggggggatct gcaagctgcc aggaagactc cgcatccagc ccgcactgtg         420
gagcagggag gacgtgctgc actggctgcg ctgggcagag caggagtact ctctgccatg         480
caccgcggag cacgggttcg agatgaacgg acgcgccctc tgcatcctca ccaaggacga         540
cttccggcac cgtgcgccca gctcaggtga cgtcctgtat gagctgctcc agtacatcaa         600
gacccagcgg cgagccctgg tgtgtgggcc cttttttgga gggatcttca ggctgaagac         660
gcccacccag cactctccag tcccccggga agaggtgact ggcccctctc agatggacac         720
ccgaaggggc cacctgctgc agccaccaga cccagggctt accagcaact tcggccacct         780
ggatgaccct ggcctggcaa ggtggacccc tggcaaggag gagtccctca acttatgtca         840
ctgtgcagag ctcggctgca ggacccaggg ggtctgttcc ttccccgcga tgccgcaggc         900
ccccattgac ggcaggatcg ctgactgccg cctgctgtgg gattacgtgt atcagctgct         960
ccttgatacc cgatatgagc cctacatcaa gtgggaagac aaggacgcca agatcttccg        1020
agttgtggat ccaaatgggc tcgccagact ctggggaaat cacaagaacc gggtgaacat        1080
gacctacgag aagatgtctc gtgccctgcg ccactattat aagcttaata tcattaagaa        1140
ggaaccgggg cagaaactcc tgttcagatt tctaaagact ccgggaaaga tggtccagga        1200
caagcacagc cacctggagc cgctggagag ccaggagcag acagaatag agttcaagga        1260 caagaggcca gaaatctctc cgtgagggc aggtggactc caggcacccg gtaccgatgg        1320
ggcagggacc gagtctccca tgaaggcaga ctcctcctcc cagagagca gcaggatccc        1380 cagccagact ctgtacccac aggattacag ccattgcttg gaaggctgg gaggcctccc        1440 atccaggaca ctgggggcag gagtgtcatc tttttgggcag ggcaatcctg gggctaaatg        1500
```

-continued

```
aggtacaggg gaatggactc tcccctactg caccccgggg agaggaagcc aggcaccgat      1560
agagcaccca gccccacccc tgtaaatgga atttaccaga tgaagggaat gaagtccctc      1620
actgagcctc agatttcctc acctgtgaaa tgggctgagg caggaaatgg gaaaaagtgt      1680
tagtgcttcc aggcggcact gacagcctca gtaacaataa aaacaatggt agctgaaaaa      1740
aaaaaaaaaa aaaaaaaaa a                                                 1761

<210> SEQ ID NO 65
<211> LENGTH: 873
<212> TYPE: DNA
<213> ORGANISM: Homo sapiens

<400> SEQUENCE: 65
atgaggatat ttgctgtctt tatattcatg acctactggc atttgctgaa cgcatttact        60
gtcacggttc ccaaggacct atatgtggta gagtatggta gcaatatgac aattgaatgc       120
aaattcccag tagaaaaaca attagacctg gctgcactaa ttgtctattg ggaaatggag       180
gataagaaca ttattcaatt tgtgcatgga gaggaagacc tgaaggttca gcatagtagc       240
tacagacaga gggcccggct gttgaaggac cagctctccc tgggaaatgc tgcacttcag       300
atcacagatg tgaaattgca ggatgcaggg gtgtaccgct gcatgatcag ctatggtggt       360
gccgactaca gcgaattac tgtgaaagtc aatgccccat acaacaaaat caaccaaaga        420
attttggttg tggatccagt cacctctgaa catgaactga catgtcaggc tgagggctac       480
cccaaggccg aagtcatctg gacaagcagt gaccatcaag tcctgagtgg taagaccacc       540
accaccaatt ccaagagaga ggagaagctt ttcaatgtga ccagcacact gagaatcaac       600
acaacaacta atgagatttt ctactgcact tttaggagat tagatcctga ggaaaaccat       660
acagctgaat tggtcatccc agaactacct ctggcacatc ctccaaatga aaggactcac       720
ttggtaattc tgggagccat cttattatgc cttggtgtag cactgacatt catcttccgt       780
ttaagaaaag ggagaatgat ggatgtgaaa aaatgtggca tccaagatac aaactcaaag       840
aagcaaagtg atacacattt ggaggagacg taa                                   873

<210> SEQ ID NO 66
<211> LENGTH: 1965
<212> TYPE: DNA
<213> ORGANISM: Homo sapiens

<400> SEQUENCE: 66
aacgcccgcc tgcaaggtcc tctgcgccct ggcagccagg agtcgccgcc acgaccgccg        60
ggtctcagtg ggtgcctgcg ccttctcccc gcccgcctgc cccgggccat ccagaaactt       120
gctctacccg ccgcgggtgc tcggcagtgc tgccccatggc ccagcccagg agcctattta      180
gggcgccgga cgggctggac agaggcgcgg ctcagtaatt gaaggcctga acgcccatg        240 tgccactgac taggaggctt ccctgctgcg gcacttcatg acccagcggc gcgcggccca       300
gtgaagccac cgtggtgtcc agcatggccg cgctgctcct gggcgcggtg ctgctggtgg       360
cccagcccca gctagtgcct tcccgccccg ccgagctagg ccagcaggag cttctgcgga       420
aagcggggac cctccaggat gacgtccgcg atggcgtggc cccaaacggc tctgcccagc       480
agttgccgca gaccatcatc atcggcgtgc gcaagggcgg cacgcgcgca ctgctggaga       540
tgctcagcct gcaccccgac gtggcggccg cggagaacga ggtccacttc ttcgactggg       600
aggagcatta cagccacggc ttgggctggt acctcagcca gatgcccttc tcctggccac       660
```

```
accagctcac agtggagaag accccgcgt atttcacgtc gcccaaagtg cctgagcgag    720
tctacagcat gaacccgtcc atccggctgc tgctcatcct gcgagacccg tcggagcgcg    780
tgctatctga ctacacccaa gtgttctaca accacatgca gaagcacaag ccctacccgt    840
ccatcgagga gttcctggtg cgcgatggca ggctcaatgt ggactacaag gccctcaacc    900
gcagcctcta ccacgtgcac atgcagaact ggctgcgctt tttccgctg cgccacatcc    960 acattgtgga cggcgaccgc tcatcaggg accccttccc tgagatccaa aaggtcgaga    1020
ggttcctaaa gctgtcgccg cagatcaatg cttcgaactt ctactttaac aaaaccaagg    1080
gcttttactg cctgcgggac agcggccggg accgctgctt acatgagtcc aaaggccggg    1140
cgcaccccca agtcgatccc aaactactca ataaactgca cgaatatttt catgagccaa    1200
ataagaagtt cttcgagctt gttggcagaa catttgactg gcactgattt gcaataagct    1260
aagctcagaa actttcctac tgtaagttct ggtgtacatc tgaggggaaa aagaatttta    1320
aaaaagcatt taaggtataa tttatttgta aaatccataa agtacttctg tacagtatta    1380
gattcacaat tgccatatat actagttata tttttctact tgttaaatgg agggcatttt    1440
gtattgtttt tcatggttgt taacattgtg taatatgtct ctatatgaag gaactaaact    1500
atttcactga aaaaaaaaaa aagatttttt ctggagacgc tatgttttt tgaatataat    1560 taacttgccc ccaactcaaa atagctgtct gtgttgcaat cattgcaaaa tctaaattct    1620
tttgttactt aaaaaaacat gttttcatg gctattacaa tcctctctct ccctctcct    1680 ttctgcattg ctctttttaa ttttttaatgt ctcattgtga tcatcagatt tatttttact    1740
tggattgtaa gatttatctc ctcggcgatt ccttgtcatt tttggaggtc acagttttac    1800
tcattcccat gtgtaaactt caagtaaaca aagcaatatt caggatggag aagcagttag    1860
tgactggcta gaggtctctt gggatccatc ttgacctcaa agaatatttg cacatgcttc    1920
tgatctcagc agttataata aagaggatta aacccttggc cttca                   1965

<210> SEQ ID NO 67
<211> LENGTH: 581
<212> TYPE: DNA
<213> ORGANISM: Homo sapiens

<400> SEQUENCE: 67
acccaccagg ccaccacaag aatgttgcat tttcattatt atgatacttc aaacaaaata     60
atggagcccc acagaccgaa tgtgaagaca gcagtgccat tgtctttgga aagctatcac    120
atatctgaag agtatggctt tcttcttcca gattctctga aagaacttcc agatcattat    180
aggccttgga tggaaattgc caacaaactt cctcaattga ttgatgctca ccagcttcaa    240
gctcatgtgg acaagatgcc cctgctgagc tgccagttcc tgaagggtca ccgggagcag    300
cgcctggccc acctggtcct gagcttcctc accatggggtt atgtctggca ggaaggagag    360
gcgcagcctg cagaggtcct gccaaggaat cttgccctc catttgtcga agtctccagg    420
aacttggggc tccctcctat cctggtccac tcagacttgg tgctgacgaa ctggaccaaa    480
aaagatccag acggagacgg agtctccctc tgtctcccag gctggagtgc agtggcatga    540
tctcggctca ctgcaacctc tgcctcctgg gtttgagcgg t                        581

<210> SEQ ID NO 68
<211> LENGTH: 2142
<212> TYPE: DNA
<213> ORGANISM: Homo sapiens

<400> SEQUENCE: 68
```

```
gaaactgaaa cttggccctc tgggggcgga gtggccactg gggatttaaa gagctgccac      60
ttccttaggc ctccagaggg cactgggaag tcacagctgc tgaggaccac ctctgctccc     120
ccgcctaagc catgcacctc tgtggggca atgggctgct gacccagaca gacccccaagg    180 agcaacaaag gcagctgaag aagcagaaga accgggcagc cgcccagcga agccggcaga     240
agcacacaga caaggcagac gccctgcacc agcagcacga gtctctggaa aaagacaacc     300
tcgccctgcg gaaggagatc cagtccctgc aggccgagct ggcgtggtgg agccggaccc     360
tgcacgtgca tgagcgcctg tgcccatgg attgtgcctc ctgctcagct ccagggctcc      420
tgggctgctg ggaccaggct gaggggctcc tgggccctgg cccacaggga caacatggct     480
gccgggagca gctggagctg ttccagaccc cgggttcctg ttacccagct cagccgctct     540
ctccaggtcc acagcctcat gattctccca gcctcctcca gtgcccctg ccctcactgt      600 cccttggccc cgctgtggtt gctgaacctc ctgtccagct gtccccagc cctctcctgt      660 ttgcctcgca cactggttcc agcctgcagg ggtcttcctc taagctcagt gccctccagc     720
ccagcctcac ggcccaaact gccctccac agccctcga gctggagcat cccaccagag       780
ggaagctggg gtcctctccc gacaacccctt cctctgccct ggggcttgca cgtctgcaga    840
gcagggagca caaacctgct ctctcagcag ccacttggca agggctggtt gtggatccca     900
gccctcaccc tctcctggcc tttcctctgc tctcctctgc tcaagtccac ttctaacctg     960
gtcttcggag ctgggttggc cccttctttg ggctcaggaa gcagccttag cacacgggcc    1020
tctcctccct cactactggg tgctgccctg cgtggctgac cagctggccc aggatttcac    1080
agtcgaaaag gaagccacca ctgatgcctc ccactgtgac aggccctgtc accaccaata    1140
tcttatttca acctcacagt tgacctgaga aatcgagatt atcactccac tttttcagac    1200
aaggaaactg aggctcaggg aagccaagtg acaagtccaa ggtcacgaag actttcttgg    1260
agcccgaaac accaccctct gctcctcctt ctcctgtcct ggcccaggca tcctaggggc    1320
tgaaatcctg gaaccgtgg gctggtgtga aaggtttgc atgctcagag cagagaaggg      1380
ctctccccac tgcttcgtga ttccagggcc agagccatgc agtccagaa accccaacct    1440 agctggggca ggtccagagt ccaagccctg gtgggtagag gccaagcaga agccctgaag    1500
tggactcttg cttcccctag tagtgttttc agtgccaaga agctgaaact gtgagctgga    1560
gttggggaga ggtctggaag aggaccatct gggatttcta cagcctgggt acccatagcc    1620
acaccaaggc ttctgggaga ttctgcaggg tcagctttcc aggctgttcc caaatagctc    1680
cctgcctccc cactgcccct aaagccacag cagaagagcc attcatctca taaacaaaaa    1740
ggaagaggaa agaatgagga aggaccctgt gcaaggttat ttgcaggcag ggatgggctt    1800
gtacctgaca gcaccaccc ctgtgtggcc cccaggccct catcaccctc agacccctcc     1860
taagcagttc cctcattgct ctttggacta ggctgacagc aggaagagca gggcccatga    1920
ccgggtggaa gttcagtttt ggtgtctgct tcaagagggg gttttacact ctgattccag    1980
gacaagcact ctgaggcggg tgggggagag aaaccctggc tcttcaccca ggtttcacac    2040
acatgtaaat gaaacactat gttagtatct aacacactcc tggatacaga acacaagtct    2100
tggcacatat gtgatggaaa taaagtgttt tgcaatcttt aa                        2142
```

<210> SEQ ID NO 69
<211> LENGTH: 2400
<212> TYPE: DNA
<213> ORGANISM: Homo sapiens

```
<400> SEQUENCE: 69
tccgctccgt tcggccggtt ctcccgggaa gctattaata gcattacgtc agcctgggac      60
tggcaacacg gagtaaacga ccgcgccgcc agcctgaggg ctataaaagg ggtgatgcaa     120
cgctctccaa gccacagtcg cacgcagcca ggcgcgcact gcacagctct cttctctcgc    180
cgccgcccga gcgcacccct tcagcccgcgc gccggccgtg agtcctcggt gctcgcccgc   240
cggccagaca acagcccgc ccgacccgt cccgaccctg gccgcccga gcggagcctg       300
gagcaaaatg atgcttcaac acccaggcca ggtctctgcc tcggaagtga gtgcttctgc   360
catcgtcccc tgcctgtccc ctcctgggtc actggtgttt gaggattttg ctaacctgac   420
gcccttttgtc aaggaagagc tgaggtttgc catccagaac aagcacctct gccaccggat  480
gtcctctgcg ctggaatcag tcactgtcag cgacagaccc ctcggggtgt ccatcacaaa   540
agccgaggta gcccctgaag aagatgaaag gaaaagagg cgacgagaaa gaataagat    600
tgcagctgca aagtgccgaa acaagaagaa ggagaagacg gagtgcctgc agaaactccc  660
aaggcccttt tgggtccaga agacctgcat atgggctgtt gactcatgca aatgaggtat  720
ctgaactgca gcttcagtat tagcagagcc acaggccgcc tctgtggcat caccagggtt  780
tctctgaaga agagggtctg catttttccta aacccagtgc tgctctccca tctcccatct  840
tcctctcgca gcttgatgag ccccggtgtg tcccaggtac accctgcat ccaggcagca    900
gcccaggcca ccccctcctc actggcccctt ggctcctttc ttgatgcctc tgttgcttgt  960
cccccaggag tcggagaagc tggaaagtgt gaatgctgaa ctgaaggctc agattgagga 1020
gctcaagaac gagaagcagc atttgatata catgctcaac cttcatcggc ccacgtgtat 1080
tgtccgggct cagaatggga ggactccaga agatgagaga aacctcttta ccaacagat  1140
aaaagaagga acattgcaga gctaagcagt cgtggtatgg gggcgactgg ggagtcctca 1200
ttgaatcctc attttatacc caaaaccctg aagccattgg agagctgtct tcctgtgtac 1260
ctctagaatc ccagcagcag agaaccatca aggcgggagg gcctgcagtg attcagcagg 1320
cccttcccat tctgccccag agtgggtctt ggaccagggc aagtgcatct ttgcctcaac 1380
tccaggattt aggccttaac acactggcca ttcttatgtt ccagatgcc cccagctggt  1440
gtcctgcccg cctttcatct ggattctaca aaaaccagg atgcccaccg ttaggattca   1500
ggcagcagtg tctgtacctc gggtgggagg gatggggcca tctccttcac cgtggctacc  1560
attgtcactc gtaggggatg tggagtgaga acagcattta gtgaagttgt gcaacggcca  1620
gggttgtgct ttctagcaaa tatgctgtta tgtccagaaa ttgtgtgtgc aagaaaacta 1680
ggcaatgtac tcttccgatg tttgtgtcac acaacactga tgtgacttt atatgctttt   1740
tctcagatct ggtttctaag agttttgggg ggcggggctg tcaccacgtg cagtatctca  1800
agatattcag gtggccagaa gagcttgtca gcaagaggag gacagaattc tcccagcgtt 1860
aacacaaaat ccatgggcag tatgatgca ggtcctctgt tgcaaactca gttccaaagt  1920
cacaggaaga aagcagaaag ttcaacttcc aaagggttag gactctccac tcaatgtctt 1980
aggtcaggag ttgtgtctag gctggaagag ccaaagaata ttccattttc ctttccttgt 2040
ggttgaaaac cacagtcagt ggagagatgt ttggaaacca cagtcagtgg agcctgggtg 2100
gtacccaggc tttagcatta ttggatgtca atagcattgt ttttgtcatg tagctgtttt  2160
aagaaatctg gcccagggtg tttgcagctg tgaagagtca ctcacactgg ccacaaggac 2220
gctggctact gtctattaaa attctgatgt ttctgtgaaa ttctcagagt gtttaattgt  2280
actcaatggt atcattacaa ttttctgtaa gagaaaatat tacttattta tcctagtatt  2340
```
cctaacctgt cagaataata aatattggaa ccaagacatg gtaaacaaaa aaaaaaaaaa    2400

<210> SEQ ID NO 70
<211> LENGTH: 3710
<212> TYPE: DNA
<213> ORGANISM: Homo sapiens

<400> SEQUENCE: 70
aggacgcgtt tccaagttcc agtgactcct cctgtttggg actcgggggg agagtgcggg      60
gagacaaata aaacctcggg cggcggcggc tggtgggaag acttgaactt gaatctcgaa     120
ccactgcatc tccgactctg cccagactct tcactccgcg gcaccctcaa accccagccc     180
aggccggggc gcacaagcca gccagcgcac ctgcagtcct cgcccggacg cgccgcgccc     240
cctcggaacc aggctctgct ccgagcagcc ttcgcccctc aagccagcca cagtccccgc     300
caggccgggt gggcgtcaag atgaaggcgg cccgcttcgt gctgcgcagc gctggctcgc     360
tcaacgcgcg cggcctggtg ccccgagagg tggagcattt ctcgcgctac agcccgtccc     420
cgctgtccat gaagcagcta ctggactttg gttcagaaaa tgcatgtgaa agaacttctt     480
ttgcattttt gcgacaagaa ttgcctgtga gactcgccaa cattctgaag gaaattgata     540
tcctcccgac ccaattagta aatacctctt cagtgcaatt ggttaaaagc tggtatatac     600
agagcctgat ggatttggtg gaattccatg agaaaagccc agatgaccag aaagcattat     660
cagactttgt agatacactc atcaaagttc gaaatagaca ccataatgta gtccctacaa     720
tggcacaagg aatcatagag tataaagatg cctgtacagt tgacccagtc accaatcaaa     780
atcttcaata tttcttggat cgattttaca tgaaccgtat ttctactcgg atgctgatga     840
accagcacat tcttatattt agtgactcac agacaggaaa cccaagccac attggaagca     900
ttgatcctaa ctgtgatgtg gtagcagtgg tccaagatgc ctttgagtgt tcaaggatgc     960
tctgtgatca gtattattta tcatctccag aattaaagct tacacaagtg aatggaaaat    1020
ttccagacca accaattcac atcgtgtatg ttccttctca cctccatcat atgctctttg    1080
aactatttaa gaatgcaatg cgggcaacag ttgaacacac ggaaaatcag ccttcccttg a  1140
caccaataga ggttattgtt gtcttgggaa aagaagacct taccattaag atttcagaca    1200
gaggaggtgg tgttccccctg agaattattg accgcctctt tagttataca tactccactg    1260
caccaacgcc tgtgatggat aattcccgga atgctccttt ggctggtttt ggttacggct    1320
tgccaatttc tcgtctgtat gcaaagtact tcaaggagat ctgaatctc tactctttat    1380
caggatatgg aacagatgct atcatctact taaaggcttt gtcttctgag tctatagaaa    1440
aacttccagt ttttaacaag tcagccttca acattatca gatgagctct gaggctgatg    1500
actggtgtat cccaagcagg gaaccaaaga acctggcaaa agaagtggcc atgtgaagag    1560
ggacactcag gacactttac gggatcaaag tgggtctaca ccagtgctgc ttcctgaatg    1620
tttgtgtgtg aacccttgtt tcctccaaaa caaacgacag caacgaaaac tccttaatca    1680
gaacactgat ccaatgagga atggagcttg tttctgtgac ccaggagaac ttagtgcaag    1740
actacaggag ttaacagatg gccagctcct tattttttaa tgtagaataa ctcctgagtt    1800
tatatcaaat cctgaagaaa taagcctcag ttttccatct gttttttgata agaataagaa    1860
agggagtgag tgtgaagatg gtggttagca gtttcactaa gactgatatt ttaggcctct    1920
tgttcacatc aaaagatatt ggtgtcagaa taccagcatt ttcctgccat gcaaaggatt    1980
aaaacttagt ttacactatg tggttacaaa tatatgtcaa tgtacatttt gaacatattt    2040

```
atgtgctatg gaaggaaatg ctggtgacta aataaggtt tactctgaaa gaggaggaat   2100
tttattcaaa gcattcaaac attttattca agtgtttcaa aattcaaagc attgtattca   2160
aagttgcagt gaaggcatca acttatgtaa aaactcagaa ggaaggctcc tctgataaaa   2220
acacagctcc tttattatgc tgcttttctt gttcacttta cacactaagt aaacacttat   2280
tgtcaggtgc ctagtcttga gtgaattgtt agatgtgcac tgaactcggg atgttgggga   2340
ttggagagag agaattgcca aagtaacagc aaaaatatct cttactttgc tttgtttata   2400
aataaattag tagattggaa aaactagtgt tagggaaaga aatcacatgt tcagagccta   2460
attcagtagg aagggctttt ctctaccctg aaatgaaggt aatccaaagg catccatttt   2520
ctaggcttaa aagatatatt tttgatatat ttaattatat tctctacact ccagcattaa   2580
tatgtctgtt taaaaattac taattctcaa atggctcaag aacattagaa tttaagtacc   2640
ttttagagta attattttaa gcaaatagcc tggacgtaag agattctcat gccagcatgc   2700
tttcatttgt cagttgttgt gactgagaga taatgaatga cacctgaaat gcatatggta   2760
tttttgggag agttaaggta taatttgaag gttggcagac cagttgcgct gattactctt   2820
agagaagaag aaatggaaaa atgaaagaag gcaggaagga aagaaaggat ataggaagag   2880
agggaagcag aaggcaggca ttttctatt ttccccacaa attatttcaa aaaaaatctg   2940
tattttctgg gatatgtcat tggcaagagg aagaactggt gttttgaaag cagtatggat   3000
tctttaaatg cctctcactc ttacaagata gtaggctttg agataataaa cttacccgtg   3060
tcaattaaca tttaaactgg catatagaaa aaaaggagga tttttctgca ttgtaaaata   3120
atcagtatgg tttatatgtt gaatttgaca tttgtgtgta atttcatggt ggcctagtgt   3180
tgtggtgctt ctggtaatgg taatagaagc tcaactattt ttttgtggat ttcagtttt   3240
atcatcagaa gtcctagaca gtgacatttc ttaatggtgg gagtccagct catgcatttc   3300
tgattataca aaacagtttg cagtaggtta tttgtcattt cagtttttta ctgaaatttg   3360
agctaaacat ttttacatgt aaatacttgt atttaccaaa gatttaaatc agttgattaa   3420
ttaattaact caaatactgt gaactatctc taaaacacta gaaaaaagaa atgttagtat   3480
ctcaattaca ccaactgtgc aaatgaactt tgataaaata gaataatct acattggcct   3540
ttgtgaaatc tggggaagag cttaggatt ctagtagatg gatactgaat actcaggccc   3600
acttaaatta ttaatgtata cattgtgttt ttgtctttat gctatgtaca gagaaatgtg   3660
ataattttt ataataaata ttttttatga tgataaaaga aaaaaaaaa            3710
```

```
<210> SEQ ID NO 71
<211> LENGTH: 3691
<212> TYPE: DNA
<213> ORGANISM: Homo sapiens
<400> SEQUENCE: 71
ggcgcaacgc tgagcagctg gcgcgtcccg cgcggcccca gttctgcgca gcttcccgag     60
gctccgcacc agccgcgctt ctgtccgcct gcagggcatt ccagaaagat gaggatattt    120
gctgtcttta tattcatgac ctactggcat ttgctgaacg catttactgt cacggttccc    180
aaggacctat atgtggtaga gtatggtagc aatatgacaa ttgaatgcaa attcccagta    240
gaaaaacaat tagacctggc tgcactaatt gtctattggg aaatggagga taagaacatt    300
attcaatttg tgcatggaga ggaagacctg aaggttcagc atagtagcta cagacagagg    360
gccccggctgt tgaaggacca gctctcctg ggaaatgctg cacttcagat cacagatgtg    420
aaattgcagg atgcaggggt gtaccgctgc atgatcagct atggtggtgc cgactacaag    480
```

| | |
|---|---|
| cgaattactg tgaaagtcaa tgccccatac aacaaaatca accaaagaat tttggttgtg | 540 |
| gatccagtca cctctgaaca tgaactgaca tgtcaggctg agggctaccc caaggccgaa | 600 |
| gtcatctgga caagcagtga ccatcaagtc ctgagtggta agaccaccac caccaattcc | 660 |
| aagagagagg agaagctttt caatgtgacc agcacactga gaatcaacac aacaactaat | 720 |
| gagattttct actgcacttt taggagatta gatcctgagg aaaaccatac agctgaattg | 780 |
| gtcatcccag aactacctct ggcacatcct ccaaatgaaa ggactcactt ggtaattctg | 840 |
| ggagccatct tattatgcct tggtgtagca ctgacattca tcttccgttt aagaaaaggg | 900 |
| agaatgatgg atgtgaaaaa atgtggcatc caagatacaa actcaaagaa gcaaagtgat | 960 |
| acacatttgg aggagacgta atccagcatt ggaacttctg atcttcaagc agggattctc | 1020 |
| aacctgtggt ttagggggttc atcggggctg agcgtgacaa gaggaaggaa tgggcccgtg | 1080 |
| ggatgcaggc aatgtgggac ttaaaaggcc caagcactga aaatggaacc tggcgaaagc | 1140 |
| agaggaggag aatgaagaaa gatggagtca acagggagc ctggagggag accttgatac | 1200 |
| tttcaaatgc ctgaggggct catcgacgcc tgtgacaggg agaaaggata cttctgaaca | 1260 |
| aggagcctcc aagcaaatca tccattgctc atcctaggaa gacgggttga gaatccctaa | 1320 |
| tttgagggtc agttcctgca gaagtgccct ttgcctccac tcaatgcctc aatttgtttt | 1380 |
| ctgcatgact gagagtctca gtgttggaac gggacagtat ttatgtatga gttttcctta | 1440 |
| tttatttga gtctgtgagg tcttcttgtc atgtgagtgt ggttgtgaat gatttctttt | 1500 |
| gaagatatat tgtagtagat gttacaattt tgtcgccaaa ctaaacttgc tgcttaatga | 1560 |
| tttgctcaca tctagtaaaa catggagtat ttgtaaggtg cttggtctcc tctataacta | 1620 |
| caagtataca ttggaagcat aaagatcaaa ccgttggttg cataggatgt cacctttatt | 1680 |
| taacccatta atactctggt tgacctaatc ttattctcag acctcaagtg tctgtgcagt | 1740 |
| atctgttcca tttaaatatc agctttacaa ttatgtggta gcctacacac ataatctcat | 1800 |
| ttcatcgctg taaccaccct gttgtgataa ccactattat tttacccatc gtacagctga | 1860 |
| ggaagcaaac agattaagta acttgcccaa accagtaaat agcagacctc agactgccac | 1920 |
| ccactgtcct tttataatac aatttacagc tatattttac tttaagcaat tcttttattc | 1980 |
| aaaaaccatt tattaagtgc ccttgcaata tcaatcgctg tgccaggcat tgaatctaca | 2040 |
| gatgtgagca agacaaagta cctgtcctca aggagctcat agtataatga ggagattaac | 2100 |
| aagaaaatgt attattacaa tttagtccag tgtcatagca taaggatgat gcgaggggaa | 2160 |
| aacccgagca gtgttgccaa gaggaggaaa taggccaatg tggtctggga cggttggata | 2220 |
| tacttaaaca tcttaataat cagagtaatt ttcatttaca aagagaggtc ggtacttaaa | 2280 |
| ataaccctga aaaataacac tggaattcct tttctagcat tatatttatt cctgatttgc | 2340 |
| ctttgccata taatctaatg cttgtttata tagtgtctgg tattgtttaa cagttctgtc | 2400 |
| ttttctattt aaatgccact aaattttaaa ttcatacctt tccatgattc aaaattcaaa | 2460 |
| agatcccatg ggagatggtt ggaaaatctc cacttcatcc tccaagccat tcaagtttcc | 2520 |
| tttccagaag caactgctac tgcctttcat tcatatgttc ttctaaagat agtctacatt | 2580 |
| tggaaatgta tgttaaaagc acgtattttt aaaatttttt tcctaaatag taacacattg | 2640 |
| tatgtctgct gtgtactttg ctatttttat ttatttagt gtttcttata tagcagatgg | 2700 |
| aatgaatttg aagttcccag ggctgaggat ccatgccttc tttgtttcta agttatcttt | 2760 |
| cccatagctt ttcattatct ttcatatgat ccagtatatg ttaaatatgt cctacatata | 2820 |

```
catttagaca accaccattt gttaagtatt tgctctagga cagagtttgg atttgtttat    2880
gtttgctcaa aaggagaccc atgggctctc cagggtgcac tgagtcaatc tagtcctaaa    2940
aagcaatctt attattaact ctgtatgaca gaatcatgtc tggaactttt gttttctgct    3000
ttctgtcaag tataaacttc actttgatgc tgtacttgca aaatcacatt ttctttctgg    3060
aaattccggc agtgtacctt gactgctagc taccctgtgc cagaaaagcc tcattcgttg    3120
tgcttgaacc cttgaatgcc accagctgtc atcactacac agccctccta agaggcttcc    3180
tggaggtttc gagattcaga tgccctggga gatcccagag tttcctttcc ctcttggcca    3240
tattctggtg tcaatgacaa ggagtaccct ggctttgcca catgtcaagg ctgaagaaac    3300
agtgtctcca acagagctcc ttgtgttatc tgtttgtaca tgtgcatttg tacagtaatt    3360
ggtgtgacag tgttctttgt gtgaattaca ggcaagaatt gtggctgagc aaggcacata    3420
gtctactcag tctattccta agtcctaact cctccttgtg gtgttggatt tgtaaggcac    3480 tttatcccett ttgtctcatg tttcatcgta aatggcatag gcagagatga tacctaattc    3540
tgcatttgat tgtcactttt tgtacctgca ttaatttaat aaaatattct tatttatttt    3600
gttacttggt acaccagcat gtccattttc ttgtttatt tgtgtttaat aaaatgttca    3660
gtttaacatc ccagtggaga aagttaaaaa a                                   3691
```

```
<210> SEQ ID NO 72
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 72
aatccttgtg accacaccga tggagataca gaaaaagtta acgactggat tctatcttca    60

<210> SEQ ID NO 73
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 73
tttagtgaac actgttctct gggtgacaat acgtaaagaa ctgaaaagaa agaaaaagtg    60

<210> SEQ ID NO 74
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 74
caaagatgca tttacctctg tatcaactca ggaaatctca taagctggta ccactcagga    60

<210> SEQ ID NO 75
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 75
```

```
gagttttcc  tatttatttt  gagtctgtga  ggtcttcttg  tcatgtgagt  gtggttgtga    60
```

<210> SEQ ID NO 76
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 76

```
ggtactgagc  agagtcttag  gtaaaagtct  tgggaaatat  ttgggcattg  gtctggccaa    60
```

<210> SEQ ID NO 77
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 77

```
tgagccctac  atcaagtggg  aagacaagga  cgccaagatc  ttccgagttg  tggatccaaa    60
```

<210> SEQ ID NO 78
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 78

```
agagtttcct  ttccctcttg  gccatattct  ggtgtcaatg  acaaggagta  ccttggcttt    60
```

<210> SEQ ID NO 79
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 79

```
agtgagctcc  agcacgccca  gaggactgtt  aataacgatg  atccatgtgt  tttactctaa    60
```

<210> SEQ ID NO 80
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 80

```
tggaagttca  gttttggtgt  ctgcttcaag  aggggttttt  acactctgat  tccaggacaa    60
```

<210> SEQ ID NO 81
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 81
gatgtcaata gcattgtttt tgtcatgtag ctgttttaag aaatctggcc cagggtgttt    60

<210> SEQ ID NO 82
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 82
atttgacatt tgtgtgtaat ttcatggtgg cctagtgttg tggtgcttct ggtaatggta    60

<210> SEQ ID NO 83
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 83
caaatttcat cactgtatac tttcaatccg aagggccagt actacagcat gttgcacaaa    60

<210> SEQ ID NO 84
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 84
aattaggttt tcaacatggg aagcatgaaa tccacttctg gatttggagc atccacttga    60

<210> SEQ ID NO 85
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 85
taaaaggttc tgttttgttt ggaatcaatg gtagctttat tgactgttct gattgtgctg    60

<210> SEQ ID NO 86
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 86
agctaagcct cacaaaagtc aatctgcagg gaagaatcta aatcatatgc ctacccatgg    60

<210> SEQ ID NO 87
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 87
gaaggagata aggttcgact tacattcttc acactgtcaa aaaatggaga aaaactacag    60

<210> SEQ ID NO 88
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 88
ttgaacccta cacgaagaaa gaactttctg ctgttacttt ccctgacatc attcgcaatt    60

<210> SEQ ID NO 89
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 89
taaagtcagt gcccaactgt tataggttgt tggataaatc agtggttatt tagggaactg    60

<210> SEQ ID NO 90
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 90
atacaggcca aagaggtgct gaaaaaatat ttggagtcca aggaggatgt ggctgatgca    60

<210> SEQ ID NO 91
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 91
agaatctttc ccttgctaga ccccagaatt ttaaatgcat ccgtcttaca ctttcacaaa    60

<210> SEQ ID NO 92
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 92
atgtctatcc acaggctaac cccactctat gaatcaatag aagaagctat gaccttttgc    60

<210> SEQ ID NO 93
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 93
aatcctaaag cataagttag tcttttcctg attcttaaag gtcatacttg aaatcctgcc    60

<210> SEQ ID NO 94
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 94
cataatgaaa gaacccagca attctgtctc ttaatgcaat gacactattc atagactttg    60

<210> SEQ ID NO 95
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 95
atctttacat tgtctgccaa ttaaagtgtt ttaaacttgc attggaatgg actccgaatg    60

<210> SEQ ID NO 96
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 96
atacatttta attcctcacg ttttatattg gagagttcgg tacagactgt ccattactgc    60

<210> SEQ ID NO 97
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 97
gtgtgtccct aagaagaact tgaactgat ttgatattga acaaaccaa aaacttccag    60

<210> SEQ ID NO 98
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 98
tccagaagat gagagaaacc tctttatcca acagataaaa gaaggaacat tgcagagcta    60

<210> SEQ ID NO 99
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 99
tttgcattgt gtcttcattt taatgtgttt gcaatcgctc cgctccagga agaacggaaa    60

```
<210> SEQ ID NO 100
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 100
agaagaatga gatactgatg tccacagttc attggcagaa tctaacccct tctgttatct      60

<210> SEQ ID NO 101
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 101
tttttagtgg catgcaggct atacctcagt atttgtggac atgcacccag gaatatgtac      60

<210> SEQ ID NO 102
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 102
ccatgtttct gaatcttctt tgtttcaaat ggtgctgcat gttttcaact acaataagtg      60

<210> SEQ ID NO 103
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 103
tgcttttaac ttccccacca tgttgcacct aaagctttgg agttttcctg tgattagtgt      60

<210> SEQ ID NO 104
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 104
tcttataaat aagtatgaag aagctgtttg tcatctggca tcatcccatc agttagttac      60

<210> SEQ ID NO 105
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 105
ctgttcctgt gatgtggagg aaattttccg caaggttcga ttttcatttg agcagccaga      60

<210> SEQ ID NO 106
```

```
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 106
tacagagtta tagtgtgttt actcctaaga tgacagttct ctttgtctat attcagcatc    60

<210> SEQ ID NO 107
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 107
ggataacatg gctggatgaa agaaatgacc ttcattctga gaccaaagta gatttacaga    60

<210> SEQ ID NO 108
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 108
aggggacaca ggcttcttaa aacaacccgg cttcctcacc ctatgtcctt tatttacaaa    60

<210> SEQ ID NO 109
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 109
tgtgacccac ttaccttgca tctcacaggt agacagtata taactaacaa ccaaagacta    60

<210> SEQ ID NO 110
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 110
gcaacaatcc atctctcaag tagtgtatca cagtagtagc ctccaggttt ccttaaggga    60

<210> SEQ ID NO 111
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 111
gctgggactc tcagcaggtc caacatctgg aaatcacctt actacacaag attctcaaat    60

<210> SEQ ID NO 112
<211> LENGTH: 60
```

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 112
ggaaaacgag ctaattccgt gccgatggag gtgttgatgg atgtccacca ctctccactt      60

<210> SEQ ID NO 113
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 113
tccaggatga gttacttgaa atttgccttg agtgtgttac ctcctttcca agctcctcgt      60

<210> SEQ ID NO 114
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 114
ttaaagggtt gctttaagtg ggatagaaaa accttaagga aagttcatag taggtcctca      60

<210> SEQ ID NO 115
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 115
aaagggttgc aaacaaaaag aactttgaga ataaggaagc ccagagttct caagccactc      60

<210> SEQ ID NO 116
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 116
accaggaaga gatggagaaa gtaaaacgtg aaaatgctac agttatggat aagacccgag      60

<210> SEQ ID NO 117
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 117
gtaacagttt actggttgtt ccattcctga atatgcaggc taatttgtac agatagggat      60

<210> SEQ ID NO 118
<211> LENGTH: 60
<212> TYPE: DNA
```

```
<213> ORGANISM: Artificial Sequence
<220> FEATURE:
<223> OTHER INFORMATION: Description of Artificial Sequence: Synthetic
      probe

<400> SEQUENCE: 118
tcagaaaaaa cagagtaagg caccactctt gggaaattaa ggtagcttgc agtaacaagt       60

<210> SEQ ID NO 119
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 119
accatcatgg cagtggagtt tgacggggc gttgtgatgg gttctgattc ccgagtgtct        60

<210> SEQ ID NO 120
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 120
aaacactaga agatctcaga aaaatgaag ataaattgaa ccatcatcag cgaattgggc        60

<210> SEQ ID NO 121
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 121
gtatcatcca aataatgggg cctatgactt gaatgaatag aaatgaataa gctggtgttt      60

<210> SEQ ID NO 122
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 122
tgtattcact tatgctctcg tacattgagt acttttattc caaaactagt gggttttctc      60

<210> SEQ ID NO 123
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 123
attacctttc ctttaggtgt tggctacagt tatcccaaac ttggacttga ggtcttgtat      60

<210> SEQ ID NO 124
<211> LENGTH: 60
<212> TYPE: DNA
<213> ORGANISM: Artificial Sequence
```

```
<220> FEATURE:
<223> OTHER INFORMATION: Description of Artificial Sequence: Synthetic
      probe

<400> SEQUENCE: 124
atggaggtga ttggttctct ttacacatta acactgtacc aagctttgca gatctttcc         60

<210> SEQ ID NO 125
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 125
agcaaagatg aagggaaaac gaactaagac agacgctagg ccatgttggc aaagtagcat         60

<210> SEQ ID NO 126
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 126
gagatgccaa ggtgaaagta cccaacttca aaatgagata caaaagctac agaagaccct         60

<210> SEQ ID NO 127
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 127
aaaggctatt tgcagaagga gctcacagat cacattgaaa gcattgcata ttcaaacatc         60

<210> SEQ ID NO 128
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 128
gagcttcagg atgtaaatat ttggactata tgcagaaaat attccatgac ttggatatgc         60

<210> SEQ ID NO 129
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 129
gccaaagctc aaatgcccac catagaacga ctgtccatga caagatattt ctacctcttt         60

<210> SEQ ID NO 130
<211> LENGTH: 60
<212> TYPE: DNA
<213> ORGANISM: Artificial Sequence
<220> FEATURE:
```

<223> OTHER INFORMATION: Description of Artificial Sequence: Synthetic
      probe

<400> SEQUENCE: 130
aagacatcag tcaggatcat gtgaagaaaa cagtgaccat tgaaaatcac cctcatctgc    60

<210> SEQ ID NO 131
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 131
tttaagtttc cagctcttca ccgaaatgtt gtattcttat ttcagtgttt ccttccagac    60

<210> SEQ ID NO 132
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 132
tatgcaagta cttttagact aaatgcctta tgcatctgag gagatacacc gtaggatcgt    60

<210> SEQ ID NO 133
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 133
gacagtttaa aagcattgta aaactcacat agcttacttc tctctctaaa gtgcaacaag    60

<210> SEQ ID NO 134
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 134
atgtgttcta tgaagatgac atttggcctg gagaaaatga gaatgggtaa gcaagattta    60

<210> SEQ ID NO 135
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 135
agcccagccc tccttaatca acttcaagga gcaccttcat tagtacagct tgcatattta    60

<210> SEQ ID NO 136
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 136
gatcaagaga atatttcaga gttttggttt acacatcaag aaacagacac acatacctag    60

<210> SEQ ID NO 137
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 137
tgagagcgag atgggaagca tagatatcta tattttatt tctactatga gggccttgta    60

<210> SEQ ID NO 138
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 138
ctggtttgcc tgaatctttt cctttaactg gtggtactga aaatttgaat acagaaacaa    60

<210> SEQ ID NO 139
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 139
gttgttgagt tttgtatacc tatgttagga atatttgttt tatactgcct tcaggtcctc    60

<210> SEQ ID NO 140
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 140
aaacaactca agcattctgg tggcaacata gagattgtag gctgcttcta agaaagttat    60

<210> SEQ ID NO 141
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 141
tctgaagctc tttatgatgc accggtgcat ttttatttaa aaaatagatt gtgactcctc    60

<210> SEQ ID NO 142
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 142
ggcttcacaa ggatgtattt tggagaacga atagtggaac cagtaatagt cattttcttt    60

<210> SEQ ID NO 143
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 143
tggatggttg aaaatctgga atatagagga gtactgtctt aactccagta agaacaaaat    60

<210> SEQ ID NO 144
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 144
cttcaaatgg ctctcaatca tatgcttcaa atcaagacag tgctaagttc cagcagcata    60

<210> SEQ ID NO 145
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 145
ctagatgtga ggtacaaaac ttgggatcaa atggaatctt gattcactaa ccaatttaag    60

<210> SEQ ID NO 146
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 146
tagagttcac agtggtaaga ctcatatgcc tgtatgtgtt gctaataaat tagattttgg    60

<210> SEQ ID NO 147
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 147
aagtacgtga aaatcaggtt tcaatagaat gtgacacaac gtgcaaggaa atgaagcgga    60

<210> SEQ ID NO 148
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

```
<400> SEQUENCE: 148
atgaaagact gttctacatt cgttgcattc ttagcactgg tttccaaaaa cggaattcca    60

<210> SEQ ID NO 149
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 149
taaactatca atggcatttc aagtcttctg aaacagcatg gctgtatgtg cgtggtccat    60

<210> SEQ ID NO 150
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 150
tgaaggcgaa atgataactt ctaaggataa tttagaagat gagactgaag atgatgacct    60

<210> SEQ ID NO 151
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 151
aaatcagcct ccatcagtat cactgcagtt atatatgatg tatgccttat tgctcaagac    60

<210> SEQ ID NO 152
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 152 tttttttcaca tttgagattg gatgatcatg atattgaggg ggtaatggta aagcagaccc    60

<210> SEQ ID NO 153
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 153
aggacacttc atctactctg gttgactgtc attttcaaca tcataattta cataaggtag    60

<210> SEQ ID NO 154
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 154
```
agatcgttat gccagtgaaa atgtcaacaa attgttggta gggaacaaat gtgatctgac      60

<210> SEQ ID NO 155
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 155
gcattttatt tcacccattt ttgttcaagc tcttacatta acattcttag cagaatgggg      60

<210> SEQ ID NO 156
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 156
ggagaaaaga aagtgggtta tcaagggtga tttgaaattt tctgcagcat taaagctggc      60

<210> SEQ ID NO 157
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 157
taacgacatg aaaatgcaag tgtcaatgga gtagtttatt accttctatt ggcatcaagt      60

<210> SEQ ID NO 158
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 158
aggatacatg attgtgggcc tatatatgac acatgacaaa tgtccctgtc acaggactca      60

<210> SEQ ID NO 159
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 159
gtggtacgat caaaggcact atgtcttcat tgaattttgt gttgaagaca gtaaggatgt      60

<210> SEQ ID NO 160
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 160
caatagcatc tgaagagaga gtacatagat tggaaatggc tattgcattt cactcaaatg    60

<210> SEQ ID NO 161
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 161 ccttttgta tttgagagaa tctactaagt tcagtccagt caagaaaaga acctaatagc    60

<210> SEQ ID NO 162
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 162
gctcagtttc tcttaaatga ggatgatgat gaccaaccta gaggactcac taaagaacag    60

<210> SEQ ID NO 163
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 163
ctgcagcagc gttcagacca actcctggat atgagctcaa ccttcaacaa gactacacag    60

<210> SEQ ID NO 164
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 164
tgctgccgaa gatgggccgg ctgaagagag tggacctgga gaagaatcag atcacagctt    60

<210> SEQ ID NO 165
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 165
tatggggacc atagtatcat tcagtgcatt gtttacatat tcaaagtggt gcactttgaa    60

<210> SEQ ID NO 166
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 166
agcaaaaggg aagacattgt gaaccaaatg acagaagcct gccttaacca gtcgctagat    60

<210> SEQ ID NO 167
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 167
gcacatgctg tttattcaa atgcctcttt tgtacatgtt catgtttagt gttttctcag    60

<210> SEQ ID NO 168
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 168
aacgttacat gactcgttga gaaagttgag gaatttcctc taccacctttt gttgcttgaa    60

<210> SEQ ID NO 169
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 169
ctcattcagc tcaaacagat ttcatagcca aagcaaaagg actggtacgg tagtctgtgg    60

<210> SEQ ID NO 170
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 170
gattattggt ccaaggggca gttgaaagca cttttttcgg aacacgaggg ttattttgga    60

<210> SEQ ID NO 171
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 171
agaatcagat gctgcagtaa aggaaaaagc cattcaggtt ggctttgttt taggtggctt    60

<210> SEQ ID NO 172
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 172
attttcagtc cagttatgaa cagcaagtgt tgaactcttt ctgcttgttt tgattcaaag    60

<210> SEQ ID NO 173
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 173
gccatggatg cagcagcctg aaacttgaga gcgaaagtga gataaatgtc aaaggtgttt      60

<210> SEQ ID NO 174
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 174
agactgtcag tactgggagc gcctgctggc caaggaatgc aggctgtact atctgcgaaa      60

<210> SEQ ID NO 175
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 175
gcttattttg gttgcagttt ccaattttta aaaatgttga ggtaatcttt cccaccttcc      60

<210> SEQ ID NO 176
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 176
acttgaatag tccattgacc gaaactcttt atagactatt gtgtaaatgt ggaatcacag      60

<210> SEQ ID NO 177
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 177
ctcaaactgg aaataaggtt catgcaattc agtgtgatgt gagggatcct gatatggttc      60

<210> SEQ ID NO 178
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 178
gcctggggac tgtagaagaa ctcgcaaatc ttgctgcttt cctttgtagt gattatgctt      60

```
<210> SEQ ID NO 179
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 179
cctgagttct gcttccttgg atgtcattgc ttaaatatag tcttgaaggg cttgttttga    60

<210> SEQ ID NO 180
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 180
ggagctgata attggcaaaa gaccactttt accactcagg ctctatttgt gccttagctt    60

<210> SEQ ID NO 181
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 181
gaattggctg gaagaagaat gtattgcctg gctaaagaga ttcctggagt atgggaaaga    60

<210> SEQ ID NO 182
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 182
gggcaataca gtaaattttc atgttactct tttatcagat cacaaactcc tagagtctac    60

<210> SEQ ID NO 183
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 183
tcctgtctgt cttccgctca ctggcgatgc tggagaagac ggtggaaaaa tgctgcatct    60

<210> SEQ ID NO 184
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 184
ctcgtgctgt caactgccgc aagaagaagt gtggtcacac caacaacctg cgtcccaaga    60

<210> SEQ ID NO 185
```

```
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 185
cttccccgcc ccgcgtccct cccccctcggc cccgcgcgtc gcctgtcctc cgagccagtc    60

<210> SEQ ID NO 186
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 186
tacgagttta aaaactgcgt tgttattttt agagatttgt gataatacaa cttgttataa    60

<210> SEQ ID NO 187
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 187
gcaacagttc aatgaatcaa aatggaatga gcactctaag cagccaatta gatgctggca    60

<210> SEQ ID NO 188
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 188 tccccctca tcgccccgcg cccacccca tcgcccctgc cccggcggc ggcctcgcgt    60

<210> SEQ ID NO 189
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 189
ggcccccaac cagccccac cgcctctcat ccgccccgct ctggctgccc cccgccacag    60

<210> SEQ ID NO 190
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 190
gccccaggcc gcgcccctg ccccacagcc gcctcagccc gcacctcagc ccctgcacc    60

<210> SEQ ID NO 191
<211> LENGTH: 60
```

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 191
ctcaccccgc ccctggtccc actcctgccc ccgccctacc tccgcccccac cccatcatct    60

<210> SEQ ID NO 192
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 192
gaagcagcca tggtttcttg gggacaagat cacctttgtg gatttcatcg cttatgatgt    60

<210> SEQ ID NO 193
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 193
cccccgcgcc cggcctcccc ccggacccct gcggctccaa ctgtgctccc cccgacgccg    60

<210> SEQ ID NO 194
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 194
cccctcctcc ccgccgcttg gagtaagaac ccaaaacccc gaagccgggc ccgcgtgcaa    60

<210> SEQ ID NO 195
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 195
cacagactca gagagaaccc accatggtgc tgtctcctgc cgacaagacc aacgtcaagg    60

<210> SEQ ID NO 196
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 196
gaggaaaggg aaaaccttct cagagagcat gaaaggctgc taaaacacaa gctgaaggta    60

<210> SEQ ID NO 197
<211> LENGTH: 60
<212> TYPE: DNA
```

```
<213> ORGANISM: Artificial Sequence
<220> FEATURE:
<223> OTHER INFORMATION: Description of Artificial Sequence: Synthetic
      probe

<400> SEQUENCE: 197
agaagagaag catttagaga gcatcagcaa tacaaaaccg ctgagttctt gagcaaactg    60

<210> SEQ ID NO 198
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 198
accatcatgg cagtggagtt tgacgggggc gttgtgatgg gttctgattc ccgagtgtct    60

<210> SEQ ID NO 199
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 199
agaattctta acttcacaag tgttttactt cgacgatgtg cctttgattt aatttgggac    60

<210> SEQ ID NO 200
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 200
ctagatcctg tgctttactc tgaagactct aggagagaag tttgctgagg aatgccttca    60

<210> SEQ ID NO 201
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 201
tggacattcg aacagagttc aagaagcatt atggctattc cctatattca gcaattaaat    60

<210> SEQ ID NO 202
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 202
taagaaaggc tggttaccat cggagtttac aaagtgcttt cacgttctta cttgttgtat    60

<210> SEQ ID NO 203
<211> LENGTH: 60
<212> TYPE: DNA
<213> ORGANISM: Artificial Sequence
```

<220> FEATURE:
<223> OTHER INFORMATION: Description of Artificial Sequence: Synthetic
      probe

<400> SEQUENCE: 203
gcagaaagag atacaatctt gcttgaccgt ttgggacatc aatcttccac atgaagtgca    60

<210> SEQ ID NO 204
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 204
gtggccaagc gtccggagca caatagatct gaagccttga aggtgtcctg tggcaagtgt    60

<210> SEQ ID NO 205
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 205
agtcacagtt accgcgtgta ctacaatgcc ggccccaagg atgaggacca ggactacatc    60

<210> SEQ ID NO 206
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 206
atgtgagcct ttgtgatacg aattcaattt gttttcctgt cttttgacat ttgactttgc    60

<210> SEQ ID NO 207
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 207
tgttgtggtc gatttacaag gttgggtaac cggtaatgga aaaggactca tctacctcac    60

<210> SEQ ID NO 208
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 208
gaatgaactg ctgaacaaac agagtgttcc tgctcatttt gtcgccttga atgggagcaa    60

<210> SEQ ID NO 209
<211> LENGTH: 60
<212> TYPE: DNA
<213> ORGANISM: Artificial Sequence
<220> FEATURE:

<223> OTHER INFORMATION: Description of Artificial Sequence: Synthetic
      probe

<400> SEQUENCE: 209
gaatcttccg tccctcatcc taacttgcag ttcacagaga aaagtgacat acccaaagct    60

<210> SEQ ID NO 210
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 210
gacaacattt gatcccaaga aaccagaat ggaaccctt cacttcaaaa actcagttat    60

<210> SEQ ID NO 211
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 211
acactgagct cacccacaga gcccgtgaag aggtctggcc gctaccactt tgtgcctgga    60

<210> SEQ ID NO 212
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 212
tgactttcat gtcactcact ataaaatagg tctcttaacc tggcaccagt ataactataa    60

<210> SEQ ID NO 213
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 213
tgaaccacca gctccaggag aaggcaactc cagtcagaac agcagaaata agcgtgccgt    60

<210> SEQ ID NO 214
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 214
atgcattgcg ggtgctgtcc aagcttggct catctggggt ttgctgggct taacacccaa    60

<210> SEQ ID NO 215
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 215
cattgatatc cactggtcac atcataactg tctatagggc aataaaatct gtgttaaact    60

<210> SEQ ID NO 216
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 216
tcgagctttt gaggttttag attcagctaa acgtgggttt cttactaagg acgagctgat    60

<210> SEQ ID NO 217
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 217
gaaatactga aacttgctgc ctattgggta tgctgaggcc cacagactta cagaagaagt    60

<210> SEQ ID NO 218
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 218
ctgtcctgga ccctgtgtgc ctcataaggg ctattctttc tttcacgtgc aaaacatttt    60

<210> SEQ ID NO 219
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 219
tatgtacagt ttacatgaat gttcctcagg acatggcata caatggcctt ggaggtccaa    60

<210> SEQ ID NO 220
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 220
atcttagaaa caccttgaag tatgccaaga aaacgtccg tgcattttgg aaactcagag    60

<210> SEQ ID NO 221
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 221
aaggaggtct acatcaagaa tgggggataag aaaggcagct gtgagagaga tgctcaatat    60

<210> SEQ ID NO 222
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 222
ggagctctgc cctgcaggga gttgcccaa ccctttccgg aactcagtct ttagaaaaga    60

<210> SEQ ID NO 223
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 223
gaccaggaaa acaagaaag acatactcaa tcctgattca agtatggaaa cttcaccaga    60

<210> SEQ ID NO 224
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 224
atacctggga ggaaggcttt tccttcacaa ttgtatacag ggggcacctg tggccaggcc    60

<210> SEQ ID NO 225
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 225
agtggtgtag tgccgaaagt gctaaaatat ttagtgcggt attgctctgt gaattcaagt    60

<210> SEQ ID NO 226
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 226
aaatgagtac gaagataacc aaatctgcta ctggcacatt agactcaagt atggtcagcg    60

<210> SEQ ID NO 227
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 227
tggtggtgga tcctggaatt ttctcacgca ggagccattg ctctcctaga gggggtctca    60

<210> SEQ ID NO 228
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 228
caagcaggat caagtttgta gaataaacac tggtttccta gccatcctct gaaaacagta    60

<210> SEQ ID NO 229
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 229
gtgtgcttta ttgaattaga aaattagtga ccattattca caggtggaca aatgttgtcc    60

<210> SEQ ID NO 230
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 230
gctgttccca catcagaact cccttcaaac acaaagattg ctgtgaaaac gaaaatgtgt    60

<210> SEQ ID NO 231
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 231
acgacctggt catcaaaagc cttgacaaat tgaaggaggt gaaggagttt ttgggtgaga    60

<210> SEQ ID NO 232
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 232
ttcgtttcag tcaagacaat gcttagttca gatactcaaa aatgtcttca ctctgtctta    60

<210> SEQ ID NO 233
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 233
gtacataaga atctatcact aagtaatgta tccttcagaa tgtgttggtt taccagtgac    60

<210> SEQ ID NO 234
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 234
gtaccagaat tgcttagaag ataccagaag gtgcggtcta gggaccagtg aataagaaga    60

<210> SEQ ID NO 235
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 235
tgagtggaga agaaacaaac atagtgggta taatcatgga tcgcttgtac ccctgtgaaa    60

<210> SEQ ID NO 236
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 236
ctgtgtttat atggaagaaa gtaaggtgct tggagtttac ctggcttatt taatatgctt    60

<210> SEQ ID NO 237
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 237
tgagaaagac agcacccatt gaaacagata tgtgtgtgaa agtatatttt tcaattccag    60

<210> SEQ ID NO 238
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 238
agtaagggaa caagttgagc tatgacttaa catagccaaa atgtgagtgg ttgaatatga    60

<210> SEQ ID NO 239
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 239
gagcattttt tacaagcctt ccacttcaat ttccatcttt aagaagaaac tcaagggtca    60

<210> SEQ ID NO 240
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 240
tgcctcttct aagtgtctat gagcttgcac catatttaat aaattgggaa tgggtttggg    60

<210> SEQ ID NO 241
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 241
tgggtgcagc cactggaggc atcttgcttc tgctggatgt ggtcagcctt gcatatgagt    60

<210> SEQ ID NO 242
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 242
cgcccccgaa attcaagatt gagtgtcagg ctttatatat attcagcatt cctcattaca    60

<210> SEQ ID NO 243
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 243
cagatgagtt catttgcttc tgtagatgtg ttttcagagc taggtacaga ggaatgtttg    60

<210> SEQ ID NO 244
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 244
agctgaccca gcatcagcca cactctgggt tggaaaatgt ttgcctgttg gaattaattt    60

<210> SEQ ID NO 245
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 245
ttgggaagaa acgtgaactc aaggaagact cactatggtc agctaaagaa atatctaaca    60

<210> SEQ ID NO 246
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 246
ctttcaagga gatctgaatc tctactcttt atcaggatat ggaacagatg ctatcatcta    60

<210> SEQ ID NO 247
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 247
aatattaacc taatcaccat gtaagcactc tggatgatgg attccacaaa acttggtttt    60

<210> SEQ ID NO 248
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 248
ctgtgtggaa ccactgacta ctggctctca ttgacttcct tactaagcat agcaaacaga    60

<210> SEQ ID NO 249
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 249
agatttgttt aagtccccta cactttctta tttctaaatg atcaagagta cacttcctgg    60

<210> SEQ ID NO 250
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 250
tcccttttca gtacctttga acagcaacca tgtgggctac tcatgatggg cttgattctt    60

<210> SEQ ID NO 251
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 251
aagttgaaca atcctagcca ttgacaatcg tgatagttat tattttccca tttgctgtct    60

<210> SEQ ID NO 252
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 252
aaagtaacgc taactttgta gggacgatgt ctcatggatt aaataatatt ctttatggca    60

<210> SEQ ID NO 253
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 253
cctcatgtat ttatgcctaa tgtaagctga cttttaaaaa gctttctttt gttgcatgcc    60

<210> SEQ ID NO 254
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 254
tggaagcaat ctgcattcat aactttgatt ggagaataaa tggtatacat ggtgctgtct    60

<210> SEQ ID NO 255
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 255
agctgatttt tacagtgggg tactctcgcg tattaggagt ctcagatgtc atcacttgga    60

<210> SEQ ID NO 256
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 256
attcgaataa agctcttgag aagggactga atcctctgaa tgcatactcc gatctcgctg    60

<210> SEQ ID NO 257
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 257
tcaaaaatct ctgcatcctg aggtgatata cttcatattt gtaatcaact gaaagagctg    60

```
<210> SEQ ID NO 258
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 258
gctgcactca tcctctgagc gggcaacttt catcgatcgt ctggccaata gccttaccaa    60

<210> SEQ ID NO 259
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 259
taaagtttat ggaactcagt gttaggaact ttggcatctg tagctgagca cagcagggga    60

<210> SEQ ID NO 260
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 260
acctgcctta cctttctgag ttgcctttag agagatgcgt ttttctagga ctctgtgcaa    60

<210> SEQ ID NO 261
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 261
cttgggtcat tgacctctca gggcctggca ggccagtgtc tgggtttttc ttgtggtgta    60

<210> SEQ ID NO 262
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 262
tttttctcgt gggacacaaa ccccaactgt accccctatg gtttcagaac agagctgtgc    60

<210> SEQ ID NO 263
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 263
gccggtataa aggatgccca aggtctttgt acgtgtgtag gagttagcgt gtttgatatt    60

<210> SEQ ID NO 264
```

<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 264
gctttccgcc tctttgagac caagatcacc caagtcctgc acttcaccaa ggatgtcaag    60

<210> SEQ ID NO 265
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 265
tagcaaattt ataagttttg acccgcagag tgcactgaga aatatggctg tgggaaaaca    60

<210> SEQ ID NO 266
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 266
ttcaggctgg tggtttgatg catgtctttc tgcaaactta aatggcaaat attatcacca    60

<210> SEQ ID NO 267
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 267
accgcacaag gggctccatc ttcattacgg aactcatcac atgcttccag aaatattctt    60

<210> SEQ ID NO 268
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 268
attttaagac gtgtttgtgt ttgtgtgtgt ttgttctttt tattgaatct atttaagtaa    60

<210> SEQ ID NO 269
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 269
acccagcgag gagccaacta tcccaaatat acctggggtg aaatatacca aattctgcat    60

<210> SEQ ID NO 270
<211> LENGTH: 60

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 270
cgttgaattg atgatgcagt tttcatatat cgagatgttc gctcgtgcag tactgttggt    60

<210> SEQ ID NO 271
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 271
tttctggtac tctgtgaaag aagagaaaag ggagtcatgc attttgcttt ggacacagtg    60

<210> SEQ ID NO 272
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 272
taaatacaga cactaagtta tagtatatct ggacaagcca acttgtaaat acaccacctc    60

<210> SEQ ID NO 273
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 273
taatgtccgt aaatcaaaaa gcaaaccatt tgataaggag gctcacagct cctcacaata    60

<210> SEQ ID NO 274
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 274
taatactaac tatttagtat actgtcagta ctgtacatct gcacactggt gttaataggg    60

<210> SEQ ID NO 275
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 275
atgagcggat gggcaaaaag ttgacagagt tgtctatgca ggatgaagag ctgatgaaga    60

<210> SEQ ID NO 276
<211> LENGTH: 60
<212> TYPE: DNA
```

```
<213> ORGANISM: Artificial Sequence
<220> FEATURE:
<223> OTHER INFORMATION: Description of Artificial Sequence: Synthetic
      probe

<400> SEQUENCE: 276
ggaagagact cacatgcttt ggttagtatc tgtgtttccg gtgggtgtaa tagggatta    60

<210> SEQ ID NO 277
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 277
aaagccatct atgtactgaa cccgggacta gaaggaaaat aaatgatcta tatgttgtgt    60

<210> SEQ ID NO 278
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 278
ggcctggcct ctgtaagcct gtgtatgtta tcaatactgt ttcttcctgt gagttccatt    60

<210> SEQ ID NO 279
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 279
ctacgtcctg gttgctcaca gtggttcagg agttatcgaa cgtgagacag ttaatgattt    60

<210> SEQ ID NO 280
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 280
catcgtgggt ctcatgcacg tcaagacctt cccacatcca aactcagctt ccagcaggga    60

<210> SEQ ID NO 281
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 281
gtttagctct tacactctat ccttcctaga aatggtaat tgagattact cagatattaa    60

<210> SEQ ID NO 282
<211> LENGTH: 60
<212> TYPE: DNA
<213> ORGANISM: Artificial Sequence
```

```
<220> FEATURE:
<223> OTHER INFORMATION: Description of Artificial Sequence: Synthetic
      probe

<400> SEQUENCE: 282
gtgagctaac atttgctaag cactgaattt gtctcaggca ccgtgcaagg ctctttacaa    60

<210> SEQ ID NO 283
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 283
atacagcagt ttatacccac acacctgtct acagtgtcat tcaataaagt gcacgtgctt    60

<210> SEQ ID NO 284
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 284
tgaaggcttt ttacccagca atgtcctcaa tgagggtctt ttctttccct caccaaaacc    60

<210> SEQ ID NO 285
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 285
acctcattcc cattgtttgg atcatgcttc tttccaacac gtgttcacaa tctccaaagg    60

<210> SEQ ID NO 286
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 286
aatagaccga atatcaggga gccctgcgg atggacctcg ctgacctgct gacacagaat     60

<210> SEQ ID NO 287
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 287
ggaatcaatt caatttggac tggtgtgctc tctttaaatc aagtccttta attaagactg    60

<210> SEQ ID NO 288
<211> LENGTH: 60
<212> TYPE: DNA
<213> ORGANISM: Artificial Sequence
<220> FEATURE:
```

<223> OTHER INFORMATION: Description of Artificial Sequence: Synthetic
      probe

<400> SEQUENCE: 288
atttgggtgg gatgggtagg atgaagtata ttgcccaact ctatgtttct ttgattctaa    60

<210> SEQ ID NO 289
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 289
ggagagtacg gtttccatga atatacagag gtcaaaacag tcacagtgaa aatctctcag    60

<210> SEQ ID NO 290
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 290
tttaagagcg atcctcatcc cttcagcaat atgtatttga gttcacacta tttctgtttt    60

<210> SEQ ID NO 291
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 291
ttggtccaag gcactacacc tgtactgcag gggctcaatg gagctgtctt caggccagaa    60

<210> SEQ ID NO 292
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 292
tgtctgccct ggagaactat aactttgaac ttgtggatgg tgtgaagttg aaaaaagaca    60

<210> SEQ ID NO 293
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 293
gactagaaga ctgtaaataa gataccaaag gcactatttt agctatgttt ttcccatcag    60

<210> SEQ ID NO 294
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 294
gaaaggtgat agcattaaat gttcatctag agttaatagt gggaggagta aaggtagcct    60

<210> SEQ ID NO 295
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 295
tggaatactc acgtgaggga acttactttg gccagcattg accttcaaag tcagatggaa    60

<210> SEQ ID NO 296
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 296
caacagtgga acaatgccac atggacagag gtctcctaca ccttctcaga ctaccccgg    60

<210> SEQ ID NO 297
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 297
tccctgccct aaaatcccag gcttaattgc cctacaaagg gttattaatt taaaactcca    60

<210> SEQ ID NO 298
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 298
ccaatgcaga caaaccaccc cttttgttg ggaaaggaat tacctttgac agtggtggta    60

<210> SEQ ID NO 299
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 299
aaatattaac atttccctgg accataagag acctttgatt aaggttttgg gaattagcag    60

<210> SEQ ID NO 300
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 300
tttttctgga aaacagacgg attttacttc tggagacatg gcatacggtt actgacttat    60

<210> SEQ ID NO 301
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 301
tattccatga agtttagtat ttggttgaca tagtgctctt caaattcatc ccattaccct    60

<210> SEQ ID NO 302
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 302
tgccccttaa aagattgaag aaagagaaac ttgtcaactc atatccacgt tatctagcaa    60

<210> SEQ ID NO 303
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 303
agagcccttc ttcccatcaa aaaggtatca aatgccttgg aagctccctg atcctacaaa    60

<210> SEQ ID NO 304
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 304
tgtgtggtag aactgaacaa cgatagactg ctaacacata ctgtctacaa aaatctcaat    60

<210> SEQ ID NO 305
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 305
gggtgaccag gtctgggttg aaaaagaccc caaaaagggt cacatttacc agggctctga    60

<210> SEQ ID NO 306
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

```
<400> SEQUENCE: 306
agaccagttt gaggcactca ctctagaaat agcctgtgtt agctgatgtg tgaaagcgta      60

<210> SEQ ID NO 307
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 307
tgagatattt aaggttgaat gtttgtcctt aggataggcc tatgtgctag cccacaaaga      60

<210> SEQ ID NO 308
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 308
tgtctcaacc ccgcatcccc catggttcag aaaatcatcg aaaagatact gaacaagggg      60

<210> SEQ ID NO 309
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 309
tgaaatatac caaattctgc atctccagag gaaaataaga ataaagatg aattgttgca       60

<210> SEQ ID NO 310
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 310
tgatgaaatg gagtcatttg agtctcttaa tagccatgta tcataattac caagtgaagc      60

<210> SEQ ID NO 311
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 311
gtcaagccat aattgttctt agtttgcagt tacactaaaa ggtgaccaat gatggtcacc      60

<210> SEQ ID NO 312
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 312
```
aaagcatttt taaagattaa tctgaattaa gctttatcag tgtactcttt atctgtgtta    60

<210> SEQ ID NO 313
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 313
tcataactgc atgaacttca tagagatggg atcctttagc atgttctctg tgcacatgct    60

<210> SEQ ID NO 314
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 314
gtgaaaatga agacgacaac gttgtcttag cctttgaaca actgagtaca acttttttggg    60

<210> SEQ ID NO 315
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 315
ctatgtactg aatttagagg ttgagaataa taggatctgt gttattctta gtacccactg    60

<210> SEQ ID NO 316
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 316
ccatgctgtg ctgtgttatt taattttcc tggctaagat catgtctgaa ttatgtatga    60

<210> SEQ ID NO 317
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 317
ccatcttcag ggttgcacag aatcctccaa gatactttgc agccttttt cccctggtc    60

<210> SEQ ID NO 318
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 318
tgaaggcgaa atgataactt ctaaggataa tttagaagat gagactgaag atgatgacct    60

<210> SEQ ID NO 319
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 319
atgtgtgtgt actcttccta gacgtacaag agacttttta atgctaaata tttgtcagtg    60

<210> SEQ ID NO 320
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 320
agttctttga aaaagttcca tgactcgaat atctgaaatg aagaaaacaa accgactcac    60

<210> SEQ ID NO 321
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 321
aggtttgatg tccttccaag aataaagtct ttccctggtg atggtctctc gctctgtctt    60

<210> SEQ ID NO 322
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 322 cgattttct tcatgacctt aacctgtgtg ggctaacaga ggacccagat cttacaggtt    60

<210> SEQ ID NO 323
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 323
ttaaggttct ccgaagaaaa gacagcaaga gctgctttcc gcctctttga agaccaagat    60

<210> SEQ ID NO 324
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 324
gctgcccgca tctatgatta cgaccccta tataaggagg cgctgcaaat gctgcgggat    60

```
<210> SEQ ID NO 325
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 325
acagcggctc cactacagac ccagccccag gttcaatgtc ctccgaagaa tgaagtcttt      60

<210> SEQ ID NO 326
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 326
gttcagacca actcctggat atgagctcag ccttcagcaa gacaacaaag accctggccc      60

<210> SEQ ID NO 327
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 327
gttgatataa tcctaccaga aggaaagcac taagaaacac tcgtttgttg tttttaaagg      60

<210> SEQ ID NO 328
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 328
gaagataatc gatagtcatg tttttttagac tctctgtatt gcttggtaag ctacgtagta     60

<210> SEQ ID NO 329
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 329
atgctctgaa ggttttgtag aagcacaatt aaacatctaa aatggctttg ttacaccaga      60

<210> SEQ ID NO 330
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 330
gtctgtggtg agcaaagttt gccttattac actgataaag tgtaattaca ctaataaagc      60
```

<210> SEQ ID NO 331
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 331
tttataataa ccgtagccca cattgtagta gtttttcagc tctttactaa gtcccaccaa      60

<210> SEQ ID NO 332
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 332
aaccaaatat ctatgtaggc agaggtaacc aggagagaag caagacttgc tgcctaaagg      60

<210> SEQ ID NO 333
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 333
gttgtaattt aaaccttgtt tgtaactgaa aggtcgattg taatggattg ccgtttgtac      60

<210> SEQ ID NO 334
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 334
aagagtggca gaggctacta caaaaagcaa cctttcatt ttcactaaga gtttaaaagc      60

<210> SEQ ID NO 335
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 335
acatggggct tacaagtgct tcttgtccaa gtagtctacc aatgaaaaga gaaattacag      60

<210> SEQ ID NO 336
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 336
gagaagccat ctatgtactg aacccaggac tagaaggaaa ataaatgatc tacatgttgt      60

```
<210> SEQ ID NO 337
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 337
gagattgtcc agagtcctat gacagacctt caaggtttta agttccacag acttggactt    60

<210> SEQ ID NO 338
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 338
ggttgacttg actcatgctt gtttcacttt cacatggaat ttcccagtta tgaaattaat    60

<210> SEQ ID NO 339
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 339
agttgcttat ggcatacaag gctaaaatta attcagctat ttaatcttaa taattattat    60

<210> SEQ ID NO 340
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 340
tggttttcat gtgcttctct tgagcagtct gaggagagaa tagaaacaga aaccccttgg    60

<210> SEQ ID NO 341
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 341
tgcaagtttc ctgtcatgac aagaagctgt catgttcagt agcaccttac acgaaaggtg    60

<210> SEQ ID NO 342
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 342
atttctcttt ctaaagggga gtaacttttt aaacccttcc tgattttagc ctggcaatgt    60

<210> SEQ ID NO 343
```

<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 343
ggaacatgct ttctgaactc acttgagagt gtatggtgta tgtcacttct catatattct    60

<210> SEQ ID NO 344
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 344
gaaaacttcc aattcaagaa ggatggacac tgcttgaaag aaatctacct tgtggatgta    60

<210> SEQ ID NO 345
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 345
aggcgctcaa tagaaattca aatctcactt taagaccatg aatttcaagt tgcaatgaag    60

<210> SEQ ID NO 346
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 346
gaagggtttc acaatgaaga tgtgtagcag gcgttatccc attgttatca ctgggcagaa    60

<210> SEQ ID NO 347
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 347
tgacctgcta aatgacctgg agaaattgag gaagcaggaa gcacatttga gaaaagaaaa    60

<210> SEQ ID NO 348
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 348
ttggcttcat atctagacta acacaaaatt aagaatcttc cataattgct tttgctcagt    60

<210> SEQ ID NO 349
<211> LENGTH: 60

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 349
cttcttctgt gactggggat aatatctgta ataacttgct agatcaaatg acaaaacaca      60

<210> SEQ ID NO 350
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 350
atctgcaaat cgtgactaag tacatcctga ttcctgcaag ccagcagcca aaggagaata      60

<210> SEQ ID NO 351
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 351
actctgagtc agttgaaata gggtaccatc taggtcagtt taagaagagt cagctcagag      60

<210> SEQ ID NO 352
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 352
ctctgtaaag ctaaaataaa gaaatagaac aaggctgagg atacgacagt acactgtcag      60

<210> SEQ ID NO 353
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 353
aagttgaggt atacataccc cagttcaaat tagaagagca ttatgaactc agatccattc      60

<210> SEQ ID NO 354
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 354
attctggatg aatatatgcg ctttctgaac tgtagaaagg gacggaagga cccttccaag      60

<210> SEQ ID NO 355
<211> LENGTH: 60
<212> TYPE: DNA
```

```
<213> ORGANISM: Artificial Sequence
<220> FEATURE:
<223> OTHER INFORMATION: Description of Artificial Sequence: Synthetic
      probe

<400> SEQUENCE: 355
ggcagaacat tgactggca ctgatttgca ataagctaag ctcagaaact ttcctactgt      60

<210> SEQ ID NO 356
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 356
accagtactg caggattgtt gcactaaatg aaatactgta tgtgaagtgc ctggcacagt      60

<210> SEQ ID NO 357
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 357
gttaatgata tgggaacgga tgagactttc cacgtggtac ctagatttgc aaattctatt      60

<210> SEQ ID NO 358
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 358
tttttcctag acccgtgacc tgagatgtgt gatttttagt cattaaatgg aagtgtttgc      60

<210> SEQ ID NO 359
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 359
catggagagt gtctgcggat acttccacag gtcccacaac cgcagcgagg agtttctcat      60

<210> SEQ ID NO 360
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 360
ccaacactgt gtgaattatc taaatgcgtc taccattttg cactagggag gaaggataaa      60

<210> SEQ ID NO 361
<211> LENGTH: 60
<212> TYPE: DNA
<213> ORGANISM: Artificial Sequence
```

```
<220> FEATURE:
<223> OTHER INFORMATION: Description of Artificial Sequence: Synthetic
      probe

<400> SEQUENCE: 361
gtatggaaca ctccaatcag aaaaaggtta tcattggtcg ttgagttatg ggaagaactt    60

<210> SEQ ID NO 362
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 362
ggaagtgaca actgaacaca ctgtgttgga tcggaggttc cgttagggga tccttcctta    60

<210> SEQ ID NO 363
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 363
acagggtctg caaggtcttt ggttcagcta agctaggaat gaaatcctgc ttcagtgtat    60

<210> SEQ ID NO 364
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 364
tgctccttcc taaaagtctg ttttcaatcc tggtaatatt aggggcactg cggcacctaa    60

<210> SEQ ID NO 365
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 365
attcacctct ctcactgact attacagttg catttttatg gagttcttct tctcctagga    60

<210> SEQ ID NO 366
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 366
acctgaactc gcacctccta cctcttcatg tttacatata cccagtatct ttgcacaaac    60

<210> SEQ ID NO 367
<211> LENGTH: 60
<212> TYPE: DNA
<213> ORGANISM: Artificial Sequence
<220> FEATURE:
```

<223> OTHER INFORMATION: Description of Artificial Sequence: Synthetic
      probe

<400> SEQUENCE: 367
caccgacaag aactcactac tgggcatgga gggtgccaac agcatctttt ccgggttcct    60

<210> SEQ ID NO 368
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 368
acagtggatc ttggagtggg atttcttggg taaattatct ttgcccttttg aaatgtctcc    60

<210> SEQ ID NO 369
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 369
caagatccag ggacctagag gcctcggcga tgacactgcg ctgaacgacg cgcgcttatt    60

<210> SEQ ID NO 370
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 370
gtggttagcc gtatcattgt gtgggacatc atggccttca atggcatcat ccatgctctg    60

<210> SEQ ID NO 371
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 371
ctgctggagg gacactgctg gcaaacggag acctattttt gtacaaagaa cccttgacct    60

<210> SEQ ID NO 372
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 372
ggagacctcc ctaccaagtg atgaaagtgt tgaaaaactt aataacaaat gcttgttggg    60

<210> SEQ ID NO 373
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 373
gtaggtatcc ctccatgccc ttctgtaata aatatctgga aaaaacatta aacaataggc    60

<210> SEQ ID NO 374
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 374
tgcaccaggg ccttgttgaa cagatccaca ctgctctaat aaagttccca tccttaatga    60

<210> SEQ ID NO 375
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 375
gttttaactc tatctgtcat acatcctagt gaatgtaaaa tgcaaaatcc tggtgatgtg    60

<210> SEQ ID NO 376
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 376
tacagaacaa gatacctgct cagacaaagt cacctgaaga aactgataaa gagaaagttc    60

<210> SEQ ID NO 377
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 377
tgaaaaatcc tgaggattca tcttgcacat ctgagatctg agccagtcgc tgtggttgtt    60

<210> SEQ ID NO 378
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 378
tgtaggtccc ctggggacac aagcaggcgc caatggtatc tgggcggagc tcacagagtt    60

<210> SEQ ID NO 379
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 379
gcttcactga attcctgcat taacccaatt gctctgtatt tggtgagcaa aagattcaaa    60

<210> SEQ ID NO 380
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 380
accatgttga ctttcctcat gtgtttcctt atgactcagt aagttggcaa ggtcctgact    60

<210> SEQ ID NO 381
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 381
tggctggata atgttcagtg tcggggcacg gagagtaccc tgtggagctg caccaagaat    60

<210> SEQ ID NO 382
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 382
gtaactgtgc tgaatgcttt agatgaggaa atgatcccca gtggtgaat gacacgccta     60

<210> SEQ ID NO 383
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 383
ttgttcgttt tgccttctgt ccttggaaca gtcatatctc aagttcaaag gccaaaacct    60

<210> SEQ ID NO 384
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 384
tatctgattg gaaacctgcc gacttagtgc ggtgatagga agctaaaagt gtcaagcgtt    60

<210> SEQ ID NO 385
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

```
<400> SEQUENCE: 385
aagatcagaa gccagtcatg gatgaccagc gcgaccttat ctccaacaat gagcaactgc    60

<210> SEQ ID NO 386
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 386
ttcactaatc aaagacacta ttttcatact agattcctga gacaaatact cactgaaggg    60

<210> SEQ ID NO 387
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 387
gatcaactca aactatgtcg accccaagtt ccctccatgc gaggaatatt cacagagcga    60

<210> SEQ ID NO 388
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 388
ctaatatgga gattatcctt tcattgagcc ttttatcctc tgttctcctt tgaagaaccc    60

<210> SEQ ID NO 389
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 389
gaagaagttc ttcctcctag aaccccagat gaaggtcgca gccctcagag cgggagccca    60

<210> SEQ ID NO 390
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 390
aagtggtgat gttgtttcaa acgttcagaa cagataccat catcctgcct ttgttagctg    60

<210> SEQ ID NO 391
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 391
```
agagggtctt agtcctggaa agtcaggcca acaagcaacg tttgcatcat gttatctctt    60

<210> SEQ ID NO 392
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 392
taatactaac tatttagtat actgtcagta ctgtacatct gcacactggt gttaataggg    60

<210> SEQ ID NO 393
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 393
aagagtttcc gaagagtgaa gggcagtaca gtggcttcaa gagtccttac tgaagccagg    60

<210> SEQ ID NO 394
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 394
agaaagtgtg gatgtatcac ttctctctaa aatgtcattg ttagcactaa ttacaggttc    60

<210> SEQ ID NO 395
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 395
cgaagtggac cacaagaaac gcaaaatccg ggaggagatt gagcattttg gaatcaagat    60

<210> SEQ ID NO 396
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 396
gtgcaatggg gagccagtca ttgagggtat tgcagagacc atcttcctgc ccagcaagaa    60

<210> SEQ ID NO 397
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 397
acttcctgtg cctttcctat cacctcgaga agtaattatc agttggtttg gattttgga    60

<210> SEQ ID NO 398
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 398
ttgatgtgtg ggagcacgct tactaccttc agtataaaaa tgtcaggcct gattatctaa    60

<210> SEQ ID NO 399
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 399
gccactcagc tacctaattc ctcaatgacc tttatctaaa atctccatgg aagcaataaa    60

<210> SEQ ID NO 400
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 400
aaggagacaa actccacctg gaaatgttct gtgaaggtca agtgtgcaaa cagacattcc    60

<210> SEQ ID NO 401
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 401
cgccaagcat gtgaacatct gggccctgac tgtgggcatc ctcatgacca ttctgctcat    60

<210> SEQ ID NO 402
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 402
caacagcctc tatgacgaca tcgagtgctt ccttatggag ctggagcagc ccgcctagaa    60

<210> SEQ ID NO 403
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 403
atttcattca cgaatctctt attttgggaa gctgttttgc atatgagaag aacactgttg    60

<210> SEQ ID NO 404
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 404
ccaaacatcc tggagagtat gcgagaacct accaagaaaa acagtctcat tactcatata      60

<210> SEQ ID NO 405
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 405
tacagaaagc ctatctccac gcacactgtg gacttcacct tcaacaagtt caacaaatcc      60

<210> SEQ ID NO 406
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 406
gggctggcta acattgctat attgaacaac aacttgaata ccttgatcca gcgttccaac      60

<210> SEQ ID NO 407
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 407
aggcgcctgg cacatttcag ggagaaactc caaagtccac acaaagattt tctaaggaat      60

<210> SEQ ID NO 408
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 408
ttctctgata acctacttgc ttactcaatg cctttaagcc aagtcaccct gttgcctatg      60

<210> SEQ ID NO 409
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 409
gatgtcctgt gctgcttgtg atgagagcct ccacactgta ctgttcaagt caatgttaat      60

<210> SEQ ID NO 410
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 410
ctcagaggac cagctatatc caggatcatt tctctttctt cagggccaga cagcttttaa    60

<210> SEQ ID NO 411
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 411
ccagctgtgc tctggacagg catgttctct gaggacacta accacgctgg accttgaact    60

<210> SEQ ID NO 412
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 412
ttggtccaag gcactacacc tgtactgcag gggctcaatg gagctgtctt caggccagaa    60

<210> SEQ ID NO 413
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 413
tgctggttgg tatctgtaaa tgtttaataa atatctgagc atgtatctat caacgccaag    60

<210> SEQ ID NO 414
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 414
tgttgagaaa cggactctga taaaagtctt cgggatccgt ttcgacatcc tggttttgg    60

<210> SEQ ID NO 415
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 415
tgagcagtgg actcaaaagc attttcaggc atgtcagaga agggaggact cactagaatt    60

```
<210> SEQ ID NO 416
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 416
ttgtcaggcg atcttgtttg aagctctatg ttgccataat taccatcaag tacacactgt    60

<210> SEQ ID NO 417
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 417
agaagatcac tgaagaaact tctgctttaa tggctttaca aagctggcaa tattacaatc    60

<210> SEQ ID NO 418
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 418
tctgtcattt gctttgaagc ccattgtgcc ttatgccaat aattcaattg ctgcaaacac    60

<210> SEQ ID NO 419
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 419
atgaaaagct ttcctgcttg gctcttattc ttccacaaga gaggactttc tcaggccctg    60

<210> SEQ ID NO 420
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 420
caattgcatc cacgttttct tttcttttgt tgattttctt gttcccgtag aagaaagaag    60

<210> SEQ ID NO 421
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 421
atcctcatga gcattctgct catcttcatc ccagtgttga tctttcaagt ctatcaatag    60

<210> SEQ ID NO 422
```

```
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 422
caaataaacc aacgggaaaa aagaaaggtt ccagttttgt ctgaaaattc tgattaagcc    60

<210> SEQ ID NO 423
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 423 acctttctc tgggacttaa gctgctatat cccctcagag ctcacaaatg cctttacatt    60

<210> SEQ ID NO 424
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 424 gggggtatt tgcaagaata ctcattttga cataataggt cctcttgtca gagatcctct    60

<210> SEQ ID NO 425
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 425
tcaatctgaa tctgcccaga gcaagatgct gagtggcatt ggaggcttcg tgctggggct    60

<210> SEQ ID NO 426
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 426
tattcctgca tttgtgaaat gatggtgaaa gtaagtggta gcttttccct tcttttctt    60

<210> SEQ ID NO 427
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 427
aaggatgttc taattctttc tgctctgaga cgaatgctat gggctgcaga tgacttctta    60

<210> SEQ ID NO 428
<211> LENGTH: 60
```

<212> TYPE: DNA
<213> ORGANISM: Artificial Sequence
<220> FEATURE:
<223> OTHER INFORMATION: Description of Artificial Sequence: Synthetic
      probe

<400> SEQUENCE: 428
gtcgattcca ttaagcaata ctaactgacg ttaagtcatg atttcgcgcc ataataaaga    60

<210> SEQ ID NO 429
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 429
gggccctgat tctgggcatc ctcatgacca ttctgctcat cgtcatccca gtgctgatct    60

<210> SEQ ID NO 430
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 430
ttgtctatat caccgatgat acatacacaa aacgacaact gttaaaaatg gaacacttgc    60

<210> SEQ ID NO 431
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 431
catttgctgt gtttcgttag catctggctc caggacagac cttcaacttc caaattggat    60

<210> SEQ ID NO 432
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 432
tgggactgtt ctgtctcatg tttatctgag ctcttatcta tgaagacatc ttcccagagt    60

<210> SEQ ID NO 433
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 433
aagcctgacg agccctctca cagtggaatg gagagcacgg tctgaatctg cacagagcaa    60

<210> SEQ ID NO 434
<211> LENGTH: 60
<212> TYPE: DNA

```
<213> ORGANISM: Artificial Sequence
<220> FEATURE:
<223> OTHER INFORMATION: Description of Artificial Sequence: Synthetic
      probe

<400> SEQUENCE: 434
aggattattc cttgctatta gtactcattt tatgtatgtt acccttcagt aagttctccc    60

<210> SEQ ID NO 435
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 435
aagcgtgaca agccctctca cagtggaatg gatgaagtgc agatgacaat ttaaggaaga    60

<210> SEQ ID NO 436
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 436
ggtgctggat tccaaggttt gtaaaggcat ctcggtaaag actgcttttt gaatgcatat    60

<210> SEQ ID NO 437
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 437
cacggtcctg ctggtggtgg acaaatgcga cgaacctctg agcatcctgg tgaggaataa    60

<210> SEQ ID NO 438
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 438
tgaggaacag ggaaatgccg ctgtgaagtc ttaaagcact tctgcttaaa ctccatgtgt    60

<210> SEQ ID NO 439
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 439
agactctaga ggcgtggacc aagggggcatg gagcttcact ccttgctggc caggggagtt    60

<210> SEQ ID NO 440
<211> LENGTH: 60
<212> TYPE: DNA
<213> ORGANISM: Artificial Sequence
```

<220> FEATURE:
<223> OTHER INFORMATION: Description of Artificial Sequence: Synthetic
      probe

<400> SEQUENCE: 440
ctgattgaga agccaaatat tgttaaccat tttccccgtc tggcacggtt cttttgcaca    60

<210> SEQ ID NO 441
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 441
ggaatgacca ggaggagaca gccggtgttg tgtccacctc cctcattagg aatggtgact    60

<210> SEQ ID NO 442
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 442
tcaacttgac ttcatgttaa aaaccctcaa caaaccaggc gtcgaaggaa catacctcaa    60

<210> SEQ ID NO 443
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 443
gattctgtgc agagcaagat gctgacagga gctaggggct tcatgctggg gctcatcatc    60

<210> SEQ ID NO 444
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 444
tggtatttgt aaaaagcaaa caaacattac aaggcagtta tctcattgct gttttgggag    60

<210> SEQ ID NO 445
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 445
aggcagagga acgcgttgtg gtgatcagca gctcggaaga ctcagatgcc gaaaactcgt    60

<210> SEQ ID NO 446
<211> LENGTH: 60
<212> TYPE: DNA
<213> ORGANISM: Artificial Sequence
<220> FEATURE:

<223> OTHER INFORMATION: Description of Artificial Sequence: Synthetic
probe

<400> SEQUENCE: 446
gcatccaagc atgatgagcc ctctcacggt gcaatggagt gcacggtctg aatctgcaca 60

<210> SEQ ID NO 447
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 447
ggtcctgact caaaacccag tgagggggat gtttttccag gacaagtgaa gagaaaatat 60

<210> SEQ ID NO 448
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 448
ttgacaagtt cttcccacca gtgctgaaca tcacgtggct gcgcaatggg gagccagtca 60

<210> SEQ ID NO 449
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 449
ggactggcta tcccaagacc tggcagatgt ggctgctcaa taaacacttg ttgaaccatc 60

<210> SEQ ID NO 450
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 450
ggaaggtcaa ttacaacttt gaagatgaga ccgtgaggaa gtttctactg agccagttgc 60

<210> SEQ ID NO 451
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 451
atttgttccg caagttccac tacctgccct tcgtgccctc agccgaggac gtctatgact 60

<210> SEQ ID NO 452
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 452
gcttcatttc ctgtgtcttt tttcactaca ttataaatgt ctctttaatg tcacaggcag        60

<210> SEQ ID NO 453
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 453
tcagccggga gctgtgctgg cgagaaggcc caggcacgga ccagactgag gcagaggccc        60

<210> SEQ ID NO 454
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 454
tacaaccagt attctcagag ataccatcag agaacaaaca ctaatgttaa ttgcccaatt        60

<210> SEQ ID NO 455
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 455
ctcagtgact gtggttgagg acgacgagga tgaggatgga gatgacctgc tccatcacca        60

<210> SEQ ID NO 456
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 456
gtccaccaac atgattcata atgagactag accttccaga tcccagtgat gctggaaatg        60

<210> SEQ ID NO 457
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 457
agaaggcaga gaaagtgaag accaagtcca gaactgaatc ctaagaaatg caggactgca        60

<210> SEQ ID NO 458
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 458
ttcaatggga tgaagcgggt gcagtacctg aacagataca tccataaacg ggaggagaac    60

<210> SEQ ID NO 459
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 459
aaagggcggt ggaggggaaa acattaagaa tttattcatt atttctcgag tactttcaga    60

<210> SEQ ID NO 460
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 460
ctgaagatga tttaaaacat gaaagtgtat tgttgtcact gtggtaattt ccttgccagt    60

<210> SEQ ID NO 461
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 461
acttaatttg agcgagtacc ttttcatttg acacttttcc tgtttctaac cttaggaaac    60

<210> SEQ ID NO 462
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 462
atcctccatg gtatctgaat cccagaatcc tacaatcctg catggtatct gaaacatact    60

<210> SEQ ID NO 463
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 463
ctagattctg cagtcaaaga tgactaatat ccttgcattt ttgaaatgaa gccacagact    60

<210> SEQ ID NO 464
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 464
tcgtgcgttg ccttgctccg ttttcccaa aaagcactgg cttcatcaag gccaccgacg    60

<210> SEQ ID NO 465
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 465
ttcgtgctgg gcctgctctt ccttggggcc gggctgttca tctacttcag gaatcagaaa    60

<210> SEQ ID NO 466
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 466
ggactatgct gtaaccaaat tattgtccaa ggctatattt ctgggatgaa tataatctga    60

<210> SEQ ID NO 467
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 467
ctgcttaagt ctgagtgtca tttcttcaat gggacggagc gggtgcggtt cctggagaga    60

<210> SEQ ID NO 468
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 468
cacgaaagtg taaagcagta ttaagatcat tactgcatgt gccctaaaaa cccaagtttt    60

<210> SEQ ID NO 469
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 469
ttctaatttc agacttggct ttttacttag aggacattct gatttgctct cagaaacatc    60

<210> SEQ ID NO 470
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 470
tggcagcttt ggggctgttt ttgagcttct cattgtgtag aatttctaga tcccccgatt    60

<210> SEQ ID NO 471
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 471
agcagaagcg gggccgggtg gacaattact gcagacacaa ctacggggtt ggtgagagct    60

<210> SEQ ID NO 472
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 472
gatcgttctc tgtgagatca ttgggcaggt gtatgcagat cctgactgcc ttccccgaac    60

<210> SEQ ID NO 473
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 473
atcttcatga ccattctgct catcatcatc ccagtgttga tcttccaagc ctatcaatag    60

<210> SEQ ID NO 474
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 474
agattacatt aattttctta taaattggaa gatttataaa tgtttgaaat tgtacacatt    60

<210> SEQ ID NO 475
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 475
gtgtctggac agattgtggg agtaagtgat tcttctaaga attagatact tgtcactgcc    60

<210> SEQ ID NO 476
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 476
agtggaataa ggcctgttgt tccttgcagt ggatcctgat ttggacaagc agcaatttgt      60

<210> SEQ ID NO 477
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 477
tggggaggga ggtgtttaac ggcactgtgg ccttggtcta acttttgtgt gaaataataa      60

<210> SEQ ID NO 478
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 478
aagaaatttc ctttagacta acgaatatat tgggggagg aatagagggg aggtgtgcag       60

<210> SEQ ID NO 479
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 479
acttaaattg ctatatctgc tcagagctca caaatgcctt tgaattattt ccctgacttc      60

<210> SEQ ID NO 480
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 480
ctggatagtc ctgtcaccgt ggagtggaag gcacagtctg attctgcccg gagtaagaca      60

<210> SEQ ID NO 481
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 481
gggattcata gcattcacct actccctgaa gtctagggac aggaagatgg ttggagacct      60

<210> SEQ ID NO 482
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 482
cctgagacta ttttaactag gattggttat cactcttctg tgatgcctgc ttatgcctgc      60

<210> SEQ ID NO 483
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 483
actctggact tcagccaaca ggtaatacct tttcatcctc tttaagaaac agatttggag        60

<210> SEQ ID NO 484
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 484
aactgtcata cgtatgggac ctacacttaa tctctatgct ttacactagc ttctgcattt        60

<210> SEQ ID NO 485
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 485
tacaggatct aaagggttt tcttagaaag ggcaatattg tccaatgaag taagcagaag         60

<210> SEQ ID NO 486
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 486
actggagtta cactcctctt cctgggtcca attattcaga aggatggcac atttcctaga        60

<210> SEQ ID NO 487
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 487
cgctcccaga tgtaaagaac gcgacttcca caaacctgga tttttatgt acaaccctga        60

<210> SEQ ID NO 488
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 488
caaccctgac cgtgaccgtt tgctatattc cttttctat gaaataatgt gaatgataat        60

<210> SEQ ID NO 489
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 489
aattcaggac tgtctcctcc aggaccaaag tggccaggta ataggagaat aggtgaaata    60

<210> SEQ ID NO 490
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 490 tcccccctatt tatttttaca tttctctatg tgcaaatgag aaaaacacta aggttcaggg    60

<210> SEQ ID NO 491
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 491
aagagatgtt gtcctgacac ttgtggcatc aaatgcctgg atcctgttga caccccaaac    60

<210> SEQ ID NO 492
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 492
gcaactaaac aaacacaaag tattctgtgt caggtattgg gctggacagg gcagttgtgt    60

<210> SEQ ID NO 493
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 493
caactgcctg tgtcaggctt gtcccccctg agatcaaagt cttacaagtg gctgtcaagg    60

<210> SEQ ID NO 494
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 494
tttccttctg atgcagacat ggtccccact ggggcaaggc tgcagttttc ttttaaaaaa    60

```
<210> SEQ ID NO 495
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 495
ctgaccgtga ccgtttgcta tattcctttt tctatgaaat aatgtgaata ataattaaac    60

<210> SEQ ID NO 496
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 496
tgttcattgt gttgtcagcc agaaagctag tctaaatcaa ctcctagatc aaagcaaggg    60

<210> SEQ ID NO 497
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 497
ttttgagtcc ggaaaaacag aattccaagt caaattctgt tccaattatc ctggccatcg    60

<210> SEQ ID NO 498
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 498
gggcaggtag gatttcaatg gcatgttaca taaccatcct ctaaagggac agaatgtaca    60

<210> SEQ ID NO 499
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 499
tttttcgccc ttagcgtgaa gatggcctcg ggacccacga gcatccgcgt gcactttcag    60

<210> SEQ ID NO 500
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 500
tggggctgct tggttttcag atttgcttag gctccattca taaatacaga tggcacactt    60

<210> SEQ ID NO 501
```

<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 501
gctgaaggga ccttgaaggg taaagaagtt tgatattaaa ggagttaaga gtagcaagtt    60

<210> SEQ ID NO 502
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 502
ggctgaacta caagtgtagg ccaccattat aatttataaa tacagcatac ttcaaaactg    60

<210> SEQ ID NO 503
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 503
ttcttagggg tggggatga ggagttaaag gtggcatctt caatcgcagg tcaaagcaga    60

<210> SEQ ID NO 504
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 504
ctctgcatct actggacaaa gtattatgac tttaaaaacc ccattattga aaagtacctg    60

<210> SEQ ID NO 505
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 505
tgcaaccaac catgtgacag agggattcc tagactggat tcccagcctc aagagacctc    60

<210> SEQ ID NO 506
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 506
cagccatcct ttttaagagt aagttggtta cttcaaaaag agcaaacact ggggatcaaa    60

<210> SEQ ID NO 507
<211> LENGTH: 60

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 507
tctgctgcag gggacagcag aggaagacca tgtggacctg tcactgtctt gtacccttgt    60

<210> SEQ ID NO 508
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 508
tactgccctc aagggcggg tgtactacct ggagcaccct gagaagctga cgctgacaga    60

<210> SEQ ID NO 509
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 509
ggagtgttcc caatgctttg tccatgatgt ccttgttatt ttattgcctt tagaaactga    60

<210> SEQ ID NO 510
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 510
aaatgaccca cagtaggttg gcagcgcttc gagtaacaaa accttatttg gacattggct    60

<210> SEQ ID NO 511
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 511
cacggtctac atgatcaaat acctcatgac gctcatcgtg ggcatcacgt cgggcttctg    60

<210> SEQ ID NO 512
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 512
ttcatgacca ttctgctcgt catcatccca gtgttggtcg tccaggccca gcgatagatc    60

<210> SEQ ID NO 513
<211> LENGTH: 60
<212> TYPE: DNA
```

<213> ORGANISM: Artificial Sequence
<220> FEATURE:
<223> OTHER INFORMATION: Description of Artificial Sequence: Synthetic
      probe

<400> SEQUENCE: 513
acagtgaatt tgatgcatt taaaataaga ttctgatgcc agactgttaa aacaggcgct    60

<210> SEQ ID NO 514
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 514
aaggaacgca agaactgga acggaatat acgttgtgaa ggaatgaccc taggagagct    60

<210> SEQ ID NO 515
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 515
tggaaaggtg tttctctcat ctctgtccta aggcttgata aagtcattaa aattgtgttc    60

<210> SEQ ID NO 516
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 516
ccgaccatgt cctggtccct gttcaacacc cacttcatga atgctgcctg ggcttcatag    60

<210> SEQ ID NO 517
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 517
aaaggtgttt gtgccatttg gaaaacagcg tgcatgtgtt caagccttag attggcgatg    60

<210> SEQ ID NO 518
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 518
tctgctcact tccgccatct aagaggaata ggtgagttgc tcatgctgat taggattgaa    60

<210> SEQ ID NO 519
<211> LENGTH: 60
<212> TYPE: DNA
<213> ORGANISM: Artificial Sequence

```
<220> FEATURE:
<223> OTHER INFORMATION: Description of Artificial Sequence: Synthetic
      probe

<400> SEQUENCE: 519
tcctgcccca ttatcttgat ccggtgcgcc atgttgaatc ccctaaccg ctgcttgaaa      60

<210> SEQ ID NO 520
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 520
agtacgtgtt actggccaag gctatttttc agaactgtta aaggtcatat gcacgttaaa      60

<210> SEQ ID NO 521
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 521
aagaaggcat acagtggcat aaacgatgct cttcctagta gcttaatagg ccacaagcta      60

<210> SEQ ID NO 522
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 522
aacactgctg ctccagtgca ggagacttta catggatgcc aaccggtcac ccaggaggat      60

<210> SEQ ID NO 523
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 523
aaatgatgag gcgccggaat atgacacagg ggcggtgcaa accagtgaac acctttgtgc      60

<210> SEQ ID NO 524
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 524
tgtcctgaaa gttggaatga aagagaccct ataagagcac tgacatgttt cagtgtcctc      60

<210> SEQ ID NO 525
<211> LENGTH: 60
<212> TYPE: DNA
<213> ORGANISM: Artificial Sequence
<220> FEATURE:
```

<223> OTHER INFORMATION: Description of Artificial Sequence: Synthetic
      probe

<400> SEQUENCE: 525
aggcgttctc tagatccttt cctctgtttc cctctctcgc tggcaaaagt atgatctaat    60

<210> SEQ ID NO 526
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 526
gagggattga catgtttcaa caaaataatg cacttcctta cctagtggcc cttcacacaa    60

<210> SEQ ID NO 527
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 527
agtaggagtg aaagcacttc agaatttaaa ccaggatact ccctgcatga tacatctgtg    60

<210> SEQ ID NO 528
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 528
acaattgcaa gtcaacaccc taataccaga ataggagttt cctctgtgg acctgaagcc    60

<210> SEQ ID NO 529
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 529
aagattttat tgtaaaacag agctgaagtc acaggaagta gggaactttg cacccaacat    60

<210> SEQ ID NO 530
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 530
tttttgcata tcagttattt tatatgtgga ggtacaattt gtataggaaa gttagaataa    60

<210> SEQ ID NO 531
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 531
cggcactatg aaaaatcata ggccaacaaa ctggataacc tagcagaaac caaagacaag      60

<210> SEQ ID NO 532
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 532
catcaagggg gtcttgtttt gctagagagt ttggggtttg gtttgtggat ttcattgtga      60

<210> SEQ ID NO 533
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 533
catccctccc cagttcattg cactttgatt agcagcggaa caaggagtca gacattttaa      60

<210> SEQ ID NO 534
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 534
ctaacagtga aaagagagaa gggagactct atttaagatt cccaaaccta atgatcatct      60

<210> SEQ ID NO 535
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 535
aggtcctttc caccctgaga cttggctcca ccactgatat cctcctttgg ggaaaggctt      60

<210> SEQ ID NO 536
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 536
tggagttttt gcttttatcg atgtgtgtct tcaaagaaac cacttcagag gcaagaaggc      60

<210> SEQ ID NO 537
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 537
aataattgcc aggagtacag tgctcttgtt gatcttgtat tcagtcaggt taaaacaacg    60

<210> SEQ ID NO 538
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 538
gtttgatgcc agcagcttcg gccatccaaa cagaggatgc tcagatttct cacatcctgc    60

<210> SEQ ID NO 539
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 539
cattctctct aaagagcctc gttcatttcc aaagcagtta aggaatggga accagagtgt    60

<210> SEQ ID NO 540
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 540
tgctgaagat gactgctttc actgaggtca aggattgtaa tattgccagc tttgtaaagc    60

<210> SEQ ID NO 541
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 541
tgctgggcag aagggcgctg ccttctcttt gatgactctt tcctgcatgc tgcgttccat    60

<210> SEQ ID NO 542
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 542
tcaaatacag agttcatcat tcttgttgtt gatagcattg acagggaacg actagctatt    60

<210> SEQ ID NO 543
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 543
aaagccatgg acttctatga tccagcaagg cacaatgagt ttgacttcat ctcaggaact    60

<210> SEQ ID NO 544
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 544
tgattcggtt tctcagagtc tcatggcatc atagttttc cagaatgaca cagtagccac    60

<210> SEQ ID NO 545
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 545
ttggcctctc gtccacgagg ggagaaacct aaaccctgtt tcacaatctg tgcggaagta    60

<210> SEQ ID NO 546
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 546
ctgttcaaca ccctcttcat gaactctggc tgcctgtgct tcacagcatt tgtgtactct    60

<210> SEQ ID NO 547
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 547
gcaggactcc tccaaaatta tgtggaccgt acggagtcga gaagcacaga gcctgagttg    60

<210> SEQ ID NO 548
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 548
tgtgcctcca aggactgtct ggcaatgact tgtattggcc accaactgta gatgtatata    60

<210> SEQ ID NO 549
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 549
ggctatgtac tttgtgcagg gaagtacatt atctacagtc acaaaaatgt ctcatgggaa    60

<210> SEQ ID NO 550
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 550
ggtgctcaaa ttaccctcca aaagcaagta gccaaagccg ttgccaaacc ccacccataa    60

<210> SEQ ID NO 551
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 551
ttcataactt tcggcgagac gtggtgagcc tcctggtgta gagttctttt gtctttgtat    60

<210> SEQ ID NO 552
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 552
gggtgacatt tgtaacattt cctctttgag actctgagtt cacctagaga agtctaagca    60

<210> SEQ ID NO 553
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 553
ccaaggcttc atgacaaggg agtttctaaa gagcctgcga aagccttttg gtgactttat    60

<210> SEQ ID NO 554
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 554
agacagtttg gtggatctga taattgacca gttagttatt cagatcaact agacagcatt    60

<210> SEQ ID NO 555
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 555

```
gacactctcg taagttacat gcaaactaaa gaaagtgaaa ttcttcctga aatggcatct      60
```

<210> SEQ ID NO 556
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 556

```
taggccaaag taacagactc aagagttatt gtacattact gaccacgctc atttgttcaa      60
```

<210> SEQ ID NO 557
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 557

```
gacatatctc taattccatc cataaatcca gttctactat ggctgagttc tggtcaaaga      60
```

<210> SEQ ID NO 558
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 558

```
catgtctgaa agtcacatat tgtgaaaatt tgaagctatc tcagtaaaaa gcagctttgg      60
```

<210> SEQ ID NO 559
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 559

```
ggttgtgaat ttccaggtac ttggactttt tgtagaagta gagagaagaa gatgaagttt      60
```

<210> SEQ ID NO 560
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 560

```
cagcttattt cctcattttt ataatgtccc ttcacaaacc cagtgtttta ggagcatgag      60
```

<210> SEQ ID NO 561
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 561

```
agtgtgcgga aatgcttctg ctacattttt agggtttgtc tacatttttt gggctctgga      60
```

<210> SEQ ID NO 562
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 562
tttaacactg gcattcctgc ctacttgctg tggtggtctt gtgaaaggtg atgggtttta        60

<210> SEQ ID NO 563
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 563
cagctcaagt accctaattt agttcttttg gactaataca attcaggaaa gaaaaaaccc        60

<210> SEQ ID NO 564
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 564
gaagaattcg ccaagtattt aaagttgcct gtttcagatg tcttgagaca acttttttgca       60

<210> SEQ ID NO 565
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 565
gtgggaccgg atcacccgct tggaaaaggg caagatctat cggcagggaa acctgtttga        60

<210> SEQ ID NO 566
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 566
gcgagtggga gcaccaggat ctcgggctcg gaacgagact gcacggattg ttttaagaaa        60

<210> SEQ ID NO 567
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 567
gccccttgaa catgaccgtg gcccaaaatt tgctattccc atgcatttg tttgtttctt        60

<210> SEQ ID NO 568
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 568
gatggatcca ctggaggtta agacatgtgg taagacagtg taataggaag ctgctcagtt    60

<210> SEQ ID NO 569
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 569
ggactgggtt agaaggtata aggttcctga tggaaaaga atgagtttg cttttaatgc    60

<210> SEQ ID NO 570
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 570
ctgctgtgcc tgatgtgggg acagacctgc tcccagatgt aaacagagca acctgcacaa    60

<210> SEQ ID NO 571
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 571
gatgagataa ggagagtcag aaacaaactt atagtgatgc gttggaaggt taatcgaaac    60

<210> SEQ ID NO 572
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 572
gggttggtgt tggcaagtca agagagtcga tgatccagct gttttagtcg cagactgagc    60

<210> SEQ ID NO 573
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 573
ttccatcacc agaaaaacta atgagatttc tctggaatac aagctgatat tgctacatcg    60

<210> SEQ ID NO 574
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 574
ctgaccccca agcagaagac agacctctgg ttttctttga cctcaagatt gacaatgaaa    60

<210> SEQ ID NO 575
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 575
gtaccgatcg tagcccctat gagaaggttt ctgcaggtaa tggtggcagc agcctctctt    60

<210> SEQ ID NO 576
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 576
gctattccaa agatttcaag ctgttctgag acatcttctg atggctttac ttcctgagag    60

<210> SEQ ID NO 577
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 577
agctccgcgt gagaagtact ggctacaatt ttttatccca ttgttggtgg tgattctgtt    60

<210> SEQ ID NO 578
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 578
taccattctt tccataggta gaagagaaag ttgattggtt ggttgttttt caattatgcc    60

<210> SEQ ID NO 579
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 579
ctttggctta atgagactgg gaccattggt gatgagaagg caaacatgtt cagaagtcaa    60

<210> SEQ ID NO 580

```
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 580
agtggctcta ttctacctgt aagaaaatga tacaaaacca cctaagatat tttgaagcct    60

<210> SEQ ID NO 581
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 581
aggtgaaaag tcaaatgaaa cagtacaatt cttgatgagt gaggtgtcat cttccaacca    60

<210> SEQ ID NO 582
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 582
ctatctcaaa ggatgacgtg atactcaatg ccttcagcaa atcagagact agcaagctgg    60

<210> SEQ ID NO 583
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 583
aacccaaact ccaaagcttt gaacattcat gactgaactg aaaacaagcc atgacttgag    60

<210> SEQ ID NO 584
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 584
atgctgaaga aacatcagtt ccagaagctc cgaaaattgc tccaatattt ggaaagaagg    60

<210> SEQ ID NO 585
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 585
caagccagag tcgatacagc aagcggagga tttggagatc cgtcaaactt aaagattaca    60

<210> SEQ ID NO 586
<211> LENGTH: 60
```

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 586
ctatcatcaa ctgcatcatc tactttaatg gtgaggtacc acagcttgtg ctgtacatgg      60

<210> SEQ ID NO 587
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 587
tggctaaatg ctttgcagaa agtgatgacc ttacaccaca accagcttct ccaggtcata      60

<210> SEQ ID NO 588
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 588
gcgattaccc tggttgcaca aaagtttata ccaagtcttc tcatttaaaa gctcacctga      60

<210> SEQ ID NO 589
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 589
gatgtgagtg tgtttcatca aacatagctc agtcctgatt atttaattgg aatatgatgg      60

<210> SEQ ID NO 590
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 590
cagagcacaa tcatcctgaa gtcttgaagg tgtcttgcaa gtgtggcaac acgttgagcc      60

<210> SEQ ID NO 591
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 591
gttcaccagc atgcccaccc tcatgcagga gtttgccaat ggcctgctga acaaggtcgt      60

<210> SEQ ID NO 592
<211> LENGTH: 60
<212> TYPE: DNA
```

```
<213> ORGANISM: Artificial Sequence
<220> FEATURE:
<223> OTHER INFORMATION: Description of Artificial Sequence: Synthetic
      probe

<400> SEQUENCE: 592
cttacttaaa cttcacacca gaaccttctg acattttctc ctgcattgtg actcacgaaa    60

<210> SEQ ID NO 593
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 593
tacattgcac cagagaagat agaaaatatc tacaacagga gtcaaccagt gttacaaatt    60

<210> SEQ ID NO 594
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 594
ttgtagatga actcttctca actctgtttt gctatgctat aattccgaaa catacaagac    60

<210> SEQ ID NO 595
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 595
atgtggcctc aaatgtcatg ccaattttca catcttccac aaactccatt tagggagaaa    60

<210> SEQ ID NO 596
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 596
ggccatacgc catgccatag cttgtgctat ctgtaaatat gagacttgta aagaactgcc    60

<210> SEQ ID NO 597
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 597
gaccaggaaa aacaagaaag acatactcaa tcctgattca agtatggaaa cttcaccaga    60

<210> SEQ ID NO 598
<211> LENGTH: 60
<212> TYPE: DNA
<213> ORGANISM: Artificial Sequence
```

```
<220> FEATURE:
<223> OTHER INFORMATION: Description of Artificial Sequence: Synthetic
      probe

<400> SEQUENCE: 598
tttaggggtc ctatctcctg ggggaagggg agatctaaga tgtcccaggt cctgggaagt      60

<210> SEQ ID NO 599
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 599
aagggacgtt gacctggact gaagttcgca ttgaactcta caacattctg tggggatata      60

<210> SEQ ID NO 600
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 600
tgctcaaagc tcaaaatgta acaaggtaca taaaacttgg tcatggtgga cactggagtc      60

<210> SEQ ID NO 601
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 601
ccagttatct ctccaaaaca cgacccacac gaggacctcg cattaaagta ttttcggaaa      60

<210> SEQ ID NO 602
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 602
taaccaaggt taggtgactg aggactggag ctgtttggtt ttctcgcatt ttccaccaaa      60

<210> SEQ ID NO 603
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 603
ctgttcctgt gatgtggagg aaattttccg caaggttcga ttttcatttg agcagccaga      60

<210> SEQ ID NO 604
<211> LENGTH: 60
<212> TYPE: DNA
<213> ORGANISM: Artificial Sequence
<220> FEATURE:
```

<223> OTHER INFORMATION: Description of Artificial Sequence: Synthetic
      probe

<400> SEQUENCE: 604
ccgaagttgc ctcttttagg aatctctttg gaattgggag cacgatgact ctgagtttga      60

<210> SEQ ID NO 605
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 605
actccagata aaatgaaaaa cctctccaag tcctggtgga agaagtactg ctgtttcgta      60

<210> SEQ ID NO 606
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 606
aaacatcatc aaaaaggaca ttcagaacat gatcgtggag gagtgtgggt gctcatagag      60

<210> SEQ ID NO 607
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 607
cggaagtgcc taagtcttta gtttccaatt tgcggatcca ctgccctctg cttgcgggct      60

<210> SEQ ID NO 608
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 608
acgtttgttt tcaaggagag ggtttaaaaa tgggatcctg taagcagact tgggcagtct      60

<210> SEQ ID NO 609
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 609
gtcacaagat ggcaaaatgc tgaaagtttt tacactgtcg atgtttccaa tgcatcttcc      60

<210> SEQ ID NO 610
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 610
tcatcagaga agtgccgctg ctgtgcctga tgttgggaga gccctgctcc cagacataaa    60

<210> SEQ ID NO 611
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 611
gaattgtcca gagaatcaag gatttttgc ggaatcttgt acccaggaca gagtcctagt    60

<210> SEQ ID NO 612
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 612
cccaagacac agggaccgtt tctccctag gagcagcggt ggggagcagg gccaaggtcc    60

<210> SEQ ID NO 613
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 613
ccgcctgggg gtgggcgcag agctgctggt cgacgtgggt cagaggctgc gccgtgggac    60

<210> SEQ ID NO 614
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 614
ctgtatctaa ctggggctgt gatcaagaag gttctgacca gcttctgcag aggataaaat    60

<210> SEQ ID NO 615
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 615
taccagataa ctgaggaggg gagaggtggg ccgtaacggg cacggatcac gatgtaaatt    60

<210> SEQ ID NO 616
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 616
acctctcatg caccatcgta gggatcatag ttctaattgt gcttctgatt gtgtttgttt    60

<210> SEQ ID NO 617
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 617 tttttttgtaa agttgatgcc ttacttttg gataaatatt tttgaagctg gtatttctat    60

<210> SEQ ID NO 618
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 618
atttgacatt tgtgtgtaat ttcatggtgg cctagtgttg tggtgcttct ggtaatggta    60

<210> SEQ ID NO 619
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 619
gtgcatgaac gtcccagaga tgatgccacc gttagaatat ctcatggata tactcccaaa    60

<210> SEQ ID NO 620
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 620
tccccgtacc ggaaacaggt ggagaaaatc cgttactgca tcaccaaact tgacagggag    60

<210> SEQ ID NO 621
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 621
acatttttca cccagacgaa ttgtacgtgg gcagaccgca gagagtttgc ctgtgcataa    60

<210> SEQ ID NO 622
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

```
<400> SEQUENCE: 622
tctaagagag aatggaatgt atgggaaaag aaagttactg gaactaatag gacacgctgt    60

<210> SEQ ID NO 623
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 623
ctgtttcaag cttctgtact ttatggaact ttggctgtga tttattttta aaggactctg    60

<210> SEQ ID NO 624
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 624
tgggcacaca aaaggattta gggtatttaa aaaatctatg tctctcccat ctcactgact    60

<210> SEQ ID NO 625
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 625
aatggcttcg gacaaaatat ctctgagttc tgtgtatttt cagtcaaaac tttaaacctg    60

<210> SEQ ID NO 626
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 626
ctgtgacttg taataaacca agctgtacaa tttagtttat aatagcagta tctgagctgc    60

<210> SEQ ID NO 627
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 627
gattatggga tatttcagat caatagccgc tactggtgta atgatggcaa aaccccagga    60

<210> SEQ ID NO 628
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 628
```
gagcatggac tcgctccaga ccgttgtcac ctgttgcatt aaacttgttt tctgttgatt    60

<210> SEQ ID NO 629
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 629
ggctggagaa gaatcttccg actctgagga cttggctaat ggttaatact taaatggtca    60

<210> SEQ ID NO 630
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 630
ccaggaaggt catcaagatg gagtctgagg aggggaagga ggcaaggttg gctcggagct    60

<210> SEQ ID NO 631
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 631
tggcttacta aaaccgagct cactgtaaaa tcatgatcca acttattgct aatctttatg    60

<210> SEQ ID NO 632
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 632
taatgtggga ataaatagag ttcaagatcc cgtaactaaa cccaagttag ttggagatgt    60

<210> SEQ ID NO 633
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 633
acaggaaatg cactggagga tttgggcctg aggttactat gccagggact gaggcaccca    60

<210> SEQ ID NO 634
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 634
cagattagac cacctcataa tgagttcttg attgcacttc agattgtctt gatggggcac      60

<210> SEQ ID NO 635
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 635
gctctattcc aaaaaggttg ctgtttcaca atacctcatg cttcacttag ccatggtgga      60

<210> SEQ ID NO 636
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 636
ccaccttttc aatgggattt catctgttag ttactgtgag tctcttattt tcccatgtgg      60

<210> SEQ ID NO 637
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 637
gtgggaggtc aatcccsttt actgtgacac agtgaaacag atctacccgt acaacaacag      60

<210> SEQ ID NO 638
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 638
cgttccagtg ccaaaaatgc gaccgagcat tttccaggtc ggaccacctc gccttacaca      60

<210> SEQ ID NO 639
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 639
agctatgagt tgaaatgttc tgtcaaatgt gtctcacatc tacacgtggc ttggaggctt      60

<210> SEQ ID NO 640
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 640
agctgctgtg cctgatgtcg ggacagccct gctcccaagt acaaatagag tgacccgtaa      60

<210> SEQ ID NO 641
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 641
gcaagctggc tttgtagcac attttacaaa tgtgtggcat tgaatattgc acagtgatgg      60

<210> SEQ ID NO 642
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 642
gcctggtaaa atcatacacc aataccagcc acatcatgca gtacggaaac gaaacgatct      60

<210> SEQ ID NO 643
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 643
tgttctaccg tactttagta gtttgaagtt ttcaagtgca taactatttt tgaccagcag      60

<210> SEQ ID NO 644
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 644
acacaaatat gccacctcaa acaagcacaa gttgaccccg gaatatctgg agctcaaaaa      60

<210> SEQ ID NO 645
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 645
tgtgtcaagg aaagggcttt atttgtgaat tttgccagaa tacgactgtc atcttcccat      60

<210> SEQ ID NO 646
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 646
ataacgtatt aaaactcttt taagtagctt aaggtattgt gcaatggcct agcctagtag      60

<210> SEQ ID NO 647
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 647
aagaatgtac ataatgttac cggagctgat ttgtttggtc attagctctt aatagttgtg    60

<210> SEQ ID NO 648
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 648
ggcatcggag aagtgcagct gctgtgcctg atgtgggaac agctcttctc ccagatgtaa    60

<210> SEQ ID NO 649
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 649
tctaaatcaa ctcctagatc aaagcaaggg ctccttttg gcaatagact gctagattga     60

<210> SEQ ID NO 650
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 650
tcctggactt ttcctctcat gtctttgctg cagaactgaa gagactaggc gctgggctc     60

<210> SEQ ID NO 651
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 651
gaagatgatc atggatgaca gcaaacgcaa ggcgaagtct tttgagggca acaacaacta    60

<210> SEQ ID NO 652
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 652
cagggaagtt tacaagctag agcgaatatc tggactgcta atatctgaca acagtaggcg    60

-continued

```
<210> SEQ ID NO 653
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 653
caccgtcatg tcctgcaaca tctccaacgc cttctcccat gtcaacatca agctgcgtgc    60

<210> SEQ ID NO 654
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 654
ccccacaggc catgaccttg aagtgaaagt cttctgttgc tattgtgggc tcaaatattt    60

<210> SEQ ID NO 655
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 655
agggatgcac gcacagtggt aatttattac tcagttccgg ttatgttttt ctccaaaacc    60

<210> SEQ ID NO 656
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 656
aatctgaatt aagctttatc agtgtactct ttatctgtgt tactagtgcc tggtatgtag    60

<210> SEQ ID NO 657
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 657
cctgttggca ctgatgaaga acccttacag ttcagggttc ctggaacttc taccagtgcc    60

<210> SEQ ID NO 658
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 658
ggaaaatgat tgacaaagcc caacaatgat ctcaggaatt acattttcca acagaccaaa    60

<210> SEQ ID NO 659
```

```
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 659
ccagggctgc atctgcaaag ggacgtcaga caagtgcagc tgctgtgcct gatgccagga      60

<210> SEQ ID NO 660
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 660
ttttgagttc cagttgactg cagaggacat gaaagccata gatggcctag acagaaatct      60

<210> SEQ ID NO 661
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 661
aagataggaa ggttatttgg agatatctgt gcctgctaaa cacaaatgca tcggcccaca      60

<210> SEQ ID NO 662
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 662
aatatttgtg taacggagat atactactgt aagttttgta ctgtactggc tgaaagtctg      60

<210> SEQ ID NO 663
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 663
atgacagaag ggttcatata aacagtatcc tgacacagtc atgcttcctg gattttggag      60

<210> SEQ ID NO 664
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 664
atgctgaacg taaactataa tgctctacca caagaaaatg gcctctcacc tggggccatt      60

<210> SEQ ID NO 665
<211> LENGTH: 60
```

<212> TYPE: DNA
<213> ORGANISM: Artificial Sequence
<220> FEATURE:
<223> OTHER INFORMATION: Description of Artificial Sequence: Synthetic
      probe

<400> SEQUENCE: 665
tgtgccaagt gtgcccacgg ctgcatctgc aaagggacgt cggagaagtg cagctgctgt      60

<210> SEQ ID NO 666
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 666
cacgtgcact ttattgaatg ccattgtaga aaagcgtgtg aggataaagg gctgatacag      60

<210> SEQ ID NO 667
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 667
tcaaggaaaa tctgggctaa gagtaggata tgagggatga tggataaggc atgagacatg      60

<210> SEQ ID NO 668
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 668
tgccaagtgt gcccagggct gcatctgcaa agggacgtca gacaagtgca gctgctgtgc      60

<210> SEQ ID NO 669
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 669
ctctgtatgc accagattat tcatctcgtt tagatattgt aagagcaaat tcaaagtcac      60

<210> SEQ ID NO 670
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 670
tctttggcaa tggccaccct ggtgttggca tattggcccc actgtaactt ttgggggctt      60

<210> SEQ ID NO 671
<211> LENGTH: 60
<212> TYPE: DNA

```
<213> ORGANISM: Artificial Sequence
<220> FEATURE:
<223> OTHER INFORMATION: Description of Artificial Sequence: Synthetic
      probe

<400> SEQUENCE: 671
actttgagaa ctctgtgaga caaggtcctt aggcacccag atatcagcca ctttcacatt      60

<210> SEQ ID NO 672
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 672
ctgtgaccag cactgtctca gtttcacttt cacatagatg tcccttctt ggccagttat      60

<210> SEQ ID NO 673
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 673
ctaagcatca gacctggaat tggagttgc aaagtgacta tcttcccatt tcccatctca      60

<210> SEQ ID NO 674
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 674
tctgcaatga atcccaaaag tatgtagttg agctgactgc aaggtgcttg agatgcaaga      60

<210> SEQ ID NO 675
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 675
actgaacggt gacttcagtg ttctcaacac tttactaaat tttactgata acttcgacga      60

<210> SEQ ID NO 676
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 676
agaacaaagt aattttctga agggaagctg cagaatatgg aaaacatata ttggagctac      60

<210> SEQ ID NO 677
<211> LENGTH: 60
<212> TYPE: DNA
<213> ORGANISM: Artificial Sequence
```

```
<220> FEATURE:
<223> OTHER INFORMATION: Description of Artificial Sequence: Synthetic
      probe

<400> SEQUENCE: 677
tgtgcaatat gtgatgtggc aaatctctat taggaaatat tctgtaatct tcagacctag    60

<210> SEQ ID NO 678
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 678
tgttcatatg ggagaagggg gagtaatgac ttgtacaaac agtatttctg gtgtatattt    60

<210> SEQ ID NO 679
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 679
gttagggctc ctattcaaca cacacatgct tccctttcct gagtcccatc cctgcgtgat    60

<210> SEQ ID NO 680
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 680
tcacaggaag tagaggaggc cacgttctta ctagtttccc ttgcatggtt tagaaagctt    60

<210> SEQ ID NO 681
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 681
ctgtattttg tgctgcctga gaccaaaaac agaacctatg cagaaatcag ccaggcattt    60

<210> SEQ ID NO 682
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 682
cacggacagg aagcacagca ggtttatcca gatgaactga gaaggtcaga ttagggcggg    60

<210> SEQ ID NO 683
<211> LENGTH: 60
<212> TYPE: DNA
<213> ORGANISM: Artificial Sequence
<220> FEATURE:
```

```
<223> OTHER INFORMATION: Description of Artificial Sequence: Synthetic
      probe

<400> SEQUENCE: 683
agatgcggta atgaaaccgg ttagtcagtg ttgtcttaat atccttgata atgctgtaaa    60

<210> SEQ ID NO 684
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 684
cagacagaca gatggaccgg cccacactcc cagagttgct aacatggagc tctgagatca    60

<210> SEQ ID NO 685
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 685
aagtgcaaat gcacctcctg caagaagagc tgctgctcct gttgcccct gggctgtgcc    60

<210> SEQ ID NO 686
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 686
tgcccaattg ccaaactaaa gacatcagtt cattggtcaa atatttgtta cctggaatgg    60

<210> SEQ ID NO 687
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 687
aatcagagag tgtcacagat ttaaccttga tctaaagaca agttgtaccc agagtatgtg    60

<210> SEQ ID NO 688
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 688
tgcttttaac ttccccacca tgttgcacct aaagctttgg agttttcctg tgattagtgt    60

<210> SEQ ID NO 689
<211> LENGTH: 60
<212> TYPE: DNA
<213> ORGANISM: Artificial Sequence
<220> FEATURE:
<223> OTHER INFORMATION: Description of Artificial Sequence: Synthetic
``` probe

<400> SEQUENCE: 689
tgggaaacat gcgtgtgacc tccacagcta cctcttctat ggactggttg ttgccaaaca    60

<210> SEQ ID NO 690
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 690
aagatcagga aatgtagaca tctagtgatt tctttagtag acagtttaat ttcccccaag    60

<210> SEQ ID NO 691
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 691
cttttggcag caaaaccacc tgcgtggcta ggatgattaa ttatgaggat gatgattttt    60

<210> SEQ ID NO 692
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 692
aattcagcaa gatatgtgat ggttctgaga atgaatttaa ttgaaataga ccagcagacc    60

<210> SEQ ID NO 693
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 693
ttgggaactc tagtctcgcc tcgggttgca atggacccca actgctcctg tgccgctggt    60

<210> SEQ ID NO 694
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 694
acctcaagtg ttgtaaaatt cgctactgca atttagaggg gccacctatc aactcatcag    60

<210> SEQ ID NO 695
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

```
<400> SEQUENCE: 695
tttgctgtta ttttatctgc tatgctattg aagttttggc aattgactat agtgtgagcc      60

<210> SEQ ID NO 696
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 696
tcctgcatgg gatctgatgg atcatgaaaa tattttgttt ctcaccatat gcttttgttg      60

<210> SEQ ID NO 697
<211> LENGTH: 4
<212> TYPE: PRT
<213> ORGANISM: Homo sapiens

<400> SEQUENCE: 697

Asp Glu Ala Asp
1
```